United States Patent
Cheng et al.

(10) Patent No.: US 7,084,162 B2
(45) Date of Patent: Aug. 1, 2006

(54) SUBSTITUTED ACID DERIVATIVES USEFUL AS ANTIDIABETIC AND ANTIOBESITY AGENTS AND METHOD

(75) Inventors: Peter T. Cheng, Princeton, NJ (US); Pratik Devasthale, Plainsboro, NJ (US); Yoon Jeon, Belle Mead, NJ (US); Sean Chen, Princeton, NJ (US); Hao Zhang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 110 days.

(21) Appl. No.: 10/655,876

(22) Filed: Sep. 5, 2003

(65) Prior Publication Data

US 2004/0171644 A1 Sep. 2, 2004

Related U.S. Application Data

(60) Division of application No. 10/080,981, filed on Feb. 22, 2002, now Pat. No. 6,653,314, which is a continuation of application No. 09/812,960, filed on Mar. 20, 2001, now Pat. No. 6,414,002, which is a continuation-in-part of application No. 09/664,598, filed on Sep. 18, 2000, now abandoned.

(60) Provisional application No. 60/155,400, filed on Sep. 22, 1999.

(51) Int. Cl.
*A61K 31/421* (2006.01)
*C07D 263/32* (2006.01)

(52) U.S. Cl. .................................. 514/374; 548/236
(58) Field of Classification Search ................. 548/236
See application file for complete search history.

(56) References Cited

U.S. PATENT DOCUMENTS

| 5,036,079 A | 7/1991 | Clark et al. |
| 5,889,025 A | 3/1999 | Lohray et al. |

FOREIGN PATENT DOCUMENTS

| EP | 0520723 B1 | 6/1994 |
| WO | WO92/22533 | 12/1992 |
| WO | WO96/38415 | 12/1996 |
| WO | WO97/27847 | 8/1997 |
| WO | WO97/27857 | 8/1997 |
| WO | WO97/28137 | 8/1997 |
| WO | WO97/28149 | 8/1997 |
| WO | WO97/31907 | 9/1997 |
| WO | WO98/00137 | 1/1998 |
| WO | WO98/00403 | 1/1998 |
| WO | WO98/27974 | 7/1998 |
| WO | WO99/07357 | 2/1999 |
| WO | WO99/08501 | 2/1999 |
| WO | WO99/11255 | 3/1999 |
| WO | WO99/15520 | 4/1999 |
| WO | WO99/16758 | 4/1999 |
| WO | WO99/20275 | 4/1999 |
| WO | WO 99/46232 | 9/1999 |
| WO | WO 00/08002 | 2/2000 |
| WO | WO 00/64676 | 11/2000 |
| WO | WO 00/64888 | 11/2000 |

OTHER PUBLICATIONS

Collins, et al, J. Med. Chem., 41, 5037–5054, 1998.
Henke, et al, J. Med. Chem., 41, 5020–5036, 1998.
Cobb, et al, J. Med. Chem., 41, 5055–5069, 1998.

*Primary Examiner*—Johann Richter
*Assistant Examiner*—Ebenezer Sackey
(74) *Attorney, Agent, or Firm*—Burton Rodney

(57) ABSTRACT

Compounds are provided which have the structure

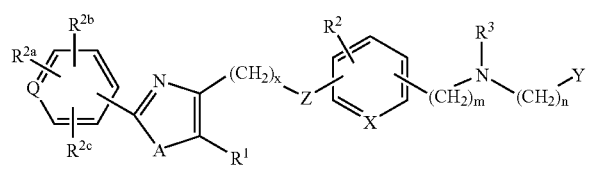

wherein Q is C or N, A is O or S, Z is O or a bond, X is CH or N and $R^1$, $R^2$, $R^{2a}$, $R^{2b}$, $R^{2c}$, $R^3$, Y, x, m, and n are as defined herein, which compounds are useful as antidiabetic, hypolipidemic, and antiobesity agents.

3 Claims, No Drawings

SUBSTITUTED ACID DERIVATIVES USEFUL AS ANTIDIABETIC AND ANTIOBESITY AGENTS AND METHOD

This is a divisional application of application Ser. No. 10/080,981 filed Feb. 22, 2002 now U.S. Pat. No. 6,653,314 which is a continuation of application Ser. No. 09/812,960 filed Mar. 20, 2001, now U.S. Pat. No. 6,414,002, which is a continuation-in-part of U.S. application Ser. No. 09/664,598 filed Sep. 18, 2000, now abandoned, which application takes priority from U.S. provisional application No. 60/155,400 filed Sep. 22, 1999.

FIELD OF THE INVENTION

The present invention relates to novel substituted acid derivatives which modulate blood glucose levels, triglyceride levels, insulin levels and non-esterified fatty acid (NEFA) levels, and thus are particularly useful in the treatment of diabetes and obesity, and to a method for treating diabetes, especially Type 2 diabetes, as well as hyperglycemia, hyperinsulinemia, hyperlipidemia, obesity, atherosclerosis and related diseases employing such substituted acid derivatives alone or in combination with another antidiabetic agent and/or a hypolipidemic agent.

DESCRIPTION OF THE INVENTION

In accordance with the present invention, substituted acid derivatives are provided which have the structure I

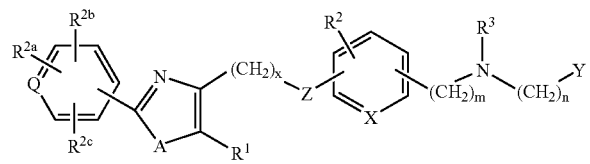

wherein x is 1, 2, 3 or 4; m is 1 or 2; n is 1 or 2;
Q is C or N;
A is O or S;
Z is O or a bond;
$R^1$ is H or alkyl;
X is CH or N;
$R^2$ is H, alkyl, alkoxy, halogen, amino or substituted amino;
$R^{2a}$, $R^{2b}$ and $R^{2c}$ may be the same or different and are selected from H, alkyl, alkoxy, halogen, amino or substituted amino;
$R^3$ is H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, alkyl(halo)aryloxycarbonyl, alkyloxy(halo)aryloxycarbonyl, cycloalkylaryloxycarbonyl, cycloalkyloxyaryloxycarbonyl, cycloheteroalkyl, heteroarylcarbonyl, heteroaryl-heteroarylalkyl, alkylcarbonylamino, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkenyloxycarbonyl, arylalkylcarbonyl, aryloxyalkyloxycarbonyl, arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl, aminocarbonylarylarylalkyl;

Y is $CO_2R^4$ (where $R^4$ is H or alkyl, or a prodrug ester) or Y is a C-linked 1-tetrazole, a phosphinic acid of the structure $P(O)(OR^{4a})R^5$, (where $R^{4a}$ is H or a prodrug ester, $R^5$ is alkyl or aryl) or phosphonic acid of the structure $P(O)(OR^{4a})_2$, (where $R^{4a}$ is H or a prodrug ester);

$X^1_x$, $X^1_n$ and $X^1_m$ which may also be referred to as $(CH_2)_x$, $(CH_2)_n$ and $(CH_2)_m$, respectively, may be optionally substituted with 1, 2 or 3 substituents;

including all stereoisomers thereof, prodrug esters thereof, and pharmaceutically acceptable salts thereof, with the proviso that where X is CH, A is O, Q is C, Z is O, and Y is $CO_2R^4$, then $R^3$ is other than H or alkyl containing 1 to 5 carbons in the normal chain.

Thus, compounds of formula I of the invention may have the structure

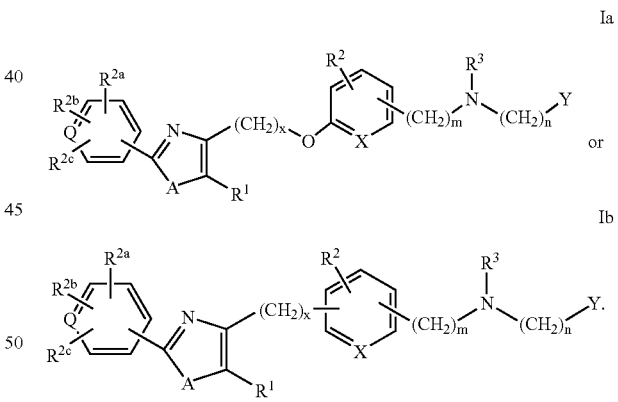

Preferred are compounds of formula I of the invention having the structure

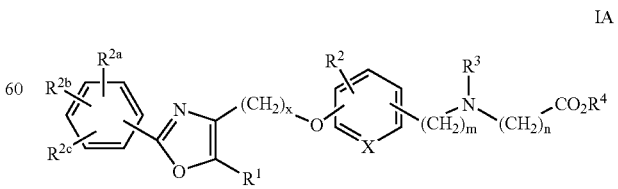

More preferred are compounds of formula I of the invention having the structures

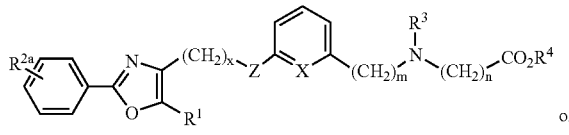
IB

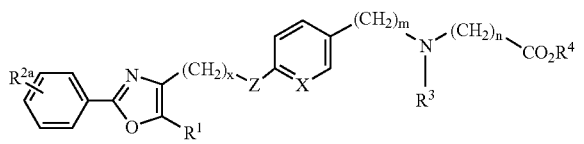
IC

In the above compounds, it is most preferred that $R^{2a}$ is alkoxy, but more preferably H, Z is a bond, but more preferably O, $X^1_x$ or $(CH_2)_x$ is $CH_2$, $(CH_2)_2$, $(CH_2)_3$, or

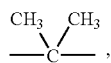

$X^1_m$ or $(CH_2)_m$ is $CH_2$, or

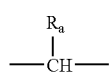

(where $R_a$ is alkyl such as methyl, or alkenyl such as

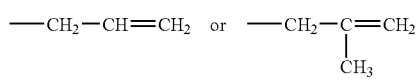

), $X^1_n$ or $(CH_2)_n$ is $CH_2$, $R^1$ is lower alkyl, preferably —$CH_3$, $R^2$ is H, $R^{2a}$ is H, $R^4$ is H, X is CH, and $R^3$ is arylalkyloxycarbonyl, arylheteroarylalkyl, aryloxyarylalkyl, arylalkyl, aryloxycarbonyl, haloaryloxycarbonyl, alkoxyaryloxycarbonyl, alkylaryloxycarbonyl, aryloxyaryloxycarbonyl, heteroaryloxyarylalkyl, heteroaryloxycarbonyl, aryloxyarylcarbonyl, arylalkenyloxycarbonyl, cycloalkylaryloxycarbonyl, arylalkylarylcarbonyl, heteroaryl-heteroarylalkyl, cycloalkyloxyaryloxycarbonyl, heteroaryl-heteroarylcarbonyl, alkyloxyaryloxycarbonyl, arylalkylsulfonyl, arylalkenylsulfonyl, alkoxyarylalkyl, arylthiocarbonyl, cycloheteroalkylalkyloxycarbonyl, cycloheteroalkyloxycarbonyl, or polyhaloalkylaryloxycarbonyl, wherein the above preferred groups may be optionally substituted.

Preferred compounds of the invention include the following:

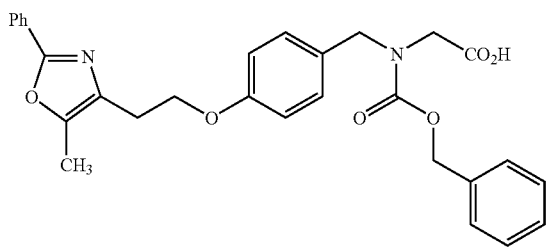

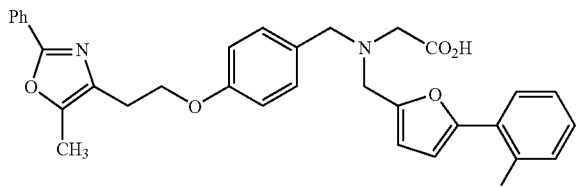

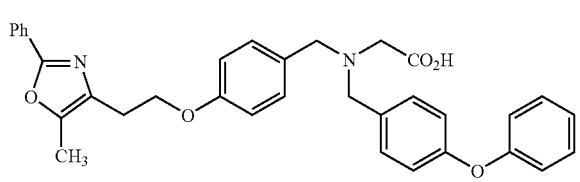

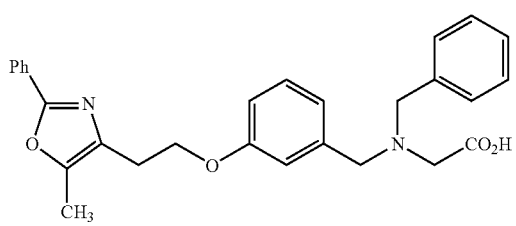

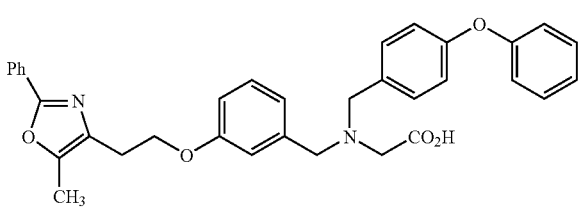

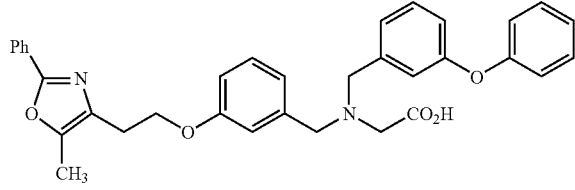

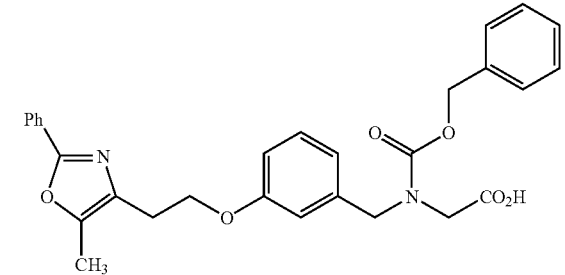

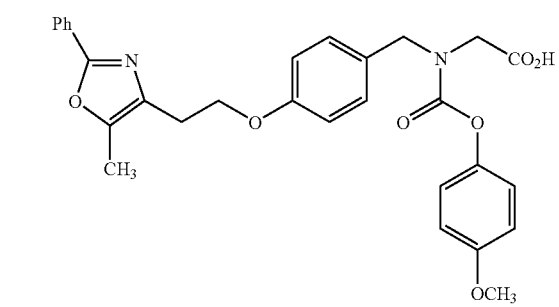

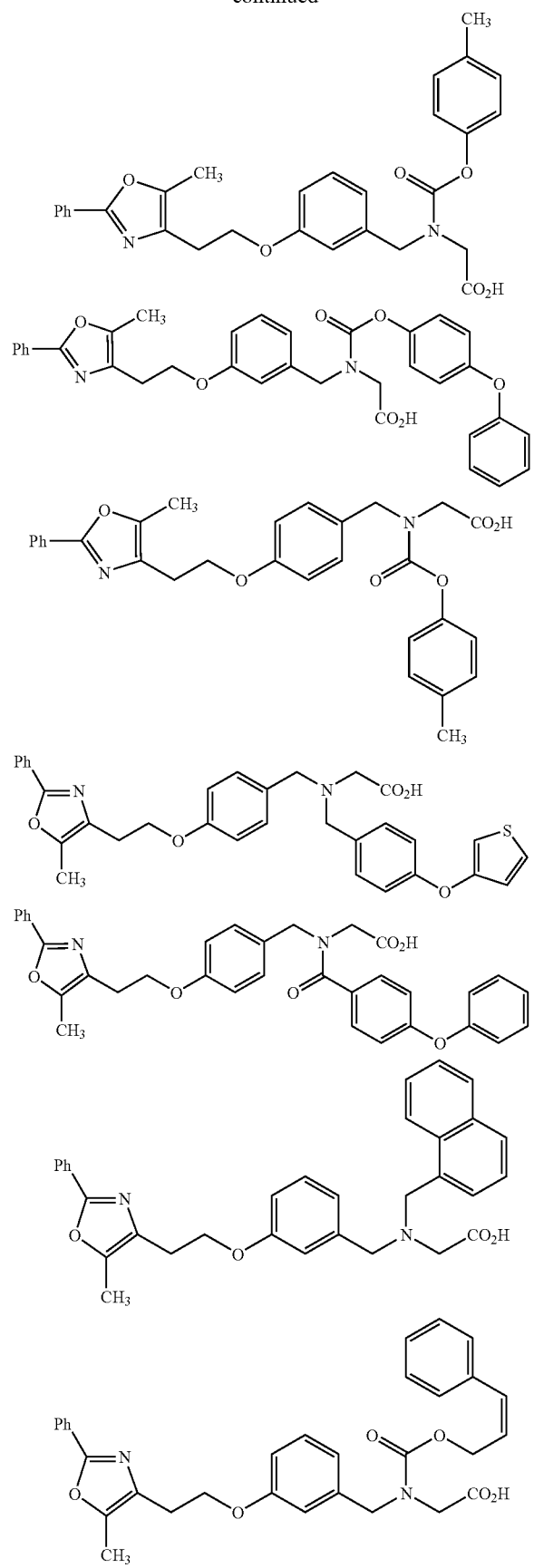
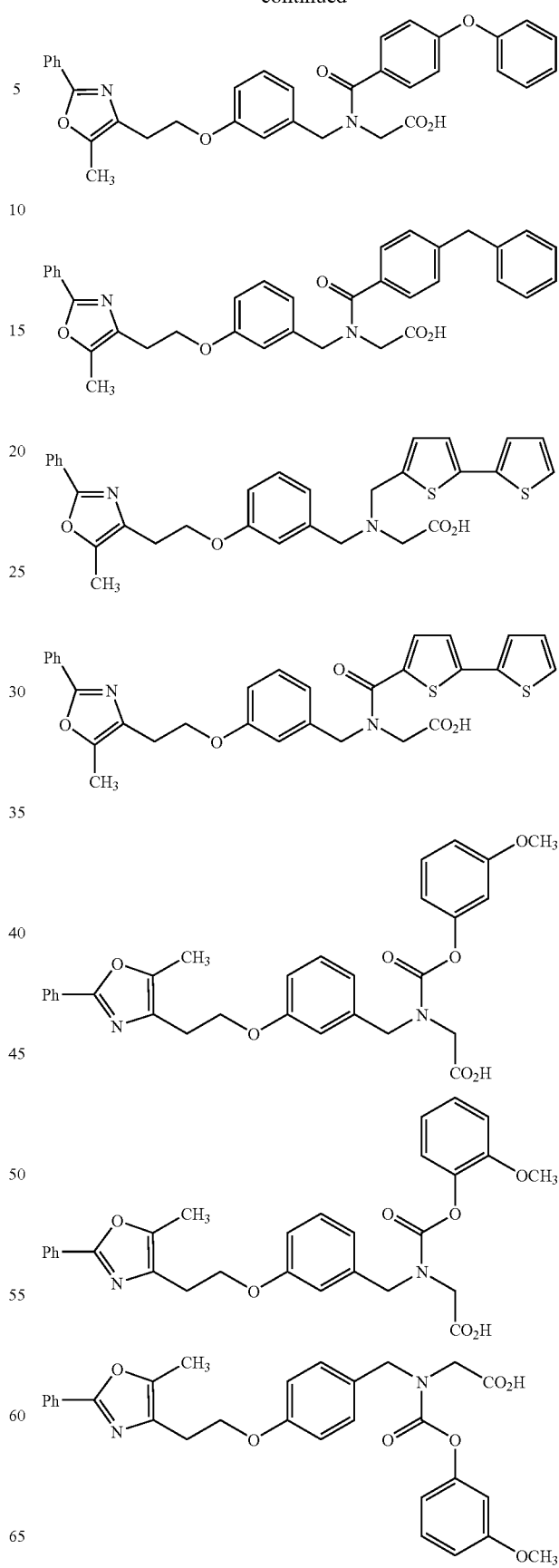

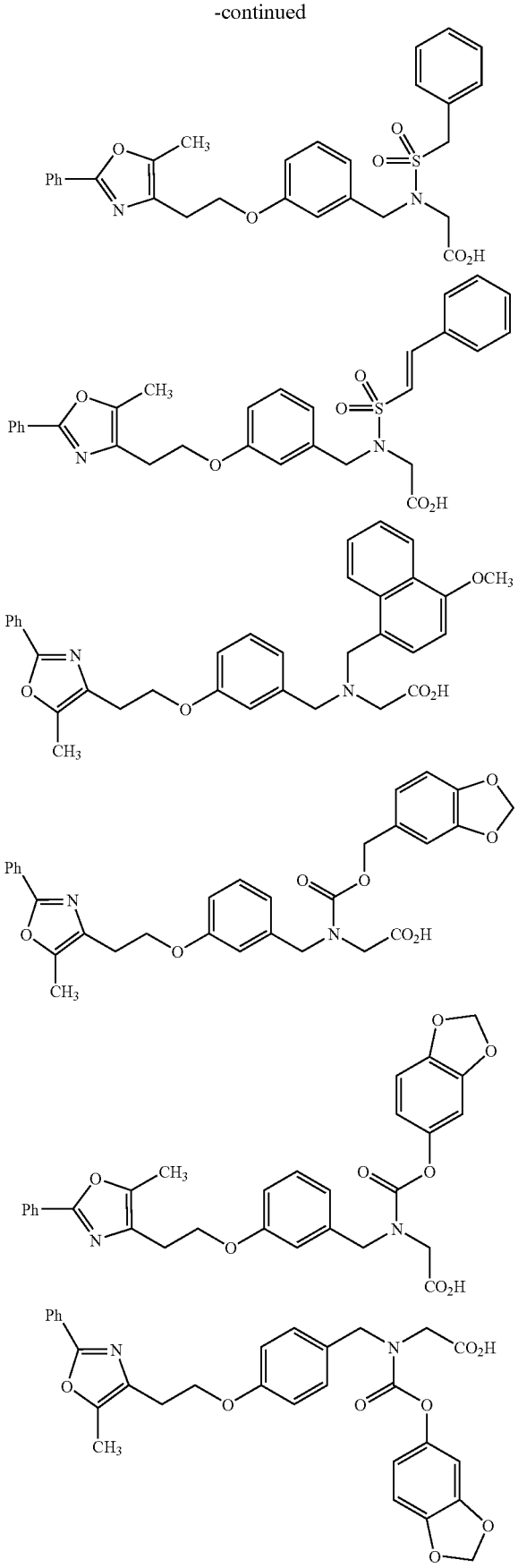
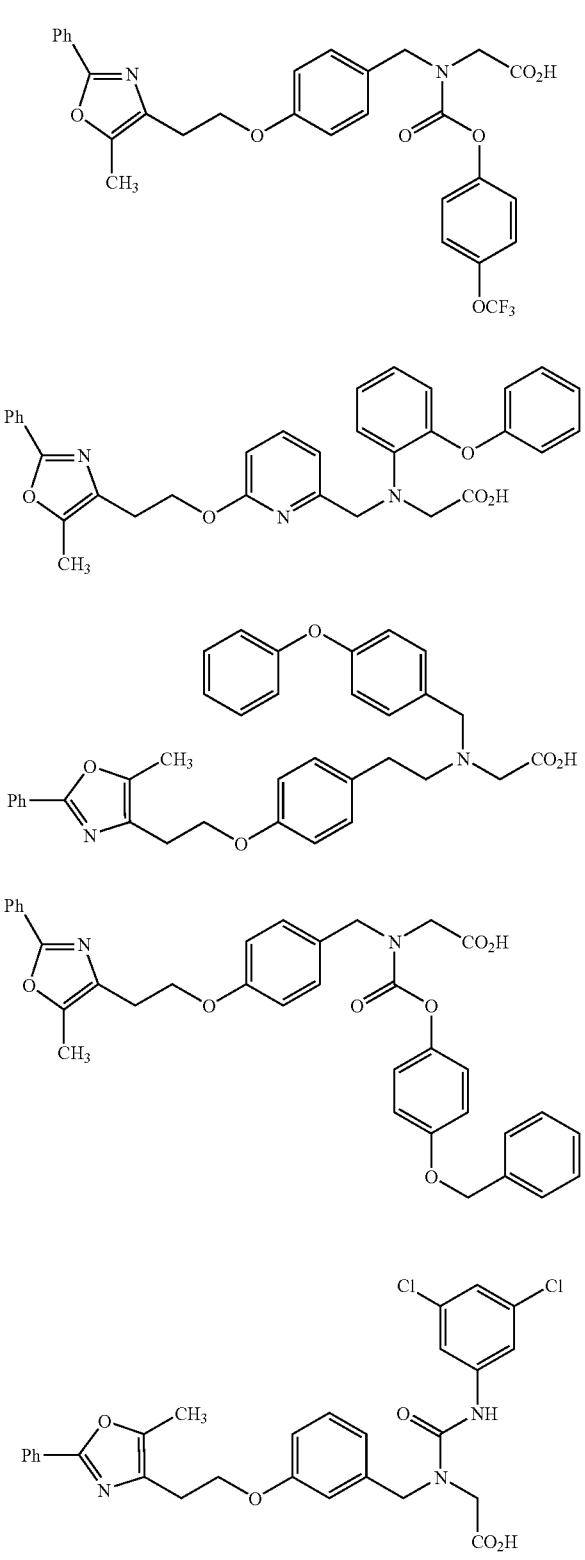

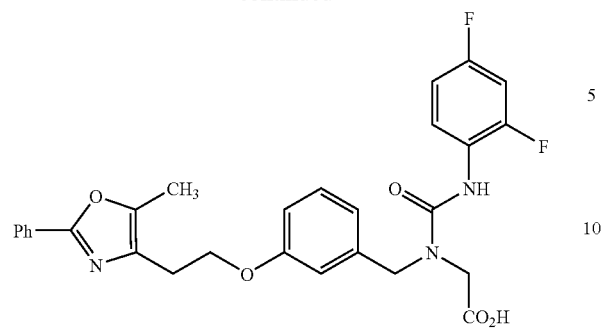
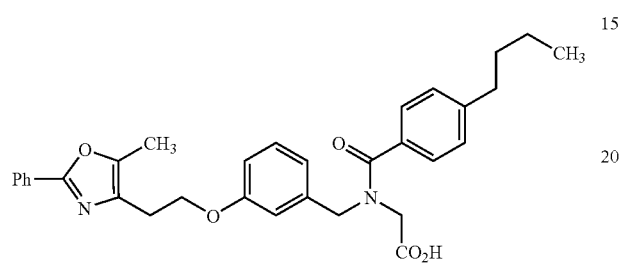
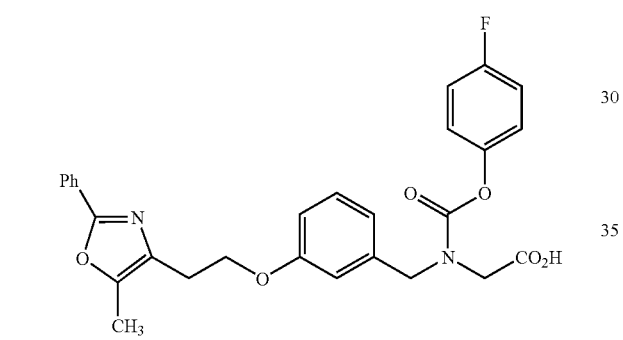
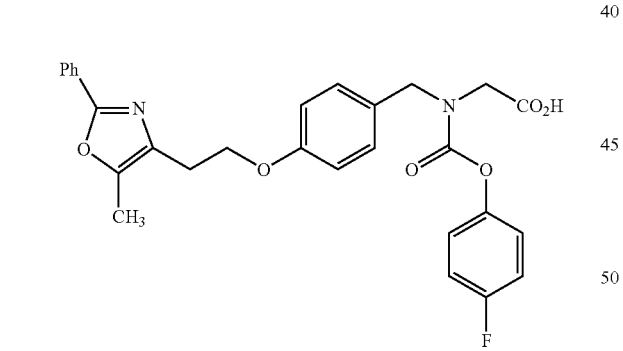
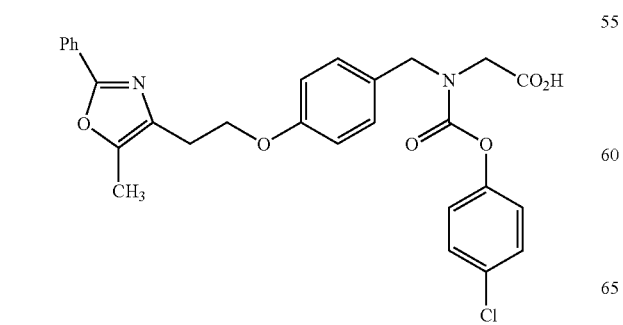
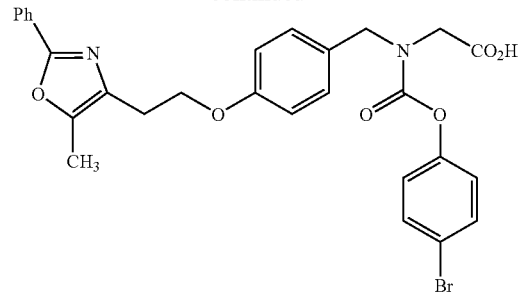
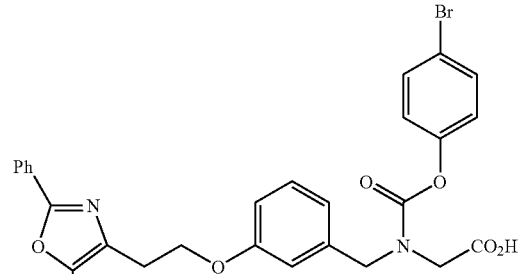
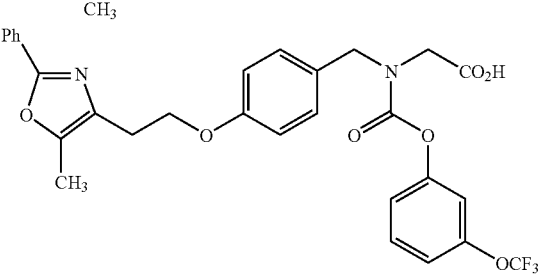
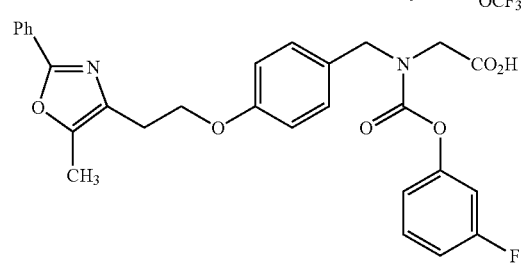
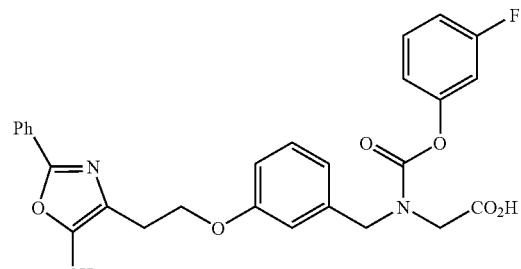
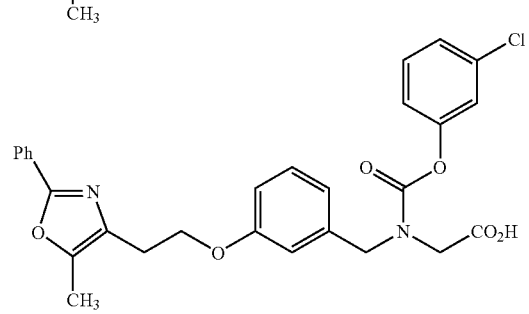

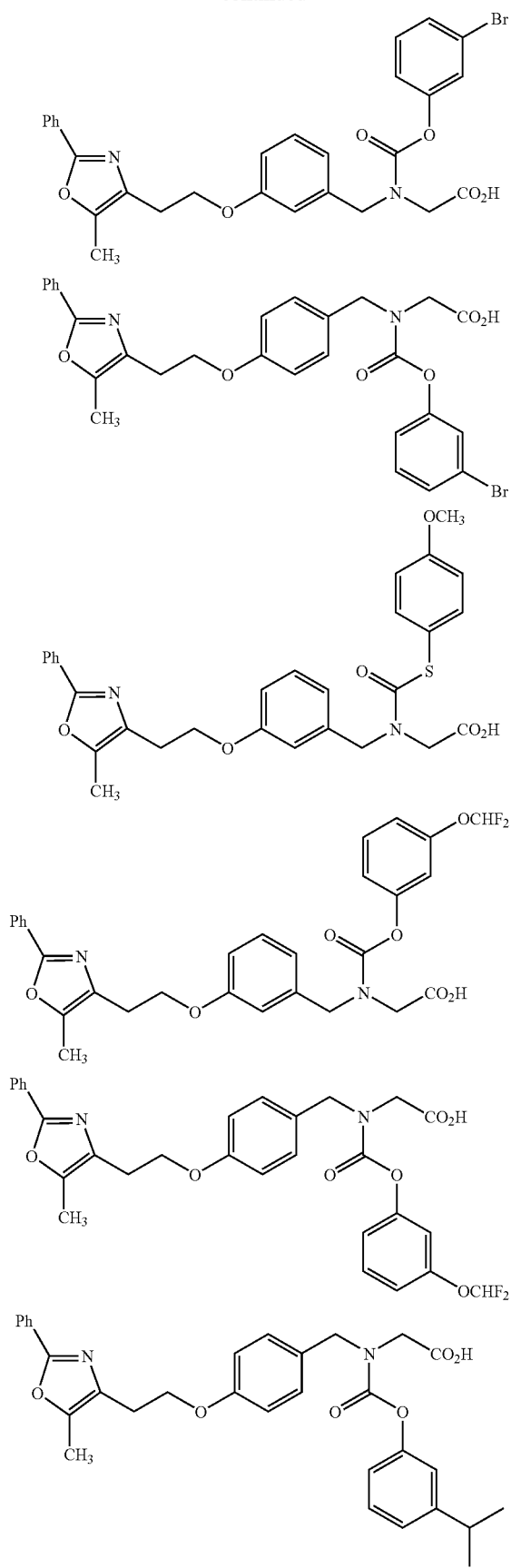
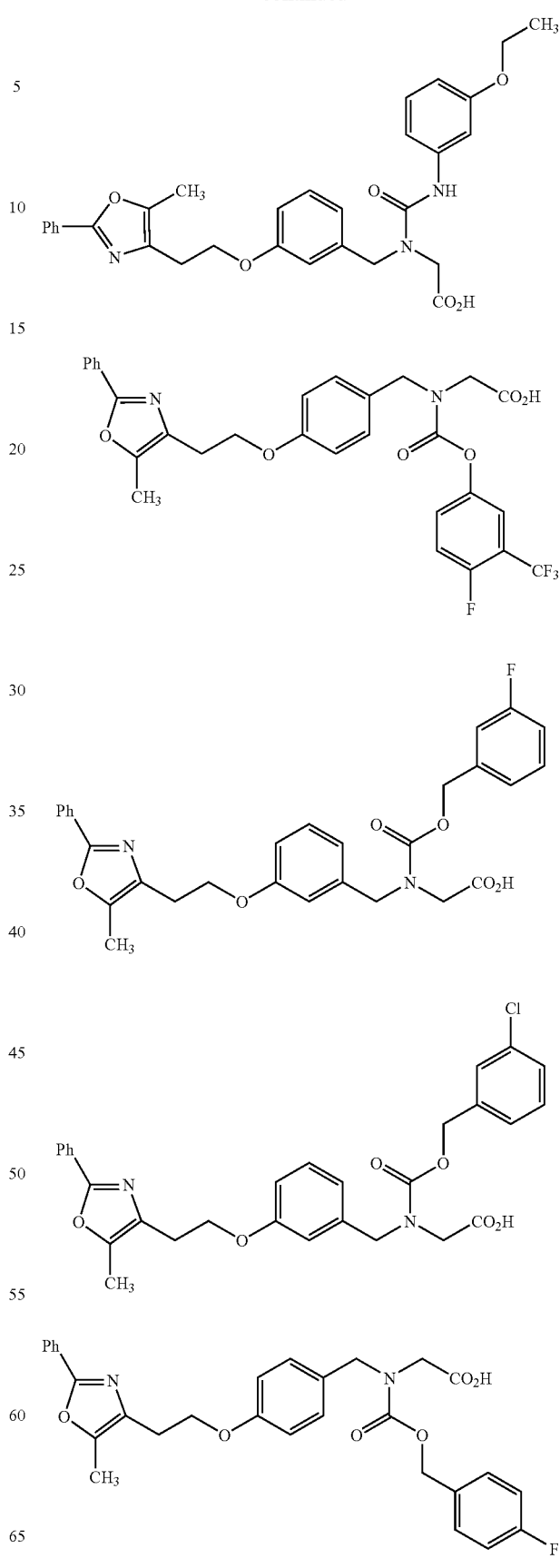

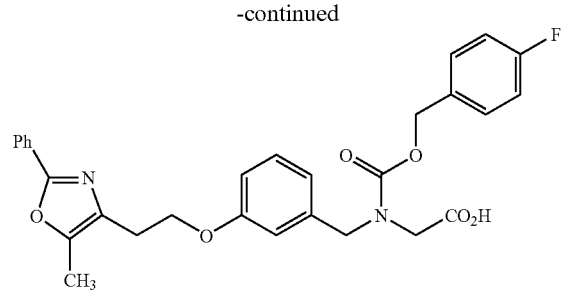
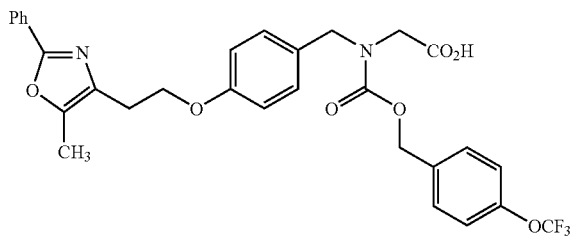
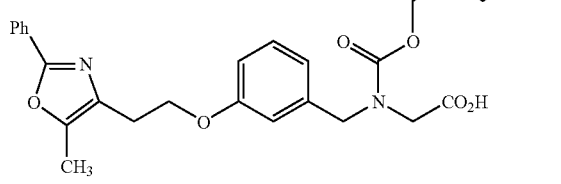
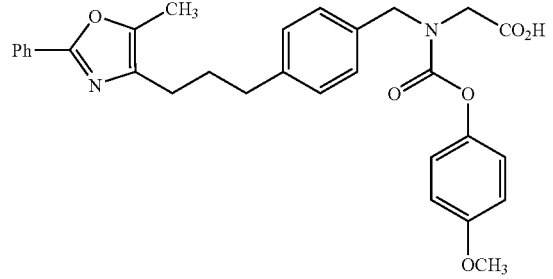
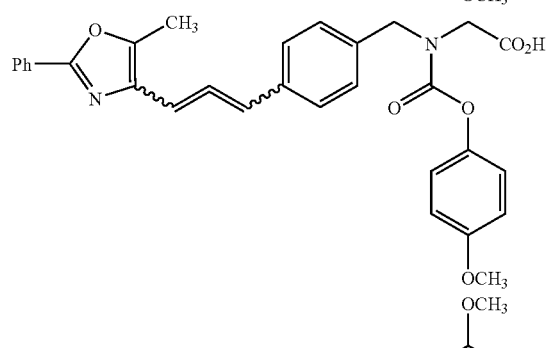
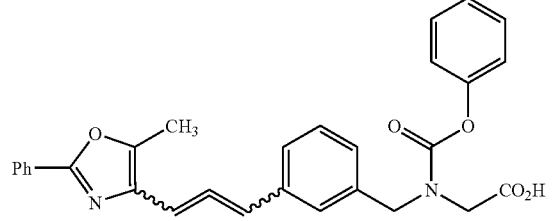
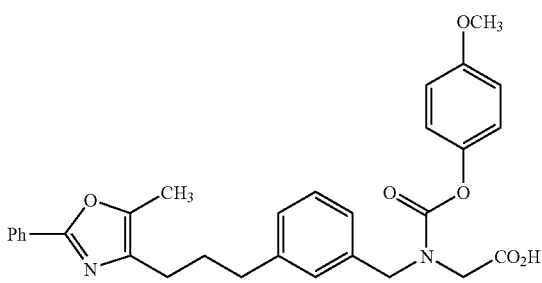
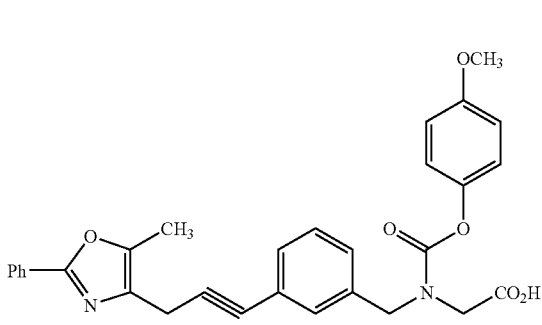
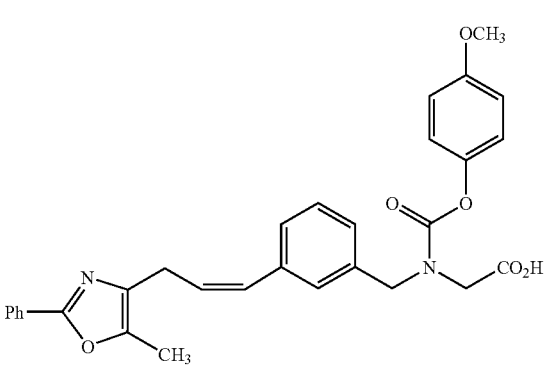
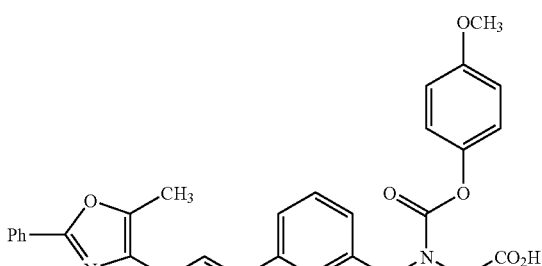
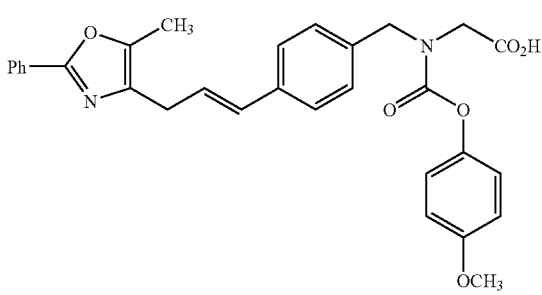

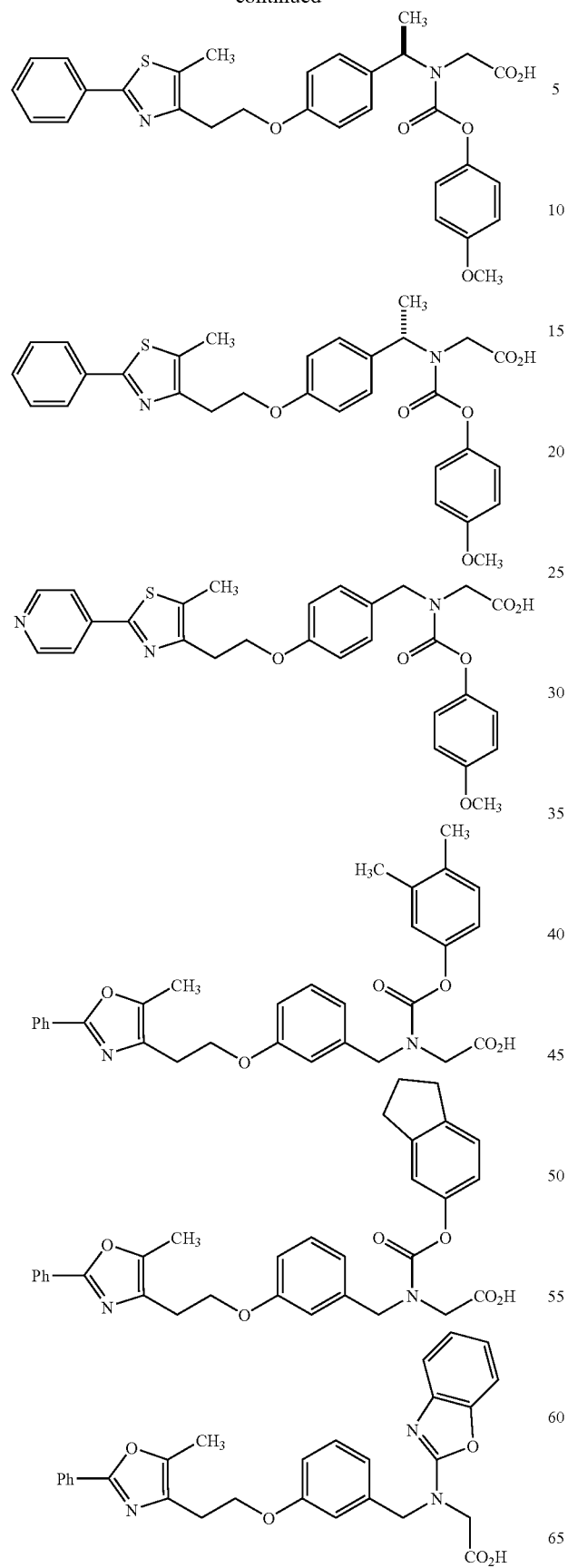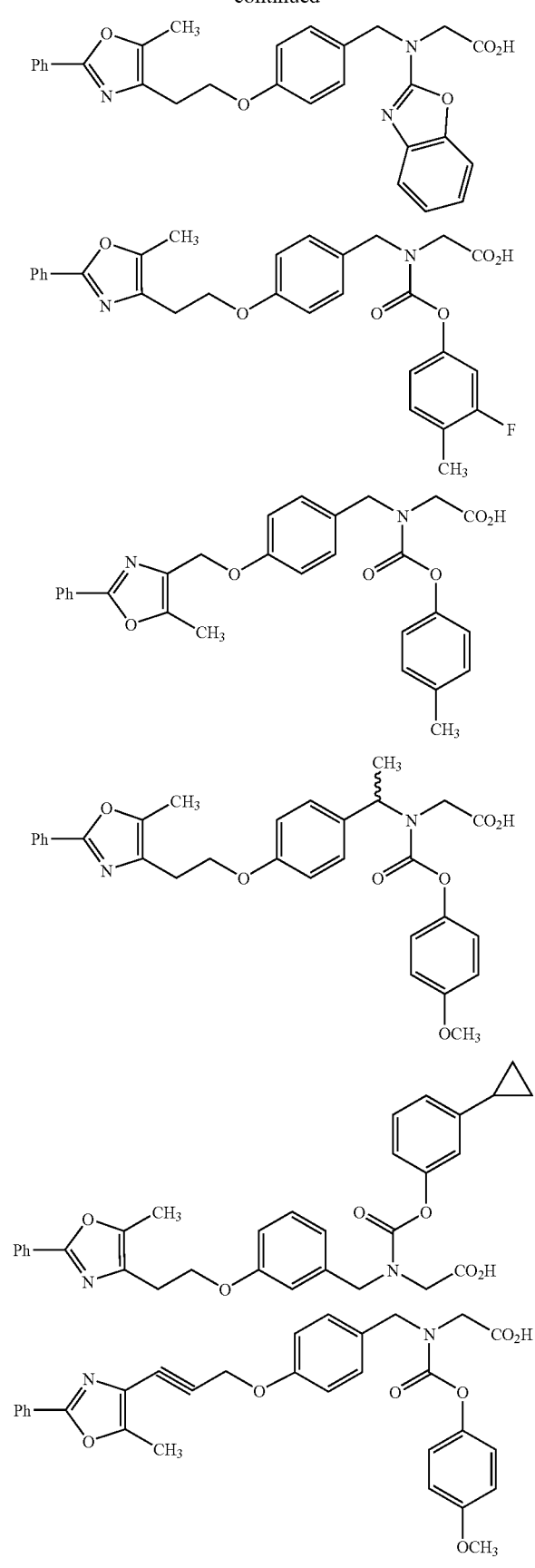

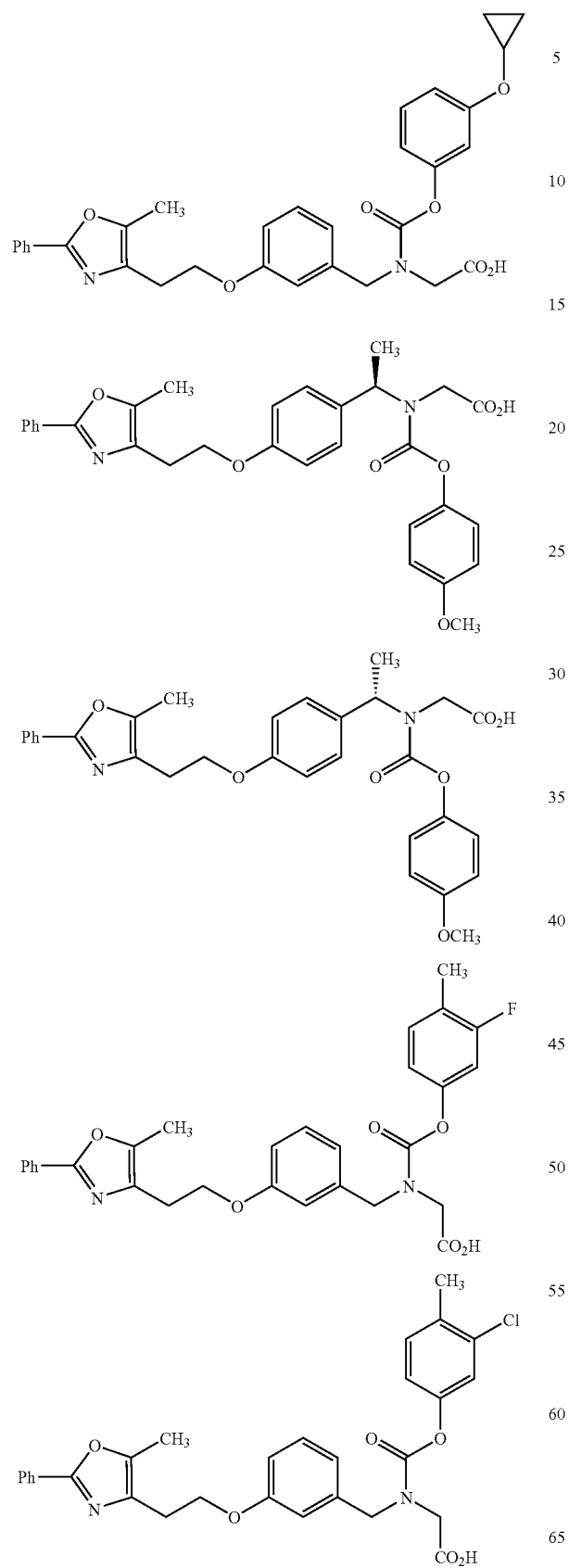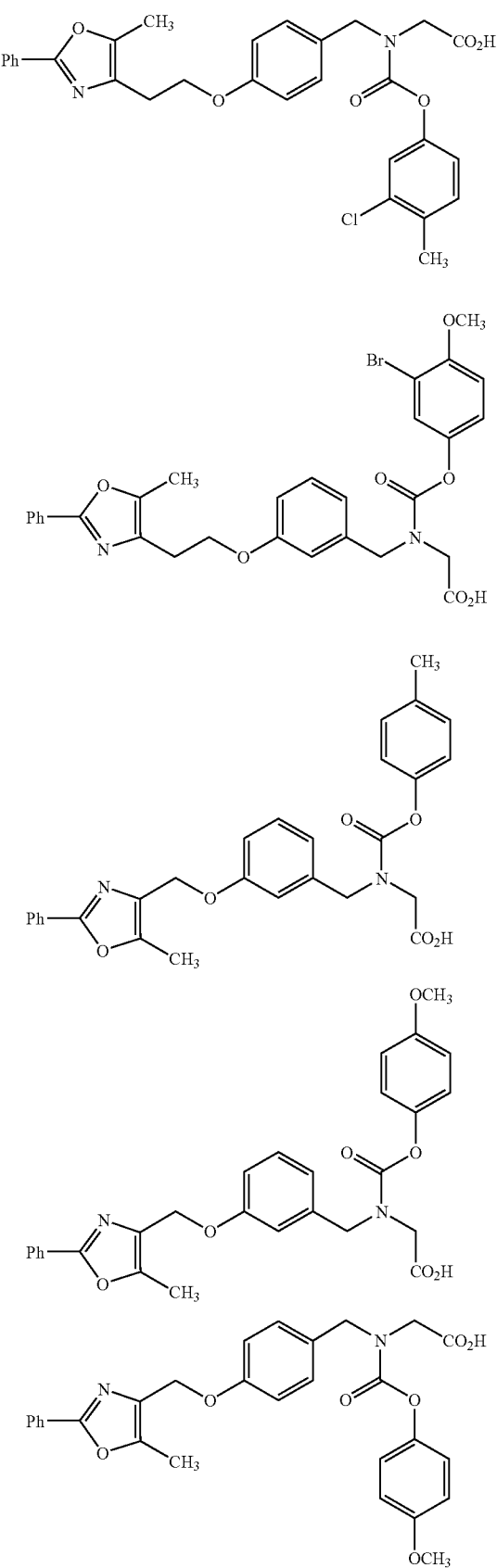

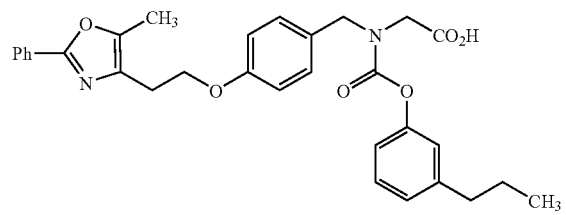
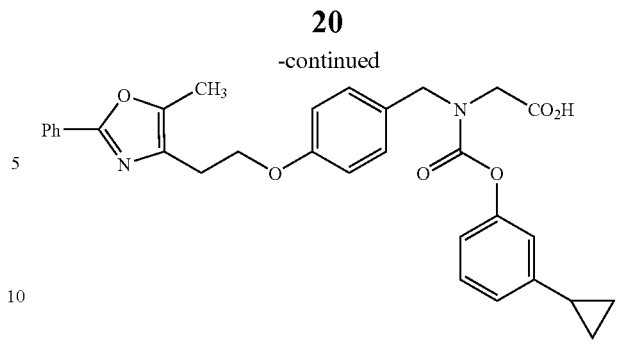
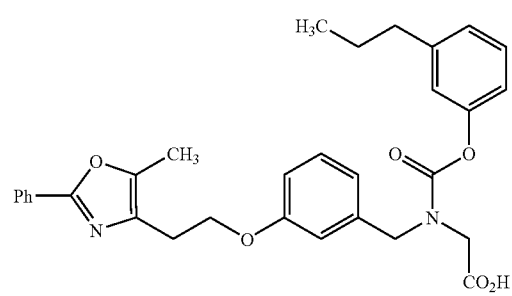
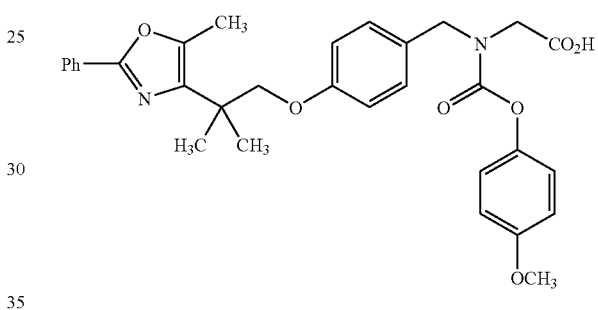
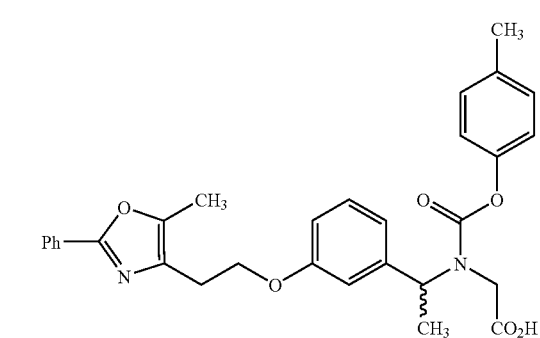
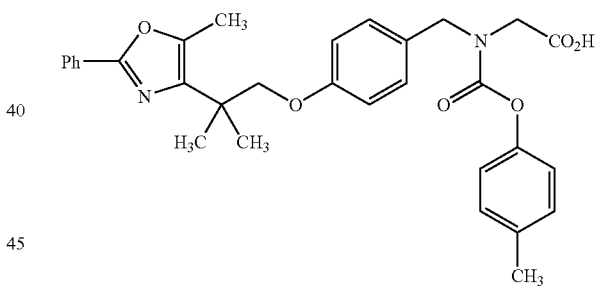
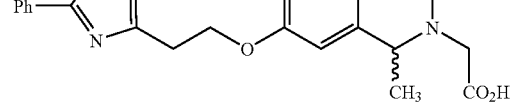
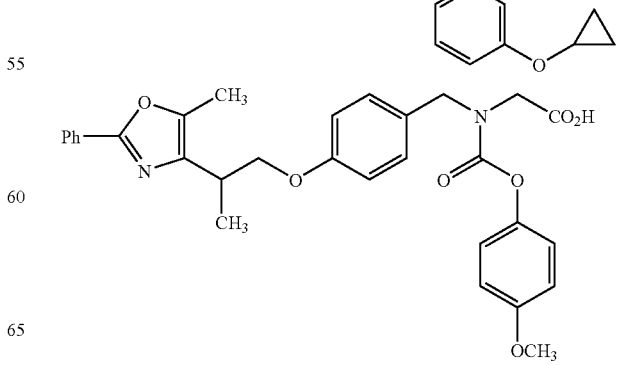

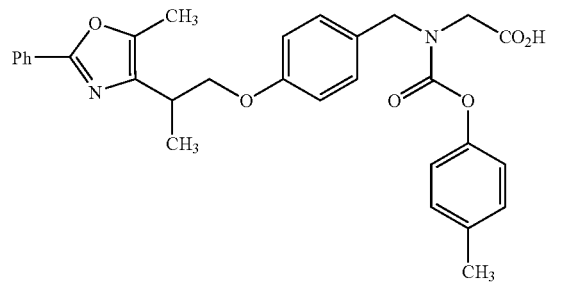
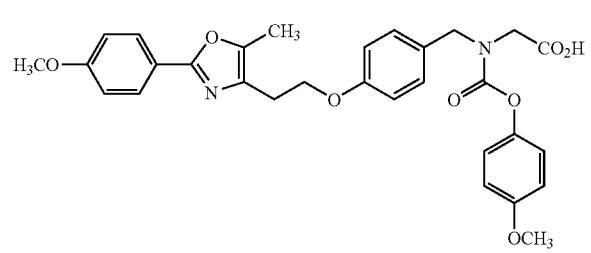
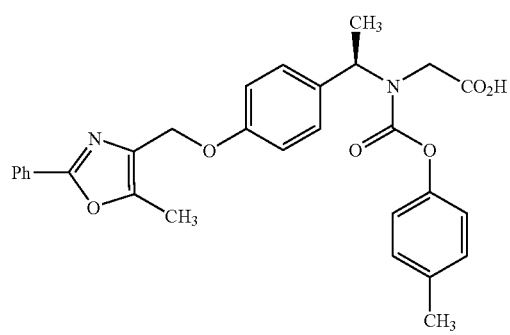
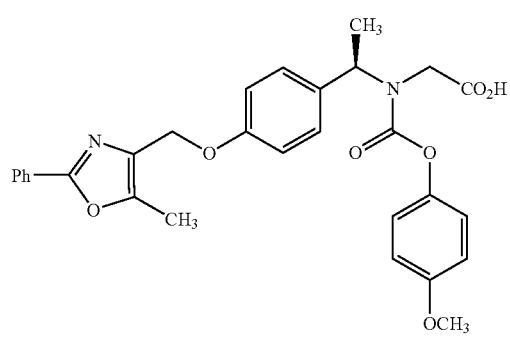
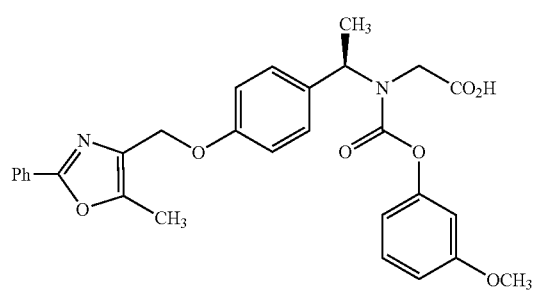
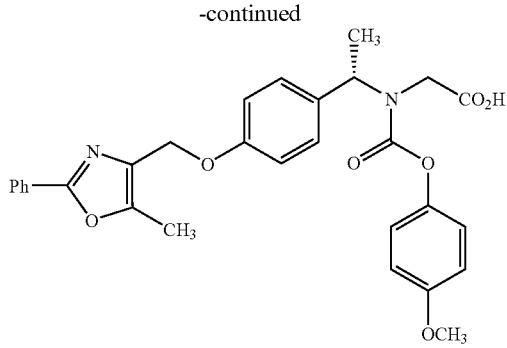
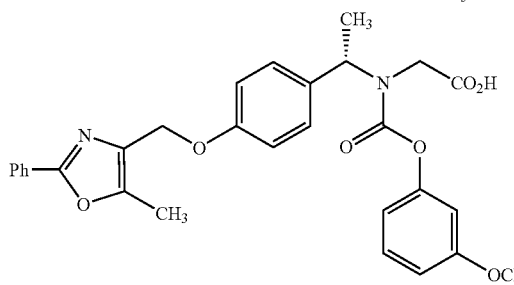
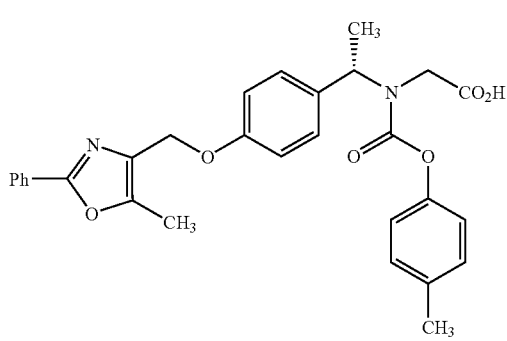

In addition, in accordance with the present invention, a method is provided for treating diabetes, especially Type 2 diabetes, and related diseases such as insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, atherosclerosis, and related diseases wherein a therapeutically effective amount of a compound of structure I is administered to a human patient in need of treatment.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis and proliferative diseases such as psoriasis, wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type antidiabetic agent and/or a hypolipidemic agent, and/or lipid modulating agent and/or other type of therapeutic agent, is administered to a human patient in need of treatment.

In the above methods of the invention, the compound of structure I will be employed in a weight ratio to the antidiabetic agent (depending upon its mode of operation) within the range from about 0.01:1 to about 100:1, preferably from about 0.5:1 to about 10:1.

The conditions, diseases, and maladies collectively referenced to as "Syndrome X" or Dysmetabolic Syndrome are detailed in Johannsson *J. Clin. Endocrinol. Metab.*, 82, 727–734 (1997) and other publications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

DETAILED DESCRIPTION OF THE INVENTION

The compounds of the formula I of the present invention may be prepared according to the following general synthetic schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, Greene, T. W. and Wuts, P. G. M., Protecting Groups in Organic Synthesis, 3$^{rd}$ Edition, 1999 [Wiley]).

Scheme 1 describes a general synthesis of the amino acids described in this invention. An alcohol II (R$^5$(CH$_2$)$_x$OH) (of which the most favored is 2-phenyl-5-methyl-oxazole-4-ethanol) is coupled with a hydroxy aryl- or heteroaryl-aldehyde III (preferably 3- or 4-hydroxybenzaldehyde) under standard Mitsunobu reaction conditions (e.g. Mitsunobu, O., *Synthesis*, 1981, 1). The resulting aldehyde IV is then subjected to reductive amination using procedures known in the literature (e.g. Abdel-Magid et al, *J. Org. Chem.* 1996, 61, 3849) with an α-amino ester hydrochloride V. PG in Scheme 1 denotes a preferred carboxylic acid protecting group, such as a methyl or tert-butyl ester. The resulting secondary amino-ester VI is then subjected to a second reductive amination using methods known in the literature (e.g. Abdel-Magid et al, *J. Org. Chem.* 1996, 61, 3849) with an R$^{3a}$ aldehyde VII. Final deprotection of the carboxylic acid ester under standard conditions known in the literature (Greene) utilizing basic conditions (for methyl esters) or acidic conditions (for tert-butyl esters) then furnishes the desired amino acid products ID.

An alternative route to the aldehyde IV is shown in Scheme 1A. The alcohol II (R$^5$(CH$_2$)$_n$OH) (of which the most favored is 2-[2-phenyl-5-methyl-oxazole-4-yl]-ethanol) is treated with methanesulfonyl chloride to give the corresponding mesylate VIII. The mesylate is then alkylated under standard basic conditions with a hydroxyaryl or hydroxyheteroaryl aldehyde III to furnish the aldehyde IV.

An alternative route to the amino acids IF is shown in Scheme 2. The secondary amino-ester VI is deprotected under standard conditions (basic conditions if the protecting group (PG) is methyl; acidic conditions if PG is tert-butyl) to furnish the corresponding amino acid IE. Reductive amination with an R$^{3a}$ aldehyde under analogous conditions as described in Scheme 1 furnishes the desired tertiary amino acid products IF.

Alternatively, as shown in Scheme 3, the tertiary amino acids IF may also be obtained by alkylation of the secondary amino-ester VI with an alkylating agent IX (with an appropriate leaving group (LG) such as halide, mesylate, or tosylate) under standard conditions known in the art followed again by standard deprotection of the carboxylic acid ester X to provide the amino acids IF.

As shown in Scheme 4, the tertiary amino acid IF may also be assembled through reductive amination first of the R$^{3a}$ aldehyde XI with an appropriate amine ester hydrochloride V. The resulting secondary amine-ester XII then is subjected to reductive amination with the appropriate alkyl, aryl or heteroaryl aldehyde IV (as in Scheme 1) followed by deprotection of the carboxylic acid ester to give the desired amino acid analogs IF.

For further substituted amino acids, a general synthetic scheme is shown in Scheme 5. Reductive amination of an appropriate amine XIII with an aryl or heteroaryl aldehyde XIV under standard conditions furnishes the corresponding secondary amine XV, which is then reacted with a halide-ester XVI (e.g. tert-butyl bromoacetate) to furnish the corresponding α-amino ester XVII. This amine-ester XVII is then deprotected under standard conditions to provide the desired amino acid analogs IF.

The synthetic route in Scheme 5 also provides a general scheme for the synthesis of the corresponding aminophosphonic acids IFA, as illustrated in Scheme 5a. The secondary amine XV is reacted with an appropriately protected halide-phosphonate XVIA to provide the corresponding amino-phosphonate ester XVIIA, which is then deprotected under standard conditions (Greene & Wuts) to furnish the amino phosphonic acid IFA. Scheme 5b illustrates the synthesis of the aminophosphinic acids IFB, which again involves the reaction of an appropriately protected halide-phosphinate ester XVIB with the secondary amine XV. Deprotection of the resulting aminophosphinate ester then provides the phosphinic acid IFB.

An alternative to the sequence in Scheme 5 is shown in Scheme 6. A hydroxyaryl or heteroaryl amine XVIII is selectively protected on nitrogen to provide protected amine XIX. A preferred R$^5$(CH$_2$)$_n$OH (II) is then reacted with XIX under Mitsunobu conditions to provide the corresponding ether, followed by deprotection of the amine, to form the free amine XX. The free amine XX is then activated with a standard activating group (2,4-dinitrobenzenesulfonamide; T. Fukuyama et al, *Tetrahedron Lett.* 1997, 38, 5831) and is then treated with an α-halo ester XVI as in Scheme 5. The 2,4-dinitrobenzenesulfonamide XXI is deprotected under literature conditions (T. Fukuyama et al, *Tetrahedron Lett.*, 1997, 38, 5831) to furnish a secondary α-amino-ester XXII which is then subjected to a reductive amination with an R$^{3a}$ aldehyde XI followed by deprotection of the ester X to furnish the desired analogs IF.

Scheme 7 describes an alternative general route to the amino acid analogs IG. A hydroxyaryl or heteroaryl aldehyde III is subjected to the usual reductive amination conditions with an appropriate amine-ester hydrochloride V. The resulting secondary amine-ester XXIII is functionalized, in this case by a second reductive amination with an $R^{3a}$ aldehyde VII to furnish the corresponding hydroxy tertiary amine-ester XXIV. This can now undergo a Mitsunobu reaction with a preferred alcohol II ($R^5(CH_2)_nOH$) which followed by deprotection of the ester XXV furnishes the desired analogs IG.

Scheme 8 describes a general synthesis of diaryl and aryl-heteroaryl-substituted amino acid analogs IH. The secondary amine-ester XXII undergoes reductive amination with an appropriately substituted formyl phenyl boronic acid XXVI under standard conditions to give the corresponding tertiary amine-ester boronic acid XXVII. The aryl boronic acid XXVII can then undergo a Suzuki coupling (e.g. conditions as described in Gibson, S. E., Transition Metals in Organic Synthesis, A Practical Approach, pp. 47–50, 1997) with aryl or heteroaryl halides XXVIII (especially bromides) to furnish the appropriate cross-coupling diaryl products XXIX. Deprotection of the amine-ester XXIX generates the desired amino acid analogs IH.

Scheme 9 describes a general synthesis of diaryl and aryl-heteroaryl ether-substituted amino acid analogs IJ. The tertiary amine-ester boronic acid XXVII which is described in Scheme 8 can be coupled with appropriately substituted phenols XXX under literature conditions (D. A. Evans et al, *Tetrahedron Lett.*, 1998, 39, 2937) to furnish the appropriate diaryl or aryl-heteroaryl ethers XXXI, which after deprotection afford the desired amino acid analogs IJ.

Alternatively, as shown in Scheme 10, reductive amination of the secondary amine-ester XXII with an appropriately substituted hydroxyaryl or hydroxyheteroaryl aldehyde XXXII furnishes the corresponding phenol-tertiary amine-ester XXXIII. The phenol XXXIII can then undergo coupling with appropriate aryl or heteroaryl boronic acids XXXIV under literature conditions (D. A. Evans et al, *Tetrahedron Lett.*, 1998, 39, 2937) to furnish the corresponding diaryl or arylheteroaryl ether-amino esters XXXI. The desired analogs IJ are then obtained after deprotection of the amine-ester XXXI.

Scheme 11 illustrates the synthesis of the carbamate-acid analogs IK. The secondary amine-ester XXII can be reacted with appropriate chloroformates XXXV under standard literature conditions (optimally in $CH_2Cl_2$ or $CHCl_3$ in the presence of a base such as $Et_3N$) to furnish the corresponding carbamate-esters. The requisite analogs IK are then obtained after deprotection of the carbamate-ester. Alternatively, the secondary amine-ester XXII can be reacted with phosgene to generate the corresponding carbamyl chloride XXXVI. This carbamyl chloride intermediate XXXVI can be reacted with $R^{3a}$—OH (XXXVII) (optimally substituted phenols) to afford the corresponding carbamate-acids IK after deprotection.

Scheme 12 illustrates the further functionalization of aryl carbamate-acid analogs IK. The secondary amine-ester XXII is reacted with an aryl chloroformate XXXVIII (containing a protected hydroxyl group) to form XXXIX. The hydroxyl group is then selectively deprotected in the presence of the ester functionality to provide XL, then alkylated with an appropriate $R^6$-LG (XLI) (where LG is halide, mesylate or tosylate, and $R^6$ is most preferably $CHF_2$—, or $CH_3CH_2$—) in the presence of base. Deprotection of the ester then furnishes the desired carbamate-acid analogs IL.

The secondary amine-ester XXIIA can be functionalized with substituted aryl or aliphatic carboxylic acids XLII, under standard peptide coupling conditions, as illustrated in Scheme 13. The amide bond-forming reactions are conducted under standard peptide coupling procedures known in the art. Optimally, the reaction is conducted in a solvent such as DMF at 0° C. to RT using 1-ethyl-3-(3-dimethylaminopropyl)carbodiimide (EDAC or EDCI or WSC), 1-hydroxybenzotriazole (HOBT) or 1-hydroxy-7-azabenzotriazole (HOAT) and a base, for example Hunig's base (diisopropylethylamine), N-methyl morpholine or triethylamine. Deprotection of the amide-ester then furnishes the desired amide-acid analogs IM.

The secondary amine-ester XXIIA can also be reacted with aliphatic or aryl isocyanates XLIII to provide the corresponding urea-esters. Deprotection of the urea-ester provides the desired urea-acid analogs IN, as shown in Scheme 14. Alternatively, as shown in Scheme 15, the carbamyl chloride intermediate XXXVI described in Scheme 11 can be reacted with appropriate aliphatic or aryl amines XLIV in the presence of a tertiary amine (e.g. $Et_3N$) to furnish tri- or tetrasubstituted urea-acid analogs IO or IP after deprotection of the ester.

The secondary amine-ester XXIIA can also be reacted with appropriate sulfonyl chlorides XLVI under standard literature conditions (optimally in the presence of a base such as pyridine, either neat or using chloroform as a co-solvent), followed by deprotection, to provide the corresponding sulfonamide-acids IQ, as shown in Scheme 16.

Replacement of the carboxylic acid functionality in these analogs with tetrazole can be achieved as shown in Scheme 17. An acid analog IK is coupled with an amine (containing an appropriate tetrazole protecting group) XLVII (preferably 3-amino propionitrile) under standard peptide coupling conditions. The resulting secondary amide XLVIII is then subjected to a Mitsunobu reaction under standard conditions with trimethylsilyl azide ($TMSN_3$) to form the protected tetrazole XLIX. Deprotection of the cyanoethyl group is achieved preferentially in the presence of base to generate the desired free tetrazole analog IR.

Scheme 18 describes a general synthesis of the hydrazide-acid analogs IS. A substituted aryl carboxylic acid 1 is treated with methanesulfonyl chloride in the presence of base; the intermediate is then reacted with a protected hydrazine-ester VA to give the corresponding acylated hydrazine 1a (ref: *Synthesis*, 1989, 745–747). The acylhydrazine 1a is coupled with an appropriately substituted aryl aldehyde IV under reductive amination conditions to give the corresponding protected hydrazide ester 3 (ref: *Can. J. Chem.*, 1998, 76, 1180–1187). Deprotection of the ester 3 then furnishes the hydrazide-acid analogs IS.

An alternative synthetic approach to hydrazide-acids IS is shown in Scheme 19. An aryl aldehyde IV can be reduced to the corresponding alcohol under standard conditions (e.g $NaBH_4$). This alcohol is then converted to the corresponding bromide 4 using standard conditions (e.g. $Ph_3P/CBr_4$ or $PBr_3$). The bromide 4 is then reacted with the hydrazine-ester 1a (ref: *Tetrahedron Lett.*, 1993, 34, 207–210) to furnish the protected hydrazide-ester 3, which is then deprotected to give the hydrazide-acid analogs IS.

The different approaches to the preparation of the α-alkylbenzyl amino acid and carbamate-acid analogs IT and IU are exemplified in the following synthetic schemes.

In Scheme 20 an appropriately substituted aryl aldehyde IV is treated with a suitable organometallic reagent (e.g. a Grignard reagent R$^{10}$MgBr) under standard conditions to give the corresponding secondary alcohol, which is then oxidized under standard conditions (e.g. Swern oxidation with (COCl)$_2$/DMSO/Et$_3$N or using pyridinium chlorochromate) to give the corresponding ketone 5. Reductive amination of the ketone 5 with an appropriately substituted amino-ester 6 provides the corresponding α-alkylbenzyl amino-ester 7. It will be understood that in the amino ester 6, the moiety

does not necessarily represent two repeating units.

Acylation of amino-ester 7 with an appropriately substituted aryl or heteroaryl chloroformate XXXV followed by deprotection provides the racemic carbamate-acid analogs IT. Reductive amination of alkylbenzyl amino-ester 7 with aryl aldehyde VII followed by deprotection provides the racemic amino-acid analogs IU.

Alternatively, as shown in Scheme 21, asymmetric reduction (e.g. using the Corey oxazaborolidine reduction protocol; review: E. J. Corey & C. Helal, Angew. Chem. Int. Ed. Engl., 1998, 37, 1986–2012.) of the aryl-ketone 5 provides each of the desired enantiomeric alcohols 8 (although only one enantiomer is represented in the scheme). Treatment of the chiral alcohol 8 with azide in a Mitsunobu-like reaction (ref: A. S. Thompson et. al., J. Org. Chem. 1993, 58, 5886–5888) gives the corresponding chiral azide (with inverted stereochemistry from the starting alcohol). The azide is then converted to the amine 9 by standard reduction methods (e.g. hydrogenation or Ph$_3$P/THF/H$_2$O). Treatment of the chiral amine 9 with an ester XVIA (containing an appropriate leaving group) provides the secondary amino-ester 10. Acylation of amino-ester 10 with an aryl or heteroaryl chloroformate XXXV followed by deprotection provides the chiral carbamate-acid analogs ITa (which may be either enantiomer depending upon the stereochemistry of 8). Reductive amination of alkyl amino-ester 10 with aryl aldehydes VII followed by deprotection provides the chiral amino-acid analogs IUa (which may be either enantiomer depending upon the stereochemistry of 8).

An alternative to Scheme 21 is shown in Scheme 22. An appropriately protected oxyaryl ketone 11 undergoes asymmetric reduction to give the chiral alcohol 12. This is converted to the chiral amine 13 via the identical sequence as in Scheme 21 (via the chiral azide). Treatment of the chiral amine 13 with an ester XVIA (LG=halogen or mesylate) gives the corresponding secondary amino-ester 14. Acylation of 14 with an aryl or heteroaryl chloroformate XXXV provides the corresponding carbamate-ester. Selective deprotection furnishes the free phenol carbamate-ester 15. Alkylation of the phenol 15 with a halide or mesylate VIII followed by deprotection provides the carbamate-acid analogs ITa. An analogous sequence (involving reductive amination of the secondary amino-ester 14 with an aryl or heteroaryl aldehyde VII, then selective deprotection, alkylation with VIII and a final deprotection) provides the amino acid analogs IUa.

It will be appreciated that either the (R)- or (S)-enantiomer of ITa or IUa may be synthesized in Schemes 21 and 22, depending upon the chirality of the reducing agent employed.

A fourth synthetic sequence is shown in Scheme 23. The substituted aldehyde IV is condensed with an amino-ester hydrochloride 6 to give the corresponding imine 16, which is then treated in situ with an appropriately substituted allylic halide 17 in the presence of indium metal (reference: Loh, T.-P., et al., Tetrahedron Lett., 1997, 38, 865–868) to give the α-allyl benzyl amino-ester 18. Acylation of amine 18 with an aryl or heteroaryl chloroformate XXXV followed by deprotection provides the carbamate-acid analogs Iv. Reductive amination of alkyl amino-ester 18 with an aryl or heteroaryl aldehyde VII followed by deprotection provides the amino-acid analogs IW.

Scheme 24 shows the preparation of the required intermediate 2-aryl-5-methyl-oxazol-4-yl methyl chloride 21 (following the general procedure described in Malamas, M. S., et al, J. Med. Chem., 1996, 39, 237–245). A substituted aryl aldehyde 19 is condensed with butane-2,3-dione monooxime under acidic conditions to give the corresponding oxazole N-oxide 20. Deoxygenation of the oxazole N-oxide 20 with concomitant chlorination furnishes the desired chloromethyl aryl-oxazoles 21. Hydrolysis of chloromethyl oxazole 21 under basic conditions furnishes the corresponding oxazole-methanol 22. Oxidation of alcohol 22 to the corresponding aldehyde is followed by conversion to the corresponding dibromoalkene 23 (e.g. Ph$_3$P/CBr$_4$). The dibromide 23 is converted to the corresponding alkynyl-lithium species (using an organolithium reagent such as n-BuLi), which can be reacted in situ with an appropriate electrophile such as formaldehyde to give the corresponding acetylenic alcohol (ref: Corey, E. J., et al., Tetrahedron Lett. 1972, 3769, or Gangakhedkar, K. K., Synth. Commun. 1996, 26, 1887–1896). This alcohol can then be converted to the corresponding mesylate 24 and alkylated with an appropriate phenol 25 to provide analogs Ix. Further stereoselective reduction (e.g. H$_2$/Lindlar's catalyst) provides the E- or Z-alkenyl analogs IY.

Scheme 25 describes a general synthesis of the amino-benzoxazole analogs IZ (general ref: Sato, Y., et al, J. Med. Chem. 1998, 41, 3015–3021). An appropriately substituted ortho-aminophenol 26 is treated with CS$_2$ in the presence of base to furnish the corresponding mercapto-benzoxazole 27. Treatment of this thiol 27 with an appropriate chlorinating agent (e.g. PCl$_5$) provides the key intermediate chlorobenzoxazole 28, which is reacted with the secondary amino-ester VI to furnish, after deprotection, the amino benzoxazole-acid analogs IZ.

The thiazole analogs IZa were synthesized according to the general synthetic route outlined in Scheme 26 (ref: Collins, J. L., et al., J. Med. Chem. 1998, 41, 5037). The secondary amino-ester XXIII is reacted with an aryl or heteroaryl chloroformate XXXV in the presence of an appropriate base (e.g. pyridine or triethylamine) to furnish the corresponding hydroxyaryl carbamate-ester 29. The hydroxyaryl ester 29 is then reacted with an appropriately substituted α-bromo vinyl ketone 29a (for S$_3$=CH$_3$, e.g. Weyerstahl, P., et. al., Flavour Fragr. J., 1998, 13, 177 or Sokolov, N. A., et al., Zh. Org. Khim., 1980, 16, 281–283) in the presence of an appropriate base (e.g. K$_2$CO$_3$) to give the corresponding Michael reaction adduct, the α-bromoketone carbamate-ester 30. The α-bromoketone 30 is then subjected to a condensation reaction with an appropriately substituted aryl amide 31 (A=O) or aryl thioamide 31 (A=S) to furnish either the corresponding oxazole (from the amide) or the thiazole (from the thioamide) (ref: Malamas, M. S., et al, J. Med. Chem., 1996, 39, 237–245). Finally, deprotection of esters 31 then provides the substituted oxazole and thiazole carbamate acid analogs IZa.

It will be appreciated that in the following schemes where the carbamate-acid analogs are prepared, the corresponding amino acid analogs may also be prepared by replacing the chloroformate reaction with an aldehyde in a reductive amination reaction (as in Scheme 20 with intermediate amine 7).

Scheme 27 describes a general synthesis of the acids IZb and IZc. A halo-substituted aryl aldehyde 32 (preferably iodide or bromide) is subjected to reductive amination using procedures known in the literature (e.g. Abdel-Magid et al, *J. Org. Chem.* 1996, 61, 3849) with an α-amino acid ester hydrochloride V. The resulting secondary amino-ester 33 is then reacted with an aryl or heteroaryl chloroformate XXXV in the presence of an appropriate base (e.g. pyridine or triethylamine) to furnish the corresponding halo-aryl carbamate-ester 34. Aryl halide 34 is then reacted with an appropriate aryl- or heteroaryl-substituted acetylene 35 (the preferred acetylene being 5-phenyl-2-methyl-oxazol-4-yl-methylacetylene) in the presence of an appropriate palladium catalyst (e.g. $(Ph_3P)_2PdCl_2$) and a copper (I) salt (e.g. CuI) in a Sonogashira coupling reaction (ref: Organocopper Reagents, a Practical Approach, R. J. K. Taylor, Ed., Chapter 10, pp 217–236, Campbell, I. B., Oxford University Press, 1994) to furnish the key intermediate, arylacetylene carbamate ester 36.

The arylacetylene ester 36 is deprotected to provide the corresponding arylacetylene acid analogs IZb. The acetylene moiety of 36 can be reduced by standard methods (e.g. hydrogenation, ref: M. Hudlicky, Reductions in Organic Chemistry, $2^{nd}$ Edition, ACS, 1996, Chapter 1) to furnish the corresponding fully saturated alkyl aryl carbamate ester, which is then deprotected to give the alkyl aryl carbamate acid analogs IZc.

Stereoselective reduction of the acetylene ester 36 by standard methods (e.g. Lindlar's catalyst; ref: Preparation of Alkenes, A Practical Approach, J. J. Williams, Ed., Chapter 6, pp 117–136, Oxford University Press, 1996) can be achieved to provide the corresponding cis-alkenyl aryl carbamate-ester, which is then deprotected to furnish the Z-alkenyl aryl carbamate acid analogs IZd (Scheme 28). Alternatively, this sequence can be reversed, i.e. the initial step being the deprotection of acetylenic ester 36 to the acetylenic acid, followed by stereoselective reduction of the acetylene moiety to provide the Z-alkene-acid analogs IZd.

The corresponding trans-alkenyl aryl carbamate acids IZe can be synthesized according to the general route in Scheme 29. An aryl- or heteroaryl-acetylene 35 (the preferred moiety again being 5-phenyl-2-methyl-oxazol-4-yl-methylacetylene) is halogenated under standard conditions (ref: Boden, C. D. J. et al., *J. Chem. Soc. Perkin Trans. I,* 1996, 2417; or Lu, W. et. al., *Tetrahedron Lett.* 1998, 39, 9521) to give the corresponding halo-acetylene, which is then converted to the corresponding trans-alkenyl stannane 37 (ref: Boden, C. D. J., *J. Chem. Soc., Perkin Trans. I,* 1996, 2417). This aryl- or heteroaryl-substituted trans-alkenyl stannane 37 is then coupled with the halo-aryl carbamate ester 34 under standard Stille coupling conditions (ref: Farina, V. et. al., "The Stille Reaction", *Organic Reactions,* 1997, 50, 1) to furnish the corresponding trans-alkenyl aryl carbamate ester 38. This carbamate-ester is then deprotected under standard conditions to give the desired trans-alkenyl aryl carbamate acid analogs IZe.

The corresponding cyclopropyl analogs IZf and IZg are synthesized according to Scheme 30. For the cis- or (Z-) cyclopropyl analogs, stereoselective reduction ($H_2$/Lindlar's catalyst) of the alkynyl moiety of intermediate alknyl ester 36 (as for analogs IZd), followed by cyclopropanation under standard conditions (Zhao, Y., et al, *J. Org. Chem.* 1995, 60, 5236–5242) and finally deprotection provides the cis-cyclopropyl carbamate-acid analogs IZf. For the trans-cyclopropyl analogs IF, analogous cyclopropanation of the E-alkene moiety of intermediate 38 followed by deprotection provides the trans-cyclopropyl carbamate-acid analogs IZg.

A preferred alternative asymmetric synthesis of ITa (Scheme 21) is shown in Scheme 31. Protection of a chiral amine 39 (with the phenol protected), preferably as a carbamate, provides intermediate 40. Removal of the phenolic protecting group of 40 provides the free phenol 41. Alkylation of phenol 41 with the mesylate VIII furnishes the protected amine 42. Deprotection of this amine then furnishes the key intermediate secondary amino-ester 9, which is then carried on to analogs ITa and IUa according to Scheme 21.

A preferred asymmetric synthesis of analogs IIA is shown in Scheme 32. The aldehyde IV is subjected to standard Wittig reaction conditions (ref: Preparation of Alkenes, a Practical Approach, J. J. Williams, Ed., Chapter 2, pp 19–58) to furnish the alkene 43. Asymmetric aminohydroxylation according to known literature procedures (ref: O'Brien, P., *Angew. Chem. Int. Ed.,* 1999, 38, 326 and Reddy, K. L., and Sharpless, K. B., *J. Am. Chem. Soc.,* 1998, 120, 1207) furnishes the desired amino-alcohol 44 as a single enantiomer. Selective protection of the amine provides the alcohol 45. Alcohol 45 is then converted to the intermediate 46, which contains a suitable leaving group (either a halide or a mesylate) for the subsequent cuprate reaction. Reaction of an appropriate higher-order cuprate (ref: L. A. Paquette, Ed., *Organic Reactions,* 1992, Vol. 41, J. Wiley & Sons) with the protected amine substrate 46 provides the coupled protected amine 47. Deprotection of the amine functionality of 47, followed by reaction with an ester XVIA (LG=halogen or mesylate), furnishes the corresponding secondary amino-ester 48. Acylation of 48 with an aryl or heteroaryl chloroformate XXXV provides the corresponding carbamate-ester, which is then deprotected to furnish the carbamate-acid analogs IIA.

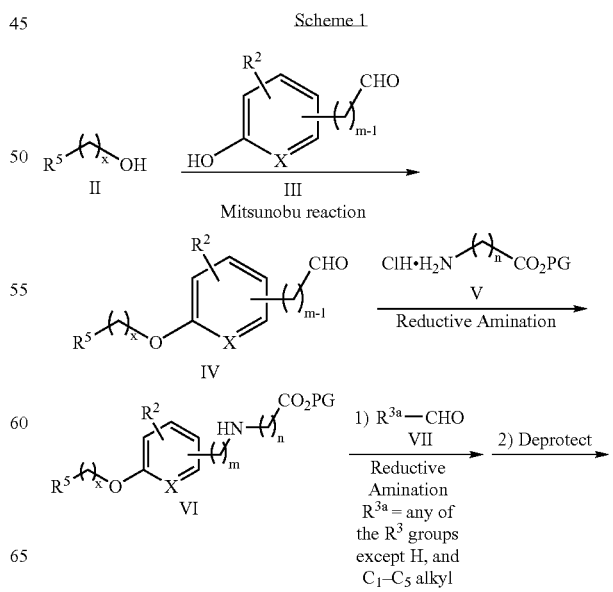

Scheme 1

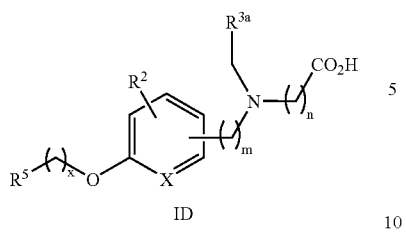
ID
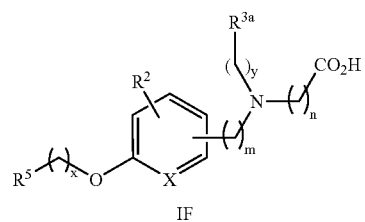
IF
In this and the following Reaction Schemes:
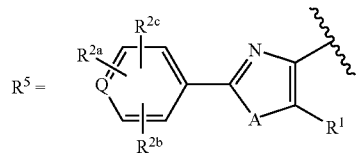
Alternative Scheme 1A for Preparing Aldehyde IV
SCHEME 1A
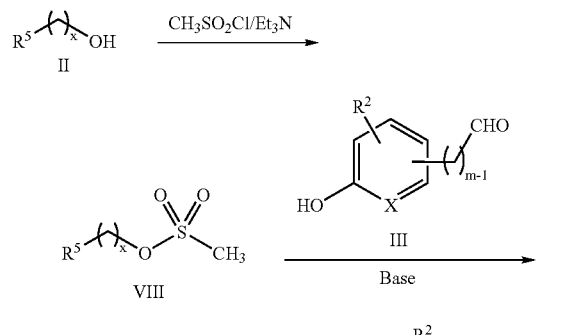
Scheme 2
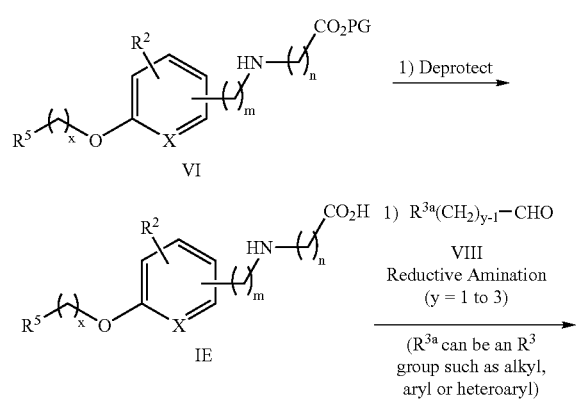
Scheme 3
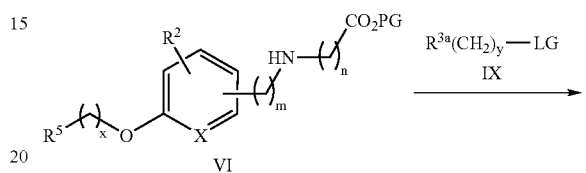
y = 1–3
LG = leaving group, e.g. halide, tosylate, etc.
Scheme 4
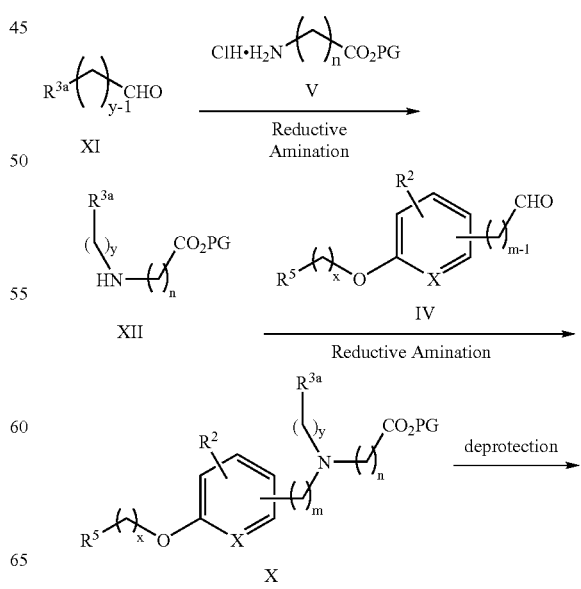

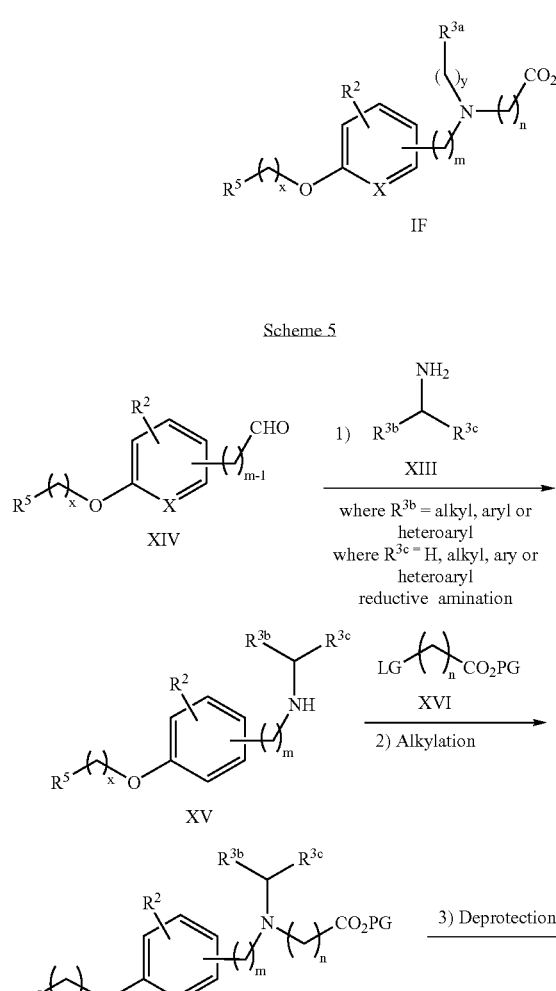
Scheme 5
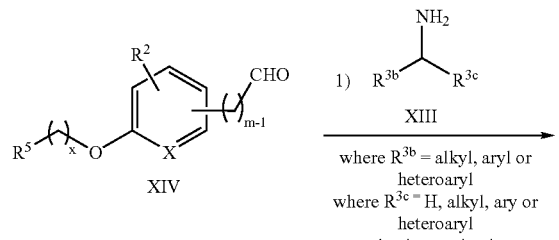
Scheme 5a
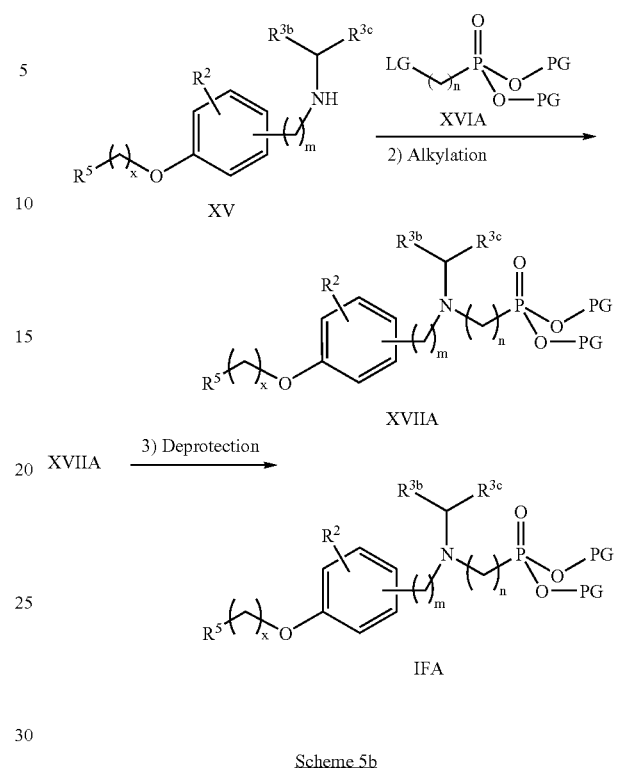
Scheme 5b
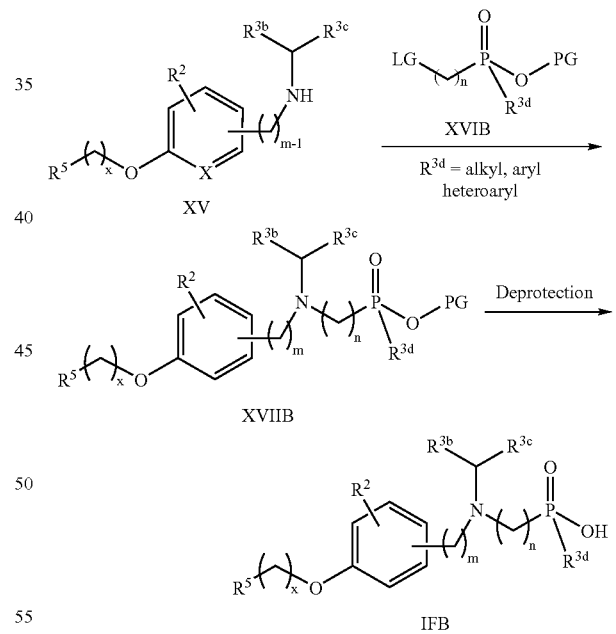
Scheme 6
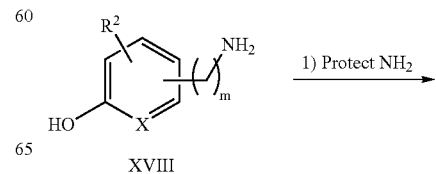

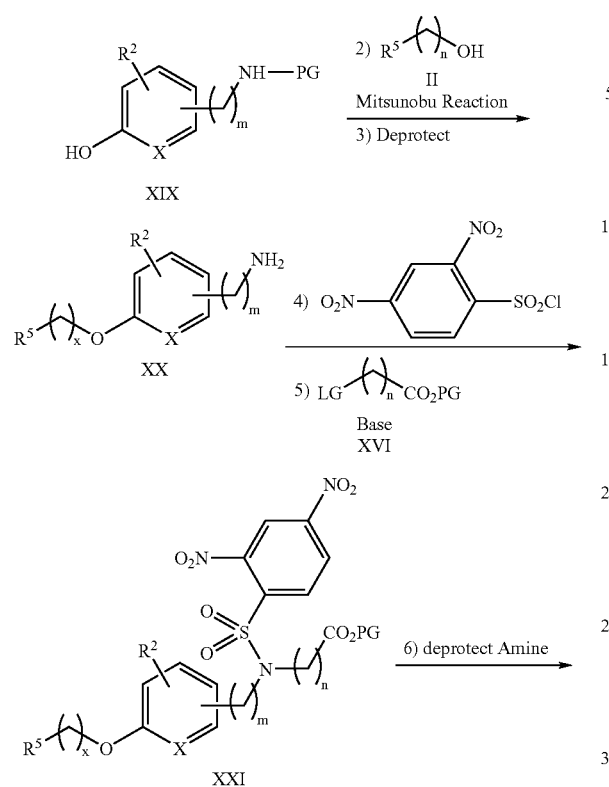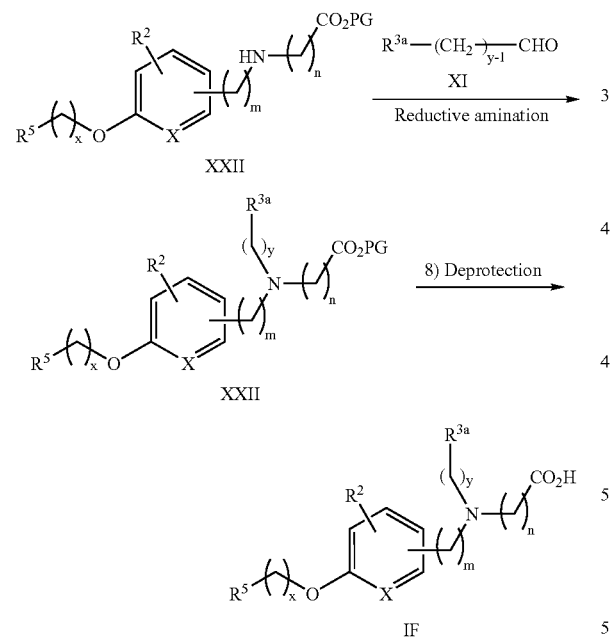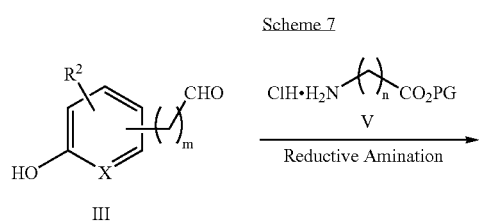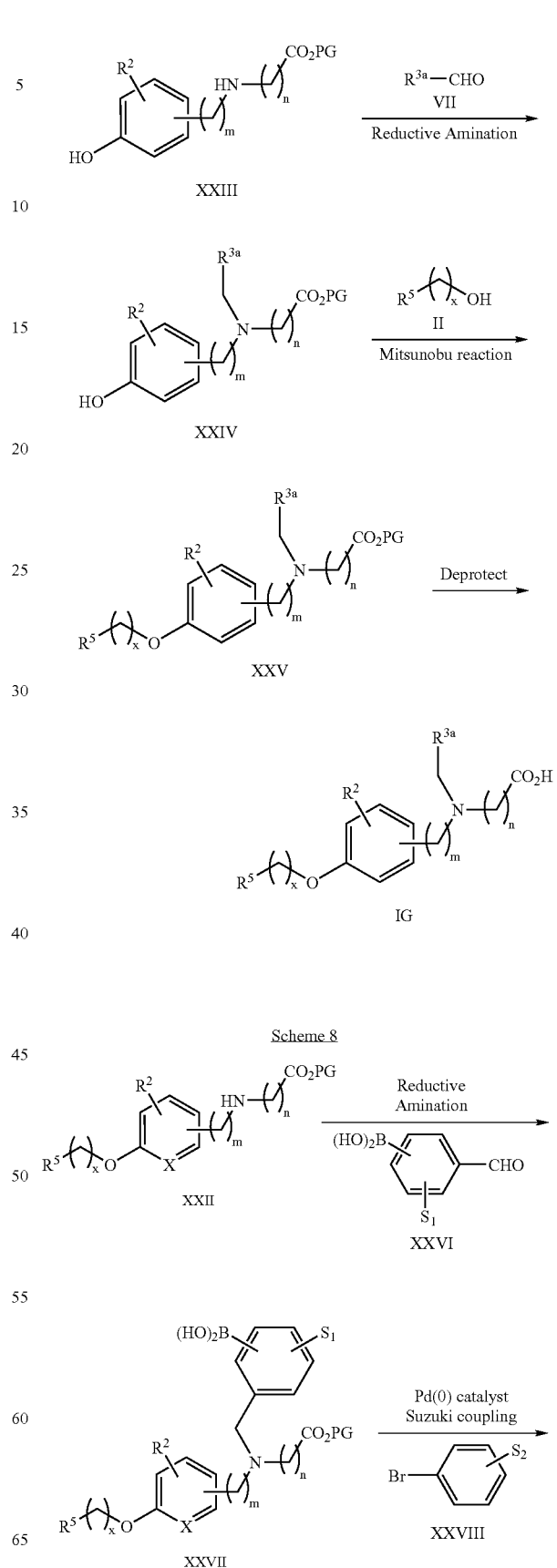

37

-continued

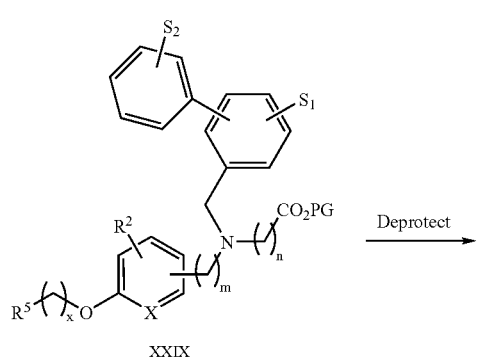

XXIX

↓ Deprotect

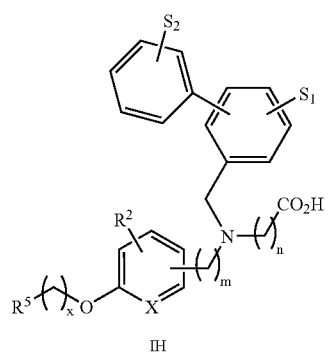

IH ($S_1$ = H, alkyl, halo, alkoxy, alkylthio, alkylamino, aryloxy, aryl, heteroaryl, alkoxycarbonyl, alkylaminocarbonyl
$S_2$ = H, alkyl, halo, alkoxy, alkylthio, alkylamino, aryloxy, aryl, heteroaryl, alkoxycarbonyl, alkylaminocarbonyl)

Scheme 9

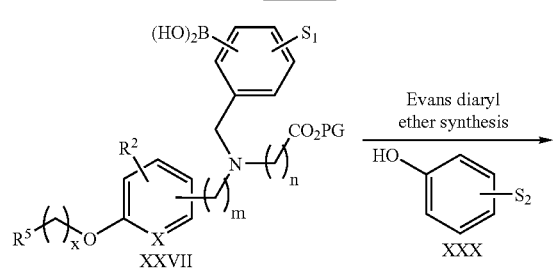

XXVII + XXX → Evans diaryl ether synthesis

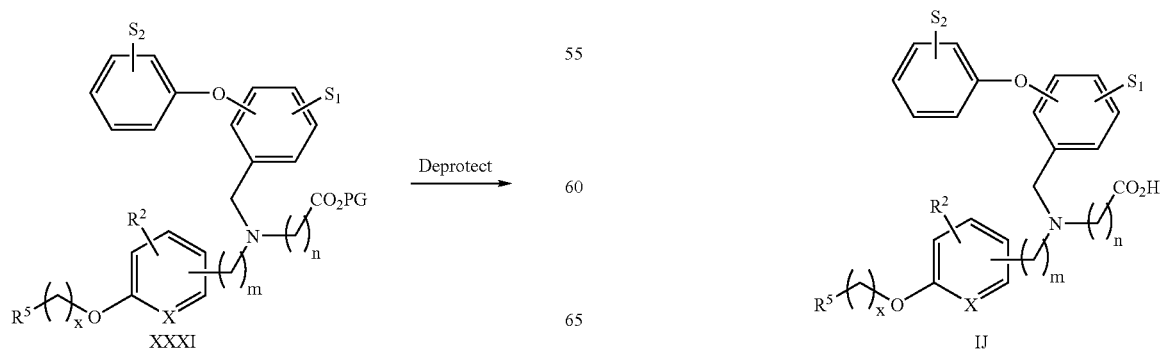

XXXI

↓ Deprotect

38

-continued

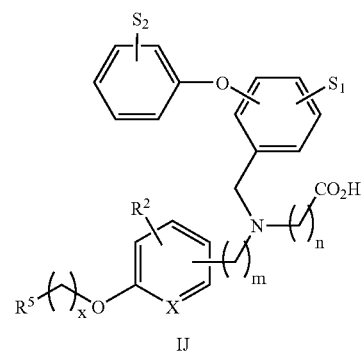

IJ

Scheme 10

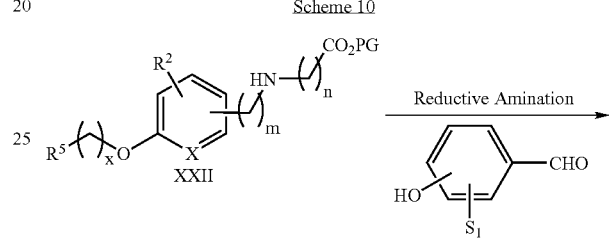

XXII → Reductive Amination

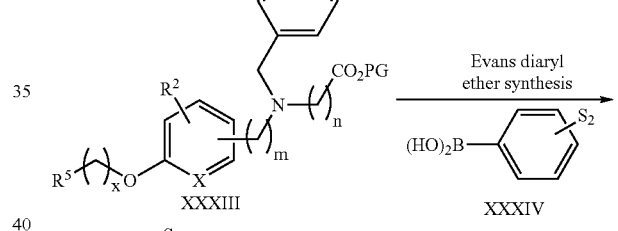

XXXIII + XXXIV → Evans diaryl ether synthesis

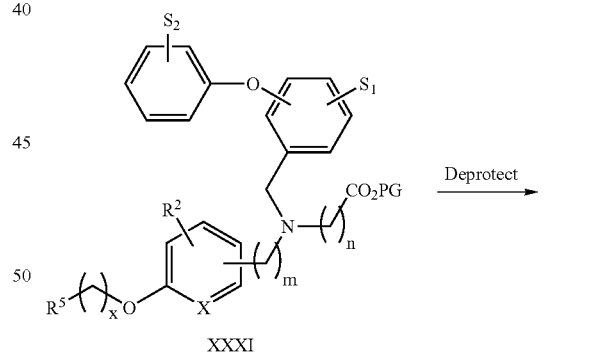

XXXI

↓ Deprotect

IJ

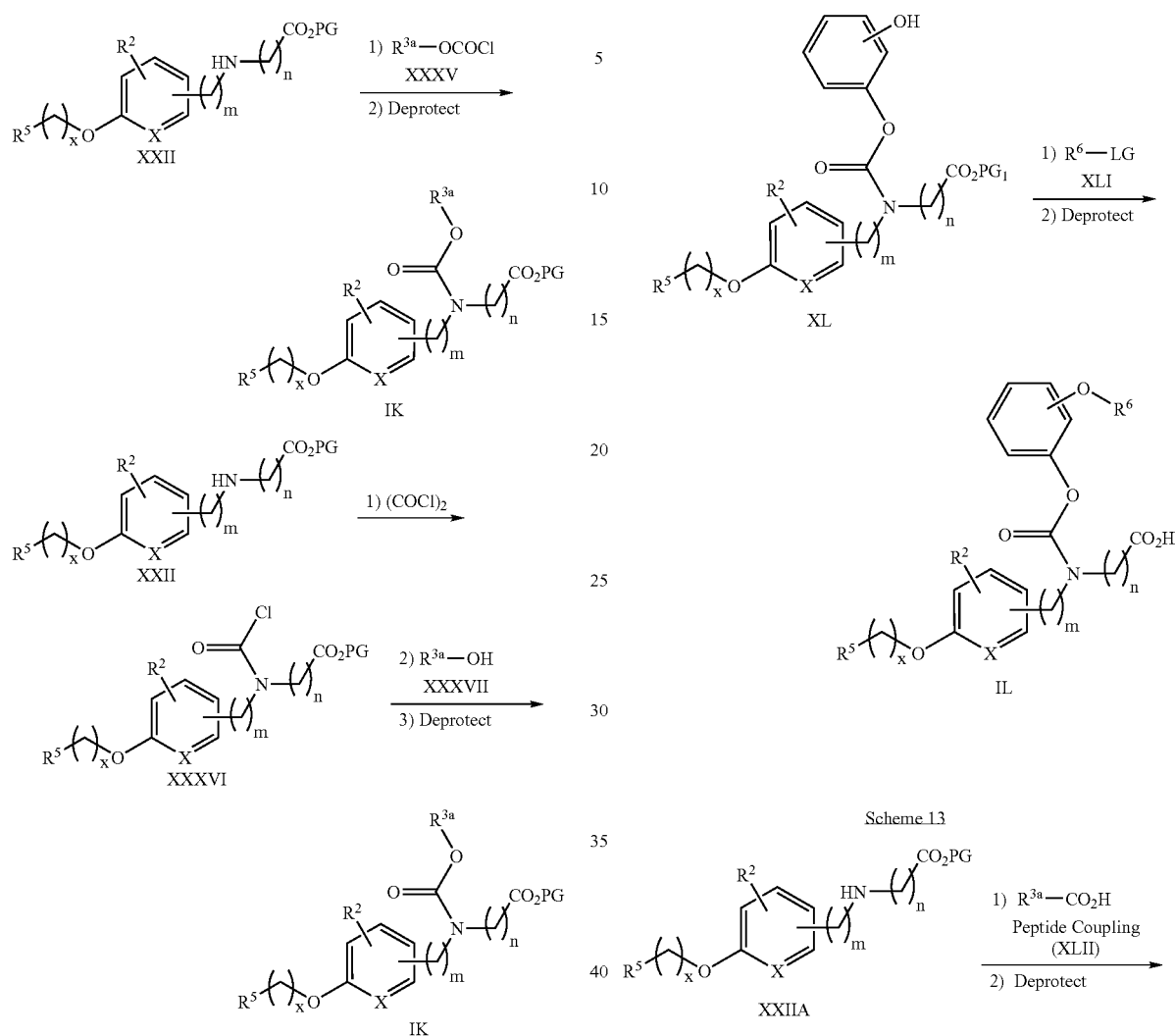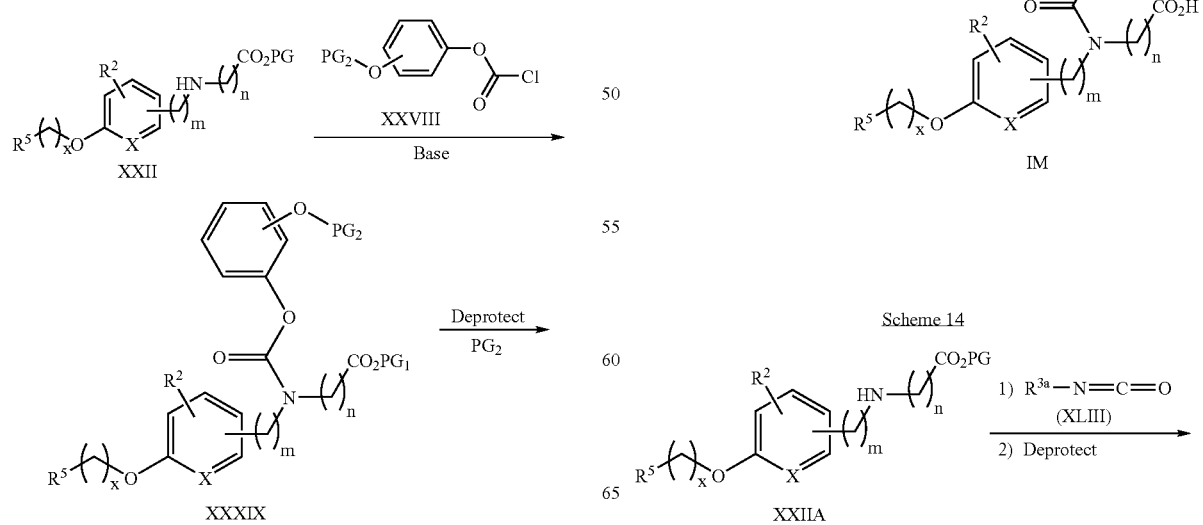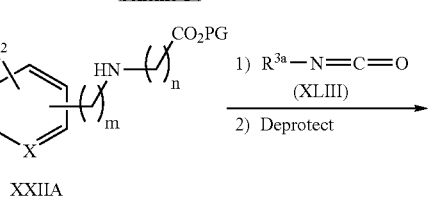

-continued
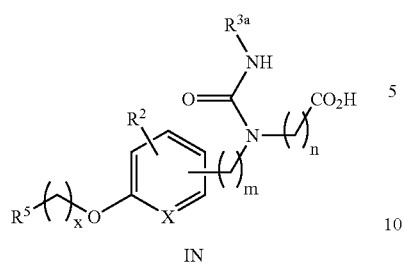
IN
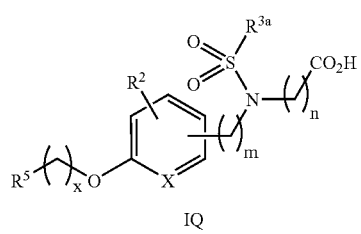
IQ
Scheme 15
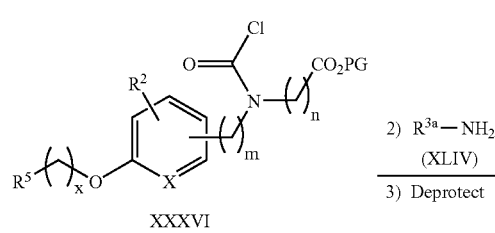
Scheme 17
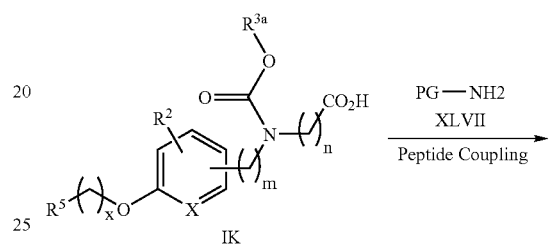
Scheme 16
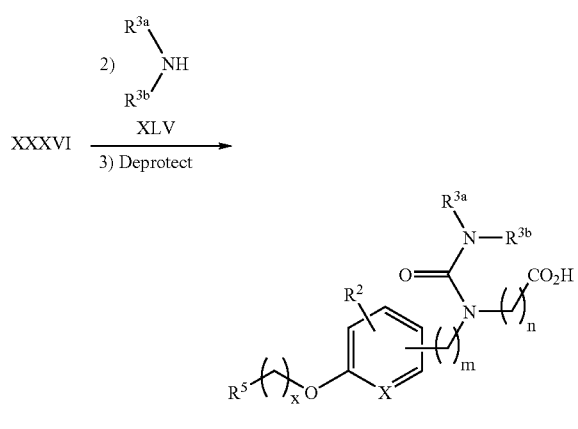
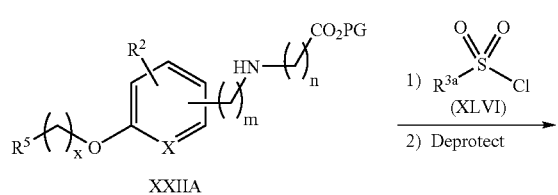
XXIIA
Scheme 18
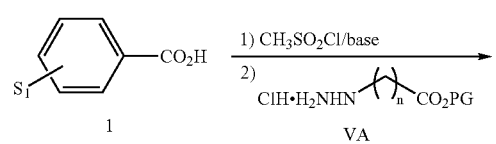

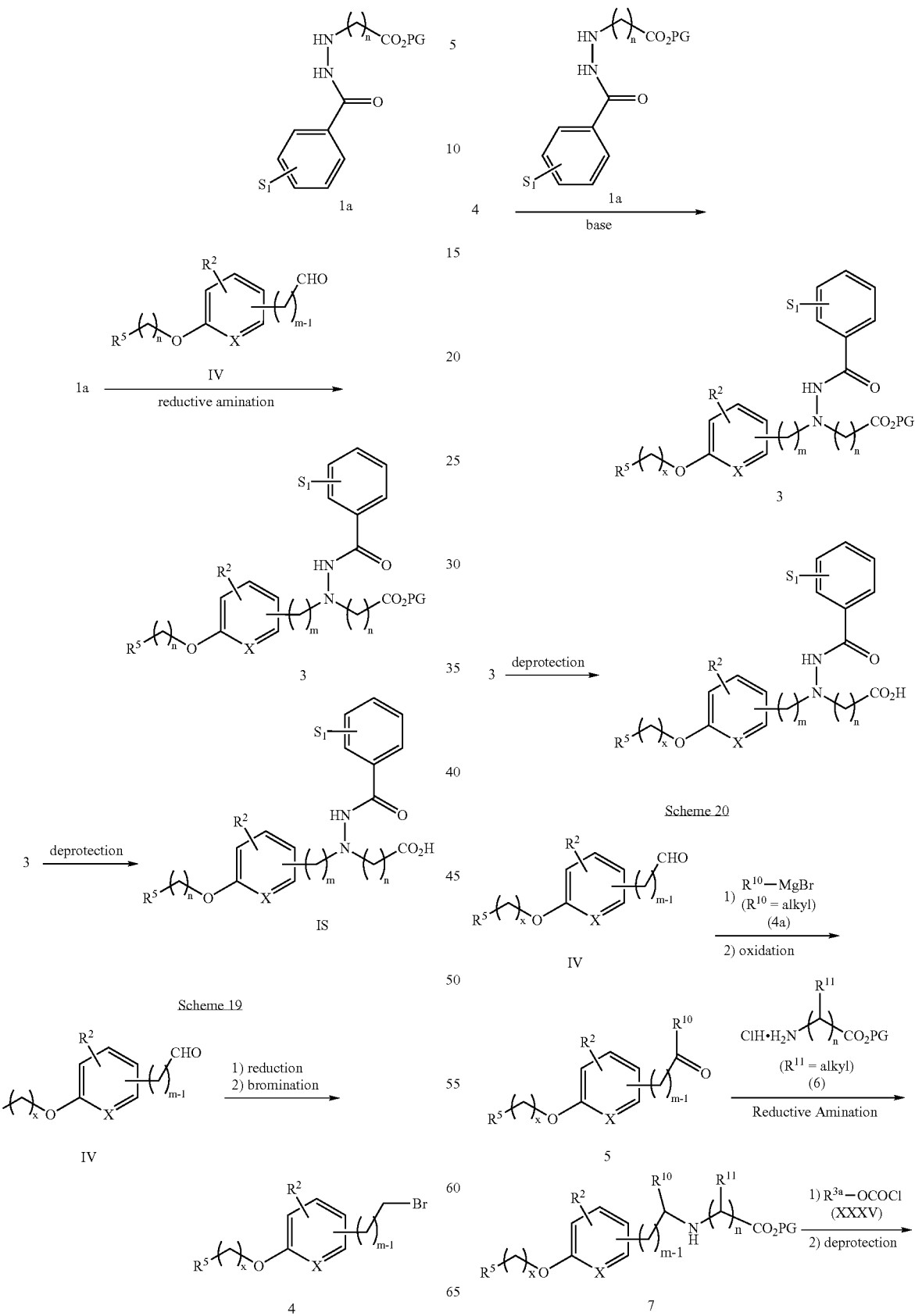

-continued

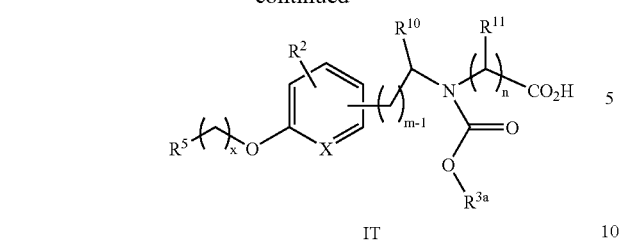

IT

1) R³ᵃ—CHO (VII) reductive amination
2) Deprotection

Scheme 21

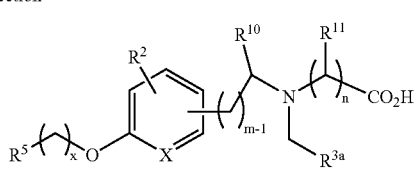

5

Asymmetric Reduction

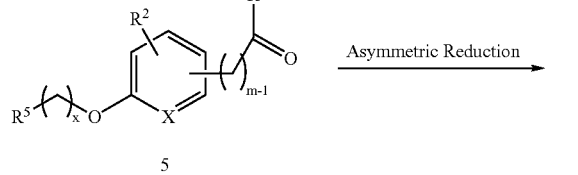

8

2) Mitsunobu reaction TMSN₃ or NaN₃
3) Azide reduction to amine


9

$$\text{LG}\overset{R^{11}}{\underset{n}{\frown}}\text{CO}_2\text{PG}$$
(XVIA)
base

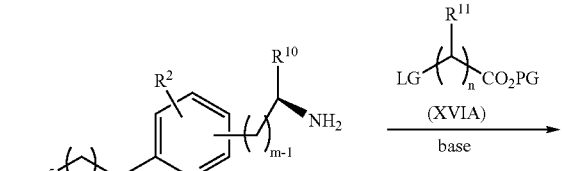

10

1) R³ᵃ—OCOCl (XXXV)
2) Deprotection

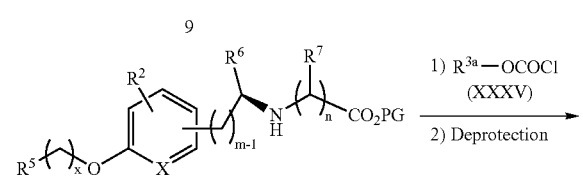

ITa

1) R³ᵃ—CHO (VII) reductive amination
2) Deprotection

-continued

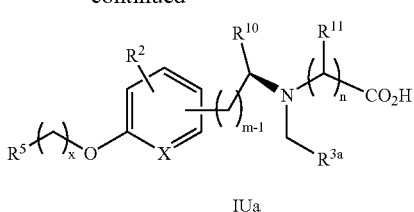

IUa

Scheme 22

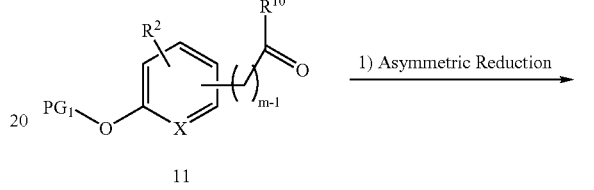

11

1) Asymmetric Reduction

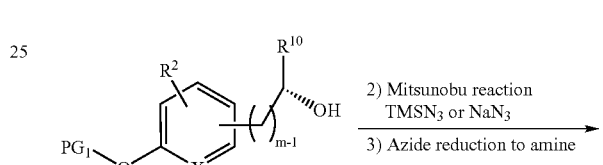

12

2) Mitsunobu reaction TMSN₃ or NaN₃
3) Azide reduction to amine $$\text{R}^2\text{—Ar—}\overset{R^{10}}{\underset{m-1}{\frown}}\text{NH}_2$$

13

$$\text{LG}\overset{R^{11}}{\underset{n}{\frown}}\text{CO}_2\text{PG}$$
(XVIA)
base

14

1) R³ᵃ—OCOCl (XXXV)
2) Deprotect PG1

15

1) Base $$\text{R}^5\overset{}{\underset{x}{\frown}}\text{OSO}_2\text{CH}_3$$
(VIII)
2) Deprotection ITa

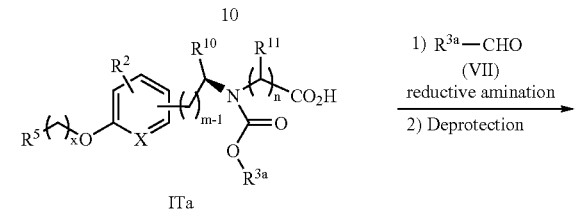

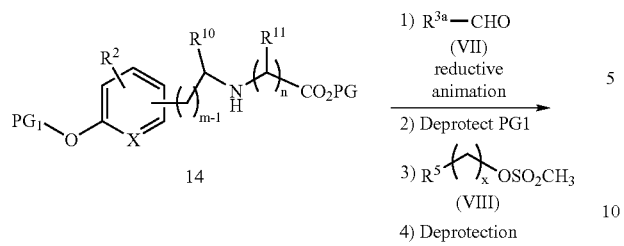
14
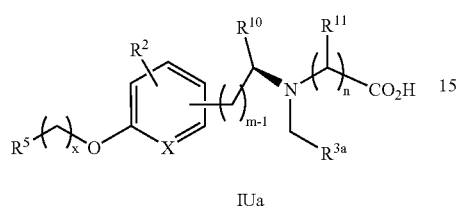
IUa
Scheme 23
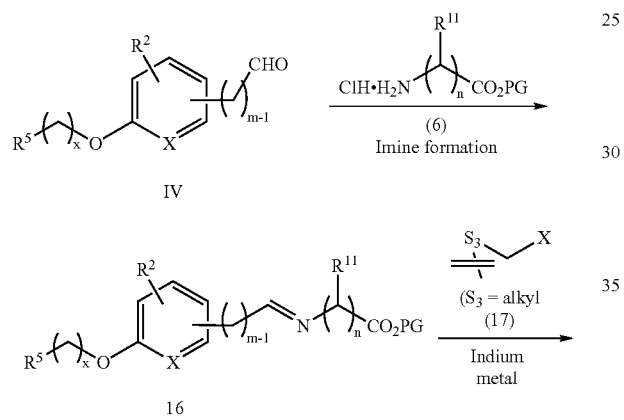
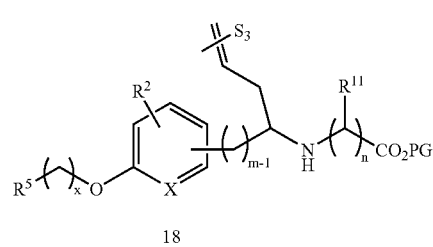
18
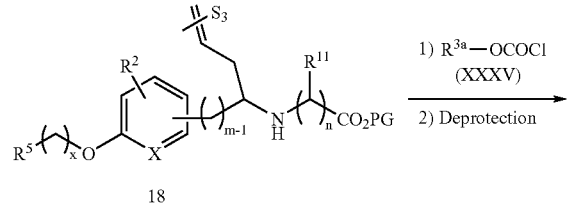
18
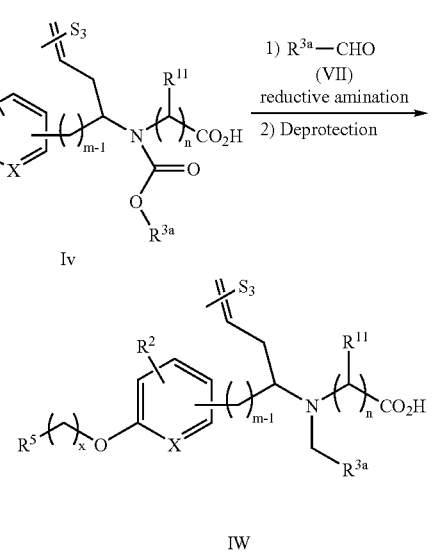
Scheme 24
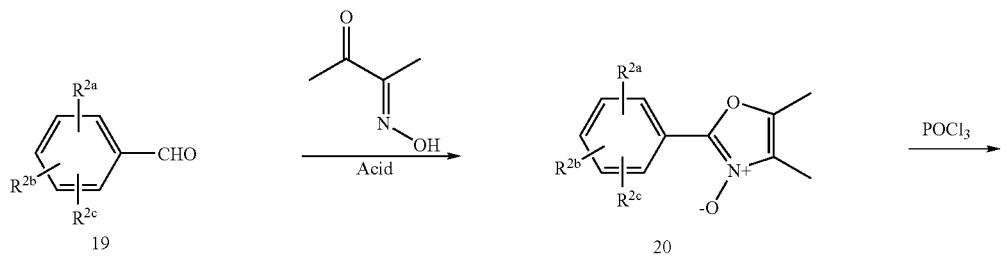
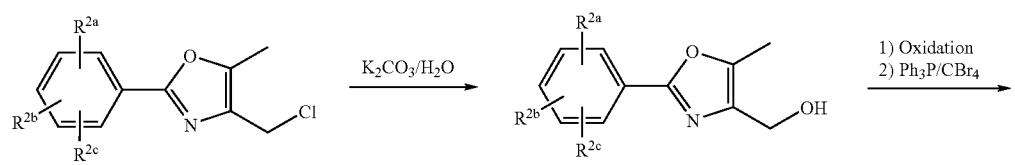

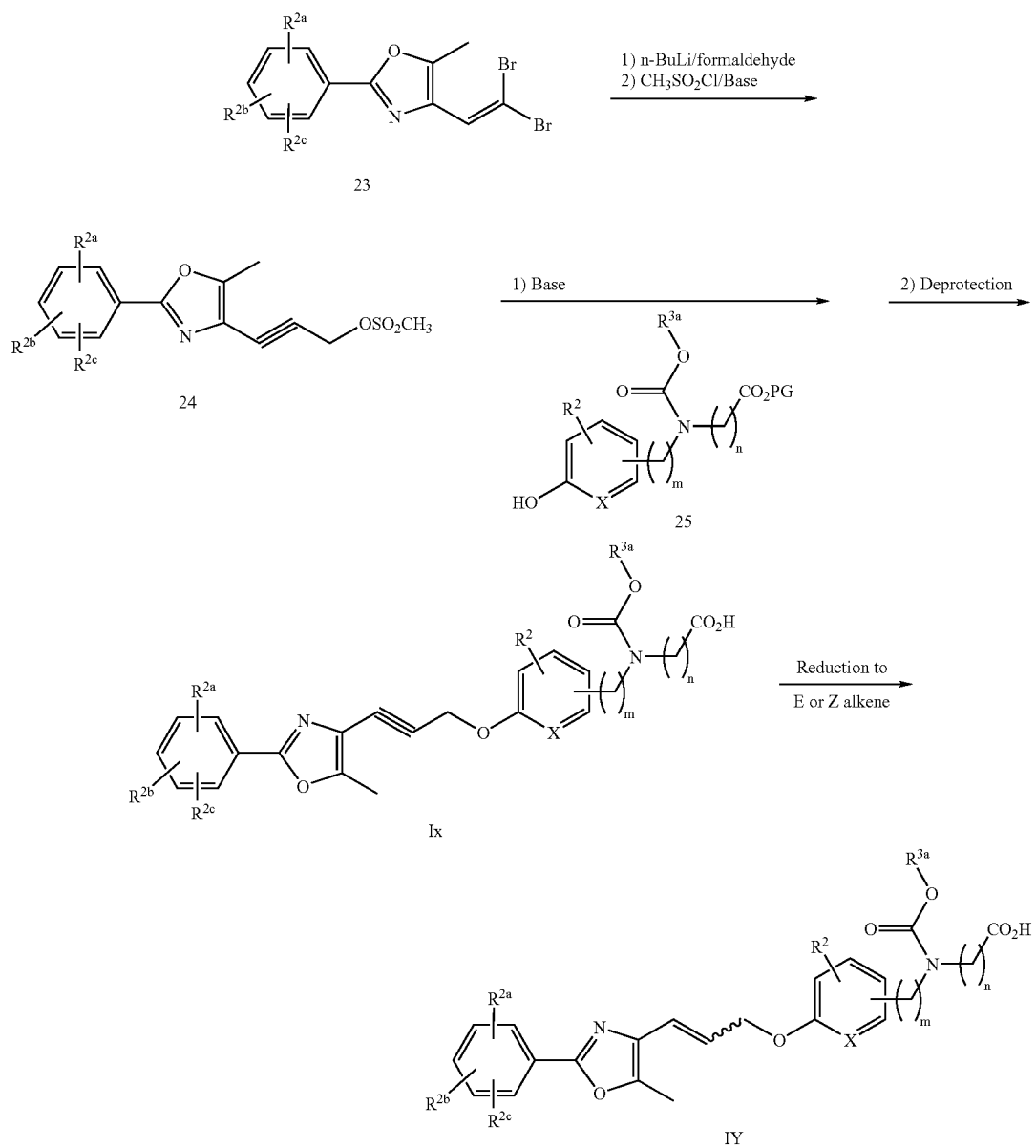
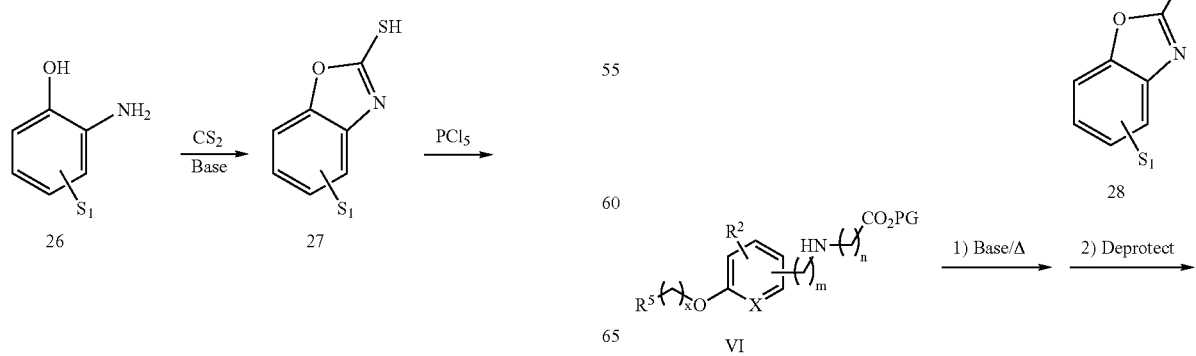
Scheme 25

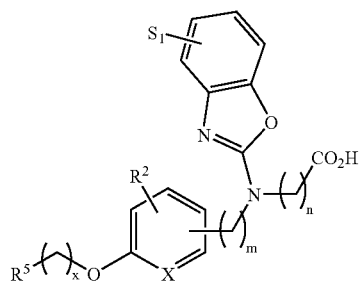
IZ
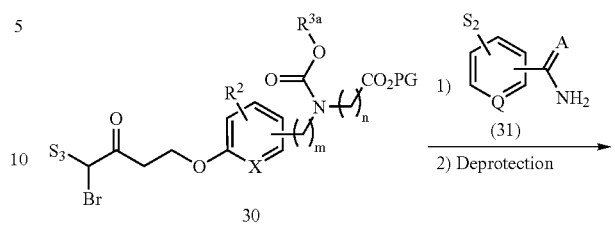
Scheme 26
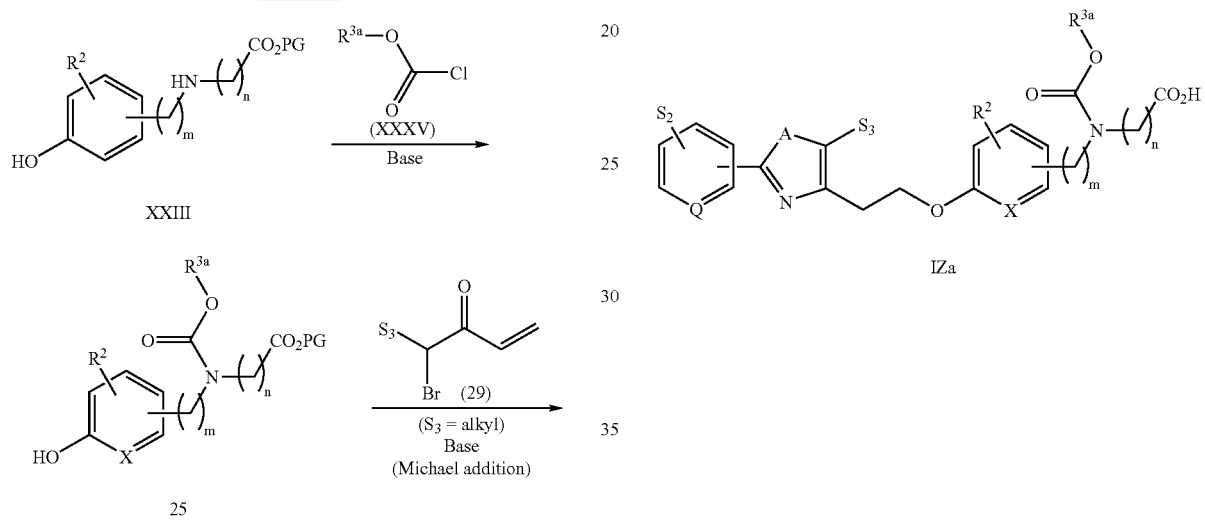
IZa
Scheme 27
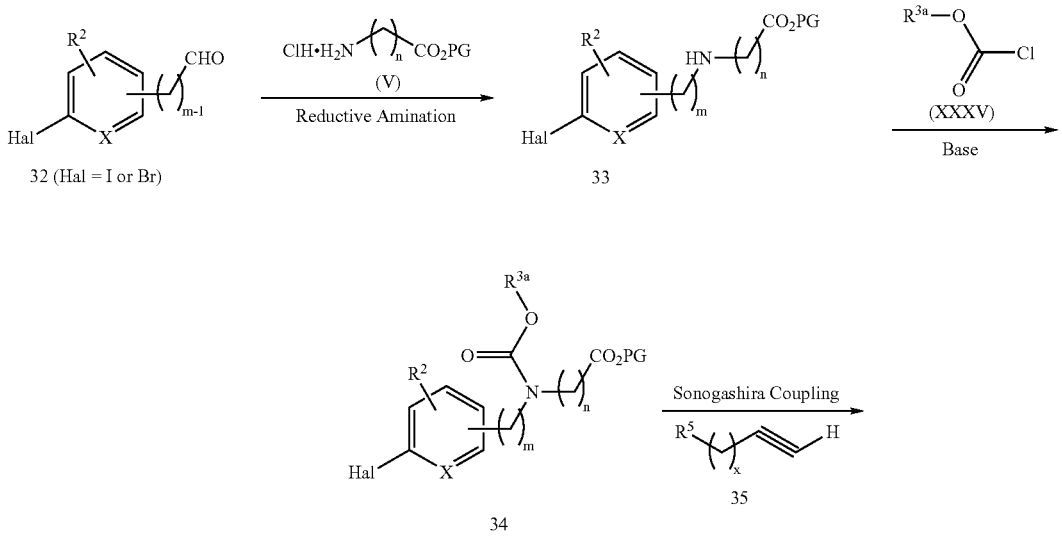

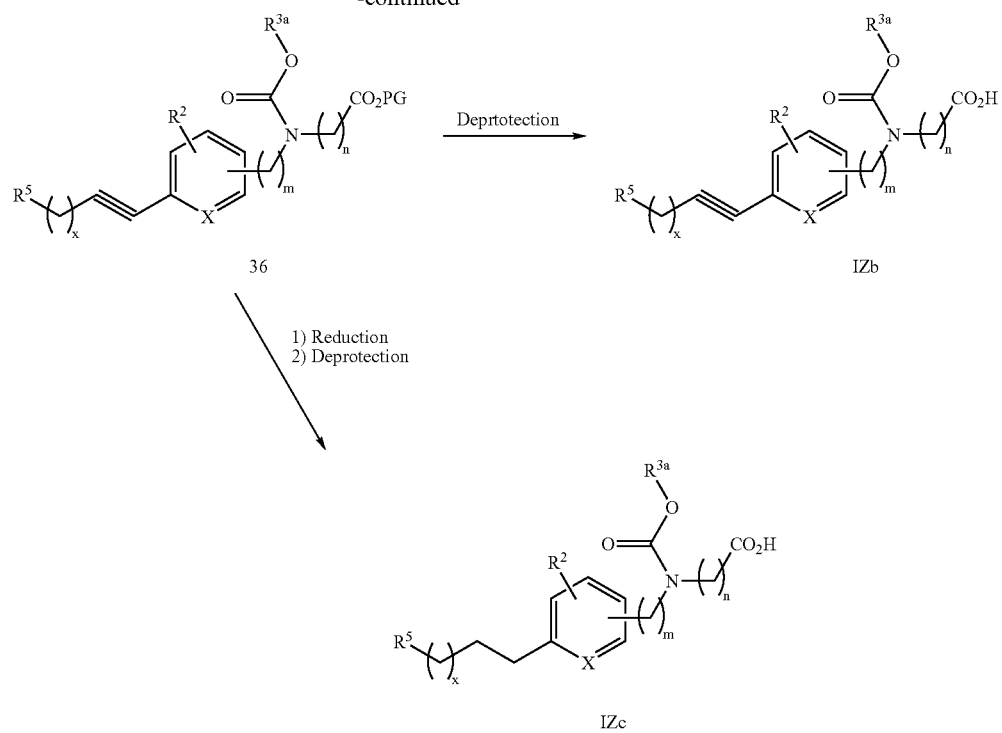
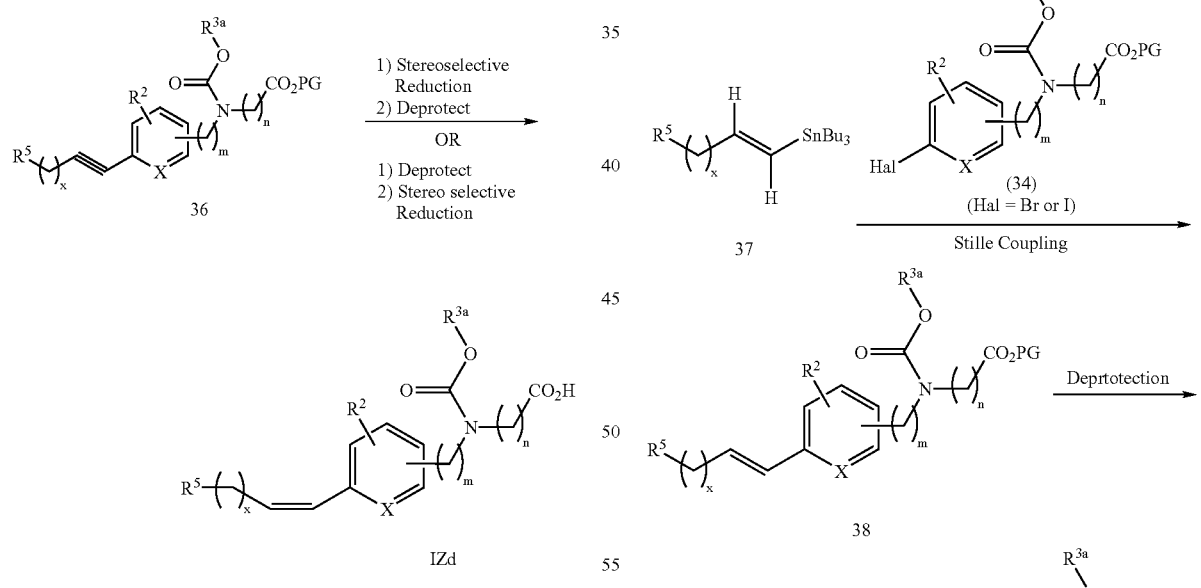
Scheme 28
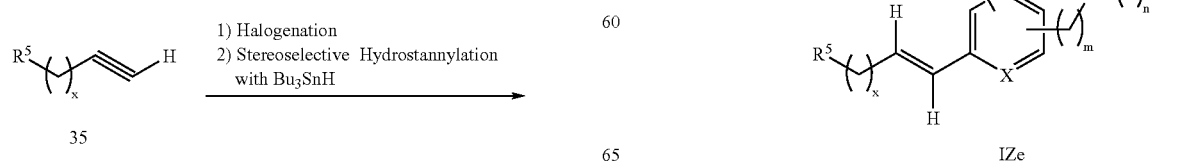
Scheme 29

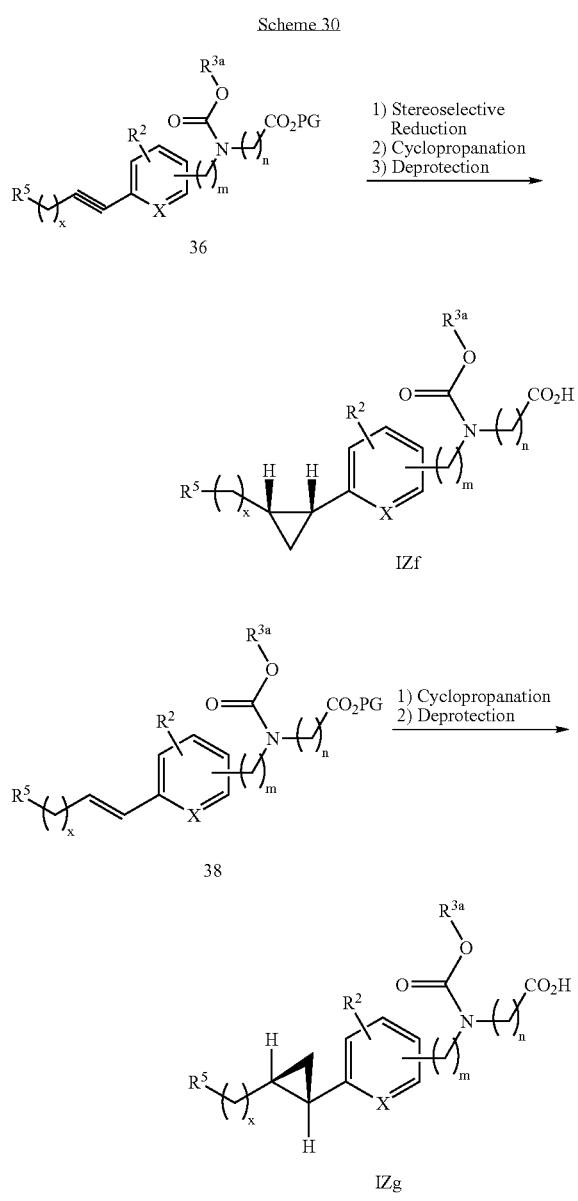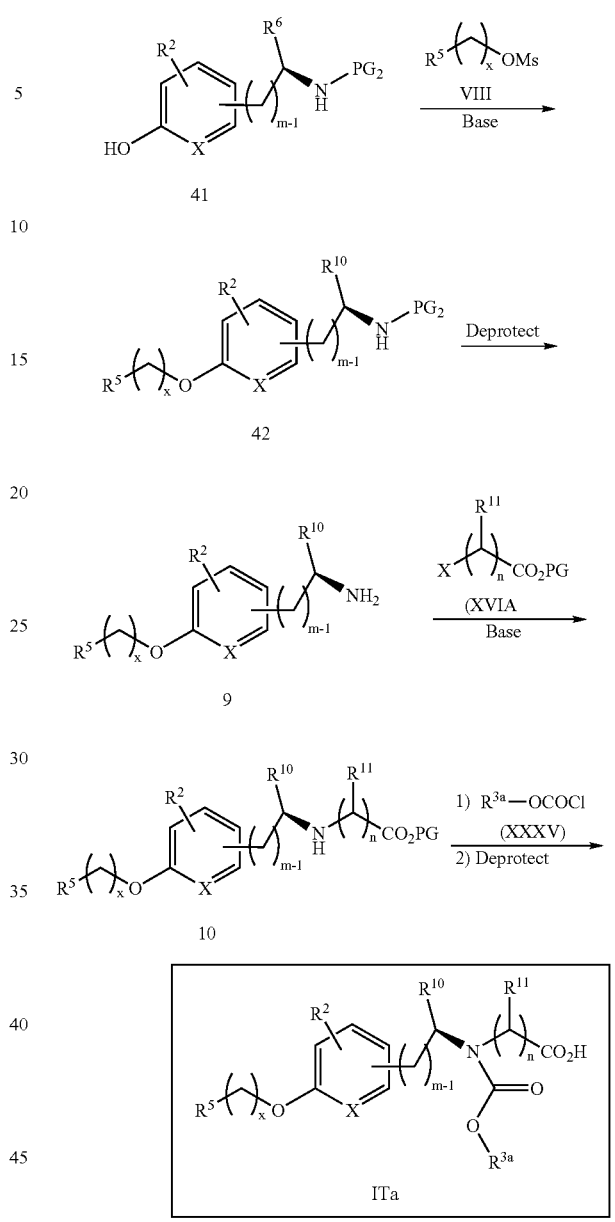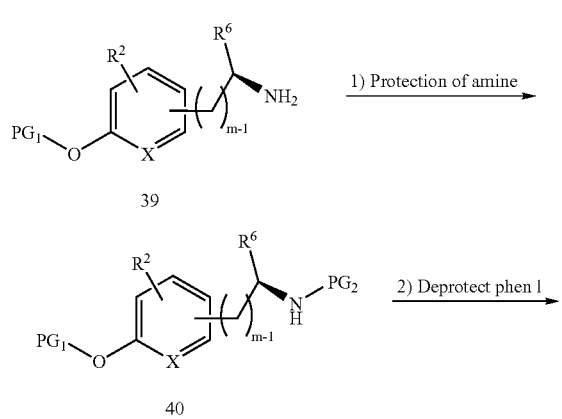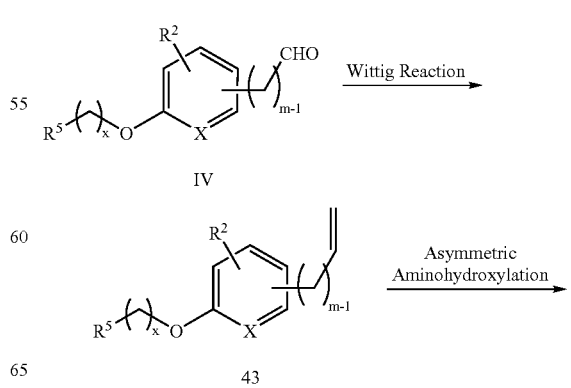

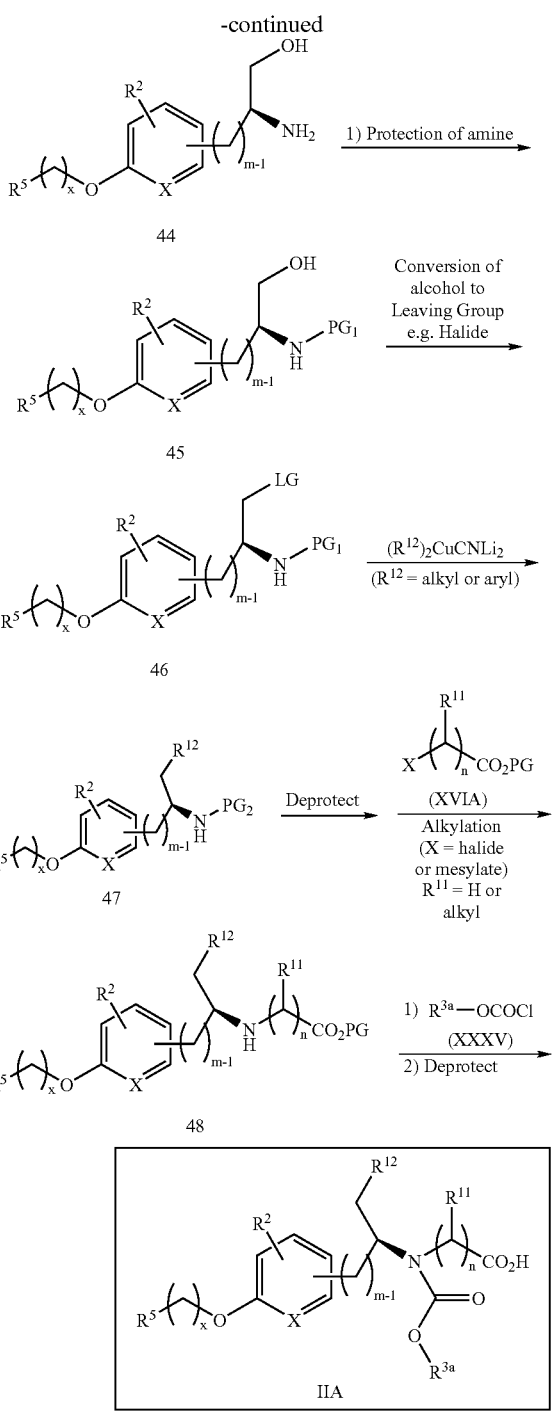

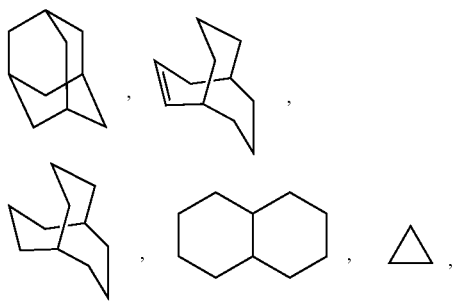

arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

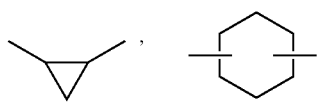

and the like, and may optionally be substituted as defined above for "cycloalkyl".

The term "alkanoyl", as used herein alone or as part of another group refers to alkyl linked to a carbonyl group.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$X^1_x$, $X^1_m$ and $X^1_n$ which may also be referred to as $(CH_2)_x$, $(CH_2)_m$, and $(CH_2)_n$, respectively, or $(CH_2)_y$, includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$ or $(CH_2)_m$ or $(CH_2)_n$ group to form a cycloalkyl group therewith.

Examples of $(CH_2)_x$, $(CH_2)_m$, $(CH_2)_n$, $(CH_2)_y$, alkylene, alkenylene and alkynylene include

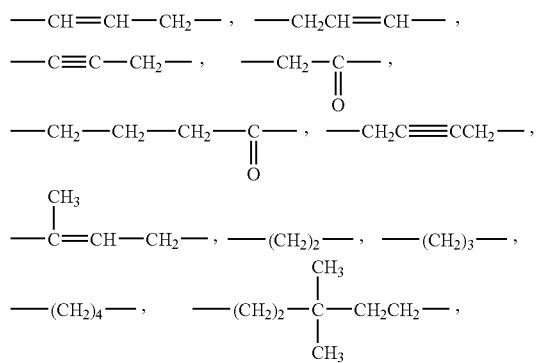

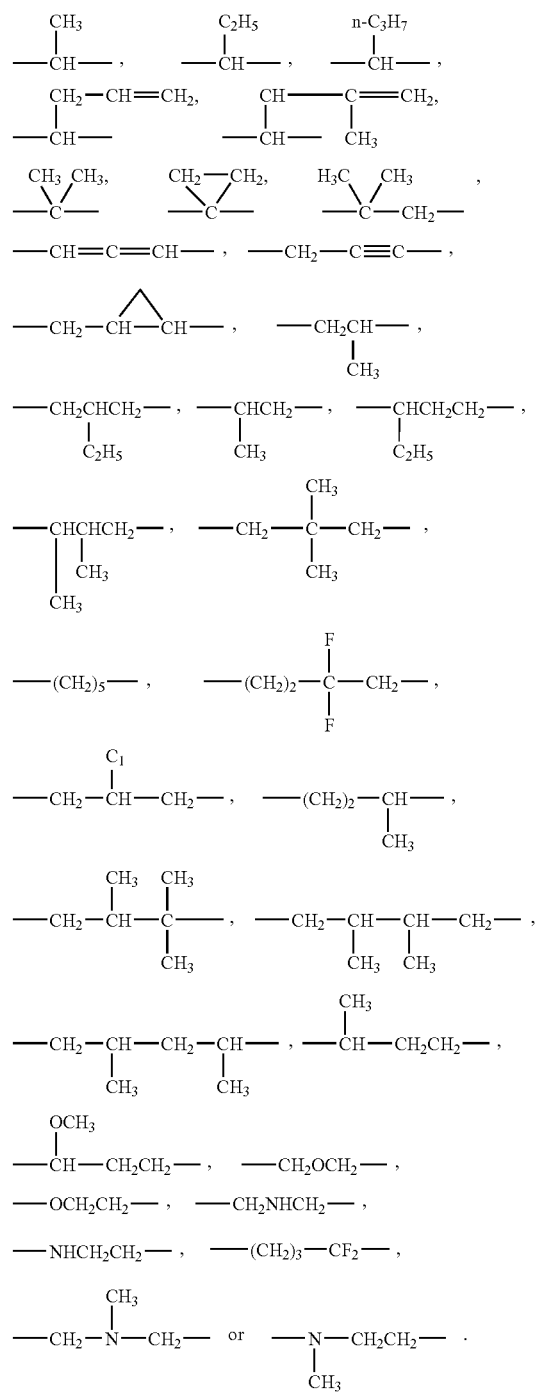

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group

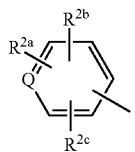

where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

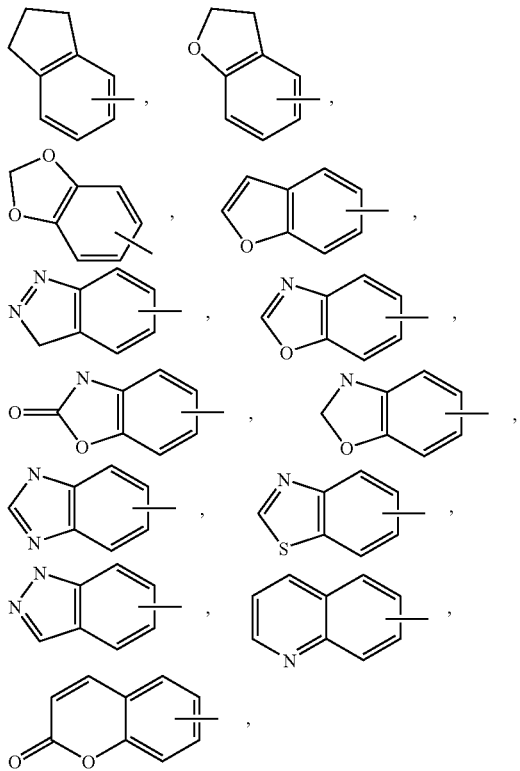

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

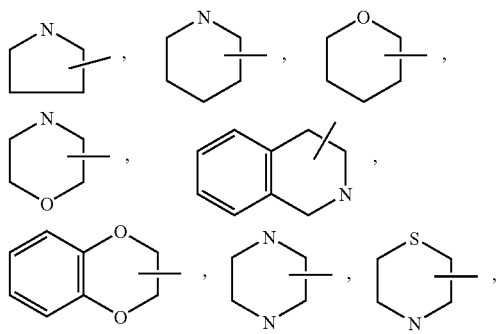

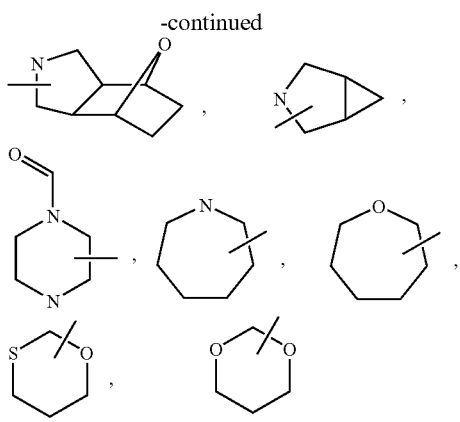

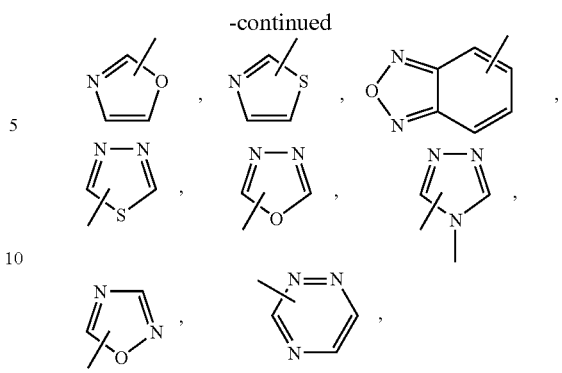

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

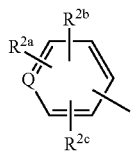

where Q is N, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents for alkyl or aryl set out above. Examples of heteroaryl groups include the following:

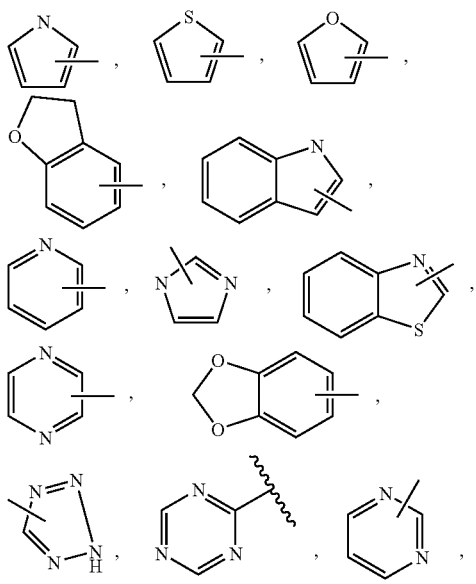

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $-(CH_2)_p-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups:

(1-alkanoyloxy)alkyl such as,

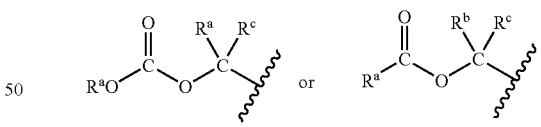

wherein $R^a$, $R^b$ and $R^c$ are H, alkyl, aryl or arylalkyl; however, $R^aO$ cannot be HO.

Examples of such prodrug esters $R^4$ include

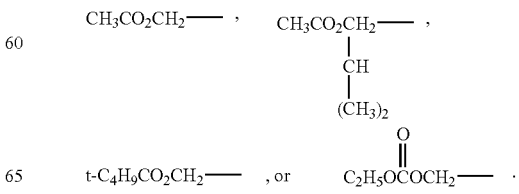

Other examples of suitable prodrug esters $R^4$ include

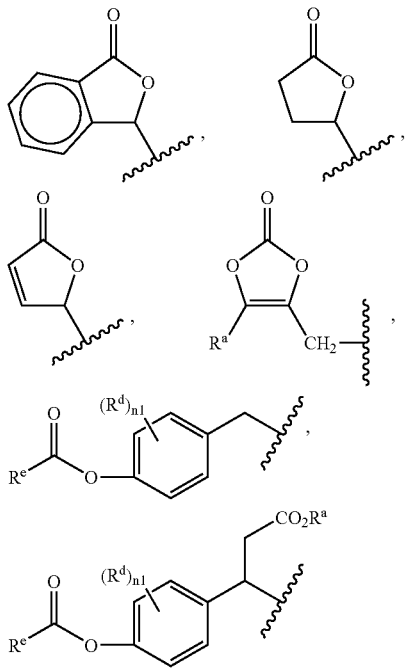

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more hypolipidemic agents or lipid-lowering agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The hypolipidemic agent or lipid-lowering agent which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

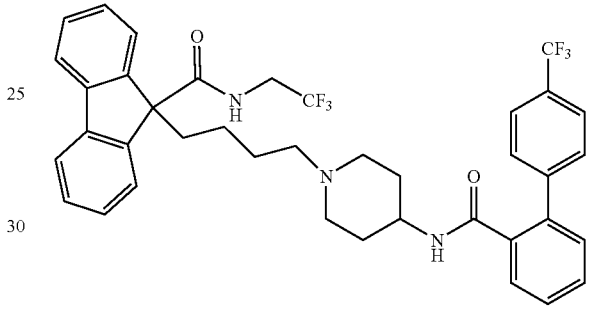

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto A J-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/W L), NN-2344 (Dr. Reddy/N N), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1 (7–36) amide, GLP-1 (7–37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. provisional application No. 60/158,773, filed Oct. 12, 1999, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. provisional application No. 60/127,745, filed Apr. 5, 1999, employing dosages as set out herein. Preferred are the compounds designated as preferred in the above application.

The antidiabetic agent may be a DP4 inhibitor such as disclosed in Provisional Application 60/188,555 filed Mar. 10, 2000, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may optionally be employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®). Dosages employed will be as set out in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following Examples represent preferred embodiments of the invention.

The following abbreviations are employed in the Examples:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
i-$Pr_2$NEt=diisopropylethylamine
$Et_3N$=triethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride
$LiAlH_4$=lithium aluminum hydride
n-BuLi=n-butyllithium
Pd/C=palladium on carbon
$PtO_2$=platinum oxide
KOH=potassium hydroxide
NaOH=sodium hydroxide
LiOH=lithium hydroxide K₂CO₃=potassium carbonate
NaHCO₃=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H₂O=1-hydroxybenzotriazole hydrate
HOAT=1-Hydroxy-7-azabenzotriazole
BOP reagent=benzotriazol-1-yloxy-tris(dimethylamino) phosphonium hexafluorophosphate
NaN(TMS)₂=sodium hexamethyldisilazide or sodium bis(trimethylsilyl)amide
Ph₃P=triphenylphosphine
Pd(OAc)₂=Palladium acetate
(Ph₃P)₄Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N₂=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLE 1

A.

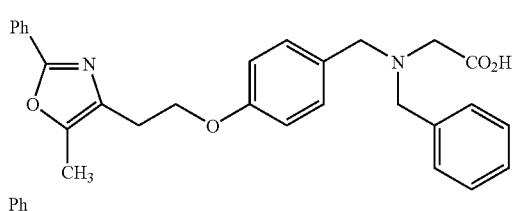

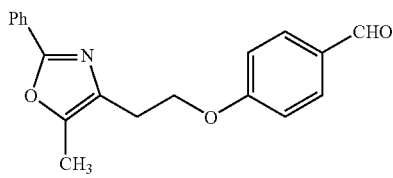

To a 0° C. solution of 4-hydroxybenzaldehyde (1.70 g, 12.3 mmol), 5-phenyl-2-methyl-oxazole-4-ethanol (Maybridge; 2.50 g, 14.0 mmol) and Ph₃P (4.20 g, 16.0 mmol) in dry THF (30 mL) was added dropwise DEAD (3.20 g, 15.0 mmol). The solution was stirred at 0° C. for 0.5 h, then was allowed to warm to RT and stirred overnight. The orange-red solution was concentrated in vacuo and the residue was chromatographed (stepwise gradient from 5:1 to 5:2 hex:EtOAc) to give Part A compound (2.47 g, 65%) as a clear, slightly yellow viscous oil.

A1. Alternative Procedure for Preparing Part A Aldehyde (1)

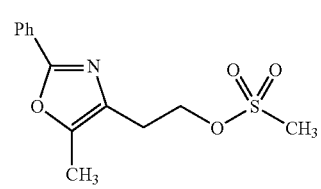

To a −5° C. solution of 5-phenyl-2-methyl-oxazole-4-ethanol (20.00 g, 0.098 mol) in CH₂Cl₂ (100 mL) was added methanesulfonyl chloride (12.40 g, 0.108 mol) in one portion (exothermic reaction). After recooling to −5° C., Et₃N (11.1 g, 0.110 mol) was added slowly over 30 min (internal temperature <3° C.). The reaction was allowed to warm to RT and stirred for 1 h (reaction monitored by analytical HPLC), at which point starting material had been consumed. The reaction was washed with aqueous HCl (2×50 mL of a 3N solution). The combined aqueous layers were extracted with CH₂Cl₂ (50 mL). The combined organic extracts were successively washed with satd. aqueous NaHCO₃ and brine (50 mL each), dried (Na₂SO₄), and concentrated to ~30 mL volume. Methyl tert-butyl ether (120 mL) was added and the mixture was stirred; a white solid was formed. The mixture was cooled to −20° C. for complete crystallization. The product was filtered and vacuum-dried to give the product mesylate (23.3 g, 85%) as a white solid. The mother liquor was concentrated in vacuo and recrystallized from methyl tert butyl ether/heptane to give a second crop of product mesylate (3.3 g, 12%; total yield=97%).

(2)

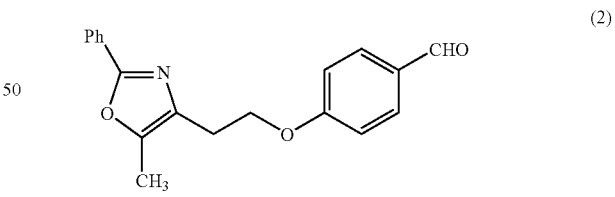

A mixture of the above mesylate (13.6 g, 0.048 mol), 4-hydroxybenzaldehyde (7.09 g, 0.058 mol) and K₂CO₃ (9.95 g, 0.072 mol) in DMF (110 mL) was heated at 100° C. for 2 h (reaction complete by analytical HPLC). The mixture was allowed to cool to RT and then poured into ice-water (400 mL) and stirred for 30 min. The solid product was filtered and washed with cold water (3×25 mL) and dried in vacuo at 50°-60° C. overnight. The crude product was crystallized from MTBE-Hexane to give (12.2 g, 82%; 2 crops) the aldehyde (Part A1 compound) as a white solid.

B.

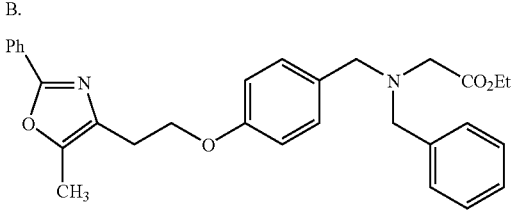

To a solution of N-benzyl glycine ethyl ester (43 mg; 0.22 mmol) and Part A1 compound (52 mg; 0.17 mmol) in DCE (10 mL) was added NaBH(OAc)$_3$ (56 mg; 0.26 mmol). The reaction mixture was stirred vigorously overnight for 12 hours. Saturated aqueous NaHCO$_3$ (10 mL) was added, and the mixture was extracted with EtOAc (3×10 mL). The combined organic extracts were washed with brine, dried (Na$_2$SO$_4$), concentrated in vacuo and chromatographed (hex:EtOAc 4:1) to give Part B compound (45 mg; 55%) as a pale yellow oil in addition to recovered starting material (14 mg; 27%).

C.

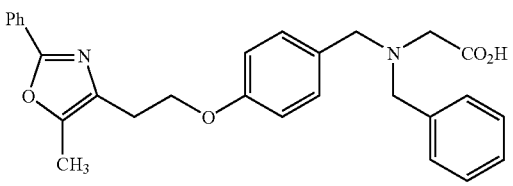

To a solution of Part B compound (45 mg) in MeOH (2 mL) was added aqueous NaOH (3 mL of a 1M solution). The solution was stirred overnight for 14 h and then acidified to pH5 with excess aqueous HCl (1M solution). The mixture was extracted with EtOAc (2×10 mL); the combined organic extracts were washed with brine, dried (Na$_2$SO$_4$), and concentrated in vacuo to give the desired acid which was still contaminated with starting material. This mixture was dissolved in MeOH (2 mL) and aqueous NaOH (3.0 mL of a 1M solution) and the resulting solution was refluxed for 1.5 h. Acidic extractive workup as above gave the desired title compound as a colorless solid (28 mg; 71%). [M+H]$^+$=457.2

EXAMPLE 2

A.

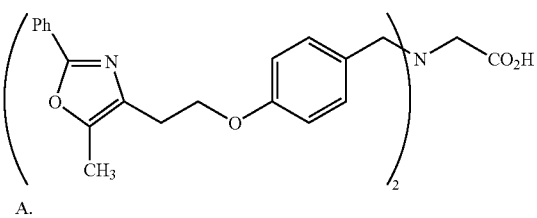

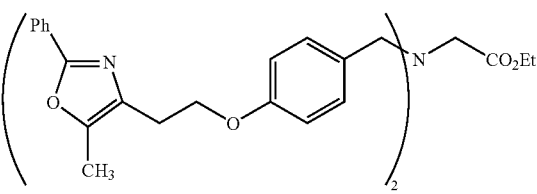

To a solution of Example 1 Part A compound (147 mg; 0.479 mmol) and glycine ethyl ester hydrochloride (73 mg; mmol) in DCE (2 mL) was added Et$_3$N and NaBH(OAc)$_3$ (156 mg; 0.74 mmol) and the reaction was stirred overnight at RT. Flash chromatography (stepwise gradient from 7:3 to 2:3 hex: EtOAc) gave 35 mg (21%) of the dibenzyl glycine ester (Example 2 Part A compound). In addition, 127 mg (67%) of the monobenzyl glycine ester (Example 3 Part A compound) was obtained.

B.

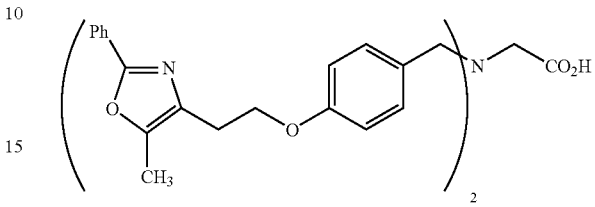

A solution of Example 1 Part A compound (35 mg; 0.051 mmol) in MeOH (2 mL) and aqueous NaOH (3 mL of a 1M solution) was heated under reflux for 12 h. The solution was adjusted to pH5 with aqueous 1M HCl and aqueous 1 M NaOH, then extracted with EtOAc (3×). The combined organic extracts were washed with brine, dried (Na$_2$SO$_4$), and concentrated in vacuo to give title compound (13 mg) as a colorless solid. [M+H]$^+$=658.2

EXAMPLE 3

A.

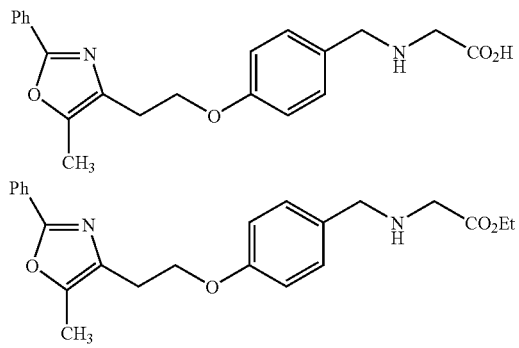

To a solution of Example 1 Part A compound (147 mg; 0.479 mmol) and glycine ethyl ester hydrochloride (73 mg; mmol) in DCE was added Et$_3$N and NaBH(OAc)$_3$ (156 mg; 0.74 mmol). Flash chromatography (stepwise gradient from 7:3 to 2:3 hex: EtOAc) gave 127 mg (67%) of the title compound. In addition, 35 mg (21%) of the bis-benzyl glycine ester (Example 2 Part A compound) was obtained as a byproduct.

B.

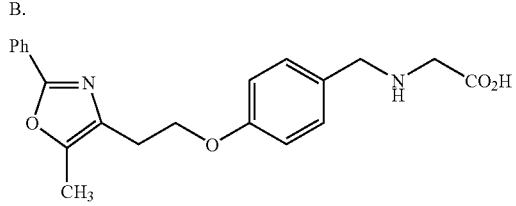

A solution of Part A compound (72 mg; 0.18 mmol) in aqueous NaOH (2 mL of a 1M solution) and MeOH (2 mL)

was refluxed for 3 h. The reaction was adjusted to pH5 with aqueous 1M HCl, and solids were filtered off. The filtrate was extracted with EtOAc (3×). The combined organic extracts were washed with brine, dried ($Na_2SO_4$) and concentrated in vacuo to give a colorless solid, which was purified by preparative HPLC (utilizing a YMC S5 ODS 20 mm×100 mm column with a continuous gradient from 70% A:30% B to 100% B for 10 min at a flow rate of 20 mL/min, where A=90:10:0.1 $H_2O$:MeOH:TFA and where B=90:10:0.1 MeOH:$H_2O$:TFA) to give title compound (10 mg; 15%) as a colorless solid. $[M+H]^+=367.2$

EXAMPLE 4

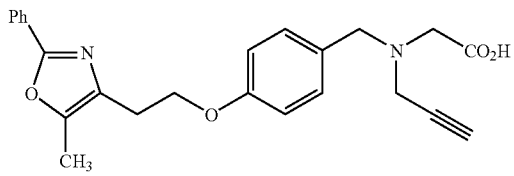

A solution of the amino t-butyl ester (0.040 g, 0.095 mmol), (prepared as described for Example 7 Part C, except that the aldehyde used in the reductive amination was Example 1 Part A instead of Example 7 Part A)

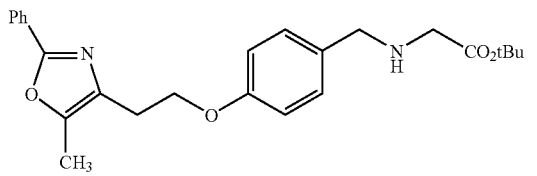

and propargyl bromide (0.014 g, 0.120 mmol) and DBU (0.5 mL; 2.96 mmol) in DCE (1 mL) was stirred at 0° C. for 5 h. TLC showed that the reaction was complete at this point. EtOAc (10 mL) was added and the organic phase was washed with $H_2O$ and concentrated in vacuo. The residual oil was dissolved in $CH_2Cl_2$/TFA (1:1, 1 mL) and stirred at RT for h, then concentrated in vacuo. The residue was purified by preparative HPLC (YMC S5 ODS 30 mm×250 mm reverse phase column; flow rate=25 mL/min; 30 min continuous gradient from 70:30 A:B to 100% B; where A=90:10:0.1 $H_2O$:MeOH:TFA and where B=90:10:0.1 MeOH:$H_2O$:TFA) to give the title compound (34 mg, 92%) as an oil. LC/MS (electrospray) gave the correct $[M+H]^+=405.2$ for the title compound.

EXAMPLE 5

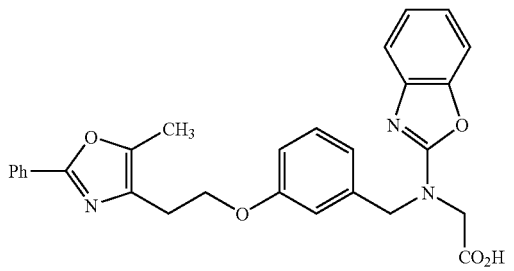

A solution of 2-chlorobenzoxazole (20 mg; 0.131 mmol), the secondary amine-methyl ester (52 mg; 0.146 mmol)

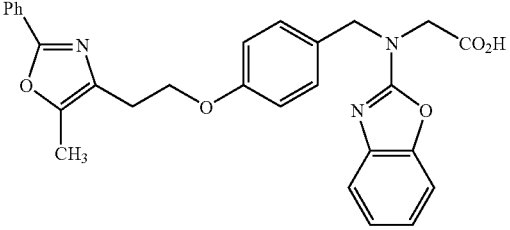

(prepared as described in Example 3 Part A except glycine ethyl ester HCl was replaced by glycine methyl ester HCl and the Example 7 Part A aldehyde was employed), and excess $Et_3N$ (0.5 mL) in THF (2.0 mL) was heated to 100° C. in a sealed tube and the reaction was monitored by LC/MS. After 4 days, starting amine had been consumed. The reaction was cooled to RT and aqueous LiOH (0.50 mL of a 1 M solution) was added to the solution. The solution was stirred at RT for 5 h, after which the hydrolysis was complete. The mixture was concentrated in vacuo to give the crude acid as an oil, which was purified by preparative HPLC (30 min continuous gradient from 70:30 A:B to 100% B, where A=90:10:0.1 $H_2O$:MeOH:TFA and B=90:10:0.1 MeOH:$H_2O$:TFA; flow rate=25 mL/min; YMC S5 ODS 30×250 mm reverse-phase column) to give the title compound (52 mg; 82%) as a solid after lyophilization from (MeOH/$H_2O$). $[M+H]^+=484.2$

EXAMPLE 6

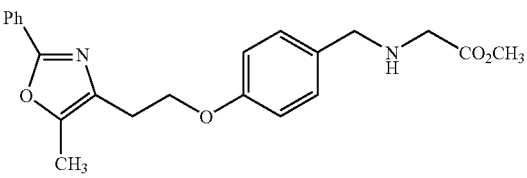

The title compound (13 mg; 21%) was prepared in an analogous fashion to Example 5 using the corresponding secondary amine-methyl ester.

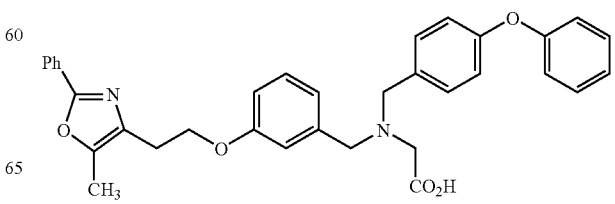

(This compound was prepared as described in Example 3 Part A except glycine ethyl ester HCl was replaced by glycine methyl ester HCl). Example 6: $[M+H]^+=484.2$

EXAMPLE 7

A.

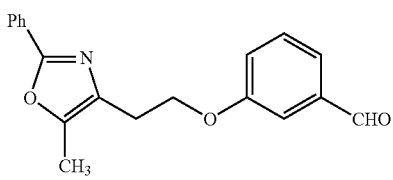

To a 0° C. solution of 3-hydroxybenzaldehyde (3.00 g; 24.6 mmol), 2-phenyl-5-methyl-oxazole-4-ethanol (5.00 g; 24.6 mmol) and Ph₃P (7.10 g; 27.1 mmol) in dry THF (75 mL) was added dropwise DEAD (4.27 mL; 27.1 mmol) over 10 min. The brown-orange solution was allowed to warm to RT and stirred at RT for 24 h. The solution was concentrated in vacuo and chromatographed (SiO₂; stepwise gradient: 100% hex to hex:EtOAc 3:1) to give Part A compound as a pale yellow viscous oil (4.01 g; 53%).

A.1. Alternative Procedure for Preparing Part A Aldehyde

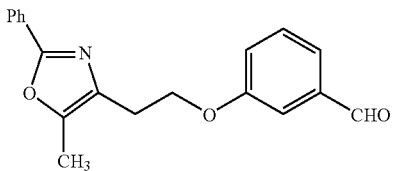

To a solution of 3-hydroxybenzaldehyde (9.1 g; 0.074 mmol) in CH₃CN (206 mL) was added K₂CO₃ (10.3 g). The mixture was heated to 90° C. in an oil bath and stirred for 18 h at 90° C. (the reaction was complete at this point by analytical HPLC). The reaction was cooled to RT, then diluted with EtOAc (500 mL), washed with H₂O, aqueous NaOH (2×100 mL of a 1 M solution) and brine. The organic phase was dried (MgSO₄) and concentrated in vacuo. The residual oil was chromatographed (SiO₂; hex:EtOAc from 9:1 to 4:1) to give the Part A aldehyde (12.7 g; 67%) as a viscous, clear, pale yellow oil.

B.

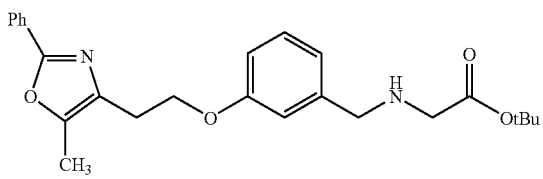

A solution of the Part A1 compound (4.00; 13.0 mmol), glycine tert-butyl ester hydrochloride (2.40 g; 14.3 mmol) and Et₃N (2.18 mL; 15.7 mmol) in MeOH (30 mL) was stirred at RT for 6 h and then cooled to 0° C. A solution of NaBH₄ (594 mg; 15.7 mmol) in MeOH (10 mL) was added portionwise at 0° C. to the solution of crude imine over ~15 min. The solution was stirred at 0° C. for 3 h, then at RT for 3 h, then concentrated in vacuo without heating to removed MeOH. The residue was partitioned between saturated aqueous NaCl and EtOAc (50 mL each). The aqueous layer was extracted with EtOAc (2×50 mL). The combined organic extracts were dried (Na₂SO₄) and concentrated in vacuo to give a yellow oil, which was chromatographed on SiO₂ (stepwise gradient; hex:EtOAc from 4:1 to 2:3) to give Part B compound as a pale viscous yellow oil (4.82 g; 88%).

C.

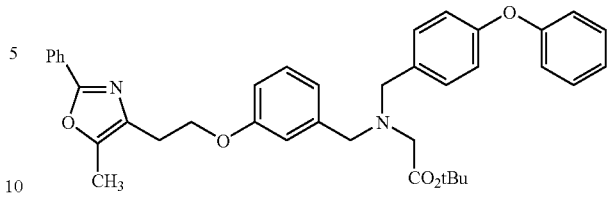

To a solution of Part B compound (0.400 g; 0.95 mmol) and 4-phenoxybenzaldehyde (0.216 g; 1.09 mmol) in DCE (5 mL) was added NaBH(OAc)₃ (0.300 g; 1.42 mmol), followed by HOAc (25 μL). The reaction was stirred at RT for 24 h. 10% unreacted starting amine was still present by analytical HPLC. Additional aldehyde (30 mg) and NaBH(OAc)₃ (60 mg) were added and the reacton was stirred at RT for a further 18 h, after which reaction was complete. The solution was partitioned between aqueous NaHCO₃ (50 mL of a 10% solution) and EtOAc (50 mL). The aqueous layer was extracted with EtOAc (2×25 mL). The combined organic extracts were washed with aqueous NaHCO₃ (2×15 mL of a 10% solution), dried (Na₂SO₄) and concentrated in vacuo to give Part C compound (521 mg crude material) as a clear, colorless oil.

D.

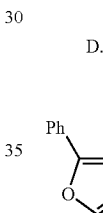

Part C compound was dissolved in CHCl₃ (2 mL) and TFA (1.5 mL) and the solution was stirred at RT for 24 h. The solution was concentrated in vacuo and the residue was purified by preparative HPLC (YMC S5 ODS 20×250 mm column; continuous gradient from 40:60 solvent A:B to 100% solvent B; where solvent A=90:10:0.1 H₂O:MeOH:TFA; solvent B=90:10:0.1 MeOH:H₂O:TFA). The purified product was lyophilized from MeOH/H₂O to give the title amino acid (312 mg; 48% over 2 steps) as its TFA salt (off-white lyophilate). [M+H]⁺ (electrospray)= 549.3

EXAMPLE 8

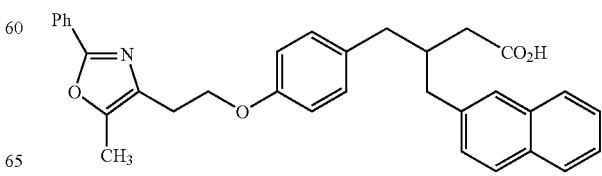

A mixture of the amino-ester (39 mg; 0.092 mmol),

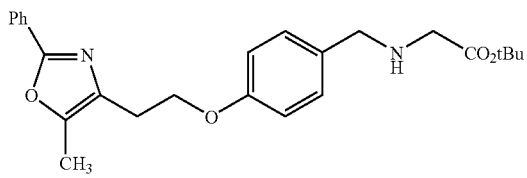

(prepared as described in Example 4), 2-naphthaldehyde (29 mg; 0.185 mmol), and NaBH(OAc)$_3$ (100 mg; 0.472 mmol) in DCE (1.5 mL) was stirred at RT for 16 h. TFA (1.0 mL) was then added to the mixture, which was stirred at RT for a further 12 h. Volatiles were removed in vacuo. The resulting residue was diluted with MeOH (1.5 mL), filtered, and purified by preparative HPLC (YMC S5 ODS 30 mm×250 mm column; continuous 30 min gradient @ 25 mL/min from 100% A to 100% B; solvent A=90:10:0.1 H$_2$O:MeOH:TFA; B=90:10:0.1 MeOH:H$_2$O:TFA) to give the desired title product (39 mg; 68%) as a clear, viscous oil. [M+H]$^+$=507.3

EXAMPLE 9

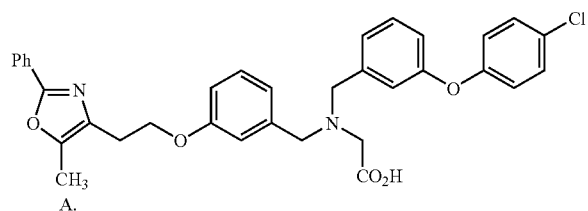

A.

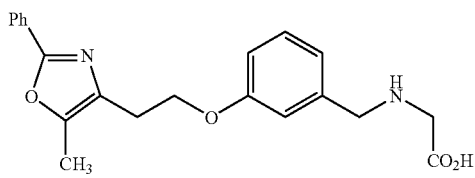

A solution of the amino acid tert-butyl ester (1.8 g, 4.27 mmol)

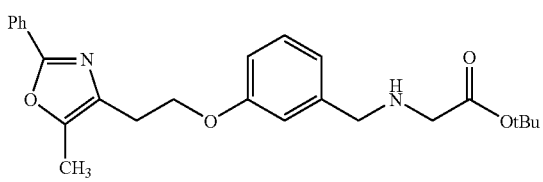

(prepared as described in Example 7 Part B), and TFA (20 mL) in CH$_2$Cl$_2$ (40 mL) was stirred at RT overnight. The solution was concentrated in vacuo, and the residue was dissolved in CH$_2$Cl$_2$ and eluted through solid NaHCO$_3$ (to remove excess TFA) with excess CH$_2$Cl$_2$. The combined filtrates were concentrated in vacuo to provide the desired amino acid Part A compound (1.48 g; 95%). [M+H]$^+$=457.2

B.

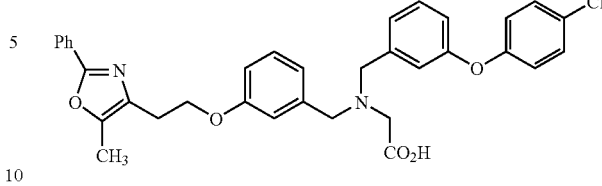

The title compound was prepared as part of a solution phase library run using the following exemplary procedure:

To a solution of the Part A amino acid compound (27 mg, 0.074 mmol; in 2 mL CH$_2$Cl$_2$) was added (4-chlorophenoxy)-3-benzaldehyde (86 mg; 0.37 mmol), NaBH(OAc)$_3$ (79 mg, 0.37 mmol) and HOAc (0.1 mL). The reaction was stirred at RT for 15 h. The product was purified via solid-phase extraction using a Varian SAX cartridge (3 g of sorbent in a 6 mL column, 0.3 meq/g) by the procedure outlined below:
1) The column was conditioned with MeOH (10 mL) and CH$_2$Cl$_2$ (20 mL)
2) The reaction mixture was loaded onto the SAX column
3) The column was rinsed with CH$_2$Cl$_2$ (10 mL)
4) The column was rinsed with 1% TFA in MeOH (3 mL)
5) The product was eluted with 1% TFA in MeOH (20 mL)

The product solution (combined fractions from step 5) was concentrated using a Speed Vac for 16 h to afford the crude product (25 mg; 49%) as a solid. Reverse-phase HPLC analysis (YMC S5 ODS 4.6×33 mm column, continuous gradient from 100% A to 100% B for 2 min at a flow rate of 5 mL/min [Solvent A=10% MeOH/90% H$_2$O/0.2% H$_3$PO$_4$; Solvent B=90% MeOH/10% H$_2$O/0.2% H$_3$PO$_4$]) indicated that the product purity was 92%. In addition, LC/MS (electrospray) gave the correct molecular ion [(M+H)$^+$=583] for the title compound.

EXAMPLE 10
(Procedure Used with Heterocyclic Aldehydes)

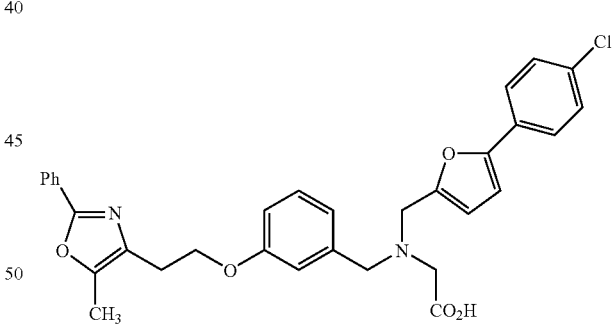

The title compound was prepared as part of a solution phase library run using the following exemplary procedure. A mixture of the amino acid (14 mg; 0.038 mmol),

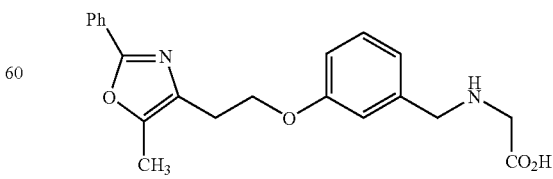

(prepared as described in Example 9 Part A), 5-(4-chlorophenyl)-2-furfural (16 mg; 0.076 mmol), and NaBH (OAc)₃ (72 mg; 0.34 mmol) in DCE (1.5 mL) was stirred at RT for 16 h. TFA (1.0 mL) was then added to the mixture, which was stirred at RT for a further 12 h. Volatiles were removed in vacuo. The resulting residue was diluted with MeOH (1.5 mL), filtered, and purified by preparative HPLC (YMC S5 ODS 30 mm×250 mm column; continuous 30 minute gradient @ 25 mL/min from 100% A to 100% B; solvent A=90:10:0.1 H₂O:MeOH:TFA; B=90:10:0.1 MeOH:H₂O:TFA) to give the desired title product (39 mg; 68%) as a clear, viscous oil.

EXAMPLE 10A

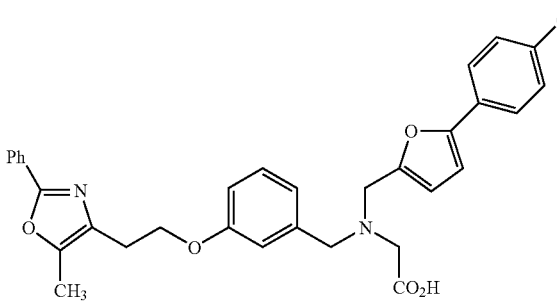

An alternative purification procedure to preparative HPLC was used as follows:

The crude reductive amination product was purified by solid-phase extraction using an SAX cartridge (United Chemicals; 3 g of sorbent in a 6 mL column, 0.3 meq/g) by the procedure outlined below:

1) The column was conditioned with MeOH (5 mL) and CH₂Cl₂ (5 mL)
2) The reaction mixture (diluted with 2 mL CH₂Cl₂) was loaded onto the SAX column
3) The column was rinsed with CH₂Cl₂ (8 mL)
4) The product was eluted with 1% TFA in MeOH (20 mL)

The product-containing fractions were concentrated in vacuo using a Speed Vac for 16 h to afford the crude product. This was dissolved in CH₂Cl₂:MeOH (95:5) and loaded onto a silica gel cartridge (1.5 g SiO₂) and the product was eluted with CH₂Cl₂:MeOH (95:5; 8 mL). The product-containing fractions were concentrated in vacuo using a Speed Vac to give the desired title product.

Reverse Phase HPLC analysis (YMC S5 ODS 4.6×33 mm column, continuous gradient from 100% A to 100% B for 2 min at a flow rate of 5 mL/min [Solvent A=10% MeOH/90% H₂O/0.2% H₃PO₄; Solvent B=90% MeOH/10% H₂O/0.2% H₃PO₄]) indicated that the product purity was 92%. In addition, LC/MS (electrospray) gave the correct molecular ion [(M+H)⁺=583] for title compound.

EXAMPLE 11

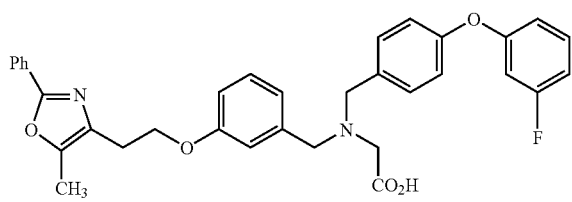

A.

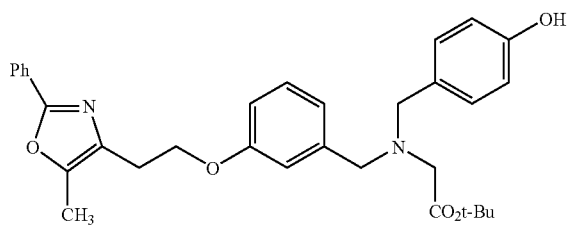

To a mixture of the amino-tert-butyl ester (0.339 g, 0.80 mmol),

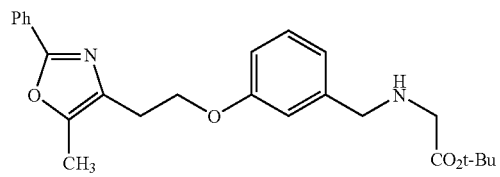

(prepared as described in Example 7, Part B), 4-hydroxybenzaldehyde (0.127 g, 1.03 mmol) and NaBH(OAc)₃ (0.510 g, 2.4 mmol) was added 7 drops of HOAc. The reaction was stirred at RT for 16 h. The mixture was diluted with EtOAc, then washed with aqueous NaHCO₃. The organic phase was dried (MgSO₄) and concentrated in vacuo. The crude product was chromatographed (SiO₂; hexanes/EtOAc 3:1 to 1:4) to provide the 4-hydroxybenzyl amino ester title compound compound (0.381 g, 90%).

B.

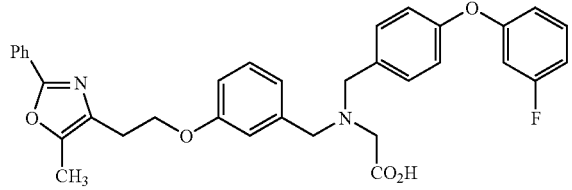

The title compound was prepared as part of a solution phase library run using the following exemplary procedure.

To a solution of Part A phenol compound (30 mg, 0.057 mmol) in CH₂Cl₂ (1 mL) was added 3-fluorophenyl boronic acid (12 mg; 0.086 mmol) and 4A molecular sieves (pre-dried at 400° C. overnight) at RT. After stirring for 5 min, Cu(OAc)₂ (1 eq), Et₃N (5 eq) and pyridine (5 eq) were added to the mixture. The vial was capped and air was allowed to pass into the reaction. The reaction was stirred at RT for 60 h and was complete by analytical HPLC and LC/MS. (For other reactions which were incomplete after this time, additional boronic acid (1.5 equivalent) was added in order to form additional desired product). The reaction mixture was filtered and concentrated in vacuo.

The product was purified via solid-phase extraction using a United Technology SCX column (2 g of sorbent in a 6 mL column) by the procedure outlined below.

1) The column was conditioned with MeOH (10 mL) and CH₂Cl₂ (10 mL)
2) The residue was dissolved in a minimal volume of CH₂Cl₂ and loaded onto the SCX column.
3) The cartridge was successively washed with CH₂Cl₂ (20 mL), CH₂Cl₂/MeOH (20% MeOH, 20 mL) and MeOH (20 mL)

4) The product was eluted with a solution of 0.5N $NH_3$ in MeOH.

The product-containing fractions were concentrated in vacuo to give the desired tert-butyl ester. (Some incomplete reactions required chromatography (on $SiO_2$) of the crude material to give esters of the requisite purity). The t-butyl ester was treated with a solution of 30% TFA in $CH_2Cl_2$ overnight. Volatiles were removed and the residue was redissolved in $CH_2Cl_2$ (1 mL) and concentrated in vacuo on a Speed Vac to afford the desired title product (30 mg; 77%). Reverse phase HPLC analysis indicated that the product purity was 90%. In addition LC/MS gave the correct molecular ion [$(M+H)^+$=567] for the desired title compound.

EXAMPLE 12

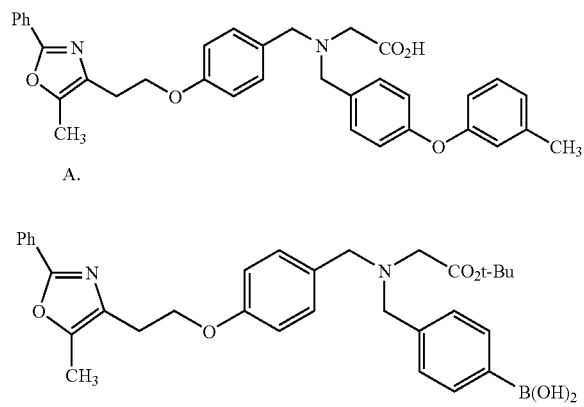

A.

To a solution of the secondary amine-tert butyl ester (110 mg; 0.26 mmol)

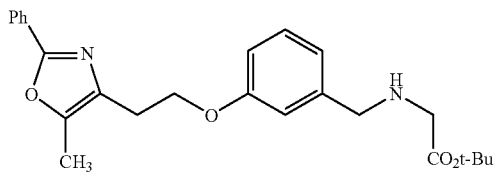

(prepared as described in Example 7, Part B), in 1,2-dichloroethane (4 mL) were successively added 4-formyl phenylboronic acid (47 mg; 0.31 mmol) and $NaBH(OAc)_3$ (165 mg; 0.78 mmol). The mixture was stirred at RT for 3 h. Analytical HPLC and LC/MS indicated that the reaction was complete at ths point. Volatiles were removed in vacuo and the residue was chromatographed ($SiO_2$; stepwise gradient from 3:1 to 1:1 hexane:EtOAc) to provide title compound (133 mg; 91%) as a white foam.

B.

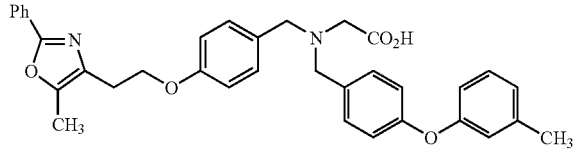

The title compound was prepared as part of a solution phase library run using the following procedure.

To a solution of the Part A boronic acid compound (40 mg, 0.072 mmol) in $CH_2Cl_2$ (1 mL) was added m-cresol (23 mg; 0.22 mmol) and 4A molecular sieves (150 mg; pre-dried at 400° C. overnight). After stirring for 5 min, $Cu(OAc)_2$ (1 eq), $Et_3N$ (5 eq) and pyridine (5 eq) were added to the mixture. The vial was capped and air was allowed to pass into the reaction, which was stirred at RT for 24 h. The reaction mixture was filtered through a pad of Celite and concentrated in vacuo.

The product was purified via solid-phase extraction using a United Technology SCX column (2 g of sorbent in a 6 mL column) by the procedure outlined below.

1) The column was conditioned with MeOH (10 mL) and $CH_2Cl_2$ (10 mL)
2) The residue was dissolved in a minimal volume of $CH_2Cl_2$ and loaded onto the SCX column.
3) The cartridge was successively washed with $CH_2Cl_2$ (20 mL) and MeOH (20 mL).
4) The product was eluted with a solution of 0.5N $NH_3$ in MeOH.
5) The product-containing fractions were concentrated in vacuo
6) The residue was dissolved in a minimum amount of $CH_2Cl_2$ and loaded onto a silica gel cartridge (2 mL)
7) The cartridge was eluted with hexane:EtOAc (3:1; 20 mL)
8) The product-containing fractions were collected and concentrated in vacuo to give the purified tert-butyl ester The t-butyl ester was treated with a solution of 1:1 TFA in $CH_2Cl_2$ overnight. Volatiles were removed and the residue was redissolved in $CH_2Cl_2$ (1 mL) and concentrated in vacuo on a Speed Vac to afford the desired title product (25 mg; 48%) as a slightly yellowish oil. Reverse phase HPLC analysis indicated that the product purity was 91%. In addition LC/MS gave the correct molecular ion [$(M+H)^+$= 563.2] for the desired compound.

EXAMPLE 13

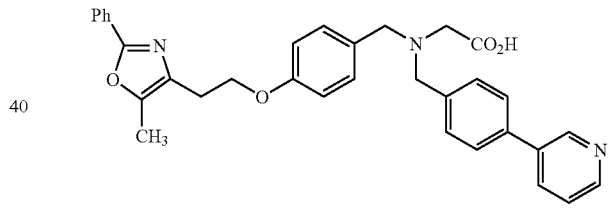

The title compound was prepared as part of a solution phase library run using the following exemplary procedure.

To a solution of 3-bromopyridine (32 mg; 0.2 mmol) in DME (1 mL) were successively added $(Ph_3P)_4Pd$ (5 mg; 0.05 mol equiv) and the Example 12 Part A boronic acid (50 mg; 0.09 mmol)

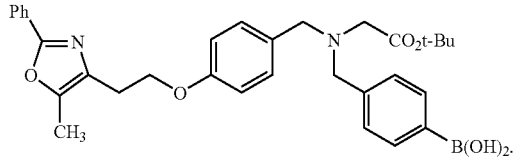

Finally, aqueous $Na_2CO_3$ (19 mg in 0.3 mL $H_2O$) was added and the mixture was heated in an oil bath at 85° C. for 5 h; LC/MS indicated that the reaction was complete at this point.

The reaction mixture was filtered and the filtrate was chromatographed on a silica gel cartridge (2 mL; EtOAc). The product-containing fractions were concentrated in vacuo and the residue was chromatographed on another silica gel cartridge (2 mL; stepwise gradient of hexanes, hex:EtOAc 3:1 and EtOAc). The product-containing fractions were concentrated in vacuo and the residue was eluted through an SCX (2 g) cartridge (20 mL each of CH$_2$Cl$_2$ and MeOH; then product eluted with 2M ammonia in MeOH). The product-containing fractions were concentrated in vacuo to give the desired biaryl amine tert-butyl ester product. This was treated with a solution of CH$_2$Cl$_2$/TFA (7:3; 1 mL) overnight for 14 h. Volatiles were removed to give title compound (39 mg; 67%) as an oil. [M+H]$^+$=534.3

EXAMPLES 14 TO 124

Following one of the above procedures, the following compounds of the invention were prepared:

TABLE 1

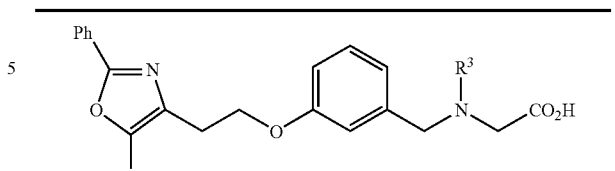

| Example No. | R$^3$ | [M + H]$^+$ |
|---|---|---|
| 14 | 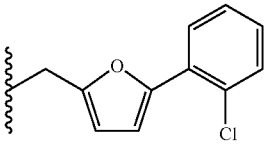 | 457.3 |
| 15 | 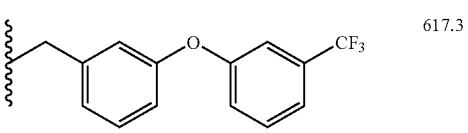 | 471.3 |
| 16 | 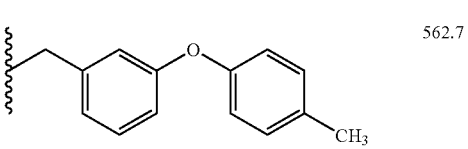 | 485.3 |
| 17 | 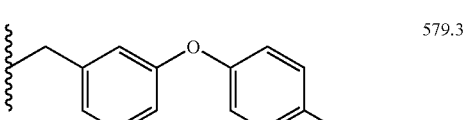 | 617.2 |
| 18 | 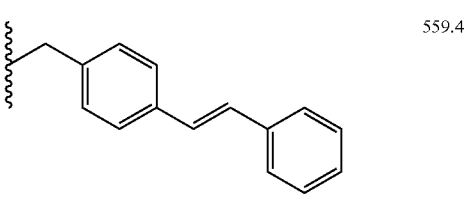 | 549.3 |
| 19 | 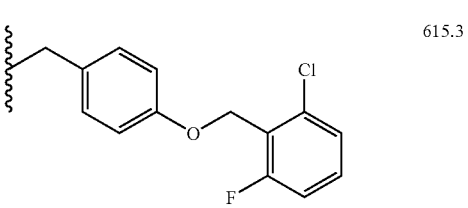 | 533.3 |

TABLE 1-continued

| Example No. | R$^3$ | [M + H]$^+$ |
|---|---|---|
| 20 | 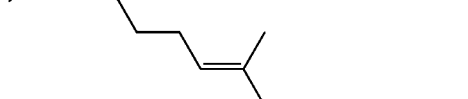 | 557.3 |
| 21 | 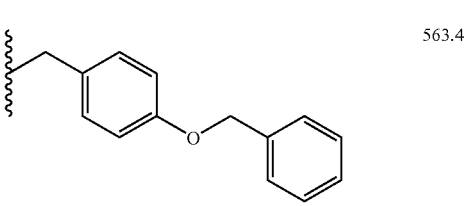 | 617.3 |
| 22 | | 562.7 |
| 23 | | 579.3 |
| 24 | | 559.4 |
| 25 | | 615.3 |
| 26 | | 503.4 |
| 27 | | 563.4 |

TABLE 1-continued

| Example No. | R³ | [M + H]⁺ |
|---|---|---|
| 28 | 4-(4-tert-butylthiazol-2-yl)benzyl | 596.3 |
| 29 | 3-phenoxythien-2-ylmethyl | 555.3 |
| 30 | 4-(furan-2-yl)but-3-enyl | 473.4 |
| 31 | 4-fluorobenzyl | 475.4 |
| 32 | 2-(4-chlorophenylthio)benzyl | 599.3 |
| 33 | 3-(3,5-dimethoxyphenoxy)benzyl | 517.4 |
| 34 | naphth-1-ylmethyl | 507.1 |
| 35 | naphth-2-ylmethyl | 507.1 |
| 36 | 1H-indol-2-ylmethyl | 496.1 |
| 37 | 2,6-dichloro-3-benzoylbenzyl | 557.1 |
| 38 | 5-(2-trifluoromethylphenyl)furan-2-ylmethyl | 591.2 |
| 39 | 5-(3-nitrophenyl)furan-2-ylmethyl | 568.2 |
| 40 | 5-(2-chloro-5-trifluoromethylphenyl)furan-2-ylmethyl | 625.2 |
| 41 | 5-(3-trifluoromethylphenyl)furan-2-ylmethyl | 591.2 |

TABLE 1-continued

| Example No. | R³ | [M + H]⁺ |
|---|---|---|
| 42 | 2-nitrophenyl-furan | 568.2 |
| 43 | benzyl 4-ethyl-3-methyl-1H-pyrrole-2-carboxylate | 622.3 |
| 44 | 5-(4-bromophenyl)furan | 601.2 |
| 45 | 5-(3-chlorophenyl)furan | 557.2 |
| 46 | 5-(1,3-dioxolan-2-yl)furan | 519.2 |
| 47 | 1-(3-chloro-5-(trifluoromethyl)pyridin-2-yl)indole | 675.2 |
| 48 | 5-(2,4-dichlorophenyl)furan | 519.2 |

TABLE 1-continued

| Example No. | R³ | [M + H]⁺ |
|---|---|---|
| 4 | (2,6-difluorophenyl)(1-methyl-1H-pyrrol-3-yl)methanone | 600.3 |
| 50 | (1-methyl-1H-pyrrol-3-yl)(phenyl)methanone | 564.2 |
| 51 | 2,2'-bithiophene | 545.3 |
| 52 | 5-bromo-3,4-dimethylthieno[2,3-b]thiophene | 625.2 |
| 53 | 5-(phenylethynyl)thiophene | 563.3 |
| 54 | (2,4-dichlorophenyl)(1-methyl-1H-pyrrol-3-yl)methanone | 632.3 |
| 55 | 1-(4-chlorophenyl)pyrrole | 556.3 |

TABLE 1-continued
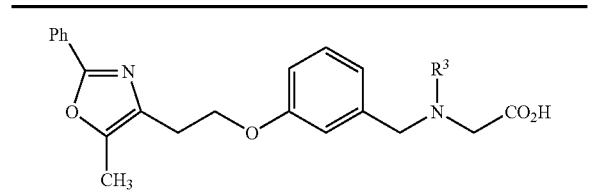
| Example No. | R³ | [M + H]⁺ |
|---|---|---|
| 56 | 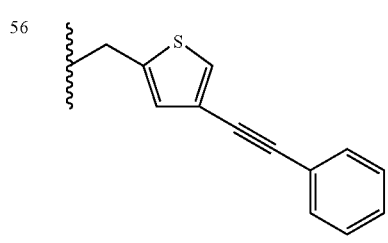 | 563.3 |
| 57 | 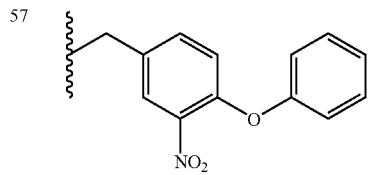 | 593.2 |
| 58 | 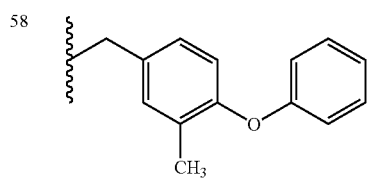 | 562.2 |
| 59 | 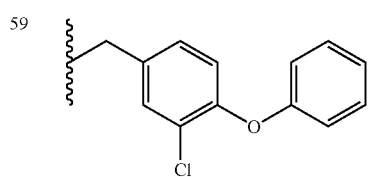 | 582.2 |
| 60 | 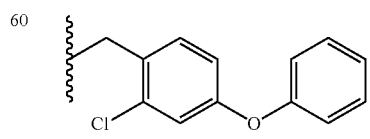 | 582.2 |
| 61 | 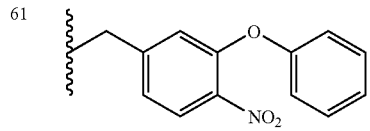 | 593.2 |
| 62 | 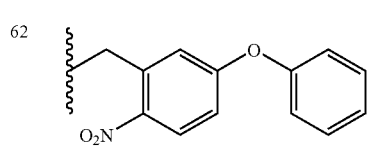 | 593.2 |
TABLE 1-continued
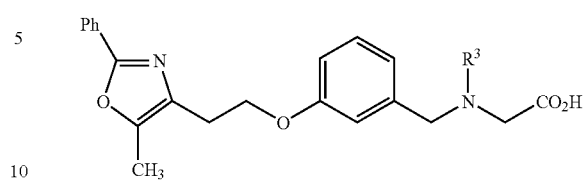
| Example No. | R³ | [M + H]⁺ |
|---|---|---|
| 63 | 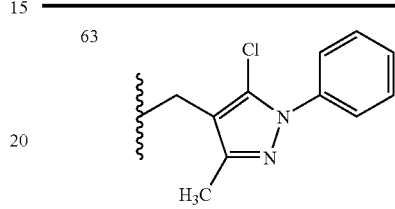 | 571.2 |
| 64 | 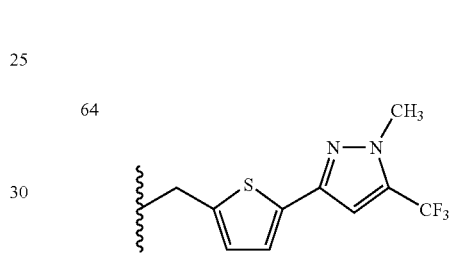 | 611.2 |
| 65 | 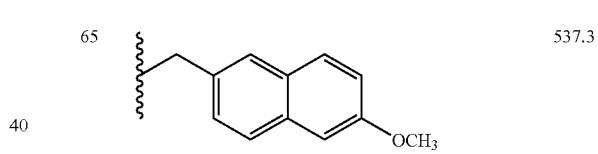 | 537.3 |
| 66 | 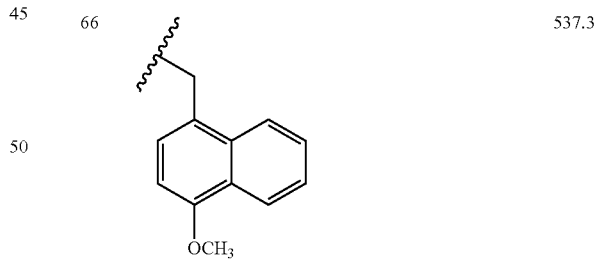 | 537.3 |
| 67 | 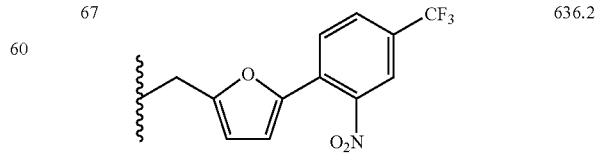 | 636.2 |

TABLE 2

| Example No. | R³ | [M + H]⁺ |
|---|---|---|
| 68 | 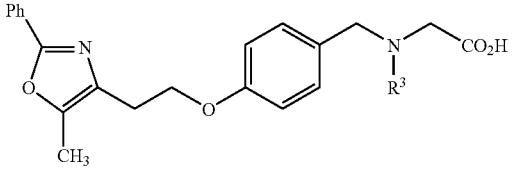 4-(pyridin-2-yl)benzyl | 534.2 |
| 69 | 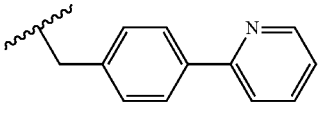 2-benzylbenzyl | 547.2 |
| 70 | 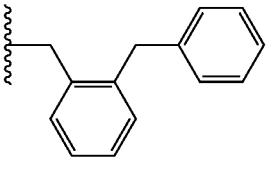 n-octyl | 465.4 |
| 71 | 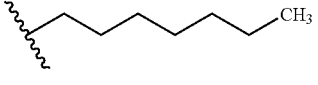 biphenyl-4-ylmethyl | 533.3 |
| 72 | 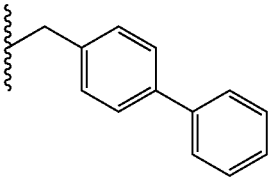 2-hydroxybenzyl | 473.3 |
| 73 | 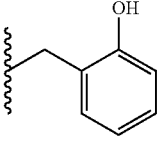 naphthalen-1-ylmethyl | 507.3 |
| 74 | 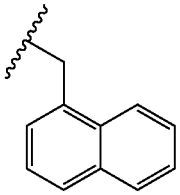 5-(2-chlorophenyl)furan-2-ylmethyl | 587.4 |
| 75 | 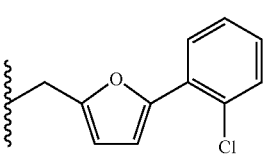 3,5-dimethoxybenzyl | 517.3 |

TABLE 2-continued

| Example No. | R³ | [M + H]⁺ |
|---|---|---|
| 76 | 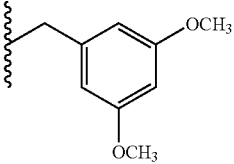 3-phenoxybenzyl | 549.3 |
| 77 | 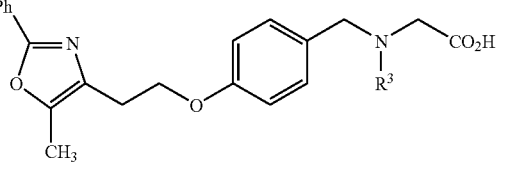 4-phenoxybenzyl | 549.3 |
| 78 | 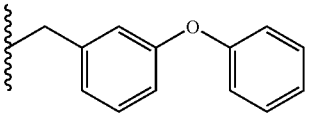 3-(4-chlorophenoxy)benzyl | 583.2 |
| 79 | 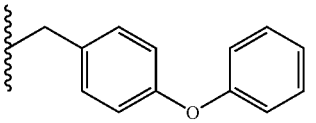 3-(3,5-dichlorophenoxy)benzyl | 617.2 |
| 80 | 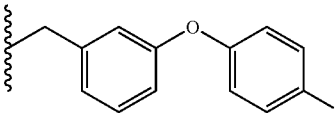 3-(4-methylphenoxy)benzyl | 563.2 |
| 81 | 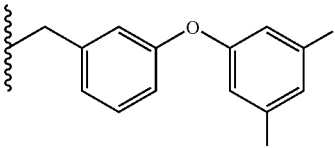 4-styrylbenzyl | 559.2 |
| 82 | 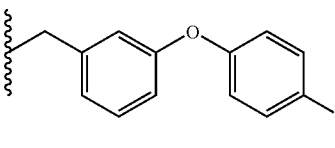 4-(2-chloro-6-fluorobenzyloxy)benzyl | 615.2 |
| 83 | 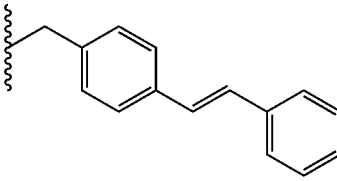 2,6-dichloro-3-benzoylbenzyl | 629.1 |

TABLE 2-continued

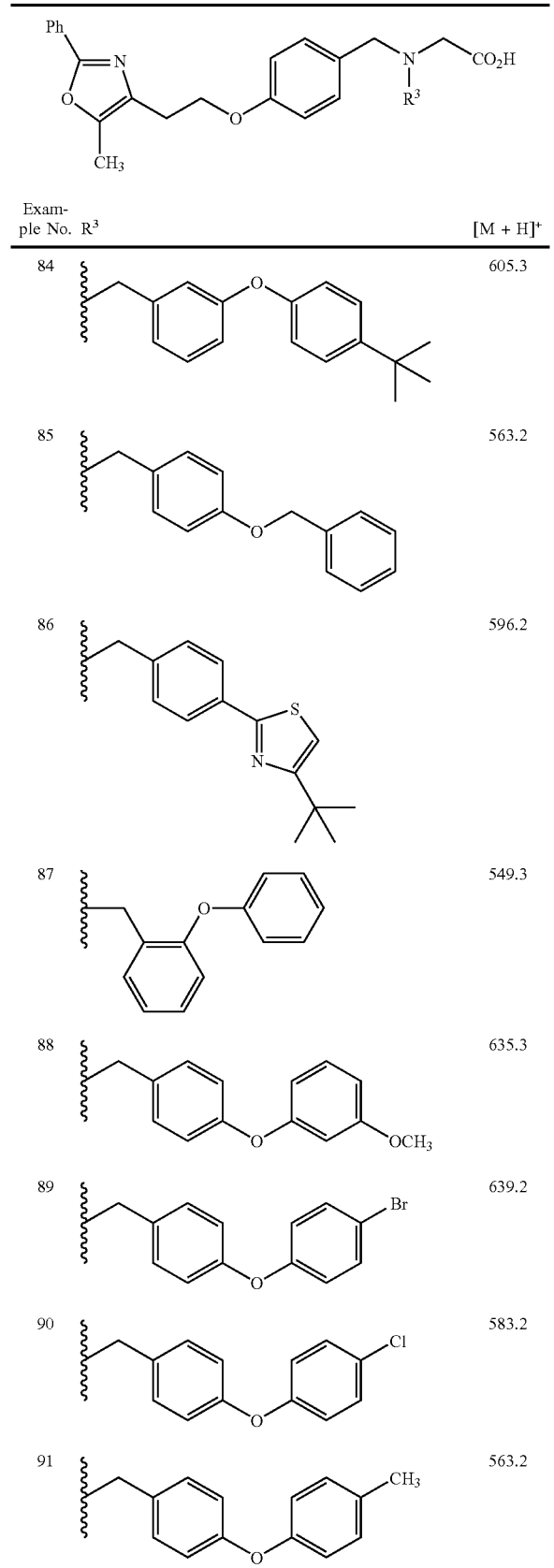
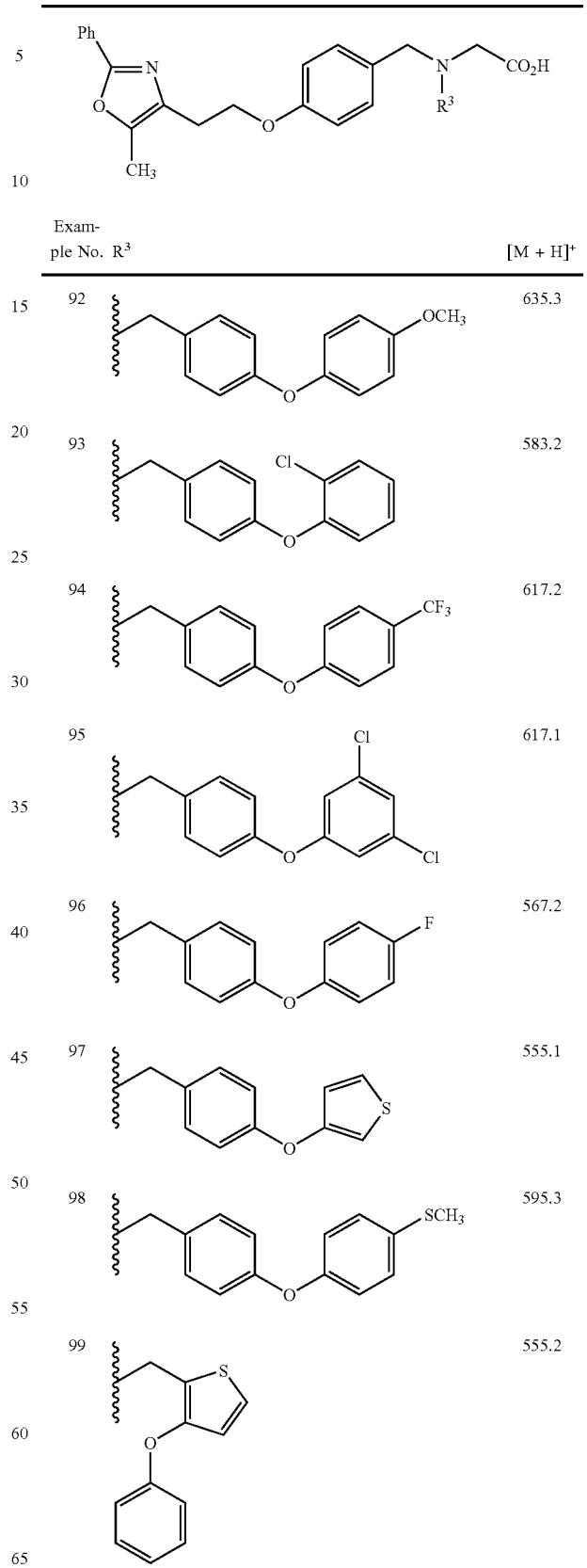

| Example No. | R³ | [M + H]⁺ |
|---|---|---|
| 84 | 3-(4-tert-butylphenoxy)benzyl | 605.3 |
| 85 | 4-benzyloxybenzyl | 563.2 |
| 86 | 4-(4-tert-butylthiazol-2-yl)benzyl | 596.2 |
| 87 | 2-phenoxybenzyl | 549.3 |
| 88 | 4-(3-methoxyphenoxy)benzyl | 635.3 |
| 89 | 4-(4-bromophenoxy)benzyl | 639.2 |
| 90 | 4-(4-chlorophenoxy)benzyl | 583.2 |
| 91 | 4-(4-methylphenoxy)benzyl | 563.2 |
| 92 | 4-(4-methoxyphenoxy)benzyl | 635.3 |
| 93 | 4-(2-chlorophenoxy)benzyl | 583.2 |
| 94 | 4-(4-trifluoromethylphenoxy)benzyl | 617.2 |
| 95 | 4-(3,5-dichlorophenoxy)benzyl | 617.1 |
| 96 | 4-(4-fluorophenoxy)benzyl | 567.2 |
| 97 | 4-(thiophen-3-yloxy)benzyl | 555.1 |
| 98 | 4-(4-methylthiophenoxy)benzyl | 595.3 |
| 99 | 3-phenoxythiophen-2-ylmethyl | 555.2 |

TABLE 2-continued

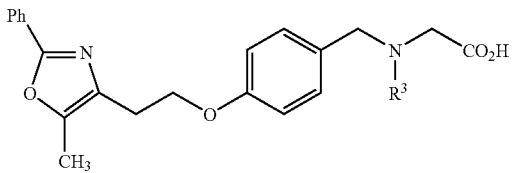

| Example No. | R³ | [M + H]⁺ |
|---|---|---|
| 100 | 4-(3-trifluoromethylphenoxy)benzyl | 617.2 |
| 101 | 4-(3-nitrophenoxy)benzyl | 594.2 |
| 102 | 4-(phenylamino)benzyl | 548.2 |
| 103 | 4-(imidazol-1-yl)benzyl | 523.3 |
| 104 | 4-(pyridin-4-yl)benzyl | 534.4 |
| 105 | 4'-carbamoylbiphenyl-4-ylmethyl | 576.2 |
| 106 | 3',5'-dichlorobiphenyl-4-ylmethyl | 601.1 |
| 107 | 3'-methoxybiphenyl-4-ylmethyl | 563.2 |

TABLE 2-continued

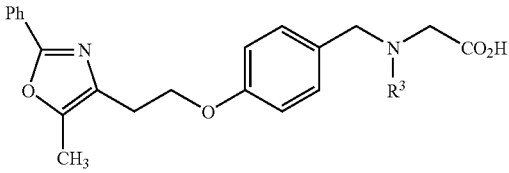

| Example No. | R³ | [M + H]⁺ |
|---|---|---|
| 108 | 3',4'-difluorobiphenyl-4-ylmethyl | 609.2 |
| 109 | 3'-fluorobiphenyl-4-ylmethyl | 551.2 |
| 110 | 4-(furan-3-yl)benzyl | 523.2 |
| 111 | 4-(thiophen-2-yl)benzyl | 539.2 |
| 112 | 3-methoxy-4-phenoxybenzyl | 579.3 |
| 113 | 3-nitro-4-phenoxybenzyl | 594.4 |
| 114 | 3-methyl-4-phenoxybenzyl | 563.3 |
| 115 | 3-chloro-4-phenoxybenzyl | 583.2 |

TABLE 2-continued

[Structure: Ph-oxazole(CH3)-CH2CH2-O-C6H4-CH2-N(R3)-CH2-CO2H]

| Example No. | R3 | [M + H]+ |
|---|---|---|
| 116 | [4-phenoxy-2-methoxybenzyl] | 579.3 |
| 117 | [4-phenoxy-2-chlorobenzyl] | 583.2 |
| 118 | [3-phenoxy-2-nitrobenzyl] | 594.3 |
| 119 | [3-phenoxy-2-nitrobenzyl isomer] | 594.3 |
| 120 | [6-methoxynaphthalen-2-ylmethyl] | 537.3 |
| 121 | [4-methoxynaphthalen-1-ylmethyl] | 537.3 |
| 122 | [4-(pyrimidin-2-yl)benzyl] | 535.2 |
| 123 | [4-(pyrimidin-5-yl)benzyl] | 535.2 |
| 124 | [indol-2-ylmethyl-CH2] | 496.1 |

EXAMPLE 125

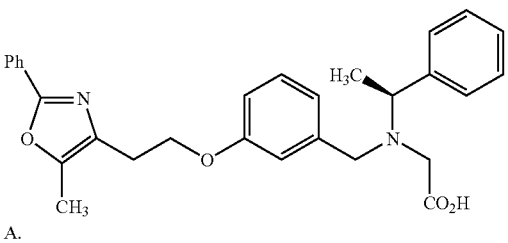

A.

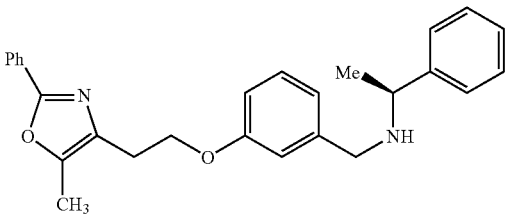

A solution of Example 7 Part A aldehyde (60 mg; 0.20 mmol) and (S)-α-methyl benzylamine (30 mg; 0.24 mmol) in MeOH (1 mL) was stirred at RT for 6 h. The solution was cooled to 0° C. and a pre-formed solution of NaBH$_4$ (9 mg; 0.24 mmol) in MeOH (0.5 mL) was added portionwise. The reaction was stirred at RT overnight, then concentrated in vacuo without heating. The residue was partitioned between aqueous NaHCO$_3$ and EtOAc (5 mL each). The aqueous layer was extracted with EtOAc (2×5 mL). The combined organic extracts were dried (Na$_2$SO$_4$) and concentrated in vacuo to give title compound as an orange yellow-oil (81 mg crude).

B

[Structure B shown]

A solution of the Part A compound (70 mg; 0.17 mmol), tert-butyl bromoacetate (66 mg; 0.34 mmol), and iPr$_2$NEt in DMF (0.5 mL) was stirred at RT for 2 days. LC/MS showed that the reaction was complete and clean. The crude reaction mixture was partitioned between H$_2$O (30 mL) and EtOAc (20 mL). The aqueous layer was extracted with Et$_2$O (2×10 mL); the combined organic extracts were dried (MgSO$_4$) and concentrated in vacuo to give the crude amino-tert-butyl ester.

This crude product was stirred in a 1:1 solution of CHCl$_3$ and TFA (2 mL) for 18 h at RT. The solution was then concentrated in vacuo and purified by preparative reverse-phase HPLC (as in Example 10). The purified material was lyophilized from MeOH—H$_2$O to give the title compound (71 mg; 71%) as a white lyophilate. [M+H]$^+$=471.2

EXAMPLE 126

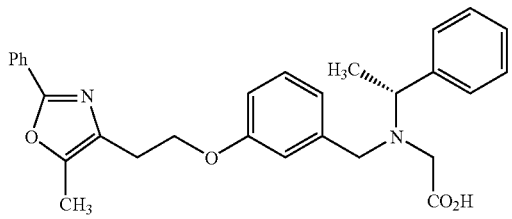

The title compound was synthesized following the same procedure as described above in Example 125 except that (S)-α-methyl benzylamine was replaced by (R)-α-methyl benzylamine in the synthesis of the part A compound. The title compound was obtained in 67% yield (66 mg) overall. $[M+H]^+=471.2$

EXAMPLE 127

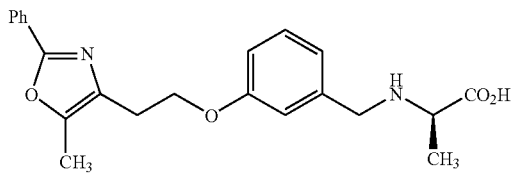

A mixture of Example 7 Part A compound (30 mg, 0.098 mmol), D-alanine tert-butyl ester hydrochloride (23 mg; 0.127 mmol), Et$_3$N (5 drops) and 4A molecular sieves in MeOH (2 mL) was stirred at RT for 4 h. NaBH$_4$ (12 mg, 0.0294 mmol) was added and the reaction was stirred at RT for 30 min. The reaction mixture was then concentrated in vacuo, diluted with CH$_2$Cl$_2$ (2 mL), and filtered through cotton. TFA (1 mL) was added to the filtrate and the reaction was stirred at RT overnight. The reaction mixture was concentrated in vacuo, diluted with EtOAc, washed several times with sat'd. aqueous NaHCO$_3$, then with brine. The organic phase was dried (MgSO$_4$) and concentrated in vacuo. The residue was purified by preparative HPLC (YMC ODS 30 mm×250 mm reverse-phase column; flow rate=25 mL/min; 30 min continuous gradient from 50:50 A:B to 100% B, where A=90:10:0.1 H$_2$O:MeOH:TFA and B=90:10:0.1 MeOH:H$_2$O:TFA) to provide the title compound (7.8 mg, 21%) as a white lyophilate.
$[M+H]^+=381.1$

EXAMPLE 128

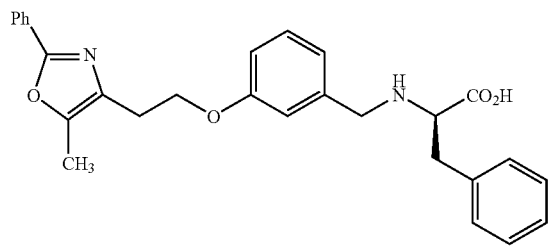

Title compound (20% overall yield) was synthesized using the same procedure as described in Example 125, using D-phenylalanine tert-butyl ester hydrochloride instead of D-alanine tert-butyl ester hydrochloride.
$[M+H]^+=457.2$

EXAMPLE 129

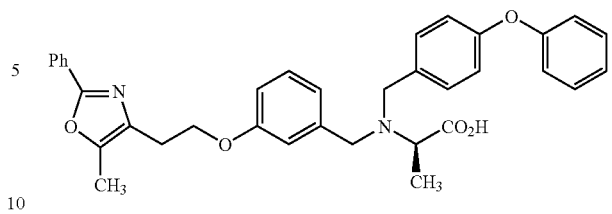

A mixture of Example 7 Part A (40 mg, 0.13 mmol), D-alanine tert-butyl ester hydrochloride (31 mg, 0.17 mmol), Et$_3$N (6 drops) and 4A molecular sieves in MeOH (2 mL) was stirred at RT for 4 h. NaBH$_4$ (15 mg, 3 equiv) was added and the mixture was stirred at RT for 30 min, then concentrated in vacuo. The residue was dissolved in CH$_2$Cl$_2$ (2 mL) and filtered. To the filtrate in a vial were added 4-phenoxybenzaldehyde (77 mg, 0.39 mmol) and NaBH(OAc)$_3$ (138 mg, 0.65 mmol). The reaction was stirred at RT for 18 h. The reaction mixture was chromatographed on SiO$_2$ using hexanes/EtOAc (9:1 to 4:1) to obtain the pure tert-butyl ester. This material was dissolved in CH$_2$Cl$_2$ (2 mL) and TFA (1 mL) was added slowly. The solution was stirred at RT overnight, then was concentrated in vacuo. The residue was redissolved in CH$_2$Cl$_2$ and filtered through solid NaHCO$_3$ to remove residual TFA. This solution was further diluted with CH$_2$Cl$_2$, washed with 1 M aq NaHSO$_4$ and brine, dried (MgSO$_4$), filtered and concentrated in vacuo to obtain the title compound (9.1 mg, 12%). $[M+H]^+=563.2$

EXAMPLE 130

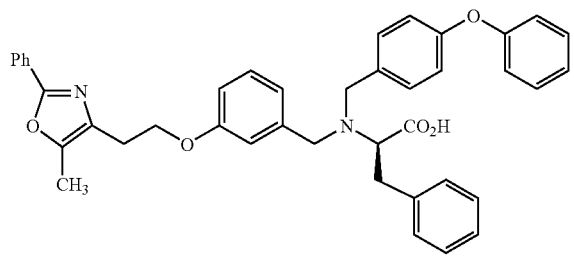

The title compound (13% overall yield) was synthesized using the same procedure as described in Example 127, using D-phenyl-alanine tert-butyl ester hydrochloride instead of D-alanine tert-butyl ester hydrochloride.
$[M+H]^+=639.2$

EXAMPLES 131 TO 135

Other analogs in this series were prepared by analogous procedures and are shown in the following table:

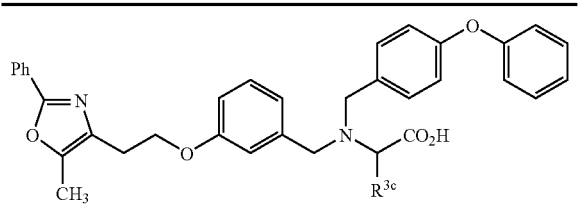

| Example No. | R³ᶜ | [M + H]⁺ |
|---|---|---|
| 131 | (S)—CH₃ | 563.2 |
| 132 | benzyl (S) | 639.3 |
| 133 | isopropyl (R) | 591.4 |
| 134 | CH₂OH (R) | 579.3 |
| 135 | OCH₂C(CH₃)₃ (R) | 635.4 |

EXAMPLE 136

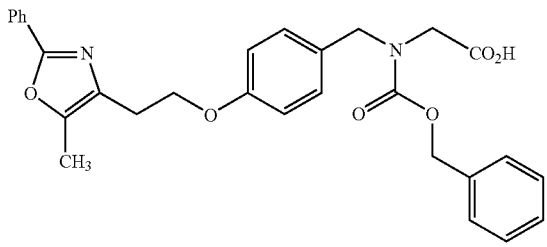

A.

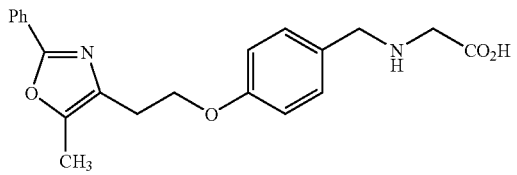

A solution of the secondary amine ethyl ester (72 mg; 0.183 mmol)

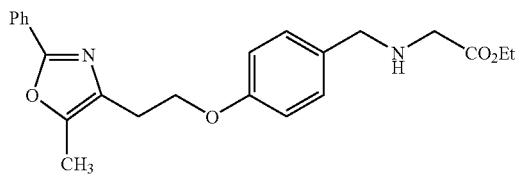

(prepared as described in Example 3 Part A) in MeOH (2 mL) and aqueous NaOH (2 mL of a 1M solution) was heated under reflux for 12 h. The pH of the solution was adjusted to 5 (with aqueous 1M NaOH and 1M HCl), upon which a colorless solid precipitated. This was filtered off and the filtrate was extracted with EtOAc (3×); the combined organic extracts were dried (Na₂SO₄) and concentrated in vacuo to give the crude title amino acid as a colorless solid (97 mg).

B

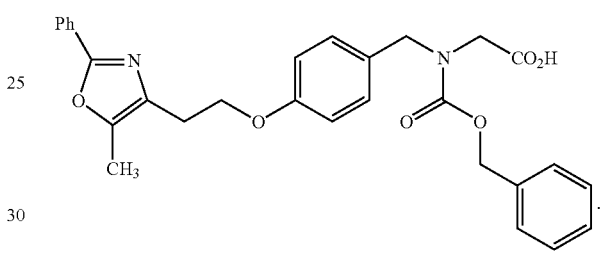

To a solution of the Part A amino acid (15 mg; 0.04 mmol) in dioxane:H₂O (1:1, 8 mL) was added K₂CO₃ (22 mg; 0.16 mmol) followed by benzyl chloroformate (15 mg; 0.09 mmol). The reaction was stirred overnight, then concentrated in vacuo and acidified with excess aqueous 1M HCl. This was extracted with EtOAc (3×); the combined organic extracts were washed with brine, dried (Na₂SO₄), and concentrated in vacuo to give title compound (13 mg; 63%) as a colorless solid. [M+H]⁺=501.3

EXAMPLE 137

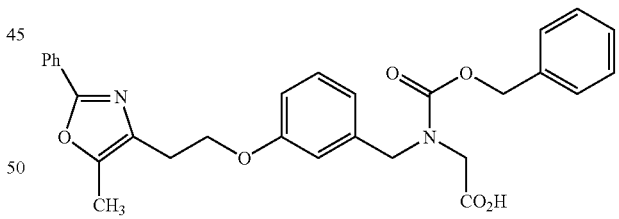

To a 0° C. solution of the amino-tert-butyl ester (75 mg; 0.18 mmol)

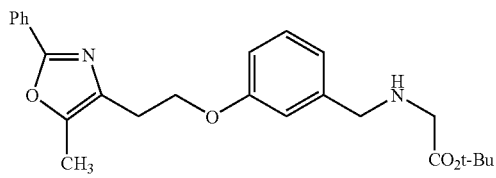

(prepared as described in Example 7 Part B), in CH₂Cl₂ (1 mL) was added CbzCl (28 µL; 0.20 mmol), followed by Et₃N (54 µL; 0.39 mmol). The reaction was allowed to warm to RT and then stirred at RT overnight for 18 h. Aqueous NaHCO₃ (2 mL of a 10% solution) was added and the aqueous layer was extracted with EtOAc (2×2 mL). The combined organic extracts were dried (Na₂SO₄) and concentrated in vacuo. The crude carbamate-ester was dissolved in CHCl₃ (3 mL) and TFA (1 mL); the solution was stirred at RT for 24 h, then concentrated in vacuo. The crude carbamate-acid was purified by reverse-phase preparative HPLC on a C-18 column (continuous gradient over 14 min; 4 min hold time; flow rate=20 mL/min from 1:1 A:B to 100% B; solvent A=90:10:0.1 H₂O:MeOH:TFA; solvent B=90:10:0.1 MeOH:H₂O:TFA). The product was lyophilized from MeOH/H₂O to give title compound as a white lyophilate. [M+H]⁺=501.3.

EXAMPLE 138

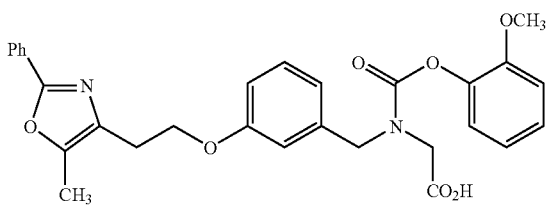

A. The required aryl chloroformates (where not commercially available) were prepared according to the following general procedure, which is exemplified by the synthesis of 2-methoxy phenyl chloroformate:

A solution of 2-methoxyphenol (2 g, 16.1 mmol), N,N-dimethylaniline (1.95 g, 16.1 mmol), phosgene (8.34 mL of a 1.93 M solution in toluene, 16.1 mmol) and a catalytic amount of DMF in chlorobenzene (5 mL) was stirred in a pressure tube for 2 h at 80° C. The organic layer was separated and concentrated in vacuo. The residue was distilled (Buchi Kugelrohr; bp=115° C. @ 10 mm Hg) to provide 2-methoxyphenyl chloroformate (1.5g; 50%) as a clear oil.

B

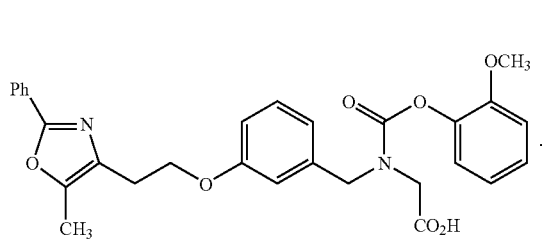

A solution of the amino-t-butyl ester (20 mg, 0.05 mmol),

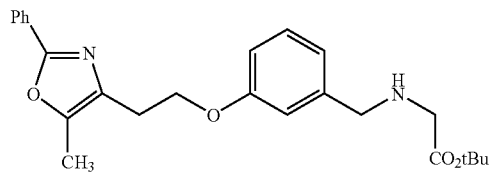

(prepared as described in Example 7 Part B), 2-methoxyphenyl chloroformate (8 mg, 0.05 mmol; prepared as above) and polyvinylpyridine (Aldrich; 16 mg, 0.3 mmol) in CH₂Cl₂ (1 mL) was stirred for 30 min at RT. Amine resin WA21J (Supelco; 200 mg) was added and the mixture was stirred at RT for 30 min in order to remove unreacted chloroformate. The reaction mixture was filtered and concentrated in vacuo to give the desired 2-methoxyphenyl carbamate-ester.

The ester was treated with a solution of 30% TFA in CH₂Cl₂ (5 mL) overnight. Volatiles were removed in vacuo to give the crude acid. This material was purified via solid-phase extraction using an anion exchange column (CHQAX13M6 column; United Technologies; 3 g of sorbent in a 6 mL column) by the exemplary procedure outlined below.

1) The column was conditioned with MeOH (10 mL) and CH₂Cl₂ (10 mL).
2) The crude acid was dissolved in a minimal volume of CH₂Cl₂ and loaded onto the SAX column.
3) The cartridge was washed with CH₂Cl₂ (10 mL), CH₂Cl₂/MeOH (10 mL of a 4:1 CH₂Cl₂:MeOH solution).
4) The product was eluted with CH₂Cl₂/MeOH (10 mL of a 4:1 CH₂Cl₂:MeOH solution).

The product-containing fractions were concentrated in vacuo on a Speed Vac to afford title compound as an oil. Analytical reverse-phase HPLC (standard conditions) indicated that the purity of the product was 90%. In addition LC/MS gave the correct molecular ion [(M+H)⁺=517.3] for the desired title compound.

EXAMPLE 139

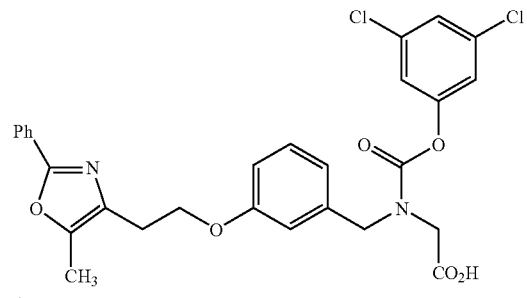

A.

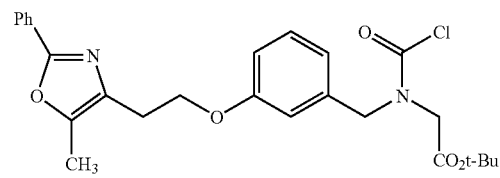

Phosgene (0.21 mL of a 1.93 M solution in toluene; 0.40 mmol) was added dropwise to a solution of the amino-tert-butyl ester (100 mg, 0.24 mmol)

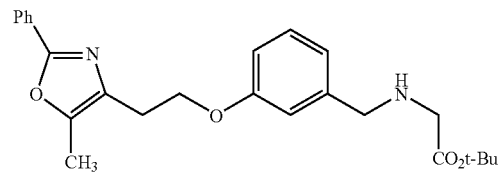

(prepared as described in Example 7 Part B), and Et₃N (30.3 mg; 0.30 mmol) in 3 ml CH₂Cl₂ at −5° C. The reaction mixture was stirred at RT for 2 h. The mixture was concentrated in vacuo to give the crude product which was chromatographed (SiO₂; hexane/EtOAc 1:5) to provide title compound (0.105 g, 91%).

B.

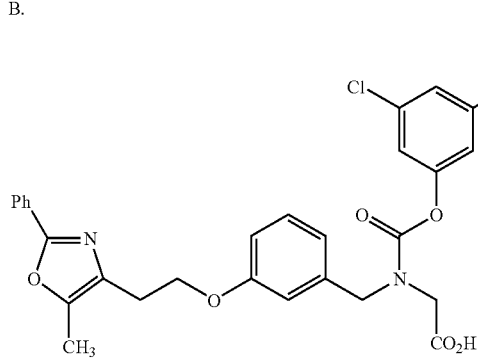

The title compound was prepared as part of a solution phase library run using the following exemplary procedure.

A mixture of the Part A carbamoyl chloride (20 mg; 0.045 mmol), 3,5-dichlorophenol (16 mg; 0.07 mmol), and pyridine (0.5 ml) was stirred at 80° C. for 16 h. Pyridine was removed in vacuo and the residue was purified via solid-phase extraction using a CHQAX1 cartridge (2 g of sorbent in a 6 ml column, 0.3 mg/g) by the procedure outlined below:

1) The column was conditioned with MeOH (10 mL) and $CH_2Cl_2$ (20 mL)
2) The reaction mixture in $CH_2Cl_2$ was loaded onto the SAX column
3) The product was eluted with $CH_2Cl_2$ (10 mL)

The product-containing fractions were concentrated in vacuo using a Speed Vac over 16 h to afford the pure aryl carbamate-tert-butyl ester which was treated with a solution of 30% TFA in $CH_2Cl_2$ overnight. Volatiles were removed using a Speed Vac for 16 h to afford the crude acid final product. The product was initially purified via solid-phase extraction using a Varian SAX cartridge (2 g of sorbent in a 6 mL column, 0.3 meq/g) by the procedure outlined below:

1) The column was conditioned with MeOH (10 mL) and $CH_2Cl_2$ (20 mL)
2) The reaction mixture in $CH_2Cl_2$ was loaded onto the SAX column
3) The column was rinsed with $CH_2Cl_2$ (10 mL)
4) The column was rinsed with 10% MeOH in $CH_2Cl_2$ (10 mL)
5) The product was eluted with 2% TFA in $CH_2Cl_2$ (10 mL)

The product-containing fractions were concentrated in vacuo using a Speed Vac for 16 h to afford the purified product (20 mg, 80%) as a solid. Reverse phase HPLC analysis (YMC S5 ODS 4.6×33 mm column, continuous gradient from 50% A to 100% B for 2 min at a flow rate of 5 mL/min [Solvent A=10% MeOH/90% $H_2O$/0.2% $H_3PO_4$; Solvent B=90% MeOH/10% $H_2O$/0.2% $H_3PO_4$]) indicated that the product purity was 96%. In addition, LC/MS gave the correct molecular ion [$(M+H)^+$=555.2] (electrospray) for the title compound.

EXAMPLE 140

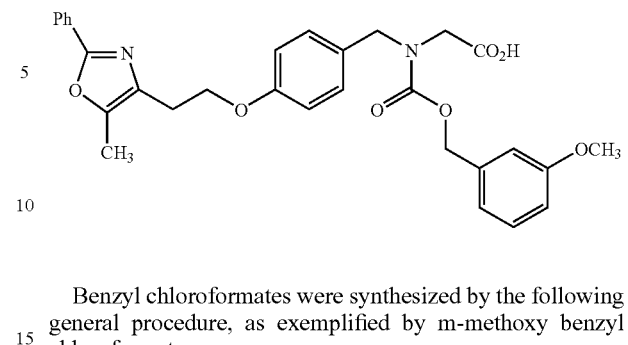

Benzyl chloroformates were synthesized by the following general procedure, as exemplified by m-methoxy benzyl chloroformate:

A.

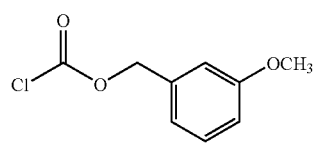

To a solution of 3-methoxybenzyl alcohol (2.0 g; 7.24 mmol), N,N-dimethylaniline (0.877 g; 7.24 mmol) in anhydrous ether (5 mL) was added phosgene dropwise (3.8 mL of a 1.93 M solution in toluene; 7.3 mmol) at 0° C. The reaction mixture was stirred at 0° C. for 2 h, after which solids were filtered off. The filtrate was concentrated in vacuo at RT. The crude chloroformate was stripped from anhydrous $Et_2O$ (2×2 mL) and used without further purification in the next reaction. Subsequently other chloroformates were also prepared using this standard procedure.

B.

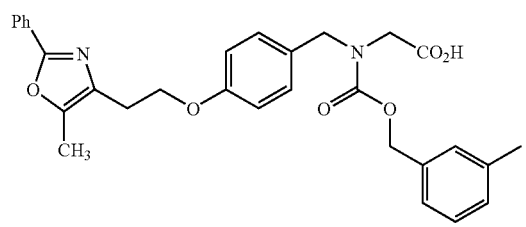

The title compound was prepared as part of a solution phase library which was run using the following standard procedure.

To a suspension of the Example 3 amino acid (trifluoroacetic acid salt)

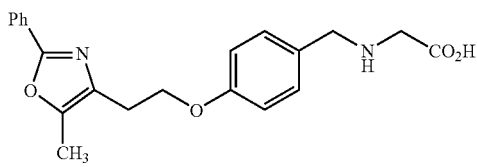

(25 mg, 0.05 mmol) in $CH_2Cl_2$ (1 mL) was added Part A compound (10 mg; 0.05 mmol) and $iPr_2NEt$ (19.4 mg; 0.15 mmol). After stirring for 30 min at RT, the reaction mixture was concentrated in vacuo.

The product was purified via solid-phase extraction using a Varian CHQAX13M6 (anion exchange) column (3 g of sorbent in a 6 mL column) by the procedure outlined below:
1) The column was conditioned with MeOH (10 mL) and CH$_2$Cl$_2$ (10 mL)
2) The residue was dissolved in a minimal volume of CH$_2$Cl$_2$ and loaded onto the SAX column.
3) The cartridge was washed successively with CH$_2$Cl$_2$ (10 mL), 20% MeOH/CH$_2$Cl$_2$ (10 mL).
4) The product was eluted with a solution of 20% MeOH/CH$_2$Cl$_2$ (10 mL).

The product-containing fractions were concentrated in vacuo using a Speed Vac to afford the title compound. Reverse Phase HPLC analysis using standard conditions indicated that the product purity was 90%. In addition, LC/MS (electrospray) gave the correct molecular ion [(M+H)$^+$=531.3] for the desired title compound.

EXAMPLE 141

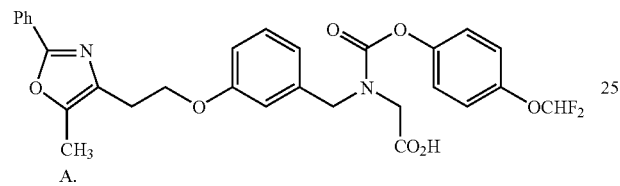

A.

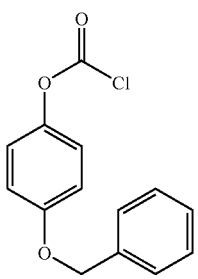

A solution of 4-(benzyloxy)phenol (2.0 g; 9.99 mmol), N,N-dimethylaniline (1.21 g; 9.99 mmol), phosgene (5.2 mL of a 1.95 M solution in toluene; 10 mmol) and a catalytic amount of DMF in chlorobenzene (5 mL) was heated at 80° C. in a pressure tube for 2.5 h. The mixture was allowed to cool to RT. The upper clear solution was separated and concentrated in vacuo to give the crude title aryl chloroformate as crystals (2 g crude product).

B.

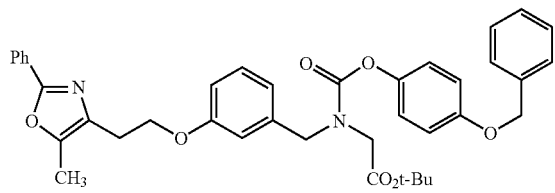

To a mixture of the Part A chloroformate (184 mg, 0.70 mmol) in CH$_2$Cl$_2$ (5 mL) and polyvinylpyridine (Aldrich; 315 mg, 1 mmol) was added a solution of the amino-tert-butyl ester (280 mg, 0.66 mmol)

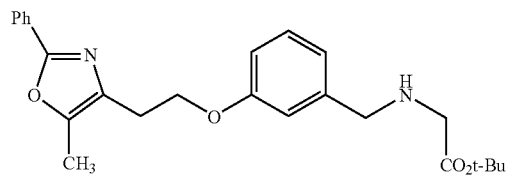

(prepared as described in Example 7 Part B), in CH$_2$Cl$_2$ (5 mL). The reaction was stirred at RT for 15 min. Resin-bound amine (WA21J, Supelco; 150 mg) was added to the mixture. The reaction mixture was stirred for another 15 min. The resin-bound amine and polyvinylpyridine were filtered off and the filtrate was concentrated in vacuo to give the crude product. The crude product was chromatographed (SiO$_2$; hexane/EtOAc 1:4) to provide title compound (0.30 g, 70%).

C.

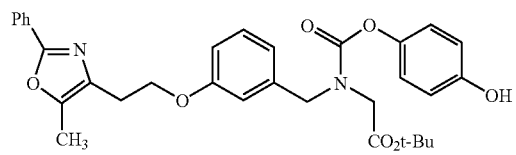

A solution of Part B compound (75 mg; 0.42 mmol) in 20 ml MeOH was hydrogenated in the presence of 20 mg of 10% Pd/C under an atmosphere of H$_2$ (balloon) for 24 h. The palladium catalyst was removed by filtration and the filtrate was concentrated in vacuo to give the crude title t-butyl ester (240 mg, 90%) which was used without further purification in the next step.

D.

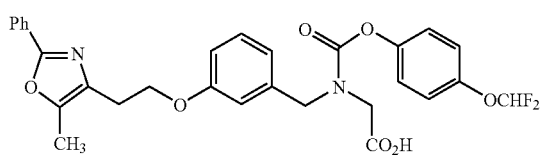

The solution of Part C phenol-tert-butyl ester (50 mg; 0.089 mmol), catalytic Bu$_4$NBr (1.5 mg, 0.0047 mmol), aq NaOH (0.7 mL of a 1 M solution) and isopropanol (2 mL) in a pressure tube was cooled to −50° C. Freon gas was bubbled into the solution for 1 min. The tube was sealed and heated to 80° C. for 12 h. The mixture was extracted with EtOAc (3×10 mL). The combined organic extracts were washed with brine, dried (Na$_2$SO$_4$) and concentrated in vacuo to give an oil, which was then treated with a solution of 30% TFA in CH$_2$Cl$_2$ overnight. Volatiles were removed in vacuo and the residue was purified using preparative HPLC (YMC S5 ODS 30×250 mm reverse phase column; 30 minute continuous gradient from 70:30 A:B to 100% B, where A=90:10:0.1 H$_2$O:MeOH:TFA, and B=90:10:0.1 MeOH:H$_2$O:TFA) to afford the desired title product (14 mg; 28%). Reverse Phase HPLC analysis indicated that the product purity was 97%. In addition LC/MS (electrospray) gave the correct molecular ion [(M+H)$^+$=553.1] for the desired compound.

EXAMPLE 142

Following the Example 141 procedure, the analogous compound was prepared [(M+H)$^+$=553.2]:

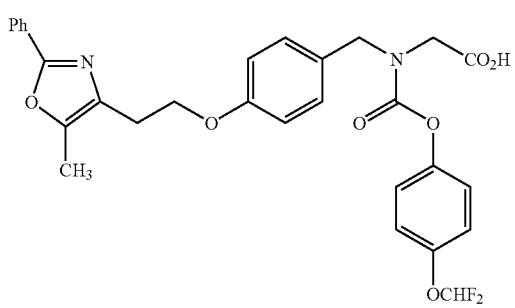

Intermediates corresponding to Example 141 Parts B and C were deprotected using the same TFA/CHCl$_3$ procedure as above and purified as usual to give the following analogs:

EXAMPLES 143

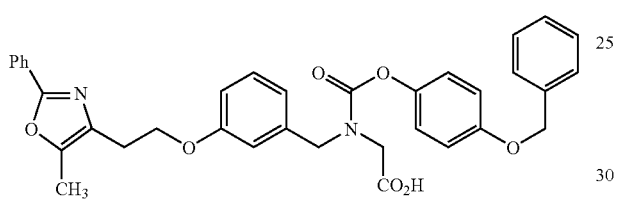

EXAMPLES 144

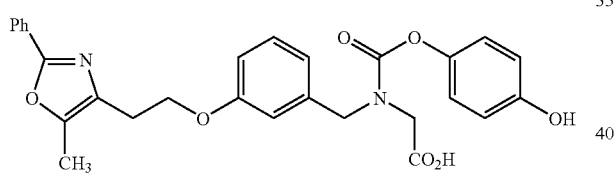

EXAMPLES 145 TO 305

The following carbamate-acid analogs in Tables 4 and 5 were synthesized according to one of the above methods:

TABLE 4

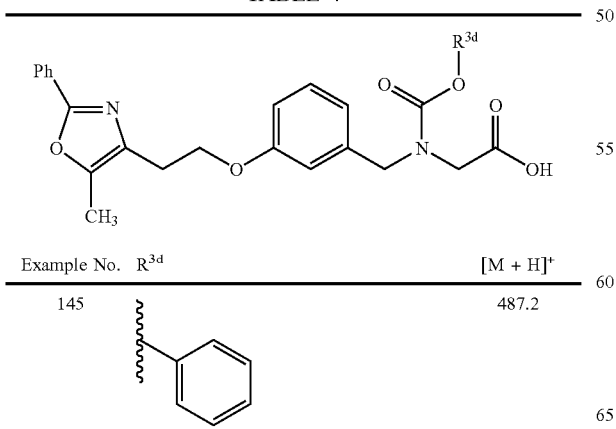

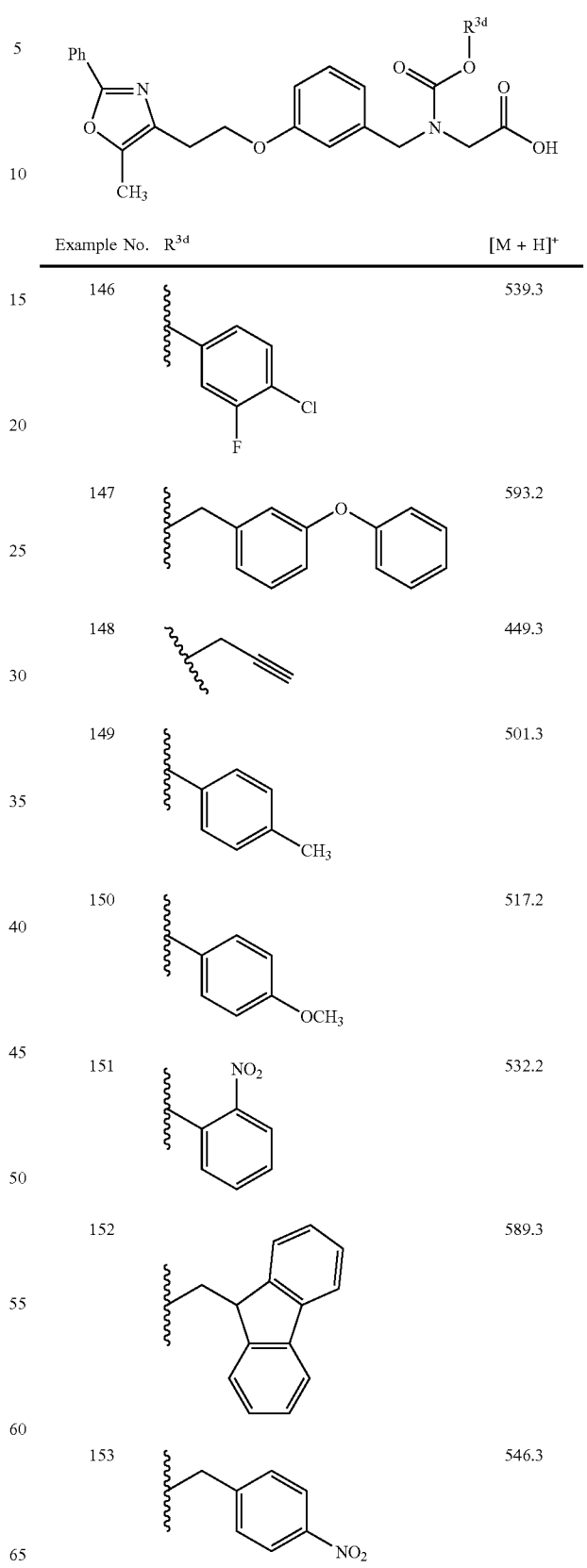

| Example No. | R$^{3d}$ | [M + H]$^+$ |
|---|---|---|
| 145 | phenyl | 487.2 |
| 146 | 4-chloro-3-fluorophenyl | 539.3 |
| 147 | 3-phenoxybenzyl | 593.2 |
| 148 | propargyl | 449.3 |
| 149 | 4-methylbenzyl | 501.3 |
| 150 | 4-methoxybenzyl | 517.2 |
| 151 | 2-nitrophenyl | 532.2 |
| 152 | 9H-fluoren-9-ylmethyl | 589.3 |
| 153 | 4-nitrobenzyl | 546.3 |

TABLE 4-continued
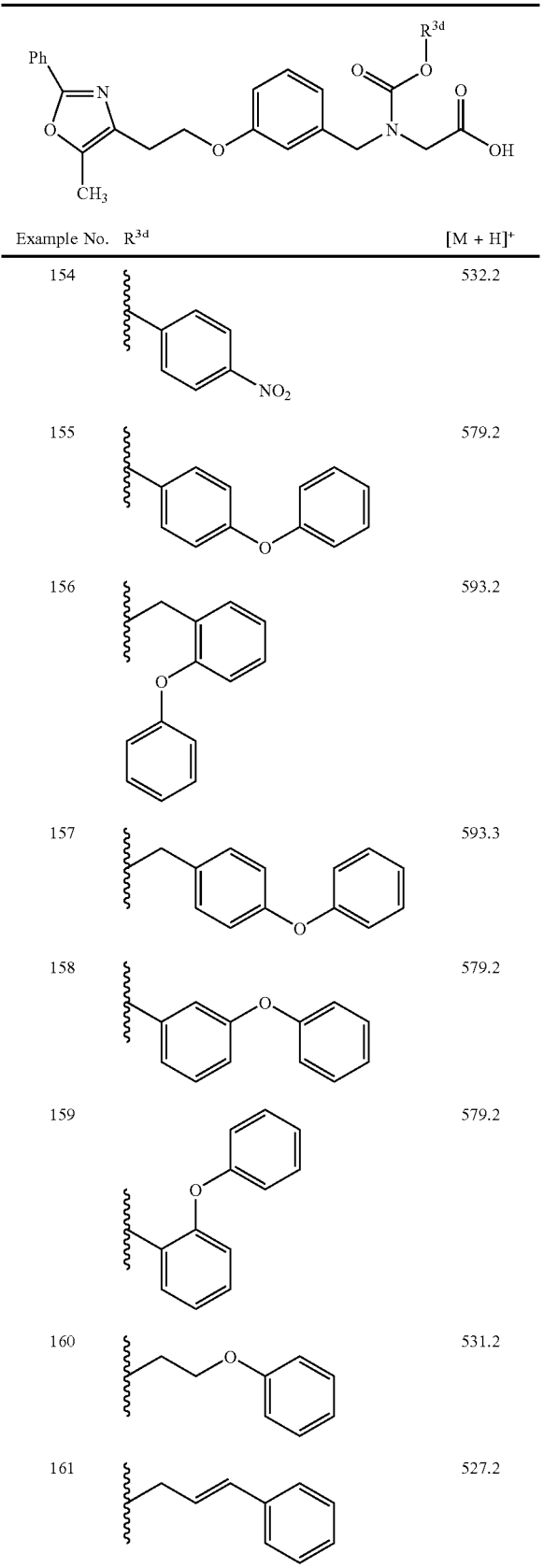
| Example No. | R3d | [M + H]+ |
|---|---|---|
| 154 | 4-NO2-C6H4- | 532.2 |
| 155 | 4-PhO-C6H4- | 579.2 |
| 156 | 2-(PhO)-C6H4-CH2- | 593.2 |
| 157 | 4-(PhO)-C6H4-CH2- | 593.3 |
| 158 | 3-PhO-C6H4- | 579.2 |
| 159 | 2-PhO-C6H4- | 579.2 |
| 160 | PhO-CH2CH2- | 531.2 |
| 161 | (E)-PhCH=CH-CH2- | 527.2 |
TABLE 4-continued
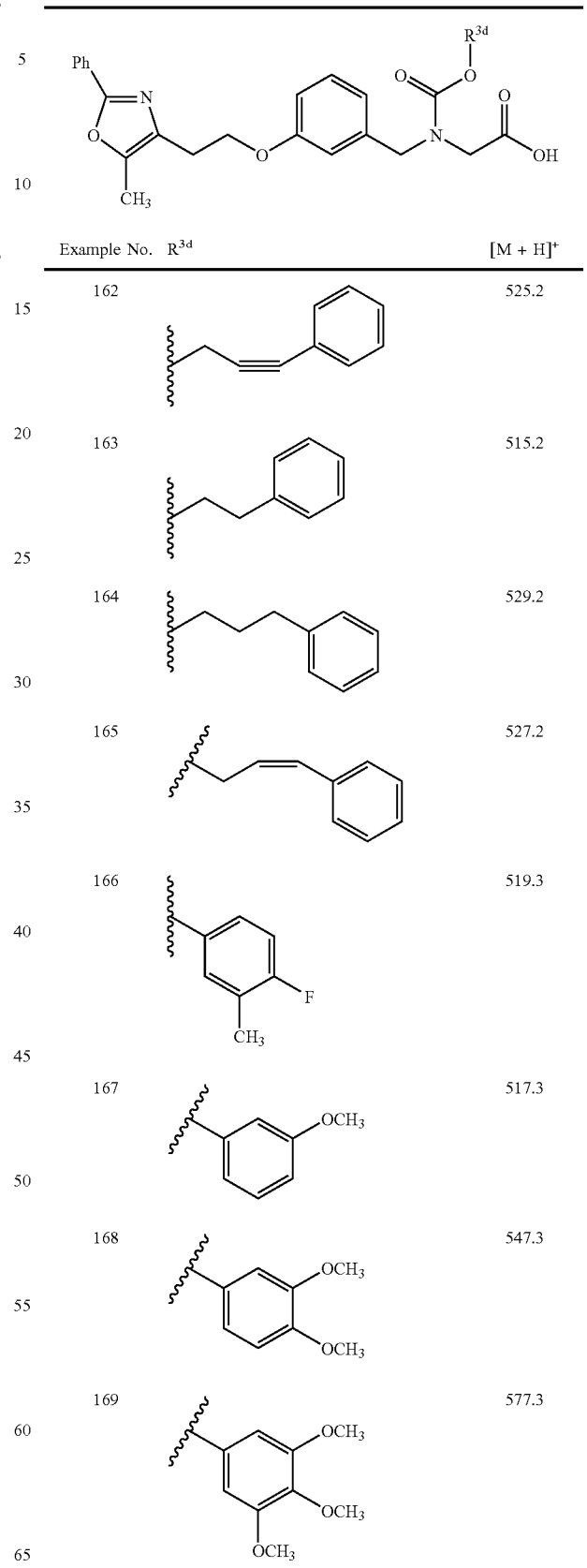
| Example No. | R3d | [M + H]+ |
|---|---|---|
| 162 | Ph-C≡C-CH2CH2- | 525.2 |
| 163 | Ph-CH2CH2- | 515.2 |
| 164 | Ph-CH2CH2CH2- | 529.2 |
| 165 | (Z)-Ph-CH=CH-CH2- | 527.2 |
| 166 | 4-F-3-CH3-C6H3- | 519.3 |
| 167 | 3-OCH3-C6H4- | 517.3 |
| 168 | 3,4-(OCH3)2-C6H3- | 547.3 |
| 169 | 3,4,5-(OCH3)3-C6H2- | 577.3 |

TABLE 4-continued
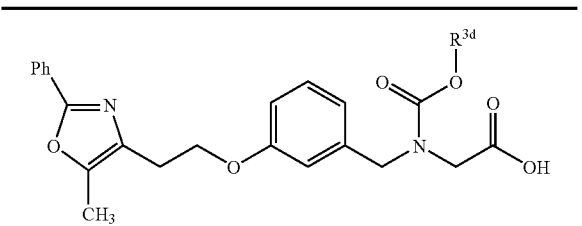
| Example No. | R³ᵈ | [M + H]⁺ |
|---|---|---|
| 170 | 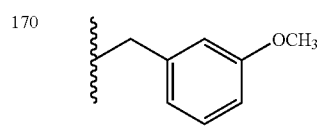 | 531.3 |
| 171 | 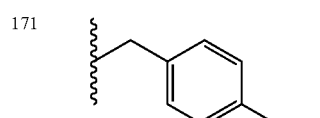 | 531.3 |
| 172 | 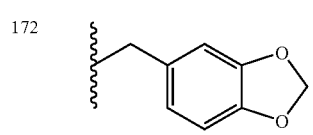 | 545.3 |
| 173 | 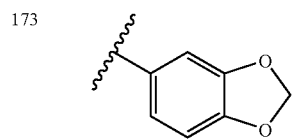 | 531.3 |
| 174 | 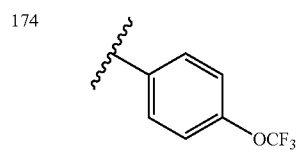 | 571.2 |
| 175 | 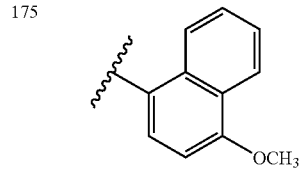 | 567.3 |
| 176 | 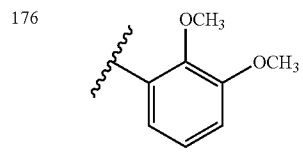 | 547.3 |
| 177 | 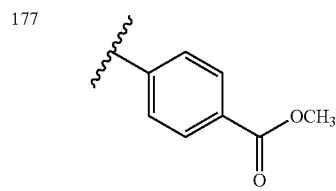 | 545.3 |
TABLE 4-continued
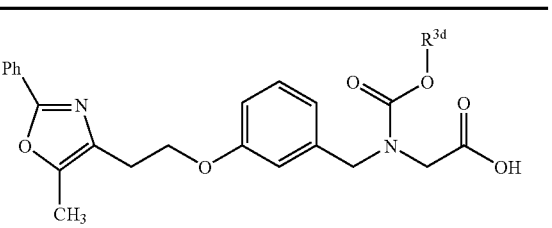
| Example No. | R³ᵈ | [M + H]⁺ |
|---|---|---|
| 178 | 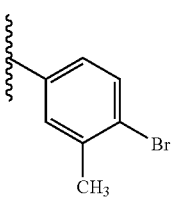 | 579.2 |
| 179 | 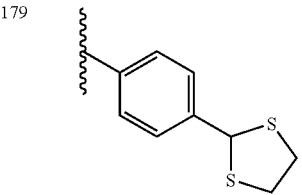 | 591.2 |
| 180 | 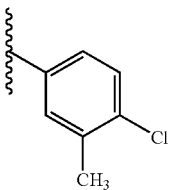 | 535.2 |
| 181 | 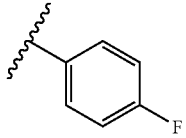 | 505.2 |
| 182 | 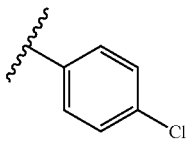 | 521.1 |
| 183 | 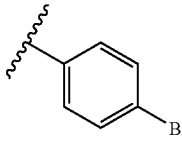 | 566 + 588 |
| 184 | 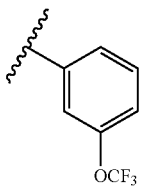 | 571.1 |

TABLE 4-continued
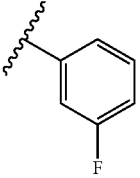
| Example No. | R³ᵈ | [M + H]⁺ |
|---|---|---|
| 185 | 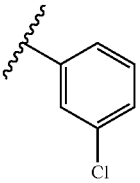 3-F-phenyl | 505.2 |
| 186 | 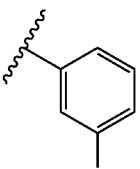 3-Cl-phenyl | 521.1 |
| 187 | 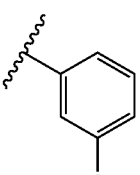 3-Br-phenyl | 566 + 588 |
| 188 | 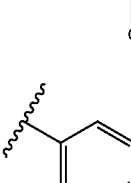 3-OC(O)CH₃-phenyl | 545.2 |
| 189 | 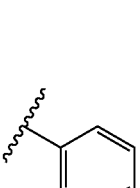 4-C(O)CH₃-phenyl | 529.1 |
| 190 | 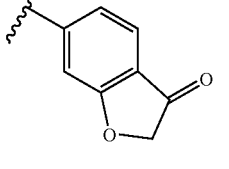 3-C(O)CH₃-phenyl | 529.1 |
TABLE 4-continued
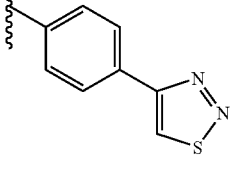
| Example No. | R³ᵈ | [M + H]⁺ |
|---|---|---|
| 191 | 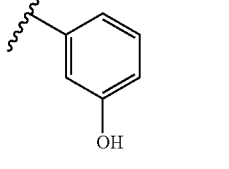 | 543.1 |
| 192 | 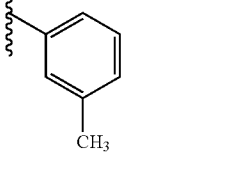 | 571.2 |
| 193 | 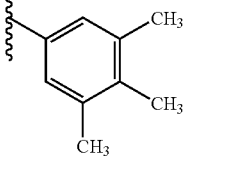 3-OH-phenyl | 503.3 |
| 194 | 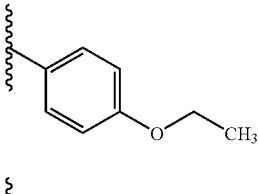 3-CH₃-phenyl | 501.3 |
| 195 | 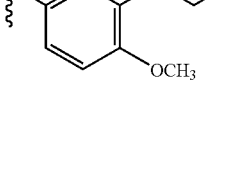 3,4,5-tri-CH₃-phenyl | 529.4 |
| 196 | 4-OCH₂CH₃-phenyl | 531.3 |
| 197 | 3-OCH₂CH₃-4-OCH₃-phenyl | 561.3 |

TABLE 4-continued
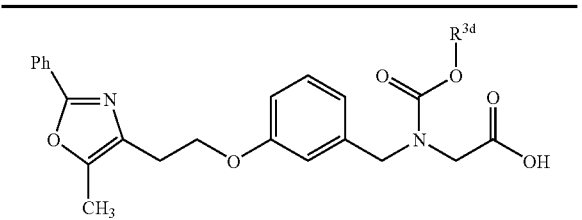
| Example No. | R³ᵈ | [M + H]⁺ |
|---|---|---|
| 198 | 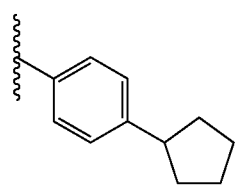 | 555.3 |
| 199 | 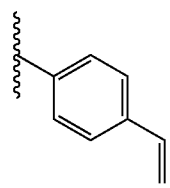 | 513.3 |
| 200 | 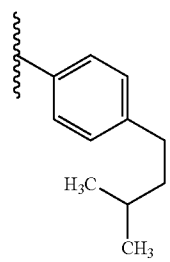 | 557.4 |
| 201 | 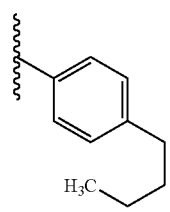 | 543.3 |
| 202 | 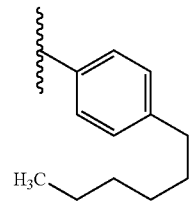 | 571.4 |
| 203 | 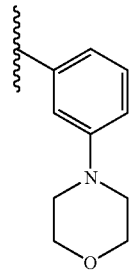 | 572.3 |
TABLE 4-continued
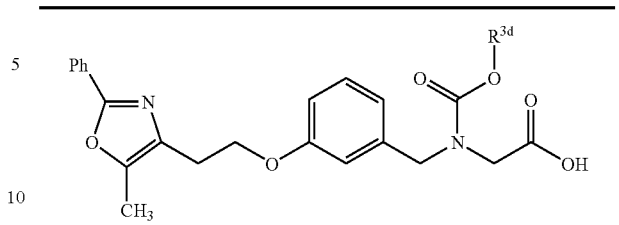
| Example No. | R³ᵈ | [M + H]⁺ |
|---|---|---|
| 204 | 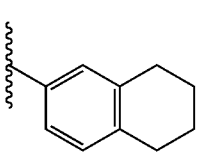 | 541.3 |
| 205 | 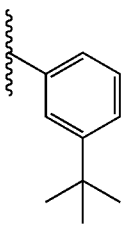 | 543.4 |
| 206 | 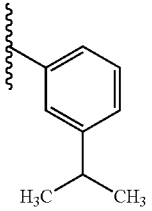 | 529.4 |
| 207 | 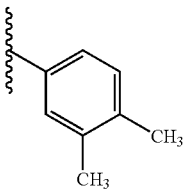 | 515.3 |
| 208 | 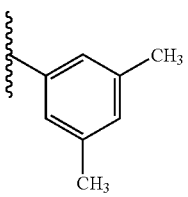 | 515.3 |
| 209 | 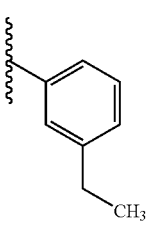 | 515.3 |

TABLE 4-continued

[Structure: Ph-oxazole(5-CH3)-CH2CH2-O-phenyl-CH2-N(C(O)OR^3d)-CH2-COOH]

| Example No. | R^3d | [M + H]^+ |
|---|---|---|
| 210 | 4-tert-butylphenyl | 543.3 |
| 211 | 4-isopropylphenyl | 529.4 |
| 212 | 4-benzylphenyl | 577.3 |
| 213 | 4-ethylphenyl | 515.3 |
| 214 | 4-propylphenyl | 529.3 |
| 215 | 2,3-dihydro-1H-inden-5-yl | 527.3 |
| 216 | 3-ethoxyphenyl | 531.3 |
| 217 | 4-pentylphenyl | 557.3 |
| 218 | 3-CF3-4-F-phenyl | 573.1 |
| 219 | 3-fluorobenzyl | 519.2 |
| 220 | 3-chlorobenzyl | 535.2 |
| 221 | 3-OCF3-benzyl | 585.2 |
| 222 | 4-fluorobenzyl | 519.2 |
| 223 | 4-chlorobenzyl | 535.2 |
| 224 | 4-OCF3-benzyl | 585.2 |
| 225 | 3,5-dimethoxybenzyl | 561.2 |

TABLE 5
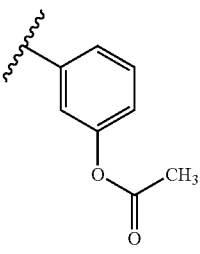
| Example No. | R³ᵈ | [M + H]⁺ |
|---|---|---|
| 226 | 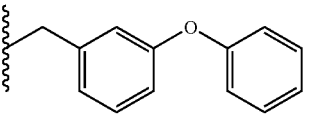 | 545.2 |
| 227 | 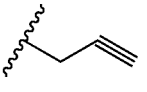 | 593.1 |
| 228 | 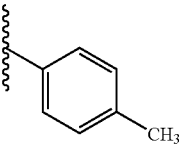 | 449.2 |
| 229 | 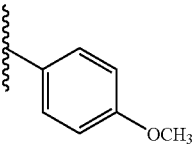 | 501.2 |
| 230 | 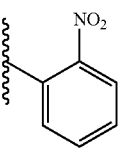 | 517.2 |
| 231 | 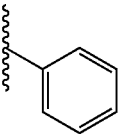 | 532.2 |
| 232 | 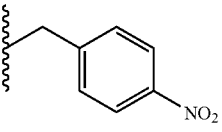 | 487.3 |
| 233 | 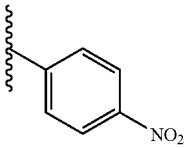 | 546.3 |
TABLE 5-continued
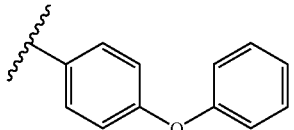
| Example No. | R³ᵈ | [M + H]⁺ |
|---|---|---|
| 234 | 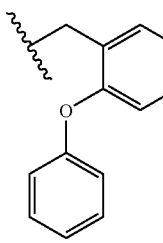 | 532.2 |
| 235 | 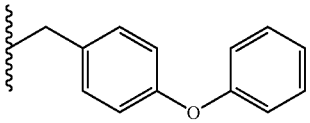 | 579.2 |
| 236 | 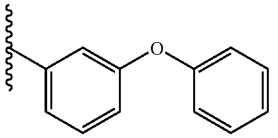 | 593.2 |
| 237 | 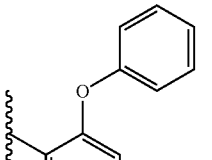 | 593.3 |
| 238 | 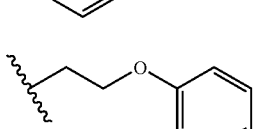 | 579.2 |
| 239 | 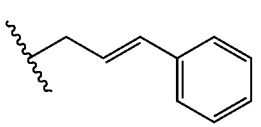 | 579.2 |
| 240 | | 531.2 |
| 241 | | 527.2 |

TABLE 5-continued
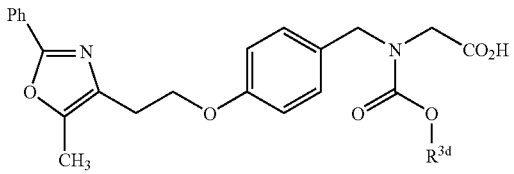
| Example No. | R³ᵈ | [M + H]⁺ |
|---|---|---|
| 242 | 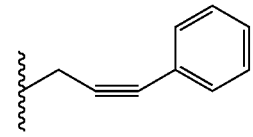 | 525.2 |
| 243 | 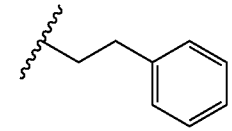 | 515.2 |
| 244 | 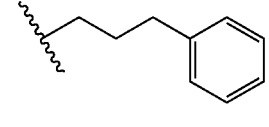 | 529.2 |
| 245 | 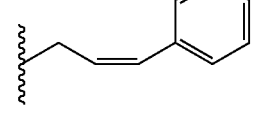 | 527.2 |
| 246 | 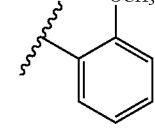 | 517.3 |
| 247 | 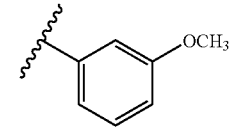 | 517.3 |
| 248 | 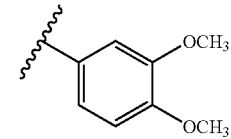 | 547.3 |
| 249 | 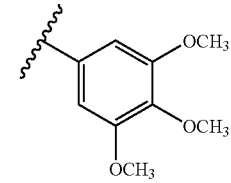 | 577.3 |
| 250 | 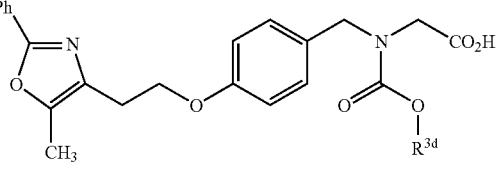 | 543.1 |
| 251 | 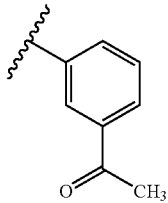 | 531.3 |
| 252 | 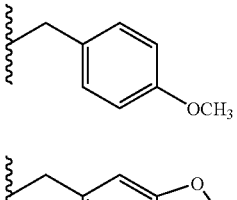 | 545.3 |
| 253 | 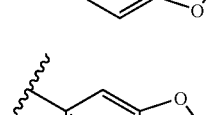 | 531.3 |
| 254 | 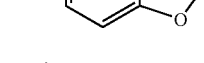 | 571.2 |
| 255 | 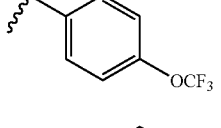 | 567.3 |
| 256 | 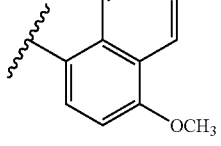 | 547.3 |
| 257 | 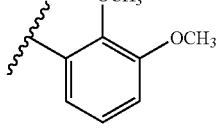 | 545.3 |

TABLE 5-continued

[Core structure: 2-phenyl-5-methyl-oxazol-4-yl-CH2CH2-O-(4-phenylene)-CH2-N(CO-O-R^{3d})-CH2-CO2H]

| Example No. | R^{3d} | [M + H]^+ |
|---|---|---|
| 258 | 4-(benzyloxy)phenyl | 593.4 |
| 259 | 4-hydroxyphenyl | 503.2 |
| 260 | 4-bromo-3-methylphenyl | 579.2 |
| 261 | 4-fluorophenyl | 505.2 |
| 262 | 4-chlorophenyl | 521.1 |
| 263 | 4-bromophenyl | 566/567 |
| 264 | 3-(trifluoromethoxy)phenyl | 571.1 |
| 265 | 3-fluorophenyl | 505.2 |
| 266 | 3-chlorophenyl | 521.1 |
| 267 | 3-bromophenyl | 566/567.0 |
| 268 | 3,5-difluorophenyl | 523.3 |
| 269 | 3-methylphenyl | 501.3 |
| 270 | 3-chloro-4-fluorophenyl | 539.2 |
| 271 | 3,4,5-trimethylphenyl | 529.3 |
| 272 | 4-chloro-3,5-dimethylphenyl | 549.2 |

TABLE 5-continued

[Structure: Ph-oxazole(CH3)-CH2CH2-O-C6H4-CH2-N(CH2CO2H)-C(=O)-O-R^{3d}]

| Example No. | R^{3d} | [M + H]^+ |
|---|---|---|
| 273 | 3,4-difluorophenyl | 523.2 |
| 274 | 4-vinylphenyl | 513.3 |
| 275 | 4-fluoro-3-methylphenyl | 519.2 |
| 276 | 4-chloro-3-fluorophenyl | 539.2 |
| 277 | 4-(methylthio)-3-methylphenyl | 547.3 |
| 278 | 4-(1H-pyrrol-1-yl)phenyl | 552.3 |
| 279 | 5,6,7,8-tetrahydronaphthalen-2-yl | 541.3 |
| 280 | biphenyl-3-yl | 563.3 |
| 281 | 3-(trifluoromethyl)phenyl | 555.3 |
| 282 | 3-tert-butylphenyl | 543.3 |
| 283 | 3-isopropylphenyl | 529.3 |
| 284 | 3,4-dimethylphenyl | 515.3 |
| 285 | 3,5-dimethylphenyl | 515.3 |

TABLE 5-continued

| Example No. | R³ᵈ | [M + H]⁺ |
|---|---|---|
| 286 | 3-ethylphenyl | 515.3 |
| 287 | 4-chloro-3-methylphenyl | 535.2 |
| 288 | 4-isopropylphenyl | 529.2 |
| 289 | 4-benzylphenyl | 577.3 |
| 290 | 4-ethylphenyl | 515.2 |
| 291 | 4-propylphenyl | 529.2 |
| 292 | 5-indanyl | 527.3 |
| 293 | 2-naphthyl | 537.3 |
| 294 | 3-ethoxyphenyl | 531.3 |
| 295 | 3,5-dichlorophenyl | 555.2 |
| 296 | 4-(1,2,3-thiadiazol-4-yl)phenyl | 571.3 |
| 297 | 4-fluoro-3-trifluoromethylphenyl | 573.2 |
| 298 | 3-methoxy-5-methylphenyl | 531.3 |
| 299 | 3-fluorobenzyl | 519.3 |
| 300 | 3-chlorobenzyl | 535.2 |

TABLE 5-continued

| Example No. | R³ᵈ | [M + H]⁺ |
|---|---|---|
| 301 | 3-OCF₃-benzyl | 585.2 |
| 302 | 4-F-benzyl | 519.2 |
| 303 | 4-Cl-benzyl | 535.2 |
| 304 | 4-OCF₃-benzyl | 585.2 |
| 305 | 3,5-di-OCH₃-benzyl | 561.2 |

EXAMPLE 149

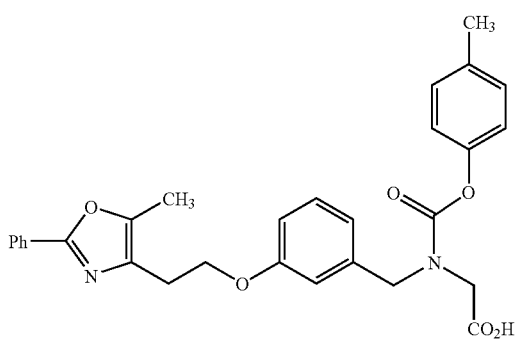

To a solution of the secondary amine-ester (2.1 g; 5.52 mmol)

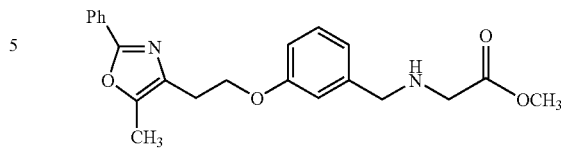

in CH₂Cl₂ (10 mL) was added 4-methylphenyl chloroformate (0.79 mL; 5.52 mmol) and polyvinyl pyridine (Aldrich; 1.74 g; 16.5 mmol). The mixture was stirred at RT for 15 min; at this point TLC showed that starting material had been consumed. The solution was filtered, concentrated in vacuo, and the residue was chromatographed (SiO₂; hex-:EtOAc 4:1) to provide the pure carbamate-ester (2 g). This was dissolved in a mixture of THF (10 mL), MeOH (1 mL) and aqueous LiOH (8 mL of a 1 M solution). The solution was stirred at RT overnight, then acidified to pH3 with excess aqueous 1 M HCl. The solution was extracted with EtOAc (2×50 mL). The combined organic extracts were washed with H₂O (2×50 mL) and brine (50 mL), dried (Na₂SO₄), and concentrated in vacuo to provide title compound as a white solid (1.75 g; 63%). [M+H]⁺=501.2

[M+H]⁺=501.2; ¹H NMR (400 MHz; CDCl₃): δ 7.93–7.99 (m, 2H), 7.38–7.43 (m, 3H), 7.23 (q, 1H, J=8 Hz), 7.02–7.12 (m, 3H), 6.98–7.02(m, 2H), 6.82–6.89 (m, 2H), 4.71 (s, 1H), 4.64 (s, 1H), 4.25 (t, 2H, J=7 Hz), 4.07 (s, 2H), 2.90–2.98 (m, 2H), 2.37 (s, 3H), 2.29 (s, 3H)

EXAMPLE 230

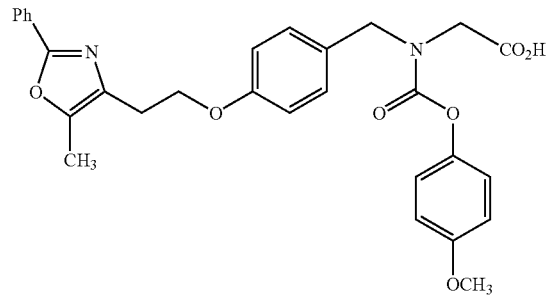

To a 0° C. solution of the secondary amine (3.0 g; 7.9 mmol)

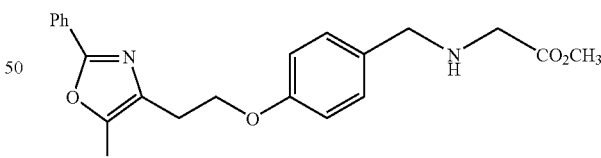

in CH₂Cl₂ (45 mL) were successively added pyridine (0.8 mL; 9.9 mmol) and 4-methoxyphenyl chloroformate (1.3 mL; 8.7 mmol). The reaction was stirred at 0° C. for 3 h, at which point starting material had been consumed (by analytical HPLC). The reaction solution was washed with aqueous HCl (2×25 mL of a 1 M solution), brine (2×), dried (Na₂SO₄), and concentrated in vacuo. The crude product was chromatographed (SiO₂; stepwise gradient from 4:1 to 3:7 hex:EtOAc) to provide the desired carbamate-ester (4.2 g; 100%). The ester was dissolved in THF:MeOH:H₂O (50 mL of a 3:1:1 solution) and LiOH.H₂O (0.5 g; 11.9 mmol) was added. The solution was stirred overnight at RT. Starting material was still present by HPLC. More LiOH.H₂O (0.2 g; 4.8 mmol) was added and the mixture was briefly heated to solubilize the LiOH, then stirred at RT for 4 h. The reaction was complete at this point, and the mixture was acidified to pH3 with excess aqueous 1 M HCl, then organic solvents were removed in vacuo. The residual aqueous phase was extracted with EtOAc (3×50 mL). The combined organic extracts were successively washed with H₂O and brine (50 mL each), dried (Na₂SO₄), filtered and concentrated in vacuo to give title compound as a colorless solid (3.07 g; 75%).

[M+H]$^+$=517.2; $^1$H NMR (400 MHz; CDCl₃): δ 7.96–7.98 (m, 2H), 7.4–7.45 (m, 3H), 7.2–7.3 (m, 2H), 7.0–7.1 (m, 2H), 6.8–7.0 (m, 4H), 4.65 (s, 1H), 4.55 (s, 1H), 4.20–4.24 (m, 2H), 4.02 (s, 2H), 3.77 (s, 3H), 3.00 (s, 2H), 2.38 (s, 3H).

The following examples (167, 187, 216, 229, 247 and 263) were all synthesized according to the methods described for Examples 149 and 230.

EXAMPLE 167

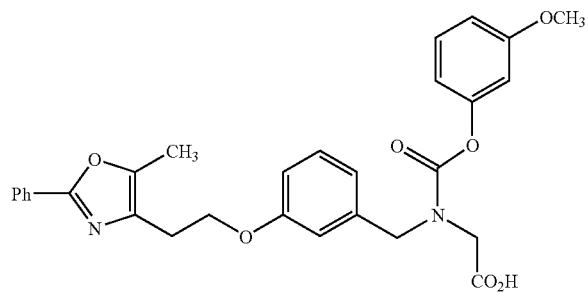

$^1$H NMR (DMSO-d₆; 500 MHz): δ 2.37 (s, 3H), 2.94 (m, 2H), 3.73 (2s, 3H), 4.06 (d, J=4.8 Hz, 2H), 4.25 (t, J=7.2 Hz, 2H), 4.66 (2s, 2H), 6.71 (m, 3H), 6.85 (m, 2H), 7.06 (d, J=16 Hz, 1H), 7.22 (m, 2H), 7.39 (m, 3H), 7.96 (m, 2H)

EXAMPLE 187

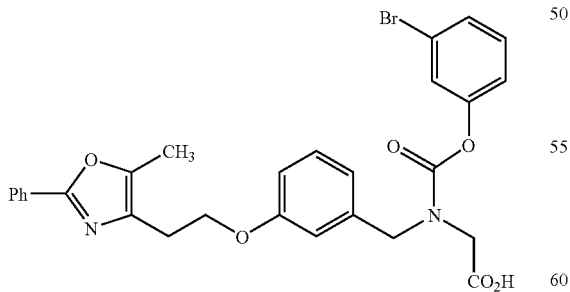

$^1$H NMR (DMSO-d₆; 500 MHz): δ 2.36 (s, 3H), 2.93 (t, J=6.6 Hz, 2H), 4.02 (2s, 2H), 4.21 (t, J=6.6 Hz, 2H), 4.55 (2s, 2H), 6.94 (m, 3H), 7.48 (m, 8H), 7.90 (m, 2H)

EXAMPLE 216

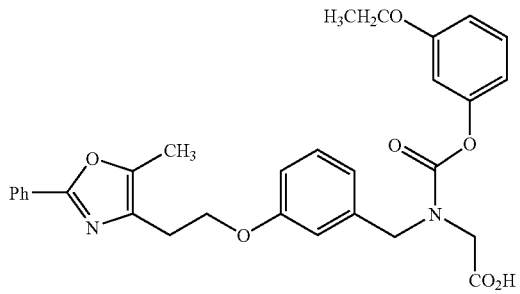

$^1$H NMR (CDCl₃; 400 MHz): δ 1.3–1.4 (m, 3H), 2.39 (s, 3H), 2.9–3.05 (m, 2H), 3.9–4.05 (m, 2H), 4.06 (br s, 2H), 4.25 (t, J=7.0 Hz, 2H), 6.85 (dd, J=11.4, 8.8 Hz, 2H), 6.99 (dd, J=15.8, 8.8 Hz, 2H), 7.18 (dd, J=8.4, 2.6 Hz, 2H), 7.38–7.50 (m, 5H), 7.99 (br d, J=7.9 Hz, 2H)

EXAMPLE 229

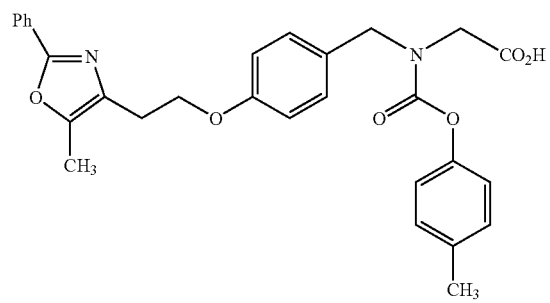

$^1$H NMR (CDCl₃; 400 MHz): δ 2.30 (2 peaks, 3H), 2.38 (2 peaks, 3H), 3.03 (dd, J=5.7, 5.7 Hz; 2H), 3.99 (s, 2H), 4.21 (dd, J=6.1, 6.1 Hz; 2H), 4.63 (2 peaks, 2H), 6.82–6.87 (m, 2H), 6.96–7.01 (m, 2H), 7.09–7.14 (m, 2H), 7.18–7.20 (m, 2H), 7.43–7.45 (m, 3H), 7.96–7.98 (m, 2H)

EXAMPLE 247

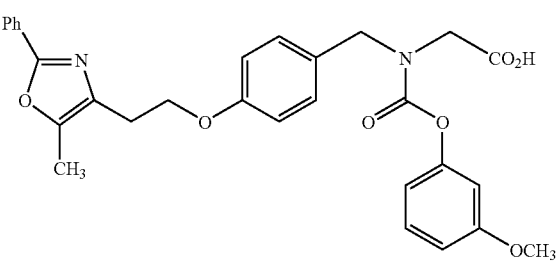

$^1$H NMR (DMSO-d₆; 500 MHz): δ 2.36 (s, 3H), 2.93 (t, J=6.6 Hz, 2H), 3.74 (s, 3H), 3.96 (2s, 2H), 4.20 (t, J=6.6 Hz, 2H), 4.55 (2s, 2H), 6.65 (m, 2H), 6.94 (m, 3H), 7.27 (m, 3H), 7.48 (m, 3H), 7.91 (d, J=6.1 Hz, 2H)

EXAMPLE 263

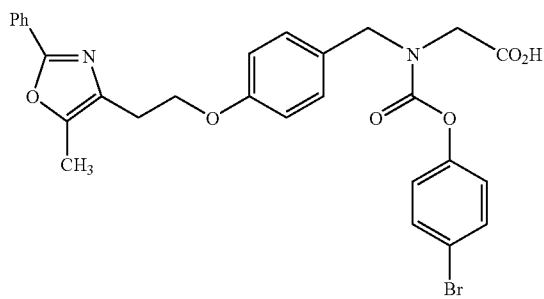

$^1$H NMR (CDCl$_3$; 400 MHz): δ 2.42 (2s, 3H; rotamers); 3.0–3.5 (m, 2H), 3.99 (br s, 2H), 4.15–4.25 (m, 2H), 4.57 (AB doublet, J=38.2 Hz, 2H), 6.85 (dd, J=11.4, 8.8 Hz, 2H), 6.99 (dd, J=15.8, 8.8 Hz, 2H), 7.18 (dd, J=8.4, 2.6 Hz, 2H), 7.38–7.50 (m, 5H), 7.99 (br d, J=7.9 Hz, 2H)

EXAMPLE 306

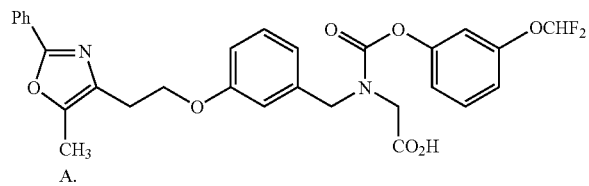

A.

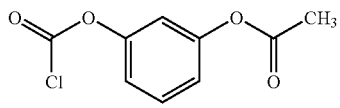

A solution of resorcinol monoacetate (2 g; 13.14 mmol), N,N-dimethylaniline (1.6 g; 13.14 mmol), phosgene (6.8 mL of a 1.95M solution in toluene; 13.1 mmol) and a catalytic amount of DMF in chlorobenzene (5 mL) was heated at 80° C. in a pressure tube for 2.5 h and then allowed to cool to RT. The clear supernatant solution was separated and concentrated in vacuo. The residue was purified via distillation in vacuo (140–150° C. @ 1.0 mm Hg) to give title compound in the form of a clear oil (2 g; 71%).

B.

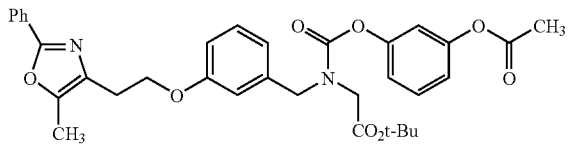

To a mixture of Part A chloroformate (50 mg, 0.237 mmol) and polyvinylpyridine (PVP) (75 mg, 0.70 mmol) was added a CH$_2$Cl$_2$ solution (2 mL) of the amino-tert-butyl ester (100 mg, 0.237 mmol),

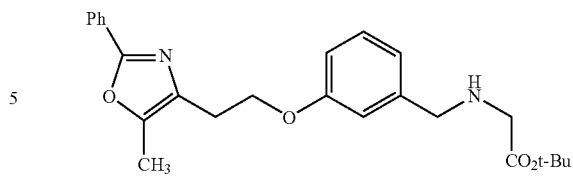

(prepared as described in Example 7 Part B).

The reaction was stirred at RT for 15 min. Resin-bound amine (WA21J, Supelco; 150 mg) was added to the mixture. The reaction mixture was stirred for another 15 min. The Resin-bound amine and PVP were removed via filtration and the filtrate was concentrated in vacuo to give the crude product. The crude product was chromatographed (SiO$_2$; hexane/EtOAc 1:4) to provide title compound (0.1 g, 70%).

C.

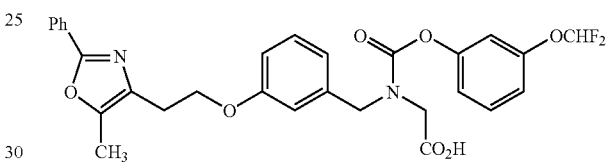

A solution of the Part B phenol-tert butyl ester compound (60 mg; 0.10 mmol), Bu$_4$NBr (0.32 mg, 0.001 mmol), aqueous NaOH (0.5 mL of a 1 M solution; 0.5 mmol) and isopropanol (1 mL) in a pressure tube was cooled to −50° C. Freon gas was bubbled into the solution for 1 min. The tube was sealed and heated to 80° C. for 12 h. The mixture was extracted with EtOAc (3×10 mL). The combined organic extracts were washed with brine, dried (Na$_2$SO$_4$) and concentrated in vacuo to give the crude difluoromethoxy ether-tert butyl ester as an oil. The crude ester was then treated with a solution of 30% TFA in CH$_2$Cl$_2$ overnight. Volatiles were removed in vacuo and the residue was purified using preparative reverse-phase HPLC (as in Example 127, except that the continuous gradient used was from A:B 70:30 to 100% B) to afford two products, the desired title difluoromethoxy ether-acid (13 mg; 23%) and the phenol-acid set out below (32 mg; 63%). Reverse phase HPLC analysis using standard conditions indicated that the product purity was >92%. In addition LC/MS (electrospray) gave the correct molecular ion [(M+H)$^+$=553.2 and 503.2 respectively] for the two compounds.

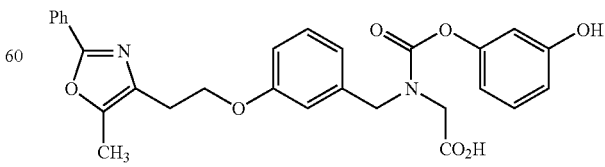

Phenol-Acid

EXAMPLES 307 AND 308

Following the above general procedure of Example 306, the following compounds were prepared:

Example 307

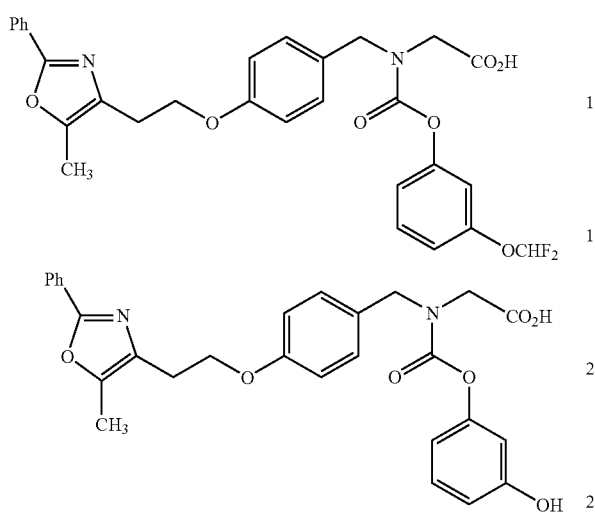

Example 307: [M+H]⁺=553.2
Example 308: [M+H]⁺=503.2

EXAMPLE 309

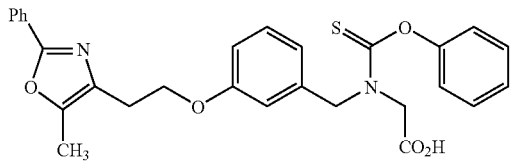

To a mixture of phenyl chlorothionoformate (11 mg, 0.063 mmol) and triethylamine (6.5 mg, 0.063 mmol) was added a solution of the amino-tert-butyl ester (20 mg, 0.053 mmol),

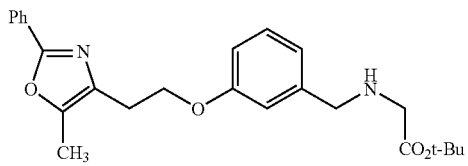

(prepared as described in Example 7 Part B) in CH$_2$Cl$_2$ (1 mL). The reaction was stirred at RT for 15 min and the mixture was concentrated in vacuo to give the crude thionocarbamate tert-butyl ester. This material was dissolved in aqueous LiOH (0.50 mL of a 1.0 M solution) and THF (2 mL) and stirred at RT for 5 h. The solution was concentrated in vacuo to give the crude acid as an oil. The crude product was purified using preparative HPLC to afford the desired title product (10 mg; 38%). [M+H]⁺=503.2

EXAMPLE 310

The corresponding thiocarbamate in the 1,4 series was prepared in the same manner as described for Example 309.

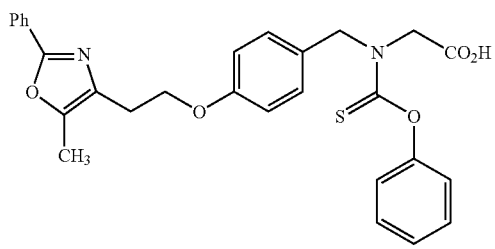

[M+H]⁺=503.2

EXAMPLE 311

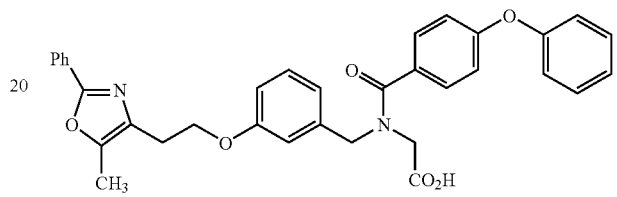

To a mixture of the amine-tert butyl ester (306 mg, 0.73 mmol)

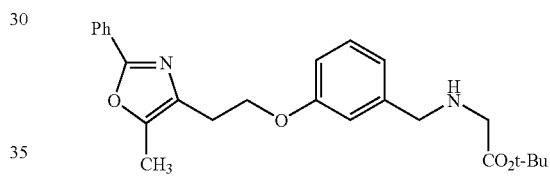

(prepared as described in Example 7 Part B), and p-phenoxybenzoic acid (220 mg; 1.02 mmol; 1.4 equiv) in CH$_3$CN (20 mL) was added BOP reagent (372 mg, 0.84 mmol, 1.15 equiv) in a single portion followed by iPr$_2$NEt (0.5 mL; 2.9 mmol; 3.9 equiv) dropwise. The reaction was stirred overnight at RT, after which volatiles were removed in vacuo. The residue was dissolved in EtOAc and washed with aqueous 1N HCl. The aqueous layer was extracted with EtOAc (2×) and the combined organic extracts were washed with H$_2$O, sat'd aqueous NaHCO$_3$ and brine, dried (Na$_2$SO$_4$) and concentrated in vacuo to give the desired product. The resulting crude amide-ester was used in the next step without further purification.

A solution of the crude amide ester in 40% TFA-CH$_2$Cl$_2$ (25 mL) was stirred for 5 h at RT. Volatiles were removed in vacuo and the crude acid was purified by Prep HPLC (YMC S5 ODS 30 mm×250 mm reverse phase column; flow rate=25 mL/min; 30 min continuous gradient from 70:30 A:B to 100% B; solvent A=90:10:0.1 H$_2$O:MeOH:TFA; solvent B=90:10:0.1 MeOH:H$_2$O:TFA) to yield title compound (238 mg; 58% yield over 2 steps) as a white solid. Analytical Reverse-phase HPLC: Retention time=7.53 min. (Continuous gradient solvent system: from 50% A:50% B to 0% A:100% B (A=90% H$_2$O/10% MeOH/0.2% H$_3$PO$_4$; B=90% MeOH/10% H$_2$O/0.2% H$_3$PO$_4$) for 8 min; detection at 220 nm; YMC S3 ODS 4.6×50 mm column). [M+H]⁺=563.3

EXAMPLE 311A

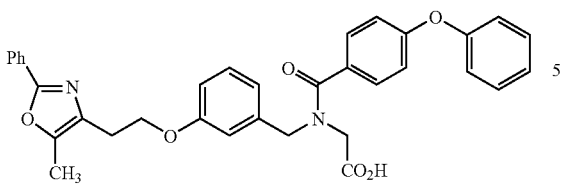

(Alternative Synthetic Procedure)

To a solution of the secondary amine tert-butyl ester (35 mg, 0.083 mmol), (prepared as described in Example 7 Part B)

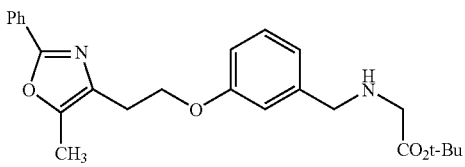

4-phenoxy benzoic acid (30 mg, 0.14 mmol) and HOAT (30 mg, 0.22 mmol) in THF/DMF (1 mL/0.05 mL) was added EDCI (20 mg, 0.10 mmol) and the mixture was stirred at RT overnight. The reaction was diluted with EtOAc, washed with aqueous 1N HCl, H$_2$O, sat'd. aqueous NaHCO$_3$ and brine, dried (Na$_2$SO$_4$) and concentrated in vacuo. The crude amide-tert butyl ester was dissolved in TFA/CH$_2$Cl$_2$ (5 mL of a 1:1 solution). The resulting pink solution was stirred overnight and concentrated in vacuo to provide the crude acid-amide as a dark brown oil. The crude product was purified by preparative HPLC (YMC S5 ODS 20×100 mm column, 10 min continuous gradient from 60:40 A:B to 100% B; solvent A=90:10:0.1 H$_2$O:MeOH:TFA; solvent B=90:10:0.1 MeOH:H$_2$O:TFA; flow rate=20 mL/min) to provide the title compound (32 mg, 69%).
[M+H]$^+$=563.3

EXAMPLE 312

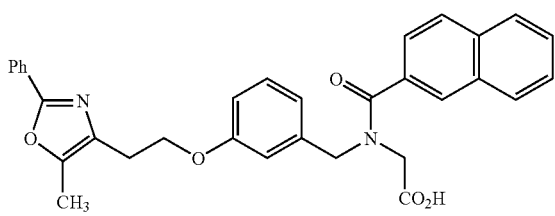

1) To a solution of the secondary amine-tert-butyl ester (25 mg; 006 mmol)

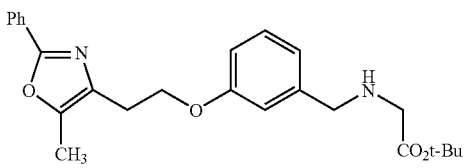

(prepared as described in Example 7 Part B), in THF (0.5 mL) was added 2-naphthalene carboxylic acid (25 mg; 0.15 mmol; 2.5 equiv).
2) HOAT (48 mg; 0.35 mmol; 5.8 equiv) was added.
3) DMF (50 gL) was added.
4) EDCI ((20 mg, 0.1 mmol, 1.8 m eq) was added.
5) The reaction vessel was shaken for 24 h at RT.
6) The reaction was diluted with MeOH (2 mL) and filtered.
7) The amide-tert butyl ester was purified by preparative HPLC (YMC S5 ODS 20×100 mm column; flow rate=25 mL/min; 10 min continuous gradient from 70:30 A:B to 100% B; solvent A=90:10:0.1 H$_2$O:MeOH:TFA; solvent B=90:10:0.1 MeOH:H$_2$O:TFA).
8) The fractions containing the purified amide-ester were treated with a solution of TFA in CH$_2$Cl$_2$ (0.5 mL of a 1:1 solution) overnight. The reaction was concentrated in vacuo (Speed Vac) to give title compound (8 mg; 25%). Reverse-phase analytical HPLC showed that the purity of the product was >88%; LC/MS (electrospray detection) gave the correct [M+H]$^+$=521.2 for the title compound.

EXAMPLE 313

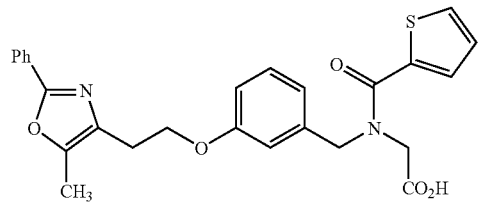

A mixture of the amino-ester (20 mg; 0.0474 mmol),

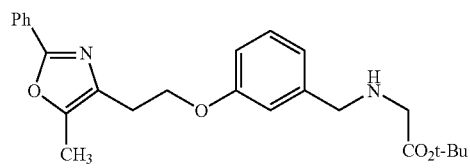

(prepared as described in Example 7 Part B), thiophene-2-carboxylic acid (9.1 mg, 0.71 mmol), EDCI (26 mg, 1.4 mmol) and DMAP (a catalytic amount) was dissolved in CH$_2$Cl$_2$ (2 mL) and stirred at RT overnight. The reaction solution was successively washed with aqueous 1N HCl (2 mL) and sat'd aqueous NaHCO$_3$ (2 mL). To the organic phase was then added 0.5 g anhydrous Na$_2$SO$_4$, and 0.2 g WA21]amine-bound resin (Supelco). The mixture was shaken for 0.5 h and the solids were filtered off. TFA (2.0 mL) was added to the filtrate and the solution was shaken at RT overnight. The reaction solution was concentrated in vacuo using a Speed Vac for 16 h to afford title compound as a yellow oil. Reverse phase analytical HPLC (YMC S5 ODS 4.6×33 mm column, continuous gradient from 100% A to 100% B for 2 min at a flow rate of 5 mL/min [Solvent A=10% MeOH/90% H$_2$O/0.2% H$_3$PO$_4$; Solvent B=90% MeOH/10% H$_2$O/0.2% H$_3$PO$_4$]) indicated that the product purity was 92.7%. In addition, LC/MS (electrospray) gave the correct molecular ion [(M+H)$^+$=477.2] for the desired title compound.

EXAMPLE 314

Another purification protocol using amine-bound resin for the amide-acid product is illustrated by the following synthesis:

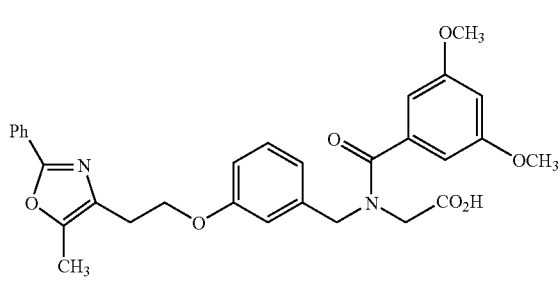

To a mixture of the amino-ester (20 mg; 0.0474 mmol),

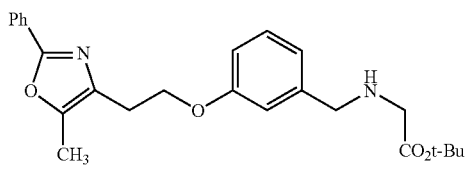

(prepared as described in Example 7 Part B), and 3,5-dimethoxybenzoic acid (13 mg, 0.071 mmol) in anhydrous $CH_3CN$ (0.5 mL) was added a solution of BOP reagent (31 mg, 0.071 mmol) in $CH_3CN$ (0.5 mL), followed by DIEA (41 µL, 0.23 mmol) in $CH_3CN$ (0.5 mL). The reaction was shaken at RT overnight. Volatiles were removed in vacuo using a Speed Vac and $CH_2Cl_2$ (2 mL) was added. The solution was washed successively with aqueous 1N HCl (2 mL) and sat'd aqueous $NaHCO_3$ (2 mL). To the organic phase was added 0.5 g anhydrous $Na_2SO_4$, and 0.2 g WA21]amine-bound resin (Supelco). The mixture was shaken for 0.5 h and the solids were filtered. TFA (2 mL) was added to the filtrate and the solution was shaken at RT overnight. The reaction solution was concentrated in vacuo using a Speed Vac for 16 h to afford the final product as a yellow gum. Reverse-phase analytical HPLC (YMC S5 ODS 4.6×33 mm column, continuous gradient from 100% A to 100% B for 2 min at a flow rate of 5 mL/min [Solvent A=10% MeOH/90% $H_2O$/0.2% $H_3PO_4$; Solvent B=90% MeOH/10% $H_2O$/0.2% $H_3PO_4$]) indicated that the product purity was 90%. In addition, LC/MS (electrospray) gave the correct molecular ion [$(M+H)^+$=531.3] for the title compound.

EXAMPLES 315 TO 391

Following one of the above procedures, the following compounds in Tables 6 and 7 of the invention were prepared.

TABLE 6

(Amide-Acids)

| Example No. | $R^{3e}$ | $[M + H]^+$ |
|---|---|---|
| 315 | 1-naphthyl | 521.2 |
| 316 | 3,4-difluorophenyl | 507.3 |
| 317 | 3-phenoxyphenyl | 563.1 |
| 318 | 4-benzylphenyl | 561.2 |
| 319 | 3,5-dimethylphenyl | 499.3 |
| 320 | 2,2'-bithienyl | 559.2 |
| 321 | 5-methylthien-2-yl | 491.1 |
| 322 | 5-nitrothien-2-yl | 522.2 |

TABLE 6-continued (Amide-Acids)

| Example No. | R³ᵉ | [M + H]⁺ |
|---|---|---|
| 323 | 5-methyl-thiophen-2-yl | 491.2 |
| 324 | 4-butoxyphenyl | 543.3 |
| 325 | 4-methoxy-3-methylphenyl | 515.3 |
| 326 | 3-chloro-4-methoxyphenyl | 535.3 |
| 327 | 3,4-dimethylphenyl | 499.3 |
| 328 | 4-methylphenyl | 485.3 |
| 329 | 3-fluoro-4-methylphenyl | 503.3 |
| 330 | 4-(methylthio)phenyl | 517.3 |
| 331 | 4-isopropylphenyl | 513.3 |
| 332 | 4-isobutylphenyl | 527.3 |
| 333 | 4-chloro-3-methylphenyl | 519.3 |
| 334 | 4-methoxy-3-methylphenyl | 515.3 |
| 335 | benzo[1,3]dioxol-5-yl | 515.3 |
| 336 | 4-isopropoxyphenyl | 529.3 |

TABLE 6-continued
(Amide-Acids)
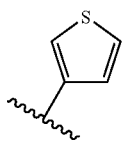
| Example No. | R³ᵉ | [M + H]⁺ |
|---|---|---|
| 337 | 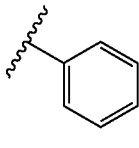 | 477.2 |
| 338 | 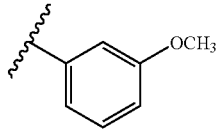 | 471.2 |
| 339 | 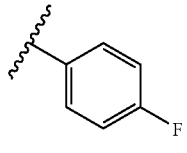 | 501.3 |
| 340 | 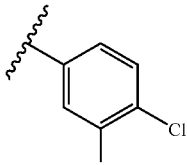 | 489.2 |
| 341 | 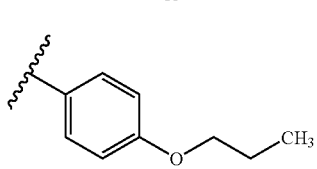 | 539.2 |
| 342 | 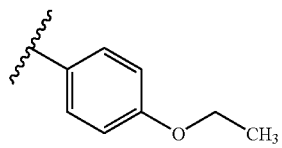 | 529.3 |
| 343 | 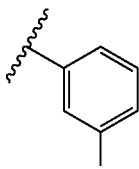 | 515.3 |
| 344 | 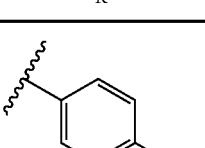 | 485.3 |
TABLE 6-continued
(Amide-Acids)
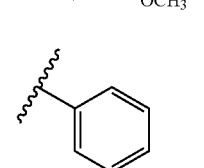
| Example No. | R³ᵉ | [M + H]⁺ |
|---|---|---|
| 345 | 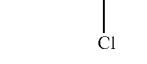 | 501.3 |
| 346 | 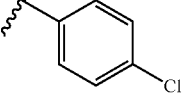 | 505.2 |
| 347 | 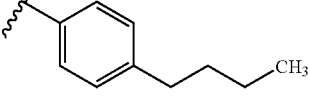 | 505.2 |
| 348 | 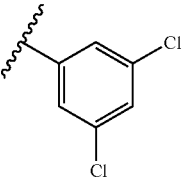 | 527.3 |
| 349 | 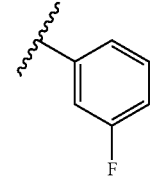 | 539.2 |
| 350 |  | 489.3 |
| 351 |  | 523.2 |

TABLE 6-continued

(Amide-Acids)

| Example No. | R³ᵉ | [M + H]⁺ |
|---|---|---|
| 352 | 3-ethoxyphenyl | 515.3 |
| 353 | 5-chlorothiophen-2-yl | 511.2 |
| 354 | 5-(methylthio)thiophen-2-yl | 523.1 |
| 355 | 4-methylbenzyl | 499.2 |
| 356 | 3-fluorobenzyl | 503.2 |
| 357 | 3,5-difluorobenzyl | 521.2 |
| 358 | benzo[1,3]dioxol-5-ylmethyl | 529.2 |
| 359 | 4-ethoxybenzyl | 529.2 |

TABLE 6-continued

(Amide-Acids)

| Example No. | R³ᵉ | [M + H]⁺ |
|---|---|---|
| 360 | 3-nitrobenzyl | 530.2 |
| 361 | 4-nitrobenzyl | 530.2 |

TABLE 7

(Amide-Acids)

| Example No. | R³ | [M + H]⁺ |
|---|---|---|
| 362 | 2-phenylethyl | 499.2 |
| 363 | biphenyl-2-yl | 547.2 |
| 364 | 4-phenoxybenzyl | 563.2 |

TABLE 7-continued
(Amide-Acids)
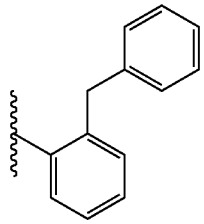
| Example No. | R³ | [M + H]⁺ |
|---|---|---|
| 365 | 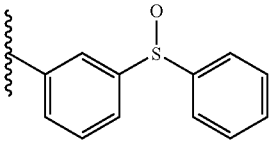 | 561.1 |
| 366 | 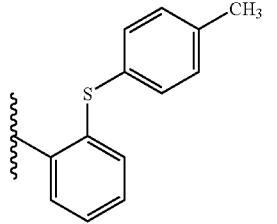 | 595.1 |
| 367 | 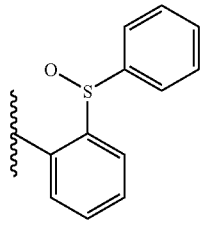 | 593.1 |
| 368 | 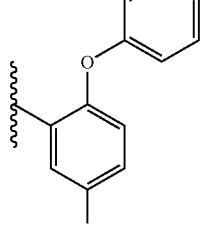 | 595.1 |
| 369 | 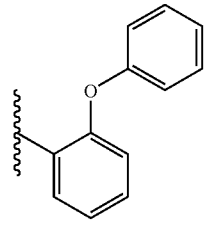 | 597.1 |
TABLE 7-continued
(Amide-Acids)
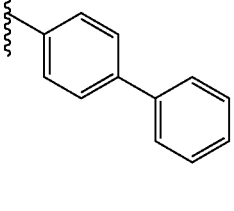
| Example No. | R³ | [M + H]⁺ |
|---|---|---|
| 370 | 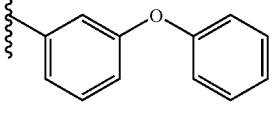 | 563.1 |
| 371 | 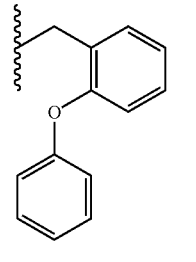 | 547.2 |
| 372 | 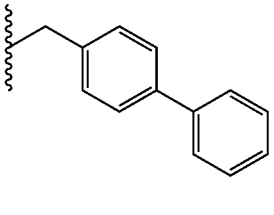 | 563.1 |
| 373 | 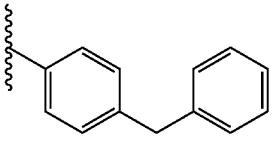 | 577.2 |
| 374 | | 561.2 |
| 375 | | 561.2 |

TABLE 7-continued (Amide-Acids)

| Example No. | R³ | [M + H]⁺ |
|---|---|---|
| 376 | 1-pyrrolyl-2-phenyl | 536.2 |
| 377 | 4-phenoxybenzyl | 577.2 |
| 378 | 3-phenoxybenzyl | 577.2 |
| 379 | 2,2'-bithiophene-5-yl | 615.3 |
| 380 | 3,4-dimethylphenyl | 499.3 |
| 381 | 4-chloro-3-methylphenyl | 519.3 |
| 382 | 3,4-difluorophenyl | 507.3 |
| 383 | 3,4-dichlorophenyl | 539.2 |
| 384 | 3-chlorophenyl | 505.2 |
| 385 | 4-chlorophenyl | 505.2 |
| 386 | 3-chloro-4-fluorophenyl | 522.7 |
| 387 | 4-isopropylphenyl | 513.3 |
| 388 | 4-isobutylphenyl | 527.3 |
| 389 | 4-propoxyphenyl | 529.3 |

TABLE 7-continued (Amide-Acids)

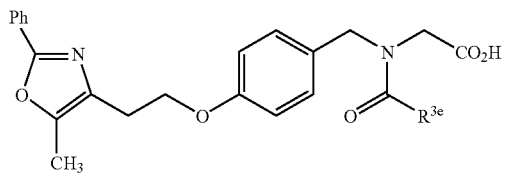

| Example No. | R³ | [M + H]⁺ |
|---|---|---|
| 390 | 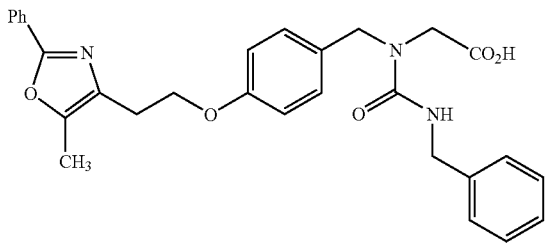 | 527.3 |
| 391 | 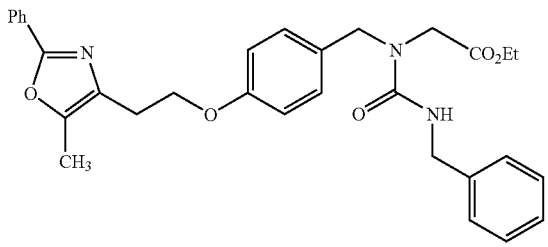 | 523.1 |

EXAMPLE 392

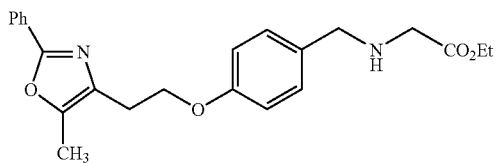

A.

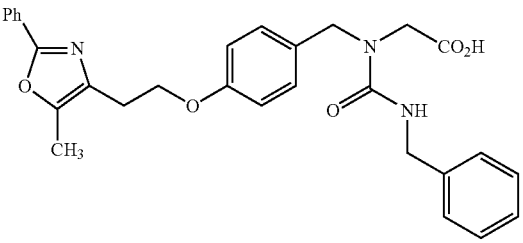

To a solution of the amine (47 mg; 0.12 mmol)

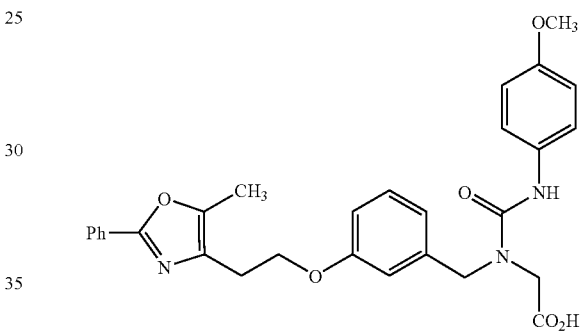

(prepared as described in Example 3 Part A), in CH₂Cl₂ (5 mL) were added iPr₂NEt (0.1 mL; 0.57 mmol) and DMAP (14 mg; 0.12 mmol) followed by benzyl isocyanate (24 mg; 0.18 mmol). The reaction was stirred for 14 h, then passed through an SCX cartridge [the 3 g SCX cartridge was prewashed successively with MeOH (10 mL) and CH₂Cl₂ (5 mL)] by eluting with CH₂Cl₂ (15 mL). The filtrate was concentrated in vacuo to give the crude urea Part A compound (53 mg; 84%), which was sufficiently pure to be used in the next step without further purification.

B.

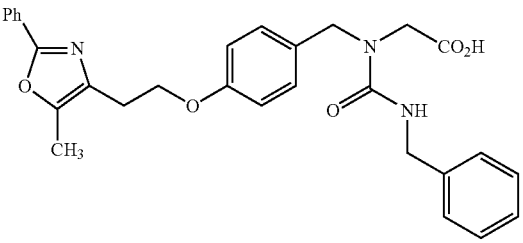

A solution of the crude Part A urea-ethyl ester (53 mg) and LiOH.H₂O (12 mg) in THF:MeOH:H₂O (3:1:1; 5 mL) was stirred at RT for 2 days. The solution was acidified to pH3 with aqueous 1M HCl, concentrated in vacuo, and purified by preparative HPLC (utilizing a YMC S5 ODS 20 mm×100 mm column; with a continuous gradient from 70% A:30% B to 100% B for 10 minutes at a flow rate of 20 mL/min, where A=90:10:0.1 H₂O:MeOH:TFA and where B=90:10:0.1 MeOH:H₂O:TFA) to give title compound (12 mg; 24%) as an off-white solid. [M+H]⁺=500.2

EXAMPLE 393

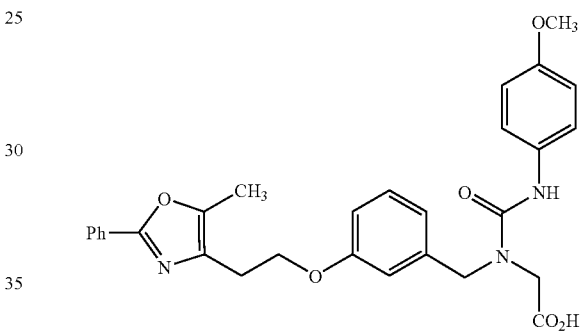

A.

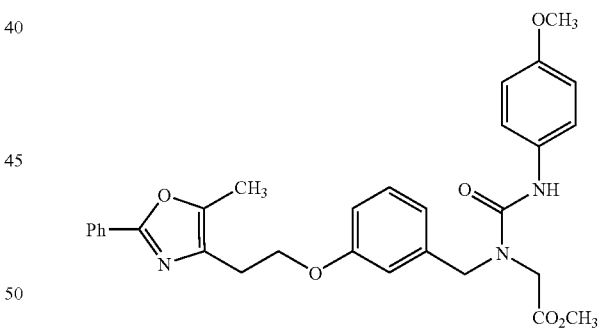

To a solution of the amine (0.25 g, 0.66 mmol)

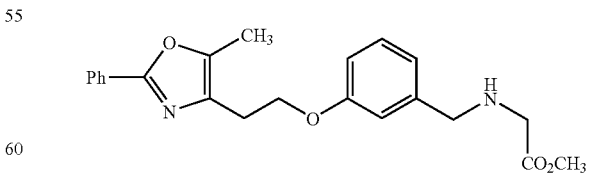

(prepared as described in Example 6), in CH₂Cl₂ (5 mL) was added 4-methoxyphenyl isocyanate (0.20 g, 1.32 mmol) in one portion and the resulting solution was stirred for 1 h at RT. The reaction mixture was then concentrated in vacuo to give an oil, which was chromatographed (SiO₂; 1.5%

MeOH/CH$_2$Cl$_2$) to provide title compound (0.34 g; 97%) as a colorless oil.

B.

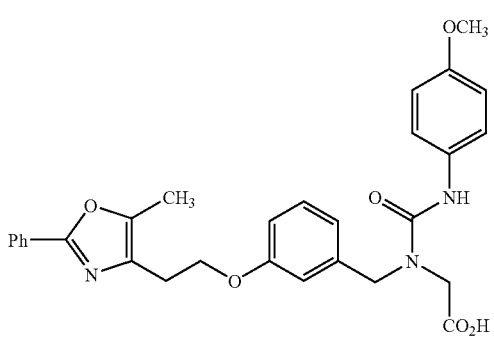

A solution of Part A compound (0.14 g, 0.26 mmol) and LiOH (0.1 g, 4.3 mmol) in H$_2$O/THF (5 ml of a 40:60 solution) was stirred for 12 h at 25° C. The reaction mixture was acidified with HOAc and extracted with EtOAc (2×). The combined organic extracts were dried (MgSO$_4$) and concentrated in vacuo to provide title compound (0.12 g; 90%) as a colorless oil. [M+H]$^+$=516

$^1$H NMR (CD$_3$OD; δ): 7.94 (m, 2H), 7.45 (m, 3H), 7.23 (m, 3H), 6.80 (m, 2H), 6.80 (m, 3H), 4.58 (s, 2H), 4.23 (t, J=7.9 Hz, 2H), 3.81 (s, 2H), 3.73 (s, 3H), 2.98 (t, J=7.9 Hz, 2H), 2.36 (s, 3H).

EXAMPLE 394

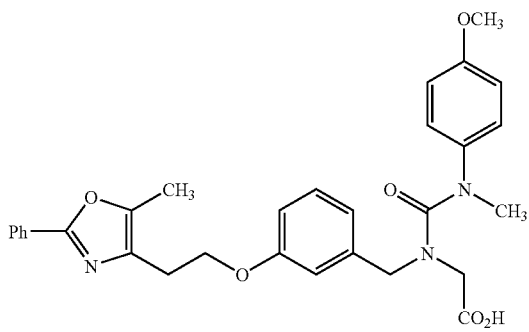

A.

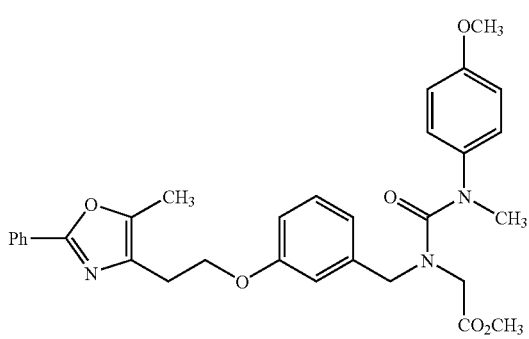

A solution of the previously described carbamoyl chloride (Example 139 Part A compound; 0.15 g; 0.34 mmol)

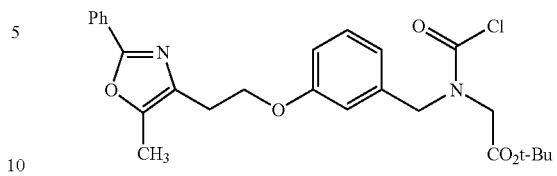

N-methyl-p-anisidine (0.14 g, 1.0 mmol) and K$_2$CO$_3$ (0.15 g, 1.1 mmol) in 5 ml of acetone was stirred at 25° C. for 12 h. The reaction mixture was concentrated in vacuo to yield an oily residue, which was chromatographed (SiO$_2$; 1.5% MeOH/CH$_2$Cl$_2$) to provide title compound (0.12 g; 65%) as a colorless oil.

B.

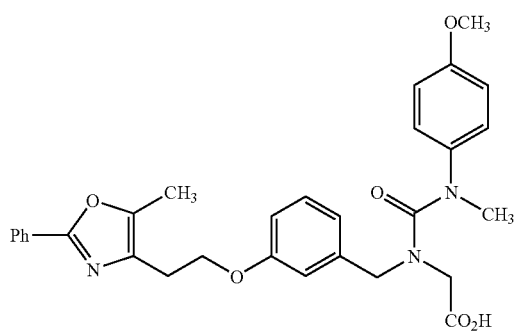

A solution of Part A compound (0.12 g, 0.22 mmol) and LiOH (0.050 g, 2.1 mmol) in H$_2$O/THF (5 mL of a 40:60 solution) was stirred at RT for 12 h. The reaction mixture was concentrated in vacuo to yield an oily residue, which was purified by preparative HPLC (YMC S5 ODS 30×250 mm column; flow rate=25 ml/min. 30 min continuous gradient from A:B=50:50 to 100% B; solvent A=90:10:0.1 H$_2$O:MeOH:TFA; solvent B=90:10:0.1 MeOH:H$_2$O:TFA) to provide title compound (59 mg, 50%) as a colorless oil. [M+H]$^+$=530.3

NMR (CDCl$_3$): 7.99 (d, 6.2 Hz, 2H), 7.45 (m, 3H), 7.24 (m, 3H), 6.82 (d, 6.2 Hz, 2H), 6.79 (m, 1H), 6.63 (m, 1H), 6.55 (s, 1H), 4.24 (s, 2H), 4.16 (t, 7.8 Hz), 2H), 3.72 (s, 3H), 3.59 (s, 2H), 3.16 (s, 2H), 3.02 (t, 7.8 Hz, 2H), 2.40 (s, 3H).

EXAMPLES 395 TO 410

Utilizing one of the above procedures, the analogs in Tables 8 and 9 were synthesized.

TABLE 8

(Urea-Acids)

| Example No. | R³ᶠ | [M + H]⁺ |
|---|---|---|
| 395 | NH-biphenyl-4-yl | 562.3 |
| 396 | NH-(3,5-dimethoxyphenyl) | 546.3 |
| 397 | NH-(3,5-dichlorophenyl) | 554.2 |
| 398 | NH-(3-methylthiophenyl) | 532.3 |
| 399 | NH-(2,4-difluorophenyl) | 522.3 |
| 400 | NH-(2,4-dimethoxyphenyl) | 546.3 |
| 401 | NH-(2-methoxyphenyl) | 516.3 |

TABLE 9

(Urea-Acids)

| Example No. | R³ᶠ | [M + H]⁺ |
|---|---|---|
| 402 | NH-biphenyl-4-yl | 562.3 |
| 403 | NH-(3,5-dimethoxyphenyl) | 546.3 |
| 404 | NH-(3,5-dichlorophenyl) | 554.2 |
| 405 | NH-(3-methylthiophenyl) | 532.3 |
| 406 | NH-(2,4-difluorophenyl) | 522.3 |
| 407 | NH-(2,4-dimethoxyphenyl) | 546.3 |
| 408 | NH-(4-methoxyphenyl) | 516.3 |

TABLE 9-continued (Urea-Acids)

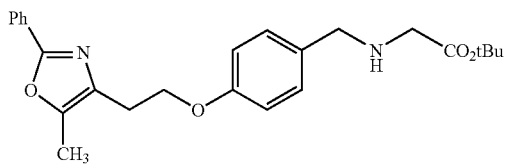

| Example No. | R³ᶠ | [M + H]⁺ |
|---|---|---|
| 409 | 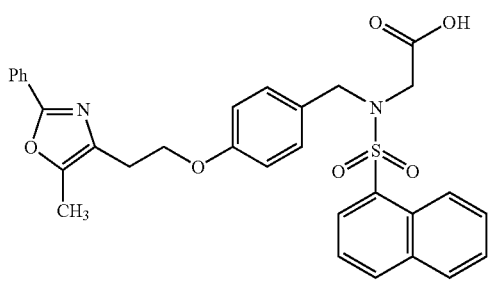 | 516.3 |

EXAMPLE 410

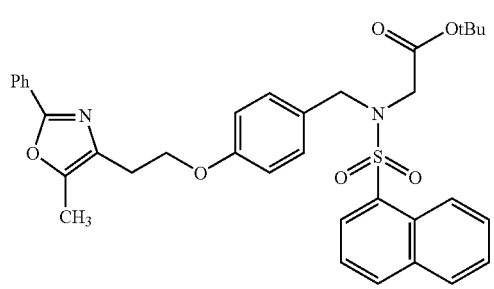

The title compound was prepared as part of a solution phase library run using the following procedure:

A.

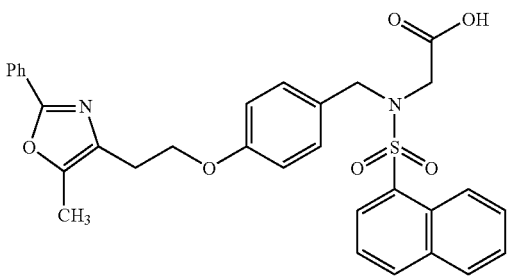

To a mixture of 1-naphthylsulfonyl chloride (26.8 mg, 0.12 mmol) and DMAP (2 mg, 0.016 mmol) in pyridine (2 mL) was added a solution of the amino-t-butyl ester (prepared as described in Example 8) (20 mg, 0.05 mmol) in pyridine (0.6 mL). The reaction was stirred at RT for 20 h. Resin-bound amine (WA21J, Supelco; 5.8 mmol/g loading;

150 mg) was added to the mixture. The reaction was stirred for a further 4 h. The resin was filtered off and the filtrate was concentrated in vacuo to give the crude product, which was chromatographed (CUSIL12M6 column; United technology; 2 g of sorbent in a 6 mL column) by the procedure outlined below.
1) The column was conditioned with hexane (20 mL).
2) The residue was dissolved in a minimal volume of EtOAc and loaded onto the silica gel column.
3) The cartridge was eluted with Hex/EtOAc(3:1), Hex/EtOAc (1:1). The desired fraction (identified by TLC) was collected and concentrated to give title compound as a viscous oil which was used in the next step without any further purification.

B.

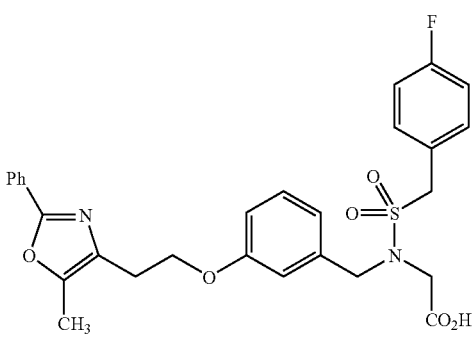

Et₃N ((0.3 ml of a 1M solution in CH₂Cl₂) and TMSI (0.3 ml of a 1M solution in CH₂Cl₂) were successively added to a solution of Part A compound in CH₂Cl₂. The reaction mixture was stirred at RT for 12 h and then was concentrated in vacuo to give the crude product. The product was purified by solid-phase extraction using a CHQAX12M6 column (United technology; 2 g of sorbent in a 6 mL column) by the procedure outlined below.
1) The column was conditioned with CH₂Cl₂ (25 mL).
2) The residue was dissolved in a minimal volume of CH₂Cl₂ and loaded onto the SAX column.
3) The cartridge was washed successively with CH₂Cl₂ (25 mL), CH₂Cl₂/MeOH (5% MeOH, 15 mL), CH₂Cl₂/MeOH (50% MeOH, 15 mL), MeOH (20 mL).
4) The product was eluted with a solution of 1% TFA in MeOH (20 mL).

The final product-containing fraction was collected and concentrated in vacuo using a Speed Vac to afford BMS-329075 (16 mg; 62%). Reverse-phase analytical HPLC indicated that the product purity was 90%. In addition, LC/MS (electrospray) gave the correct molecular ion [(M+H)⁺=557.1] for the desired compound.

EXAMPLE 411

-continued

A.

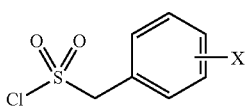

(X=halogen, alkyl, $CF_3$, $CF_3O$, ect.)

The following general procedure was utilized for the preparation of the requisite substituted benzyl sulfonyl chlorides:

$Cl_2$ gas was bubbled into a 0° C. solution of 4-fluorobenzyl mercaptan (1.0 g, Lancaster) in glacial acetic acid (100 mL) and $H_2O$ (5.0 mL) for 1 h. The reaction mixture was then poured into ice-$H_2O$ and immediately extracted with $CH_2Cl_2$ (200 mL); the organic phase was cautiously washed successively with $H_2O$ (200 mL), aqueous saturated $NaHCO_3$ (2×100 mL), and finally brine (200 mL). The organic phase was dried ($MgSO_4$) and concentrated in vacuo to furnish 4-fluorobenzyl sulfonyl chloride as a colorless solid (1.3 g; 89%).

B.

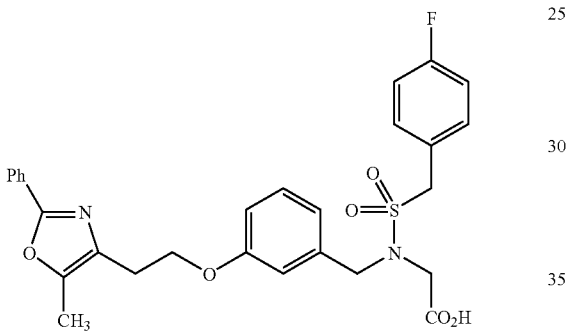

To a solution of the secondary amine methyl ester (25 mg; 0.066 mmol)

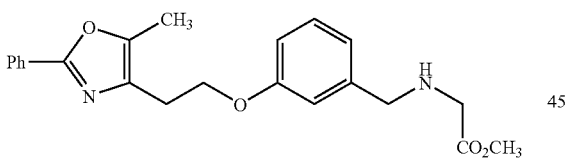

(prepared as described in Example 6), in pyridine (0.8 mL) was added 4-fluorobenzyl sulfonyl chloride (68 mg; 0.33 mmol; 5 equiv). The mixture was heated to 75° C., stirred overnight at 75° C., and then concentrated in vacuo. The black residue was treated with aqueous LiOH (1.0 mL of a 0.3 M solution) in $H_2O$/MeOH/THF for 18 h, then concentrated in vacuo. The residue was acidified with 1.0 M aqueous HCl to pH=1–2 and extracted with EtOAc (2×), dried ($Na_2SO_4$) and concentrated in vacuo to give the crude product. Purification by preparative HPLC (YMC S5 ODS 20 mm×250 mm reverse-phase column; 15 min continuous gradient from 60:40 A:B to 100% B with 10 min hold time, where A=90:10:0.1 $H_2O$:MeOH:TFA and B=90:10:0.1 MeOH:$H_2O$:TFA; flow rate=25 mL/min) gave the title compound (12 mg; 34%) as a white solid. $[M+H]^+$ (LC/MS)= 539.1

EXAMPLES 412 TO 456

Utilizing one of the above procedures, the analogs in Tables 10 and 11 were synthesized.

TABLE 10

(Sulfonamide-Acids)

| Example No. | $R^{3g}$ | $[M + H]^+$ |
|---|---|---|
| 412 | phenyl | 507.3 |
| 413 | 2,5-dichlorophenyl | 575.2 |
| 414 | 4-fluorophenyl | 525.2 |
| 415 | benzyl | 521.2 |
| 416 | cinnamyl (PhCH=CH-CH2-) | 533.2 |
| 417 | -CH2CF3 | 513.2 |
| 418 | 2,5-dimethylphenyl | 535.3 |
| 419 | 3,4-dichlorophenyl | 575.2 |
| 420 | 2,5-dichlorothien-3-yl | 581.1 |

TABLE 10-continued

(Sulfonamide-Acids)

Structure: 2-Phenyl-5-methyl-oxazole connected via ethyl-O to a meta-substituted phenyl bearing CH2-N(SO2R3g)-CH2CO2H

| Example No. | R3g | [M + H]+ |
|---|---|---|
| 421 | 5-(pyridin-2-ylsulfonyl)thiophen-2-yl | 590.3 |
| 422 | 3-(trifluoromethyl)benzyl | 589.2 |
| 423 | 3-methylbenzyl | 535.3 |
| 424 | 2-fluorobenzyl | 539.1 |
| 425 | 4-chlorobenzyl | 541.2 |
| 426 | 3,4-dichlorobenzyl | 589.0 |
| 427 | 2-chloro-6-fluorobenzyl | 573.2 |
| 428 | 4-chlorobenzyl | 555.2 |
| 429 | 2-chlorobenzyl | 555.3 |
| 430 | 2,4-dichlorobenzyl | 589.2 |
| 431 | 2-methylbenzyl | 535.3 |
| 432 | 4-(trifluoromethoxy)benzyl | 605.3 |
| 433 | 4-tert-butylbenzyl | 577.4 |

TABLE 11

(Sulfonamide-Acids)

Structure: 2-Phenyl-5-methyl-oxazole connected via ethyl-O to a para-substituted phenyl bearing CH2-N(SO2R3g)-CH2CO2H

| Example No. | R3g | [M + H]+ |
|---|---|---|
| 434 | 4-ethylbenzyl | 549.4 |

TABLE 11-continued

(Sulfonamide-Acids)

| Example No. | R³ᵍ | [M + H]⁺ |
|---|---|---|
| 435 | 1-naphthyl | 557.3 |
| 436 | phenyl | 506.3 |
| 437 | 2,4,6-trimethylphenyl | 549.3 |
| 438 | 4-chlorophenyl | 541.2 |
| 439 | benzyl | 521.3 |
| 440 | styryl (trans-2-phenylethenyl) | 533.3 |
| 441 | 2,5-dimethylphenyl | 535.4 |
| 442 | 3,4-dichlorophenyl | 575.3 |
| 443 | 4-(2-chloro-6-nitrophenoxy)phenyl | 678.3 |
| 444 | dibenzofuran-2-yl | 597.4 |
| 445 | 3-(trifluoromethyl)benzyl | 589.2 |
| 446 | 3-methylbenzyl | 535.3 |
| 447 | 2-fluorobenzyl | 539.1 |
| 448 | 4-fluorobenzyl | 539.1 |
| 449 | 3,4-dichlorobenzyl | 589.0 |
| 450 | 2-chloro-6-fluorobenzyl | 573.2 |

TABLE 11-continued (Sulfonamide-Acids)

[Structure: Ph-oxazole(CH3)-CH2CH2-O-C6H4-CH2-N(CH2CO2H)-SO2-R³ᵍ]

| Example No. | R³ᵍ | [M + H]⁺ |
|---|---|---|
| 451 | 4-Cl-benzyl | 555.2 |
| 452 | 2-Cl-benzyl | 555.3 |
| 453 | 2,4-diCl-benzyl | 589.2 |
| 454 | 2-CH3-benzyl | 535.3 |
| 455 | 4-OCF3-benzyl | 605.3 |
| 456 | 4-tBu-benzyl | 577.4 |

EXAMPLE 457

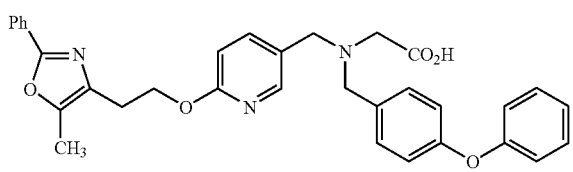

-continued

A.

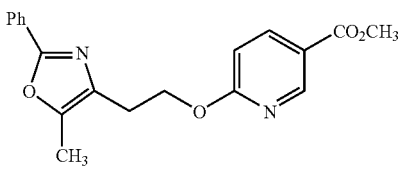

To a 0° C. solution of methyl 2-hydroxypyridine-5-carboxylate (0.2 g, 1.3 mmol), 2-(5-methyl-2-phenyloxazol-4-yl)ethanol (0.32 g, 1.56 mmol) and Ph₃P (0.38 g, 1.56 mmol) in CH₂Cl₂ (10 mL) was added DEAD (0.2 mL, 1.95 mmol) dropwise and the reaction was stirred at 25° C. for 12 h. The solution was concentrated in vacuo, and chromatographed on SiO₂ (4:1 hex:EtOAc) to provide title compound (0.28 g, 63%) as an oil.

B.

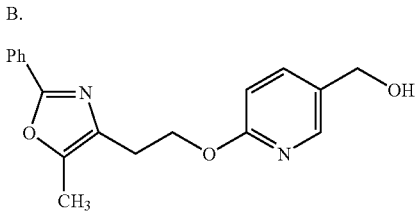

To a −78° C. solution of Part A compound (0.289., 0.82 mmol) in THF (10 mL) was added DIBALH (2.0 mL of a 1 M solution in CH₂Cl₂; 1.95 mmol) and the reaction was stirred at −78° C. for 4 h. TLC of an aliquot of the reaction showed the presence of both the corresponding aldehyde and alcohol. The reaction was warmed to 25° C. and stirred at RT for 1 h, after which only the alcohol was observed by TLC. The reaction was quenched with water and diluted with EtOAc. The organic layer was washed with brine, dried (MgSO₄), and concentrated in vacuo to furnish title compound as an oil. This crude material was used in the next reaction without further purification.

C.

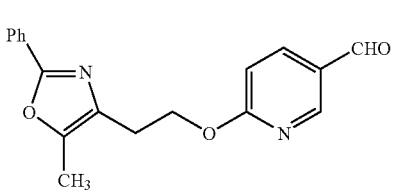

To a −78° C. solution of oxalyl chloride (0.22 mL, 2.6 mmol) and DMSO (0.37 mL, 5.2 mmol) in CH₂Cl₂ (15 mL) was added dropwise a solution of Part B compound (0.42 g of crude material in 5 mL CH₂Cl₂). The reaction mixture was stirred for 2 h at −78° C. and then Et₃N (1 mL) was added dropwise. The reaction mixture was stirred for an additional 0.5 h at −78° C. and then was slowly warmed to 25° C. The reaction mixture was diluted with EtOAc (200 mL) and washed successively with aqueous NaHCO₃ and brine. The organic layer was dried (MgSO₄), then concentrated in vacuo to provide title compound (0.40 g; 95%) as an oil, which was used in the next step without further purification.

D.

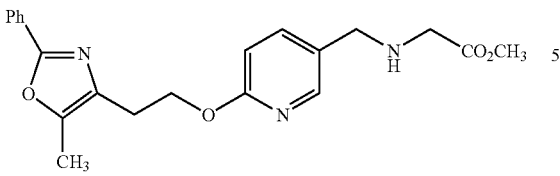

A mixture of Part C compound (<0.82 mmol), glycine methyl ester hydrochloride (0.5 g., 4.0 mmol), NaBH(OAc)$_3$ (0.85 g., 4.0 mmol) and DCE (10 mL) was stirred at 25° C. for 12 h. The reaction mixture was then diluted with EtOAc (50 mL) and washed successively with aqueous NaHCO$_3$ and brine. The organic layer was dried (MgSO$_4$), then concentrated in vacuo to give title compound (0.31 g; 82%) as an oil (>95% pure by analytical reverse-phase HPLC) which was used in the next step without further purification.

E.

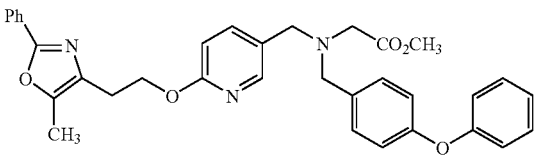

A mixture of Part D compound (0.050 g; 0.13 mmol), 4-phenoxybenzaldehyde (0.048 g; 0.26 mmol), NaBH(OAc)$_3$ (0.082 g; 0.39 mmol) in DCE (10 mL) was stirred at 25° C. for 12 h. The reaction mixture was diluted with EtOAc (50 mL) and washed successively with aqueous NaHCO$_3$ and brine. The organic layer was dried (MgSO$_4$), then concentrated in vacuo to give the tertiary amino methyl ester as an oily residue. To this residue, LiOH (0.050 g) and H$_2$O/THF (2 mL of a 60/40 solution) were added and the reaction was stirred at RT for 12 h. Preparative HPLC (YMC S5 ODS 30×250 mm column-continuous gradient over 30 min; flow rate=25 mL/min from 30:70 A:B to 100% B; A=90:10:0.1 H$_2$O:MeOH:CF$_3$CO$_2$H; B=90:10:0.1 MeOH:H$_2$O:CF$_3$CO$_2$H) provided title compound (0.021 g; 30%) as a TFA salt.

$^1$H NMR (CDCl$_3$) δ: 8.18 (s, 1H), 7.94 (d, 6.6 Hz, 2H), 7.86 (d, 8.8 Hz, 1H), 7.45 (m, 3H), 7.34 (m, 3H), 7.14 (t, 7.4 Hz, 1H), 7.02–6.92 (m, 5H), 6.81 (t, 8.8 Hz, 1H), 4.51 (m, 6H), 3.59 (s, 2H), 3.06 (t, 6.2 Hz, 2H)

EXAMPLE 458

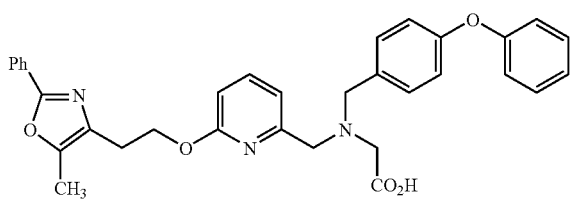

A.

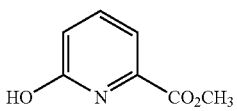

A mixture of 2-hydroxypyridine-6-carboxylic acid (1.30 g, 9.4 mmol), concentrated H$_2$SO$_4$ (0.5 mL) and MeOH (20 mL) was heated to reflux for 12 h. The reaction was complete at this point by analytical HPLC. The reaction mixture was concentrated in vacuo to give a light yellow oil, which was diluted with EtOAc and washed with aqueous NaHCO$_3$. The organic phase was dried (MgSO$_4$) and concentrated in vacuo to yield title compound as a solid (0.43 g, 30%).

B.

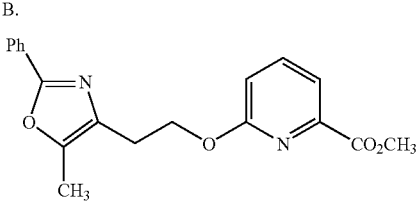

To a solution of Part A compound (0.43 g, 2.8 mmol), 2-(5-methyl-2-phenyloxazol-4-yl)ethanol (0.68 g, 3.3 mmol) and Ph$_3$P (1.0 g, 4.07 mmol) in THF (10 mL) was added DEAD (0.66 mL, 4.2 mmol) and the reaction was stirred at RT for 12 h. The solution was concentrated in vacuo and the residue was chromatographed (SiO$_2$; 20% acetone/hexanes) to provide title compound as an oil (0.92 g; 97%).

C.

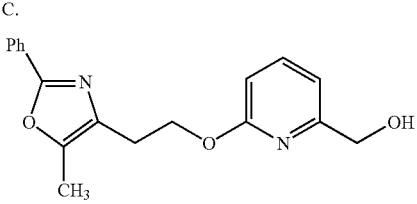

To a solution of Part B compound (0.92 g, 2.7 mmol) in THF (50 mL) was added LiAlH$_4$ (5 mL of a 1.0 M solution in THF, 5 mmol) dropwise at −78° C. and the resulting reaction was allowed to warm to 0° C. over 2 h. The reaction was then quenched by adding a few pieces of ice into the mixture. The reaction mixture was partitioned between EtOAc (200 mL) and brine (50 mL). The organic phase was dried (MgSO$_4$) and concentrated in vacuo to give an oil (0.92 g; 95%) which was used in the next reaction without further purification.

D.

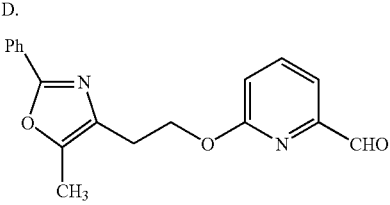

To a solution of oxalyl chloride (0.47 mL, 5.4 mmol) and DMSO (0.36 mL, 10.8 mmol) in CH$_2$Cl$_2$ (15 mL) was added dropwise a solution of Part C compound (0.92 g; >2.7 mmol) in CH$_2$Cl$_2$ (10 mL) at −78° C. The reaction mixture was stirred for 2 h and then Et$_3$N (1 mL) was added dropwise. The reaction mixture was allowed to stir for an additional 0.5 h at −78° C. and then slowly warmed to 25° C. The reaction mixture was then diluted with EtOAc (200 mL) and washed successively with aqueous NaHCO$_3$ and brine. The organic layer was dried (MgSO$_4$) and then concentrated in vacuo to yield title compound (0.90 g; >90% pure by $^1$H NMR analysis) as an oil. This material was used in the next step without further purification.

E.

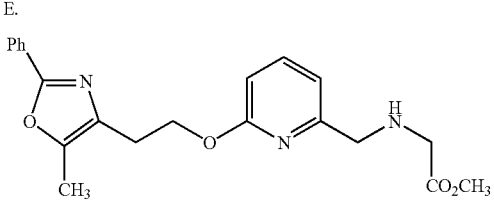

To a solution of Part D compound (0.90 g; 2.7 mmol), glycine methyl ester hydrochloride (1.7 g, 13.5 mmol) in 1,2 dichloroethane (10 mL) was added NaBH(OAc)$_3$ (1.7 g, 8.1 mmol) in one portion. The resulting solution was stirred at 25° C. for 12 h. The reaction mixture was concentrated in vacuo to give an oil, which was chromatographed (SiO$_2$; 30% acetone in hexane) to provide title compound (0.86 g; 83%) as a colorless oil.

F.

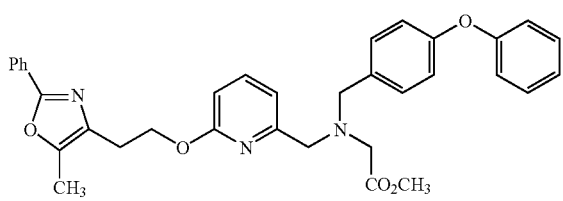

A solution of Part E compound (0.040 g, 0.1 mmol), 4-phenoxybenzaldehyde (0.030 g, 0.15 mmol) and NaBH(OAc)$_3$ (0.060 g, 0.3 mmol) in DCE (10 mL) was stirred at RT for 12 h. The reaction mixture was concentrated in vacuo and the oily residue was chromatographed (SiO$_2$; 30% acetone in hexane) to provide the amino-ester title compound (56 mg; >95%) as a colorless oil.

G.

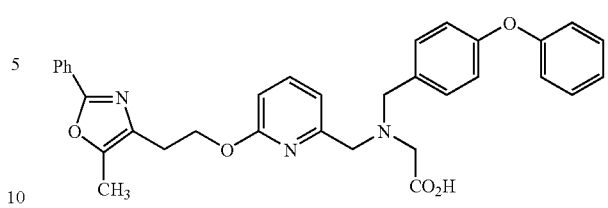

A solution of Part F compound (56 mg; 0.1 mmol) and LiOH (0.050 g; 0.21 mmol) in H$_2$O/THF (2 mL of a 6:4 solution) was stirred at RT for 12 h. The reaction mixture was concentrated in vacuo to give a white solid, which was dissolved in MeOH and purified by preparative HPLC (YMC S5 ODS 30×250 mm column; continuous gradient over 30 min; flow rate=25 mL/min from 30:70 A:B to 100% B; A=90:10:0.1 H$_2$O:MeOH:TFA; B=90:10:0.1 MeOH:H$_2$O:TFA). Title compound (41 mg; 72%) was obtained as a TFA salt.

$^1$H NMR (MeOH-D$_4$): 7.90 (m, 2H), 7.71 (t, 8.4 Hz, 1H), 7.51 (d, 8.7 Hz, 2H), 7.44 (m, 3H), 7.36 (t, 8.7 Hz, 2H), 7.17 (t, 8.4 Hz, 1H), 6.96 (m, 5H), 6.82 (d, 8.4 Hz, 1H), 4.62 (t, 6.2 Hz, 2H), 4.56 (s, 2H), 4.50 (s, 2H), 4.17 (s, 2H), 3.00 (t, 6.2 Hz, 2H), 2.36 (s, 3H). C$_{34}$H$_{31}$N$_3$O$_5$=550.23 (M+H$^+$) by LC/MS (electrospray).

EXAMPLE 459

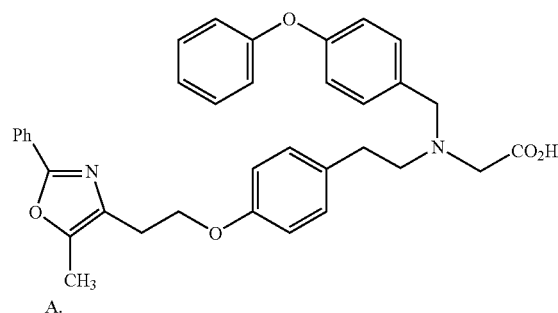

A.

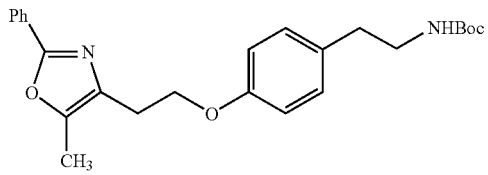

To a 0° C. solution of 2-(5-methyl-2-phenyloxazol-4-yl) ethanol (1.07 g, 5.25 mmol), Ph$_3$P (1.38 g, 5.25 mmol) and N-Boc-4-hydroxyphenylethylamine (1.24 g, 5.25 mmol) in THF (36 mL) was added DEAD (0.83 mL, 5.25 mmol). The reaction was allowed to warm to RT and stirred for 15 h. The reaction mixture was concentrated in vacuo, and the residue was chromatographed (SiO$_2$; stepwise gradient from 95:5 to 4:1 hex:EtOAc) to obtain title compound (1.43 g, 65%).

B.

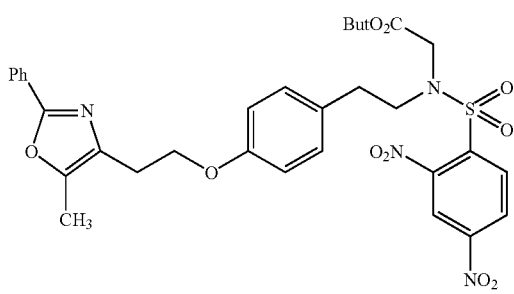

A solution of Part A compound (1.01 g, 2.37 mmol) and TFA (8 mL) in CH$_2$Cl$_2$ (30 mL) was stirred at RT for 4.5 h. The solution was concentrated in vacuo, and the residue was dissolved in CH$_2$Cl$_2$ and filtered through a pad of solid K$_2$CO$_3$. The filtrate was concentrated in vacuo to give the corresponding crude amine. To a solution of the crude amine in THF (11.9 mL) were added pyridine (0.383 mL, 4.74 mmol) and 2,4-dinitrobenzenesulfonyl chloride (0.85 g, 3.19 mmol) and the solution was stirred at RT for 15 h. Since some starting material still remained at this point, more sulfonyl chloride (0.32 g, 1.2 mmol) was then added. After a further 4 h, HPLC analysis indicated that all starting material had been consumed. The reaction mixture was diluted with Et$_2$O, washed with 1N aq HCl, saturated aq NaHCO$_3$ and brine, dried (MgSO$_4$), filtered and concentrated in vacuo to provide the crude 2,4-dinitrobenzenesulfonamide

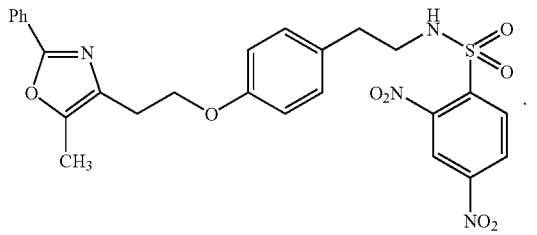

To a solution of the crude 2,4-dinitrobenzenesulfonamide in CH$_3$CN (3 mL) were added K$_2$CO$_3$ (excess) and tert-butyl bromoacetate (7.11 mmol). The reaction was stirred at RT overnight. HPLC analysis indicated the ratio of product to starting material was 2/1. More DMF (3 mL), K$_2$CO$_3$ and tert-butyl bromoacetate were added to the reaction mixture. The reaction was complete in 2 h. The reaction mixture was diluted with Et$_2$O, washed with 1N aq HCl, saturated NaHCO$_3$ and brine, dried (MgSO$_4$), and concentrated in vacuo to provide the crude tert-butyl ester. This crude material was chromatographed (SiO$_2$; hexanes/EtOAc; stepwise gradient from 9:1 to 2:1) to give title compound (0.663 g, 42% overall).

C.

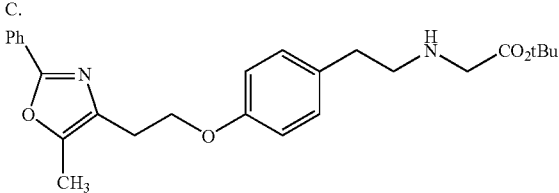

To a solution of Part B compound (0.663 g, 0.995 mmol) in THF (2.5 mL) were added Et$_3$N (0.208 mL, 1.49 mmol) and mercaptoacetic acid (0.090 mL, 1.29 mmol). The reaction was stirred at RT overnight. The reaction mixture was then diluted with Et$_2$O, washed with 1N aq HCl, saturated NaHCO$_3$ and brine, dried (MgSO$_4$), and concentrated in vacuo. The residue was chromatographed (SiO$_2$; hexanes/ EtOAc; stepwise gradient from 9:1 to 2:1) to give title compound (0.265 g, 61%).

D.

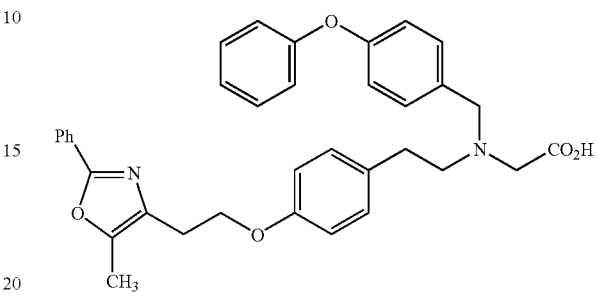

To a solution of Part C compound (0.015 g, 0.0344 mmol) in DCE (1 mL) were added 4-phenoxybenzaldehyde (0.103 mmol) and NaBH(OAc)$_3$ (0.0365 g, 0.172 mmol). The reaction was stirred at RT for 15 h. The reaction mixture was filtered through a cotton plug to provide a clear solution, which was diluted with CH$_2$Cl$_2$, washed with saturated aq NaHCO$_3$ and brine, dried (MgSO$_4$), and concentrated in vacuo. The crude product was purified by preparative HPLC (YMC S5 ODS 30×250 mm column: flow rate 25 mL/min, gradient 20% B to 100% B over 25 min, 100% B hold for 15 min, Retention time=29.1 min) to furnish the tert-butyl ester. A solution of this material was dissolved in CH$_2$Cl$_2$ (1.3 mL) and TFA (0.5 mL) was added slowly. The reaction was stirred at RT overnight and was then concentrated in vacuo. The residue was then dissolved in CH$_2$Cl$_2$, washed with H$_2$O, saturated aq NaHCO$_3$ and brine, dried (MgSO$_4$) and concentrated in vacuo to give title compound (0.012 g, 61%). LC/MS gave the correct [M+H]$^+$=563.3

Further analogs (as shown in the table below) were synthesized by the same reductive amination procedure as described in Example 459 Part D using Example 459 Part C compound and different aromatic aldehydes. In addition carbamate-acids such as Example 461 compound were also synthesized using the general method described previously for the synthesis of the Example 136 compound.

TABLE 12

| Example No. | R$^3$ | [M + H]$^+$ |
|---|---|---|
| 460 | | 571.3 |

TABLE 12-continued

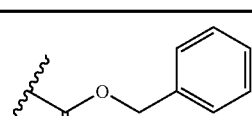

| Example No. | R³ | [M + H]⁺ |
|---|---|---|
| 461 | 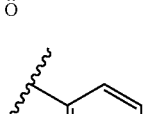 | 515.3 |
| 462 | 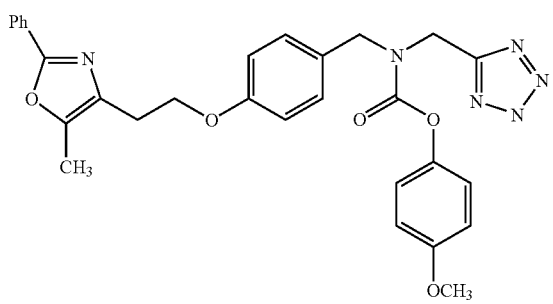 | 471.3 |

EXAMPLE 463

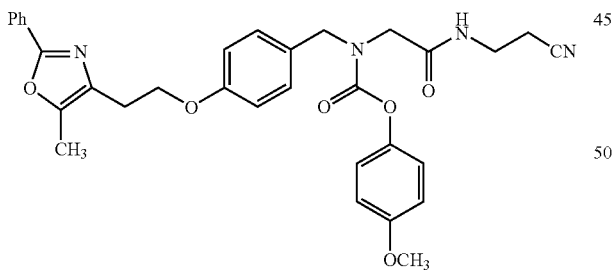

A.

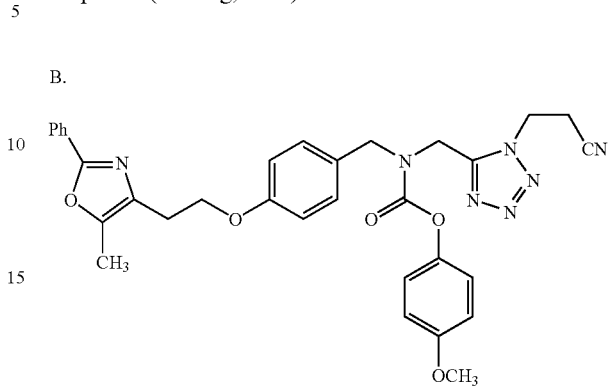

To a solution of the Example 230 acid (240 mg, 0.47 mmol) in DMF (2.0 mL) were added HOAT (68 mg, 0.49 mmol), EDAC (94 mg, 0.49 mmol) and 2-cyanoethylamine (34 mg, 0.49 mmol). The solution was stirred at RT for 18 h; analysis of the reaction by LC-MS showed that starting material was still present. Additional 2-cyanoethylamine (34 mg, 0.49 mmol) was added and the reaction mixture was stirred at RT for 48 h. Volatiles were removed in vacuo and the residue was dissolved in $CH_2Cl_2$ (40 mL) and washed successively with water (2×30 mL) and brine (30 mL). The organic phase was dried ($MgSO_4$) and concentrated in vacuo. The resulting white residue was dissolved in a minimum amount of $CH_2Cl_2$ (3 mL) and precipitation by the cautious addition of EtOAc furnished the amide product title compound (184 mg; 70%) as a white solid.

B.

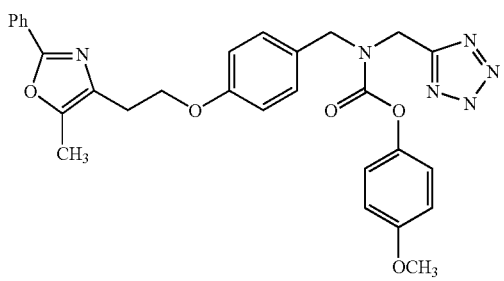

To a 0° C. solution of Part A compound (180 mg; 0.32 mmol) in $CH_2Cl_2$ (1.5 mL) were successively added $Ph_3P$ (83 mg; 0.32 mmol), DEAD (100 μL, 0.64 mmol) and $TMSN_3$ (85 uL, 0.64 mmol). The reaction mixture was stirred at RT for 24 h. LC-MS analysis showed that a significant amount of starting material still remained. The reaction mixture was then concentrated in vacuo to ⅔ of the original volume and additional $Ph_3P$, DEAD and $TMSN_3$ (1 equivalent of each reagent) were added. The reaction mixture was stirred at RT for another 24 h and then diluted with EtOAc (40 mL). The solution was treated with 5% aqueous CAN solution (10 mL) and stirred for 15 min. The reaction solution was washed with water (30 mL) and brine (30 mL), dried ($MgSO_4$) and concentrated in vacuo. The residue was chromatographed ($SiO_2$; ether:$CH_2Cl_2$ 3:7) to furnish the title compound (100 mg; 53%) as a white solid.

C.

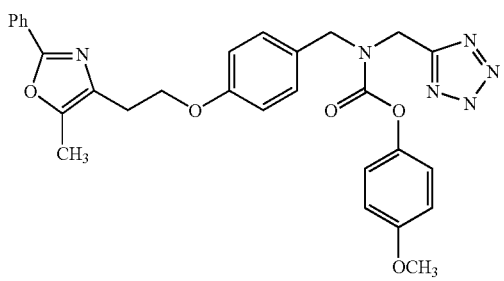

To a solution of Part B compound (100 mg, 0.17 mmol) in THF/1,4-dioxane (6:1, 1.4 mL) was added aqueous NaOH solution (0.6 mL of a 1.0 M solution, 3.5 equiv). The mixture was stirred at RT for 14 h and then acidified to ~pH2 with 1.0 M aqueous $H_3PO_4$ solution. EtOAc (30 mL) was added, and the organic phase was washed with water (15 mL) and brine (15 mL), dried ($MgSO_4$) and concentrated in vacuo. The residue was chromatographed ($SiO_2$; 4% MeOH/$CH_2Cl_2$) to give the title tetrazole (35 mg; 38%) as a white foam. LC/MS (electrospray) gave the correct molecular ion: $[M+H]^+=541.3$

EXAMPLE 464

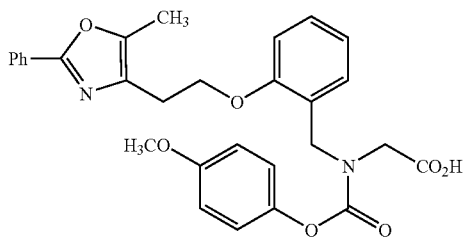

A.

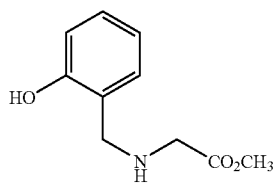

A mixture of 2-hydroxybenzaldehyde (500 mg, 4.09 mmol), glycine methyl ester hydrochloride (544 mg, 4.09 mmol) and Et$_3$N (495 mg, 4.9 mmol) in dry MeOH (5 mL) was stirred at RT for 3 h. NaBH$_4$ (155 mg, 4.09 mmol) was then added in three portions. The reaction was stirred at RT for another 30 min. Saturated aqueous Na$_2$CO$_3$ (1 mL) was added to destroy the remaining NaBH$_4$ and then aqueous HCl (10 mL of a 1N solution) was added. The aqueous phase was washed with EtOAc (3×20 mL), then carefully basified with 1N aq NaOH to pH=7–8. The aqueous phase was then extracted with EtOAc (3×20 mL). The orange-red solution was concentrated in vacuo to give title compound as a yellow viscous oil.

B.

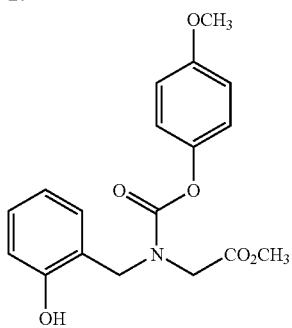

Part A compound (38 mg, 0.195 mmol), 4-methoxyphenyl chloroformate and pyridine (39 mg, 5 mmol) was dissolved in 0.1 mL CH$_2$Cl$_2$, for 5 min. The reaction mixture was then washed with aqueous HCl (2×2 mL of a 1N solution). The organic phase was washed with brine, dried (Na$_2$SO$_4$), concentrated in vacuo and chromatographed (SiO$_2$; hex:EtOAc=7:3) to give title compound (40 mg; 59%) as a pale yellow oil.

C.

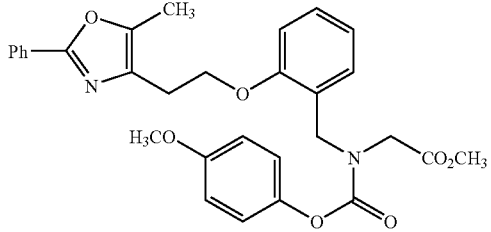

To a solution of Part B compound (40 mg, 0.116 mol), 2-[2-phenyl-5-methyl-oxazole-4-yl]-ethanol (Maybridge; 24 mg, 0.116 mmol) and Ph$_3$P (40 mg, 0.151 mol) in dry THF (3 mL) was added dropwise DEAD (26 mg, 0.151 mmol). The solution was stirred at RT overnight. The orange-red solution was concentrated in vacuo and the residue was purified by Prep-HPLC (continuous gradient from 50% A:50% B to 100% B; A=90% H$_2$O :10% MeOH+ 0.1% TFA); (B 90% MeOH/10% H$_2$O+0.1% TFA) for 10 min; YMC SH-343-5 ODS 20×100 mm (5 µm) column) to provide title compound (30 mg, 47%) as a yellow viscous oil.

D.

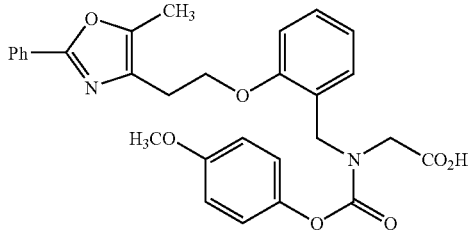

Part C compound was dissolved in MeOH (3 mL) and H$_2$O (0.3 mL). To this solution was added LiOH (3 mg) and the reaction was stirred at RT for 3 h. Volatiles were removed in vacuo and the solution was acidified with 1N aqueous HCl to pH=~3–4. The aqueous phase was extracted with EtOAc (3×10 mL). The combined organic extracts were washed with brine, dried (Na$_2$SO$_4$) and concentrated in vacuo to give title compound as a white solid (18 mg; 64%). LC/MS (electrospray) gave the correct molecular ion [(M+H)$^+$= 516].

$^1$H NMR (δ): 2.27–2.32 (m, 3H), 2.96–2.98 (m, 2H), 3.65–3.69 (d, 3H), 4.06–4.20 (m, 4H), 4.55–4.63 (d, 2H), 6.74–6.93 (m, 4H), 7.19–7.35(m, 2h), 7.88–7.90 (m, 2H).

EXAMPLE 465

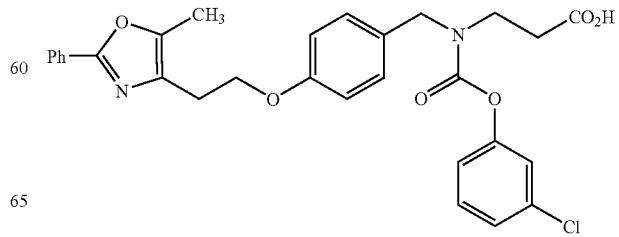

A.

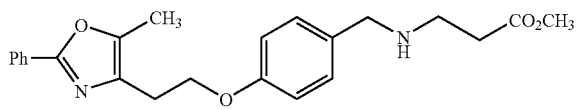

A mixture of β-alanine methyl ester hydrochloride (51 mg; 0.363 mmol), Et₃N (50 μL; 0.363 mmol) and the aldehyde (100 mg; 0.33 mmol)

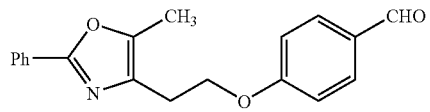

in MeOH (1 mL) was stirred at RT for 3 h. NaBH₄ (14 mg; 0.363 mmol) was then added and the reaction was stirred at RT for another 1 h. Volatiles were removed in vacuo and the residue was partitioned between saturated aqueous Na₂CO₃ and EtOAc (20 mL each). The organic phase was concentrated in vacuo to give Part A compound as a yellow oil which was used in the next step without further purification.

B.

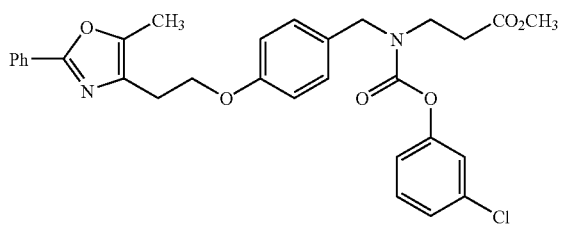

To a solution of Part A compound (20 mg; 0.050 mmol) and pyridine (0.50 mL) in CH₂Cl₂ (2 mL) was added 3-chlorophenyl chloroformate (14 mg; 0.070 mmol). The reaction was stirred at RT for 2 h, then volatiles were removed in vacuo. The residue was purified by preparative HPLC (YMC S5 ODS 20×75 mm reverse phase column; continuous gradient from 50:50 A:B to 100% B, where A=90:10:0.1 H₂O:MeOH:TFA and B=90:10:0.1 MeOH:H₂O:TFA) to give Part B compound.

C.

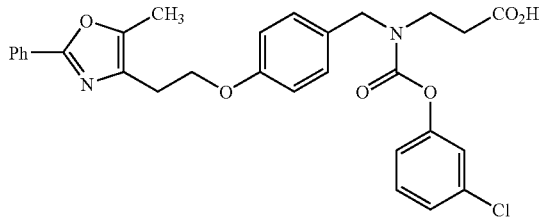

A solution of Part B compound and LiOH.H₂O (5 mg) in THF:H₂O (4:1) was stirred at RT for 1 h. The reaction solution was acidified to pH3 with aqueous HCl, then extracted with EtOAc. The combined organic extracts were concentrated in vacuo to give title compound (5 mg; 18%) as a white solid. [M+H]⁺=535.2; 537.2

EXAMPLE 466

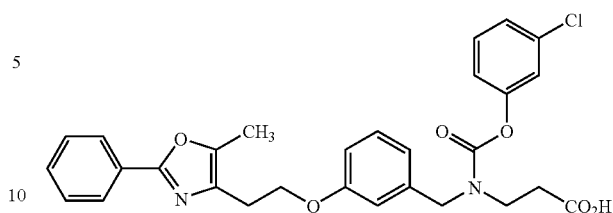

Title compound was synthesized using the same sequence as in Example 465 with the exception that the aldehyde

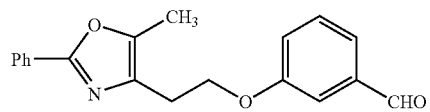

was used. [M+H]⁺=535.2; 537.2

Following procedures as described above, Examples 467 to 472 compounds were prepared.

EXAMPLES 467 TO 469

| Example No. | R³ | [M + H]⁺ |
|---|---|---|
| 467 | ![structure] | 501.3 |
| 468 | ![structure] | 563.3 |
| 469 | ![structure] | 515.3 |

EXAMPLES 470 TO 472

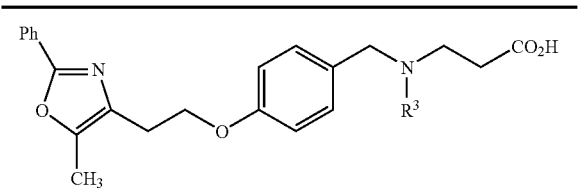

| Example No. | R³ | [M + H]⁺ |
|---|---|---|
| 470 | 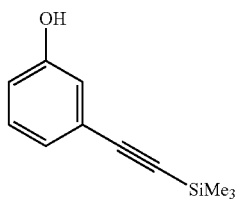 | 501.3 |
| 471 | | 563.3 |
| 472 | 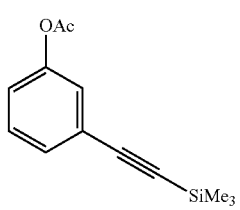 | 515.3 |

EXAMPLE 473

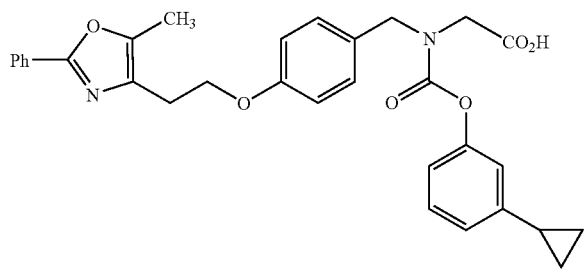

A.

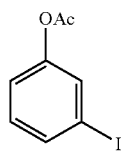

A mixture of 3-iodophenol (2.0 g; 9.1 mmol), acetic anhydride (4.6 g; 45.5 mmol) and pyridine (3.6 g; 45.5 mmol) was stirred in $CH_2Cl_2$ (20 mL) for 3 h. The resulting mixture was washed with saturated aqueous $NH_4Cl$ (3×100 mL), dried ($MgSO_4$) and concentrated in vacuo to give Part A compound (2.30 g; 97%) as a yellow oil.

B.

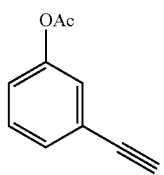

A mixture of Part A compound (1.00 g; 4.0 mmol), trimethylsilylacetylene (780 mg; 8 mmol), CuI (15 mg; 0.08 mmol) and $(Ph_3P)_2Pd_2Cl_2$ (28 mg; 0.04 mmol) in diethylamine (10 mL) was stirred at RT for 3 h. Volatiles were removed in vacuo and the residue was chromatographed ($SiO_2$; hexane:EtOAc 4:1) to give crude Part B compound, which was used in the next step without further purification.

C.

To a solution of crude Part B compound in $CH_2Cl_2$ (2 mL) were added pyridine (3 mL; 37 mmol)) and acetic anhydride (4 mL; 42 mmol). The reaction was stirred at RT for 2 h, then was partitioned between saturated aqueous $NH_4C$ (30 mL) and $CH_2Cl_2$. The organic phase was washed with additional saturated aqueous $NH_4Cl$ (30 mL) and $H_2O$ (100 mL), dried ($Na_2SO_4$) and concentrated in vacuo to give Part C compound, which was used in the next step without further purification.

D.

A solution of crude Part C compound and $Bu_4NF$ (1.1 g; 12 mmol) in THF (10 mL) was stirred at RT for 1.7 h, after which all starting material had been consumed. The reaction solution was washed with $H_2O$, Celite® was added, and volatiles were removed in vacuo. The solids were chromatographed ($SiO_2$; hexane:EtOAc 9:1) to give Part D compound (400 mg; 63% over 3 steps).

E.

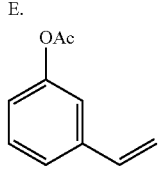

A mixture of Part D compound (400 mg; 2.5 mmol) and Pd/CaCo₃/Pb catalyst (40 mg; Aldrich) in MeOH (20 mL)

was stirred under an atmosphere of H$_2$ for 30 min. The mixture was filtered through Celite® and the filtrate was concentrated in vacuo. The residue was chromatographed (SiO$_2$; hexane:EtOAc 95:5) to give Part E compound (310 mg; 77%) as a colorless oil.

F.

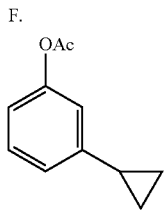

To a 0° C. solution of Part E compound (310 mg; 1.9 mmol) in DCE (10 mL) were successively added dropwise neat diethylzinc (491 µL; 4.8 mmol; Aldrich) and ICH$_2$Cl (700 µL; 9.6 mmol). The reaction mixture was allowed to warm to RT and then stirred at RT for 3 h, after which it was partitioned between saturated aqueous NH$_4$Cl and EtOAc (50 mL each). The organic phase was washed with saturated aqueous NH$_4$Cl and H$_2$O (50 mL each) and concentrated in vacuo. The residue was chromatographed (SiO$_2$; hexane:EtOAc 9:1) to furnish Part F compound (230 mg; 69%) as a colorless oil.

G.

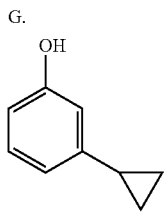

A mixture of Part F compound (100 mg; 0.57 mmol) and K$_2$CO$_3$ (157 mg; 1.1 mmol) in MeOH (5 mL) was stirred at RT overnight (no reaction). Aqueous LiOH (1.1 mL of a 1 M solution; 1.1 mmol) was added and the solution was stirred at RT overnight. Volatiles were removed in vacuo and the residue was partitioned between aqueous 1 M HCl and EtOAc. The organic phase was concentrated in vacuo and the residue was chromatographed (SiO$_2$; hexane:EtOAc 4:1) to furnish Part G compound (70 mg; 92%) as a yellow oil.

H.

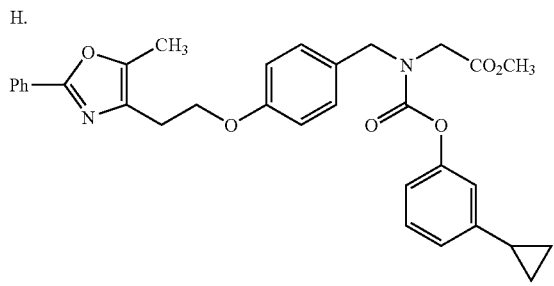

To a solution of Part G compound (6 mg; 0.045 mmol) in DMF (0.2 mL) was added potassium t-butoxide (5 mg; 0.05 mmol). The reaction was stirred for 2 min at RT, after which the carbamoyl chloride (20 mg; 0.045 mmol)

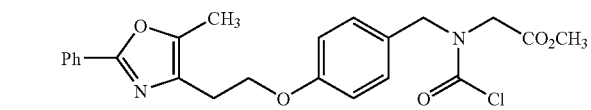

was added and the reaction was stirred at RT for a further 15 min. Volatiles were then removed in vacuo and the residue was chromatographed (SiO$_2$; hexane:EtOAc 7:3) to furnish Part H compound (11 mg; 45%) as a yellow oil.

I.

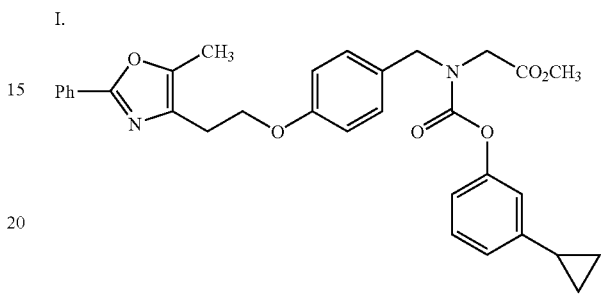

A solution of Part H compound and LiOH.H$_2$O in MeOH/H$_2$O (10 mL of a 9:1 mixture) was stirred at RT overnight. The solution was then acidified to pH~3 with aqueous HCl and extracted with EtOAc. The combined organic extracts were concentrated in vacuo and purified by preparative HPLC to give title compound (10.1 mg; 95%) as an off-white lyophilate. [M+H]$^+$=527.3

EXAMPLE 474

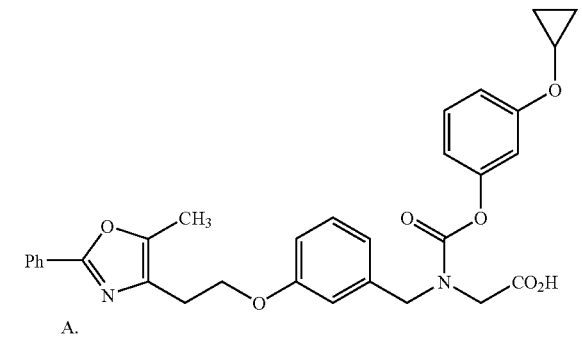

A.

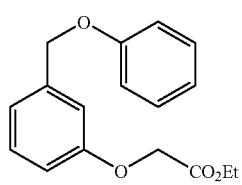

A mixture of 3-benzyloxybenzaldehyde (2.00 g; 1.0 mmol), ethyl bromoacetate (1.67 g; 1.0 mmol) and Cs$_2$CO$_3$ (3.25 g; 1.0 mmol) in DMF (20 mL) was stirred at RT for 8 h. The reaction mixture was partitioned between H$_2$O (300 mL) and EtOAc (100 mL). The aqueous phase was extracted with EtOAc (2×100 mL). The combined organic extracts were washed with brine, dried (Na$_2$SO$_4$) and concentrated in vacuo. The residue was chromatographed (SiO$_2$; 85:15 hex:EtOAc) to obtain Part A compound (3.48 g; >100%) as a colorless oil.

B.

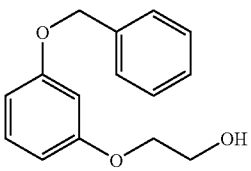

To a solution of Part A compound (3.4 g; 11.9 mmol) in dry THF (50 mL) under Ar was added LiAlH$_4$ (36 mL of a 0.5 M solution in THF; 17.8 mmol) dropwise. The reaction was stirred at RT for 1 h. The reaction was quenched by slow addition of saturated aqueous NH$_4$CL (1 mL). Volatiles were removed in vacuo and the residue was partitioned between EtOAc (100 mL) and 1 M aqueous HCl. The organic phase was dried (Na$_2$SO$_4$) and concentrated in vacuo to give Part B compound (2.4 g; 98%) as a white solid.

C.

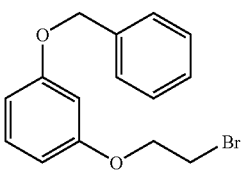

To a solution of Part B compound (2.4 g; 9.8 mmol) and Ph$_3$P (3.1 g; 14.7 mmol) in CH$_2$Cl$_2$ was added CBr$_4$ (4.80 g; 14.7 mmol). The reaction was stirred at RT overnight, then concentrated in vacuo. The residue was chromatographed (SiO$_2$; 95:5 hex:EtOAc) to give Part C compound (2.8 g; 93%) as a white solid.

D.

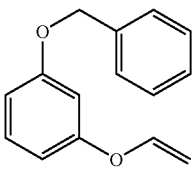

A mixture of Part C compound (310 mg; 1.0 mmol) and potassium tert-butoxide (113 mg; 2.0 mmol) in toluene (20 mL) was heated at 105° C. for 20 min. Additional KOtBu (56 mg; 1.0 mmol) was added and the reaction heated at 105° C. for another 10 min. The mixture was cooled to RT and partitioned between H$_2$O (100 mL) and EtOAc (100 mL). The organic phase was washed with H$_2$O (2×100 mL), dried (Na$_2$SO$_4$) and concentrated in vacuo. The reaction was repeated with additional Part C compound (500 mg; 1.63 mmol) and KOtBu (182 mg; 16 mmol). The combined crude reaction products were chromatographed (SiO$_2$; hexane) to give Part D compound (590 mg; 89%) as a colorless oil.

E.

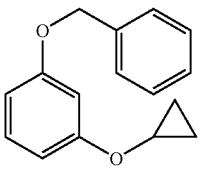

To a 0° C. solution of Part D compound (1.4 g; 62 mmol) in DCE (100 mL) was added neat diethylzinc (1.6 mL; 16 mmol) dropwise, followed by ICH$_2$Cl (5.46 g; 31 mmol). The reaction mixture was allowed to warm to RT and stirred at RT overnight, then washed with 1M aqueous HCl. The organic phase was dried (Na$_2$SO$_4$) and concentrated in vacuo. The crude residue was chromatographed twice (SiO$_2$; hexane) to give Part E compound (510 mg; 30%) in addition to recovered starting material Part D compound (250 mg; 18%).

F.

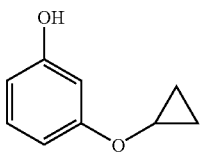

To a −78° C. solution of Part E compound (510 mg; 2.2 mmol) in liquid NH$_3$ (30 mL) was added Na (500 mg; 22 mmol). The dark blue solution was stirred at −78° C. for 4 h, then was allowed to warm to RT overnight. The remaining solid residue was partitioned between 1 M aqueous HCl and EtOAc (50 mL each). The organic phase was dried (Na$_2$SO$_4$) and concentrated in vacuo. The crude product was chromatographed (SiO$_2$; 9:1 hexane:EtOAc) to give Part F compound (240 mg; 75%) as a yellow oil.

G.

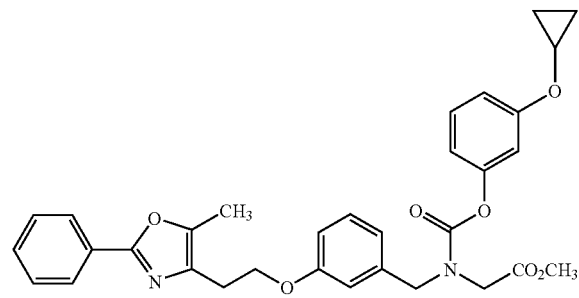

To a solution of Part F compound (150 mg; 1.0 mmol) in DMF (10 mL) were successively added KOtBu (112 mg; 1.0 mmol) and a solution of the following carbamoyl chloride (44 mg; 1.0 mmol) in DMF (0.5 mL).

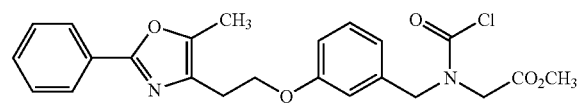

(prepared as described in Examples 5 and 139). The reaction was stirred at RT for 15 min, after which analytical HPLC indicated that all starting material had been consumed. The mixture was partitioned between H$_2$O and EtOAc (100 mL each). The organic phase was washed with H$_2$O (2×100 mL), dried (Na$_2$SO$_4$) and concentrated in vacuo. The crude product was chromatographed (SiO$_2$; 9:1 hexane:EtOAc) to give impure Part G compound as a yellow oil.

H.

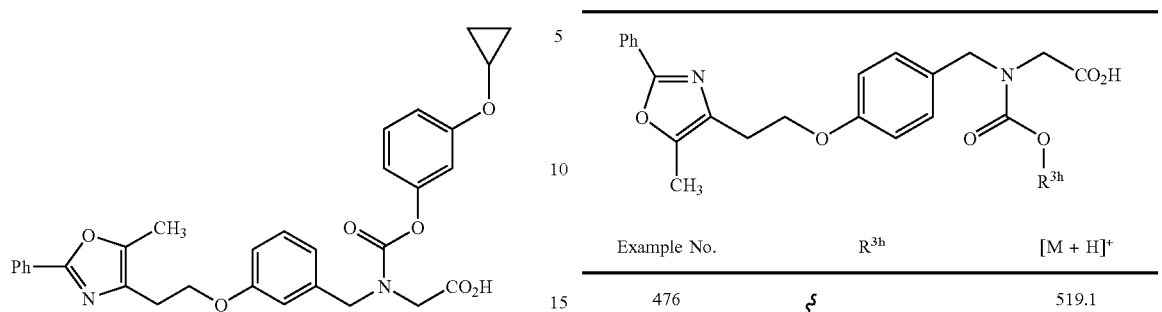

A solution of Part G compound (556 mg; 1.0 mmol) and LiOH.H₂O (116 mg; 2.8 mmol) in 10:1 MeOH:H₂O (10 mL) was stirred at RT for 2 h. Volatiles were removed in vacuo and the residue was acidified to pH2 with aqueous 1 M HCl, then extracted with EtOAc (3×40 mL). The combined organic extracts were dried (Na₂SO₄) and concentrated in vacuo. The crude product was purified by preparative HPLC (YMC S5 ODS 50×250 mm column; flow rate=25 mL/min; continuous 20 min gradient from 70:30 B:A to 100% B, where A=90:10:0.1 H₂O:MeOH:TFA and B=90:10:0.1 MeOH:H₂O:TFA) to give (120 mg; 30% over 2 steps) as a colorless oil. [M+H]⁺=543.2

EXAMPLE 475

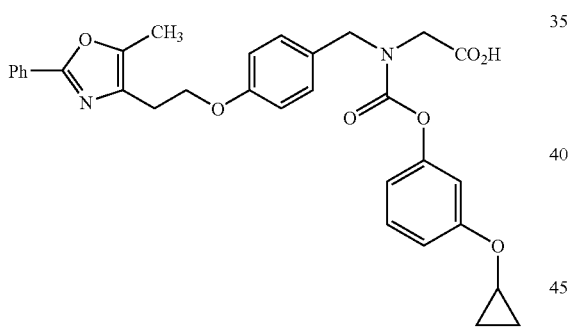

Title compound was synthesized from Example 474 Part F compound (150 mg; 1.0 mmol) and the carbamoyl chloride (440 mg; 1.0 mmol)

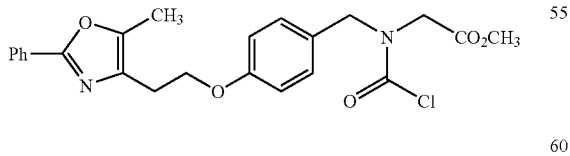

(prepared as described in Examples 6 and 139) followed by LiOH/H₂O hydrolysis in the same manner as in Example 474. The title compound was isolated and purified as a colorless oil (340 mg; 92% over 2 steps). [M+H]⁺=543.3

Following the procedures described above, the Examples 476 to 494 compounds were prepared.

EXAMPLES 476 TO 484

![General structure with R³ʰ substituent on oxazole-containing scaffold]

| Example No. | R³ʰ | [M + H]⁺ |
|---|---|---|
| 476 | 4-(3-F, 4-CH₃)phenyl | 519.1 |
| 477 | 4-(3-Cl, 4-CH₃)phenyl | 535.1 |
| 478 | 4-(3-Br, 4-CH₃)phenyl | 579.1; 581.0 |
| 479 | 4-(3-F, 4-OCH₃)phenyl | 535.3 |
| 480 | 4-(3-Cl, 4-OCH₃)phenyl | 551.3 |
| 481 | 4-(3-Br, 4-OCH₃)phenyl | 595.3; 597.3 |

-continued
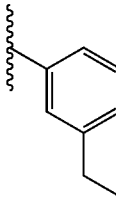
| Example No. | R^{3h} | [M + H]^+ |
|---|---|---|
| 482 | 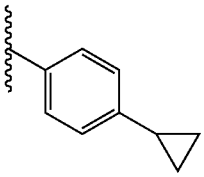 | 529.3 |
| 483 | 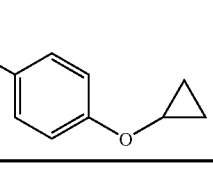 | 527.3 |
| 484 | 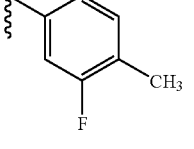 | 543.4 |
EXAMPLES 485 TO 494
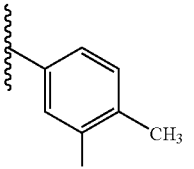
| Example No. | R^{3h} | [M + H]^+ |
|---|---|---|
| 485 | 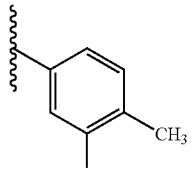 | 519.1 |
| 486 | 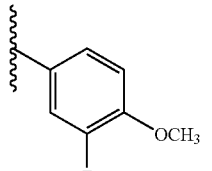 | 535.1 |
-continued
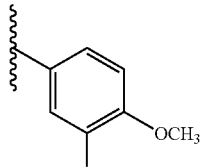
| Example No. | R^{3h} | [M + H]^+ |
|---|---|---|
| 487 | 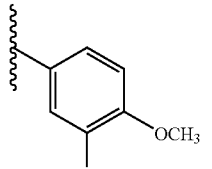 | 579.1; 581.0 |
| 488 | 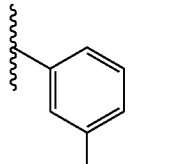 | 535.3 |
| 489 | 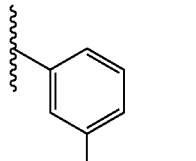 | 551.3 |
| 490 | | 595.2; 597.2 |
| 491 | | 529.3 |
| 492 | | 527.3 |

-continued

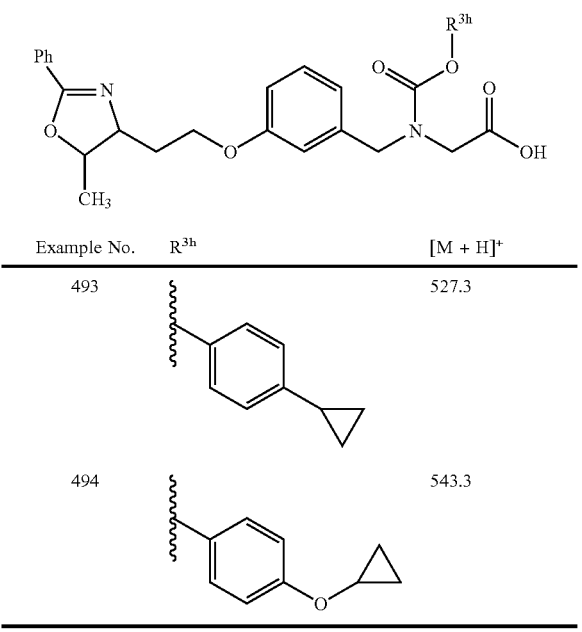

| Example No. | R³ʰ | [M + H]⁺ |
|---|---|---|
| 493 | 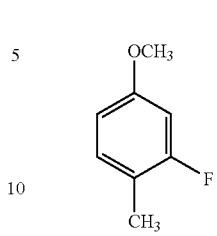 | 527.3 |
| 494 | 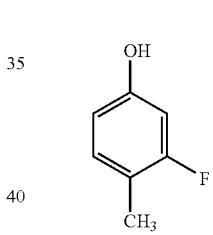 | 543.3 |

EXAMPLE 492

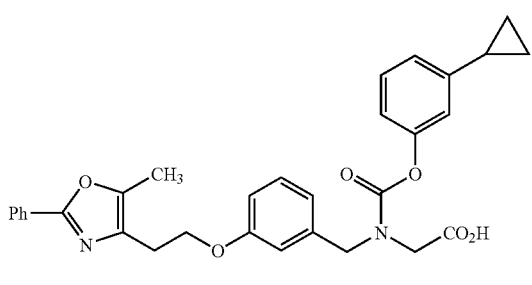

Example 492 was synthesized according to the procedures described hereinbefore.

¹H NMR (CDCl₃; 400 MHz): δ 0.68 (t, J=4.4 Hz; 2H), 0.94 (t, J=4.4 Hz; 2H), 1.87 (m, 1H), 2.42 (s, 3H), 3.06 (s, 2H), 4.02 (t, J=5.2 Hz, 2H), 4.22 (t, J=5.2 Hz, 2H), 4.60 (2 peaks, 2H), 6.84–6.89 (m, 4H), 7.15–7.26 (m, 4H) 7.40–7.47 (m, 3H), 7.98–8.00 (m, 2H).

The required (commercially unavailable) phenols and chloroformates for the synthesis of the above carbamate-acid analogs were prepared as follows:

3-Fluoro-4-methyl-phenyl chloroformate

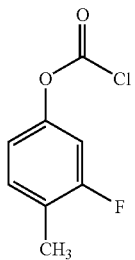

-continued

A.

A mixture of 5-methoxy-2-methyl aniline (5.0 g; 36 mmol), HCl (7.6 mL of a 12 M solution; 91 mmol) and H₂O (11 mL) was heated at 60° C. for 15 min until complete dissolution had occurred. The reaction was cooled to 0° C. and an aqueous solution of NaNO₂ (2.5 g; 36 mmol) was added dropwise (internal temperature ≦7° C.). The reaction was stirred at 0° C. for 30 min and a 0° C. solution of HBF₄ (5.3 mL of a 48% solution; 40 mmol) was added cautiously. The reaction was stirred at 0° C. for 20 min, and the resultant brown solid was filtered, washed with ice water (3×10 mL) and H₂O (2×10 mL). The solid was dried under high vacuum for 20 h, then heated (heat gun) until evolution of BF₃ (white fumes) had ceased. The resulting brown oil was partitioned between EtOAc and H₂O. The organic phase was dried (Na₂SO₄), concentrated in vacuo and distilled by Kugelrohr to give 3-fluoro-4-methyl anisole (1.6 g; 31%) as a colorless oil.

B.

To a −70° C. solution of 3-fluoro-4-methyl anisole (1.62 g; 11.6 mmol) in CH₂Cl₂ (10 mL) was added dropwise BBr₃ (10 mL; 12 mmol). The reaction mixture was stirred at −70° C. for 10 min, then allowed to warm to 0° C. and stirred at 0° C. for 2 h. The reaction was allowed to warm to RT and concentrated in vacuo and the residue was partitioned between H₂O and EtOAc. The organic phase was washed with H₂O, dried (Na₂SO₄) and concentrated in vacuo to give 3-fluoro-4-methyl phenol (1.1 g; 75%) as an oil.

A solution of 3-fluoro-4-methyl phenol (1.1 g; 8.7 mmol), phosgene (5.9 mL of a 1.93 M solution in toluene; 8.7 mmol), DMF (10 μL) and N,N-dimethylaniline (1.27 g; 8.7 mmol) in chlorobenzene (10 mL) in a sealed tube was stirred at RT for 2 h, then at 80° C. for 2 h. The reaction was cooled to RT, stirred for RT for 1 h, then was concentrated in vacuo. The residue was distilled by Kugelrohr to furnish 3-fluoro-4-methyl phenyl chloroformate (800 mg; 49%) as a clear oil.

3-chloro-4-methyl-phenyl chloroformate

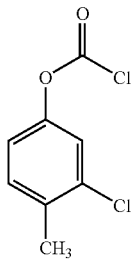

3-chloro-4-methyl phenyl chloroformate (600 mg; 45% overall for 2 steps) was synthesized from 3-chloro-4-methyl anisole (1.0 g) using the same route (BBr$_3$-mediated methyl ether cleavage followed by treatment with phosgene) as above.

3-bromo-4-methyl-phenyl chloroformate

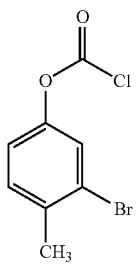

To a 0° C. mixture of 3-bromo-4-methyl aniline (5 g; 27 mmol) and H$_2$SO$_4$ (5.5 mL of a 16 M solution) in H$_2$O (7.5 mL) was added dropwise a solution of aqueous NaNO$_2$ (1.93 g; 28 mmol in 7.5 mL H$_2$O). The reaction was stirred at 0° C. for 30 min, then was heated at 50° C. for 2 h, then was cooled to RT and extracted with EtOAc (2×). The combined organic extracts were washed with H$_2$O, dried (Na$_2$SO$_4$) and concentrated in vacuo to give 3-bromo-4-methyl phenol (1.72 g; 34%) as an oil. This phenol was converted to 3-bromo-4-methyl phenyl chloroformate (1.9 g; 82%) using the same procedure (phosgene/dimethylaniline/heat) as for 3-fluoro-4-methyl phenyl chloroformate above.

2-Methoxyphenyl chloroformate (1.5 g) and 3-methoxyphenyl chloroformate (1.5 g) were both synthesized in the same way as for 3-fluoro-4-methyl phenyl chloroformate (phosgene/dimethylaniline/heat) from 2-methoxyphenol (2 g) and 3-methoxyphenol (2 g) respectively.

3-chloro-4-methoxy phenol

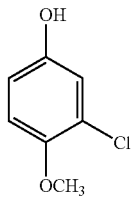

To a 0° C. solution of 3-chloro-4-methoxy aniline (1.0 g; 6.4 mmol) in 1:1 H$_2$O:conc. H$_2$SO$_4$ (100 mL) was added very slowly a solution of NaNO$_2$ (0.5 g; 7.6 mmol) in H$_2$O (10 mL). Thick yellow fumes were emitted, and the black solution was then heated to reflux for 30 min. The mixture was extracted with EtOAc (4×50 mL) and the combined extracts were concentrated in vacuo. The residue was chromatographed (SiO$_2$; 4:1 hex:EtOAc) to obtain 3-chloro-4-methoxy phenol (300 mg; 30%) as a yellow oil.

3-Fluoro-4-methoxy-phenol

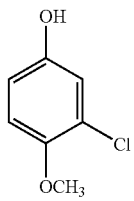

A solution of 3'-fluoro-4'-methoxyacetophenone (10 g; 59 mmol) and m-chloroperbenzoic acid (50% purity; 30 g; 89 mmol) in CH$_2$Cl$_2$ (300 mL) was stirred at RT overnight. The solution was washed with saturated aqueous Na$_2$CO$_3$, then filtered through a pad of SiO$_2$ (CH$_2$Cl$_2$ as eluent) and finally chromatographed (SiO$_2$; hex:EtOAc 4:1) to give the crude product (3'-fluoro-4'-methoxy phenyl acetate; 63 g). A solution of this crude material and LiOH.H$_2$O (5 g; 120 mmol) in MeOH:H$_2$O (100 mL of a 9:1 mixture) was stirred at RT overnight. Volatiles were removed in vacuo, and the residue was partitioned between excess aqueous 1 M HCl and EtOAc (aqueous layer pH~3). The aqueous phase was extracted with EtOAc (2×). The combined organic extracts were dried (Na$_2$SO$_4$) and concentrated in vacuo to give 3-fluoro-4-methoxy phenol (6.1 g; 72%) as an oil.

3-bromo-4-methoxy phenol (4.39 g; 47% for 2 steps) was synthesized using the exact analogous sequence starting from 3-bromo-4-methoxy benzaldehyde.

3-propyl phenol

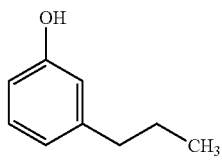

-continued

A.

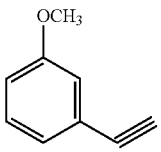

A mixture of 3-iodoanisole (2 g; 8.5 mmol), trimethylsilylacetylene (1.67 g; 17 mmol), CuI (32 mg; 0.17 mmol) and (Ph$_3$P)$_2$PdCl$_2$ (59 mg; 0.085 mmol) in diethylamine (10 mL) was stirred at RT for 1 h. Volatiles were removed in vacuo, and the residue was partitioned between EtOAc and brine. The organic phase was washed with brine (2×10 mL) and then filtered through a pad of SiO$_2$. Volatiles were removed in vacuo to give the crude product (3-trimethylsilylethynyl anisole) as a light yellow oil. A solution of this crude product and tetrabutylammonium fluoride (6.6 g; 26 mmol) in THF (10 mL) was stirred at RT for 15 min. Volatiles were removed in vacuo and the residue was chromatographed (SiO$_2$; 9:1 hex:EtOAc) to furnish Part A compound (1.0 g; 89%) as a yellow oil.

B.

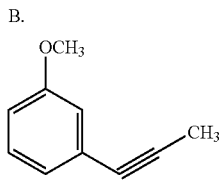

To a 0° C. solution of Part A compound (1.0 g; 7.6 mmol) in anhydrous THF (5 mL) was added dropwise n-BuLi (4.5 mL of a 2.0 M solution in hexane; 9.1 mmol). The resulting yellow solution was stirred at 0° C. for 30 min. Methyl iodide (1.6 g; 11.4 mmol) was then added and the reaction was allowed to warm to RT and stirred at RT for 30 min. Volatiles were removed in vacuo and the residue was partitioned between aqueous 1N HCl and EtOAc. The aqueous phase was extracted with EtOAc (3×20 mL), and the combined organic extracts were dried (MgSO$_4$) and concentrated in vacuo to give Part B compound (1.0 g; 92%) as a yellow oil.

C.

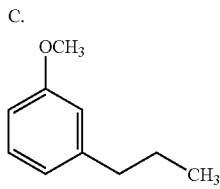

A solution of Part B compound (1.0 g) in MeOH (5 mL) was stirred over 10% Pd/C (10 mg) under an atmosphere of H2 overnight. The catalyst was removed by filtration through a pad of Celite® and the filtrate was concentrated in vacuo to give Part C compound (1.0 g; 100%) as a yellow oil.

D.

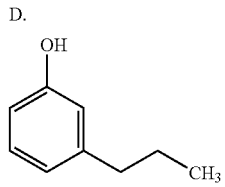

To a −78° C. solution of Part C compound (1.0 g; 6.6 mmol) in CH$_2$Cl$_2$ (10 mL) was added BBr$_3$ (4.8 mL of a 1 M solution in CH$_2$Cl$_2$). The reaction was allowed to warm to RT and was stirred at RT for 3 h, after which it was cautiously partitioned between aqueous 1 M HCl and CH$_2$Cl$_2$. The organic phase was washed with aqueous NH$_4$Cl, dried (MgSO$_4$) and concentrated in vacuo to give 3-propyl phenol (900 mg; 100%) as a yellow oil.

EXAMPLE 495

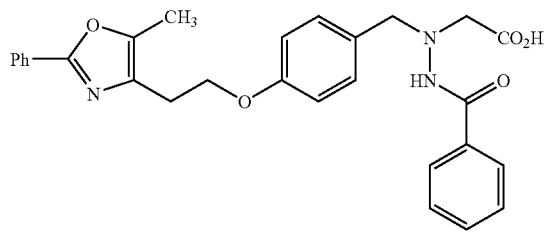

A.

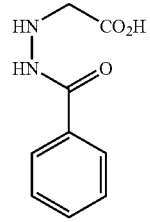

A mixture of benzoic acid (1.22 g; 10 mmol), methanesulfonyl chloride (1.15 g; 10 mmol), K$_2$CO$_3$ (5.52 g; 40 mmol) and benzyltriethylammonium chloride (0.23 g; 1 mmol) in toluene was stirred at 80° C. for 2 h. Ethyl hydrazine acetate hydrochloride (1.55 g; 10 mmol) was then added and the reaction was stirred for a further 30 min, then cooled to RT. Solids were filtered off and the filtrate was concentrated in vacuo. The residue was chromatographed (SiO$_2$; stepwise gradient from 3:1 to 1:1 hexane:EtOAc) to give Part A compound (350 mg; 16%) as a white solid.

B.

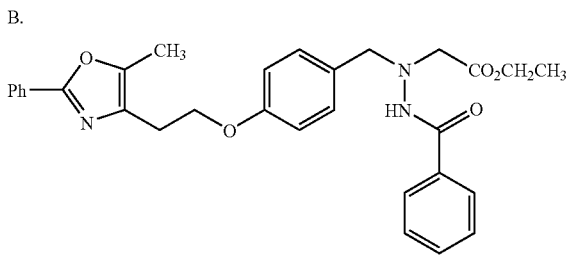

To a 0° C. solution of Part A compound (49 mg; 0.22 mol) and the aldehyde (50 mg; 010 mmol)

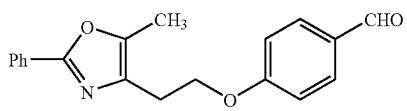

in DCE (3 mL) was added NaBH(OAc)$_3$ (30 mg; 0.42 mmol). The reaction was allowed to warm to RT and stirred at RT for 2 h, then at 60° C. for 18 h. The mixture was cooled to RT and concentrated in vacuo. The residue was purified by preparative HPLC (YMC S5 ODS 30×250 mm column; flow rate=25 mL/min; 20 min continuous gradient from 70:30 B:A to 100% B, where solvent A=90:10:0.1 H$_2$O:MeOH:TFA and solvent B=90:10:0.1 MeOH:H$_2$O:TFA) to give Part B compound.

C.

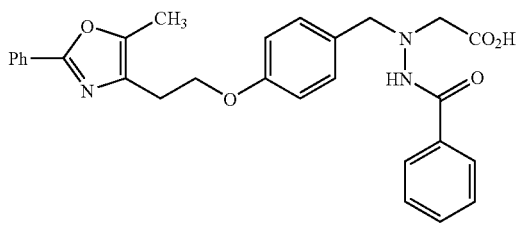

A solution of crude Part B compound in THF (1 mL) and aqueous LiOH (0.3 mL of a 1 M solution; 0.3 mmol) was stirred at RT for 3 h, then acidified to pH~3 with aqueous 1 M HCl. The aqueous phase was extracted with EtOAc (2×); the combined organic extracts were concentrated in vacuo. The residue was purified by preparative HPC (YMC 5S ODS 30×250 mm column; flow rate=25 mL/min; 22 min continuous gradient from 70:30 B:A to 100% B, where solvent A=90:10:0.1 H$_2$O:MeOH:TFA and solvent B=90:10:0.1 MeOH:H$_2$O:TFA) to give title compound (26 mg; 33% yield over 2 steps) as a white solid. [M+H]$^+$=486.3

EXAMPLE 496

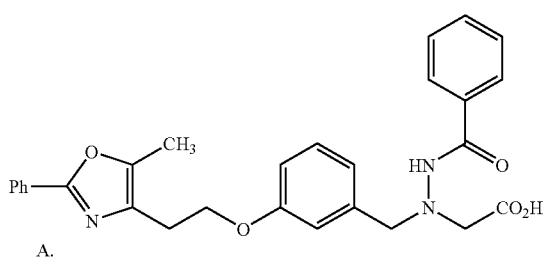

A.

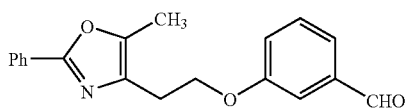

To a 0° C. solution of the aldehyde (200 mg; 0.65 mmol)

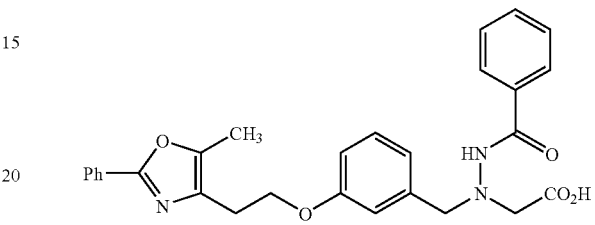

in MeOH (2 mL) was added portionwise NaBH$_4$ (24 mg; 0.65 mmol), after which the reaction was allowed warm to RT and stirred at RT for 1 h. Volatiles were removed in vacuo and the residue was partitioned between H$_2$O and EtOAc. The organic phase was dried (Na$_2$SO$_4$) and concentrated in vacuo to give the intermediate alcohol as an oil. A solution of the alcohol in CH$_2$Cl$_2$ (2 mL) and PBr$_3$ (1 mL of a 1M solution in CH$_2$Cl$_2$) was stirred at RT for 30 min. Volatiles were removed in vacuo and the residue was partitioned between aqueous saturated NaHCO$_3$ and EtOAc. The organic phase was washed with H$_2$O, dried (Na$_2$SO$_4$) and concentrated in vacuo to give Part A compound (150 mg; 62%) as an oil.

B.

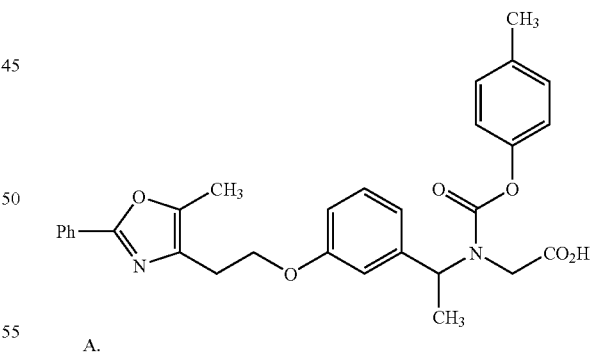

A solution of Part A compound (42 mg; 0.11 mmol), Example 500 Part A compound (25 mg; 0.11 mmol) and K$_2$(100 mg; 0.71 mmol) in DMF (1 mL) was stirred at RT for 3 days. The reaction mixture was partitioned between EtOAc and H$_2$O. The organic phase was washed with H$_2$O (2×) and concentrated in vacuo. The residual oil was dissolved in THF (1 mL) and aqueous LiOH (0.3 mL of a 1 M solution) was added. The reaction was stirred at RT for 3 h, then acidified to pH~3 with aqueous 1 M HCl. The aqueous phase was extracted with EtOAc (2×); the combined organic extracts were concentrated in vacuo. The residue was purified by preparative HPC (YMC S5 ODS 30×250 mm column; flow rate=25 mL/min; 20 min continuous gradient from 70:30 B:A to 100% B, where solvent A=90:10:0.1 H$_2$O:MeOH:TFA and solvent B=90:10:0.1 MeOH:H$_2$O:TFA) to give title compound (15 mg; 27% yield over 2 steps) as a white solid. [M+H]$^+$=486.4

EXAMPLE 497

A.

A mixture of 3-hydroxyacetophenone (650 mg; 4.78 mmol), K$_2$CO$_3$ (660 mg; 4.78 mmol) and the 2-phenyl-5- methyl-4-oxazole-ethanol mesylate (1.12 g; 3.98 mmol)

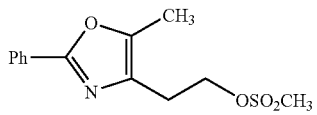

in MeCN (40 mL) was refluxed overnight. Volatiles were removed in vacuo, and the residue was partitioned between EtOAc (100 mL) and 1.0 M aqueous NaOH (80 mL). The organic phase was washed with brine (100 mL), dried (MgSO$_4$) and concentrated in vacuo. The residue was chromatographed (SiO$_2$; hexane:EtOAc 3:1) to give Part A compound (850 g; 67%) as a yellow solid.

B.

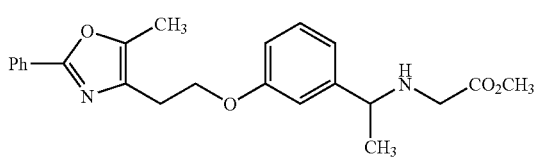

To a solution of Part A compound (850 mg, 2.65 mmol) in DCE (15 mL) were successively added glycine methyl ester hydrochloride (333 mg, 2.65 mmol), Et$_3$N (554 μL, 4.0 mmol), NaBH(OAc)$_3$ (786 mg; 3.7 mmol) and acetic acid (152 μL; 2.65 mmol). The reaction mixture was stirred at RT for 6 days, then partitioned between aqueous 1 M NaOH and CH$_2$Cl$_2$. The aqueous phase was washed with H$_2$O, then concentrated in vacuo. The residue was partitioned between EtOAc and 1 M aqueous HCl. The organic phase was washed with brine, dried (MgSO$_4$) and concentrated in vacuo to give recovered starting material (Part A compound). The pH of the aqueous HCl phase was adjusted to 10 with excess solid NaOH. This aqueous phase was extracted with EtOAc (60 mL). The organic extract was washed with brine (60 mL), dried (MgSO$_4$) and concentrated in vacuo to give the crude Part B compound (400 mg; 39%) as an oil, which was used in the next step without further purification.

C.

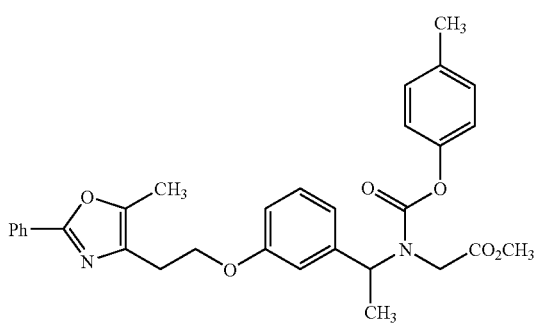

To a solution of Part B compound (29 mg; 0.074 mmol) in pyridine (1.0 mL) were added 4-tolyl chloroformate (14 μL; 0.089 mmol) and DMAP (10 mg). The solution was heated at 61° C. for 2 h, then cooled to RT and concentrated in vacuo to give crude Part C compound (36 mg) as a syrup.

D.

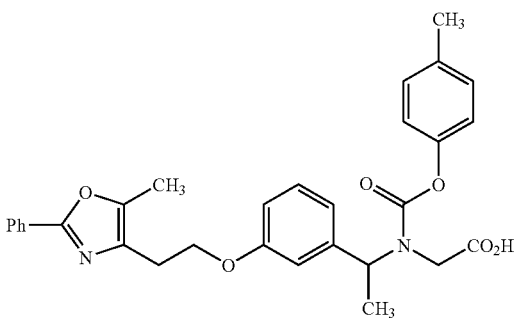

A solution of crude Part C compound (36 mg; 0.68 mmol) and LiOH.H$_2$O (12 mg; 0.28 mmol) in THF:MeOH:H$_2$O (1 mL of a 1:1:1 solution) was stirred at RT for 2 h. Volatiles were removed in vacuo and the residue was acidified to pH2 with aqueous 1 M HCl, then extracted with EtOAc (3×40 mL). The combined organic extracts were dried (Na$_2$SO$_4$) and concentrated in vacuo. The crude product was purified by preparative HPLC (YMC S5 ODS 50×250 mm column; flow rate=25 mL/min; continuous 20 min gradient from 70:30 B:A to 100% B, where A=90:10:0.1 H$_2$O:MeOH:TFA and B=90:10:0.1 MeOH:H$_2$O:TFA) to give title compound (28 mg; 72% over 2 steps) as a white solid.

[M+H]$^+$=515.3

EXAMPLE 498

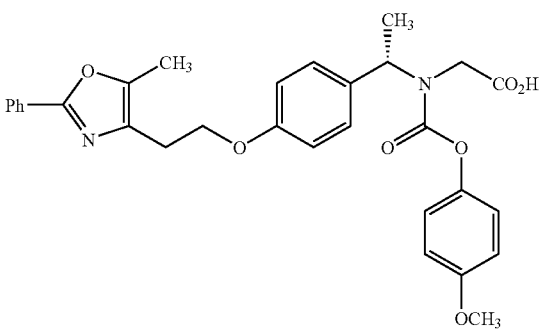

A.

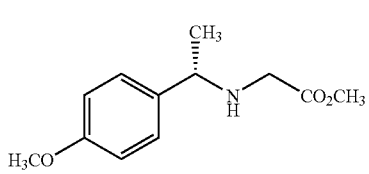

A solution of (S)-1-(4-methoxyphenyl)ethylamine (11.9 g, 79 mmol), methyl bromoacetate (11.5 g; 75 mmol) and Et$_3$N (12.6 mL; 90 mmol) in THF (156 mL) was stirred at RT for 15 h. The reaction was partitioned between EtOAc and H$_2$O. The organic phase was washed with brine, dried (MgSO$_4$), and concentrated in vacuo to give crude Part A compound, which was used in the next step without further purification.

B.

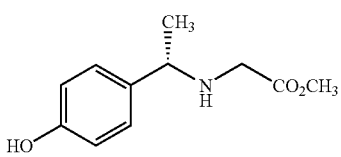

To a 0° C. solution of the crude Part A compound from above in CH₂Cl₂ (198 mL) was slowly added dropwise BBr₃ (12.0 mL; 127 mmol). The reaction was stirred at 0° C. for 3 h, then poured cautiously into a 0° C. mixture of saturated aqueous NH₄Cl and EtOAc. The aqueous phase was neutralized by slow addition of solid NaHCO₃, then extracted with EtOAc (2×). The combined organic extracts were washed with brine, dried (MgSO₄) and concentrated in vacuo to furnish Part B compound (7.29 g; 44% over 2 steps).

C.

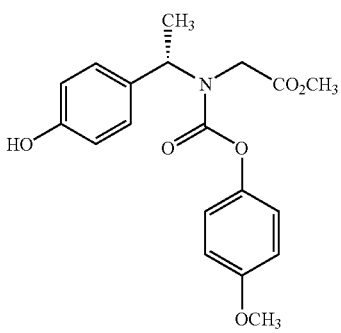

To a solution of Part B compound (6.13 g; 29.3 mmol) in dioxane:H₂O (98 mL of a 1:1 solution) were successively added NaHCO₃ (3.2 g; 38 mmol) and 4-methoxy-phenyl chloroformate (3.92 mL; 26.4 mmol). The reaction was stirred at RT for 2 h, then partitioned between EtOAc and H₂O. The organic phase was washed with brine, dried (MgSO₄), and concentrated in vacuo to give crude Part C compound (10.0 g; 95%).

D.

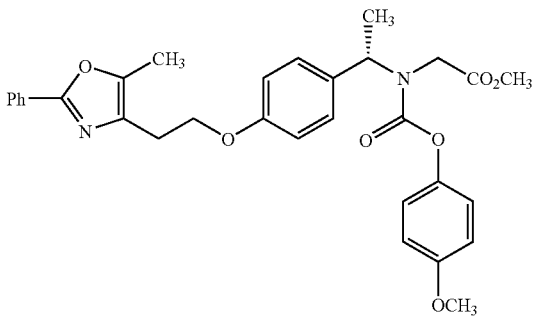

To a solution of Part C compound in MeCN (59 mL) were successively added K₂CO₃ (2.43 g; 17.6 mmol) and the mesylate (4.93 g; 17.6 mmol).

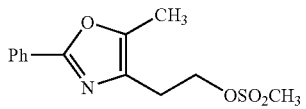

The reaction was heated at 90° C. for 20 h, then cooled to RT. The mixture was partitioned between EtOAc and H₂O. The organic phase was washed with brine, dried (MgSO₄) and concentrated in vacuo. The residue was chromatographed (SiO₂; stepwise gradient from 8:1 to 3:1 to 1:1 hexane:EtOAc) to give Part D compound (3.4 g; 36%).

E.

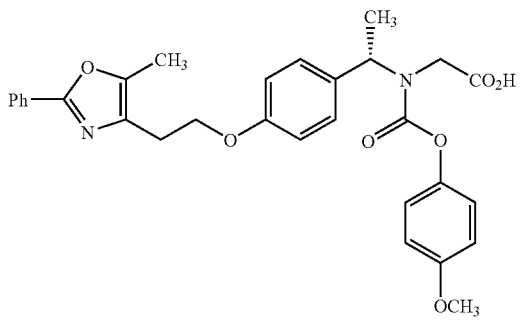

To a solution of Part D compound (3.4 g; 6.25 mmol) in THF:H₂O (31 mL of a 2:1 solution) was added LiOH.H₂O (0.525 g; 125 mmol). The reaction was stirred at RT overnight for 14 h. EtOAc was added and the solution was acidified with 1 N HCl solution to pH~2. The organic phase was washed with brine, dried (MgSO₄) and concentrated in vacuo. The residue was purified by preparative HPLC (YMC S5 ODS 30×250 mm column; flow rate=25 mL/min; 22 min continuous gradient from 70:30 B:A to 100% B, where solvent A=90:10:0.1 H₂O:MeOH:TFA and solvent B=90:10:0.1 MeOH:H₂O:TFA; retention time=17.8 min) to give the title compound (2.1 g; 63% yield) as a white solid. [M+H]⁺=531.3; ¹H NMR (DMSO-d₆; 400 MHz): δ 1.50 (2d, J=6.6 Hz; 3H), 2.37 (s, 3H), 2.94 (t, J=7.0 Hz, 2H), 3.74 (s, 3H), 3.81 (m; 2H), 4.21 (t, J=6.2 Hz, 2H), 5.36 (m, 1H), 6.93 (m, 6H), 7.28 (m, 2H), 7.50 (m, 3H), 7.91 (m, 2H)

EXAMPLE 499

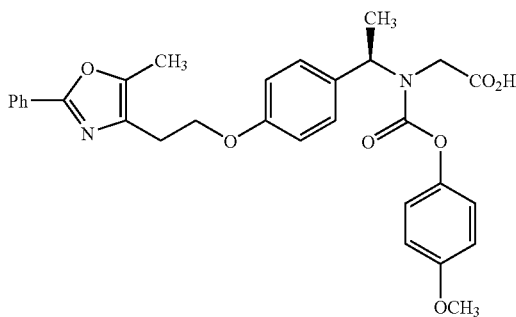

The synthesis of title compound was done using the identical sequence described for Example 498 compound except that (R)-4-methoxy-α-methyl benzylamine was used instead of the (S) isomer. [M+H]⁺=531.3;

¹H NMR (DMSO-d₆; 400 MHz): δ 1.50 (2d, J=7.0 Hz; 3H), 2.37 (s, 3H), 2.94 (t, J=6.6 Hz, 2H), 3.74 (s, 3H), 3.84

(m; 2H), 4.21 (t, J=6.6 Hz, 2H), 5.35 (m, 1H), 6.93 (m, 6H), 7.29 (m, 2H), 7.50 (m, 3H), 7.91 (m, 2H)

Alternative Synthesis of Examples 498 and 499

EXAMPLE 498A

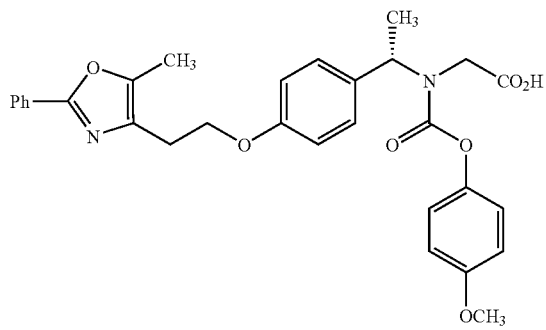

A.

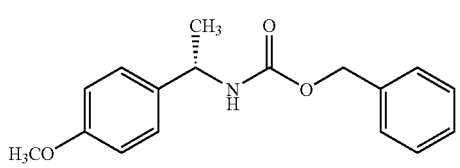

To a RT mixture of (S)-1-(4-methoxyphenyl)ethylamine (5.45 g, 36 mmol) in THF (50 mL) and aqueous NaHCO$_3$ (6.05 g in 25 mL H$_2$O) was added dropwise benzyl chloroformate (6.20 mL; 43 mmol). The reaction was stirred at RT for 30 min; the organic phase was isolated and concentrated in vacuo. The residue was partitioned between EtOAc and H$_2$O (100 mL each); the organic phase was washed with brine, dried (MgSO$_4$), and concentrated in vacuo to about 30 mL volume. An equivalent volume of hexane (30 mL) was added and Part A compound (9.12 g; 89%) crystallized as colorless needles.

B.

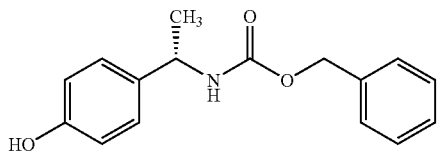

To a −78° C. solution of Part A compound (2.50 g; 8.8 mmol) in anhydrous CH$_2$Cl$_2$ (11 mL) was added dropwise a solution of BBr$_3$ in CH$_2$Cl$_2$ (11.4 mL of a 1.0 M solution; 11.4 mmol) over 25 min. The reaction was allowed to warm to 0° C. and stirred at 0° C. for 6 h, then quenched carefully at −78° C. by dropwise addition of excess MeOH (6 mL). The solution was allowed to warm to 0° C. and stirred at 0° C. for 5 min. The solution was partitioned between CH$_2$Cl$_2$ (60 mL) and H$_2$O (50 mL). The organic phase was washed successively with brine and 5% aqueous NaHCO$_3$ (50 mL each), dried (MgSO$_4$) and concentrated in vacuo. The residue was chromatographed (SiO$_2$; stepwise gradient from 4:1 to 1:1 hex:EtOAc) to furnish Part B compound (1.30 g; 63% yield based on 650 mg (26%) of recovered unreacted Part A compound) as a white solid.

C.

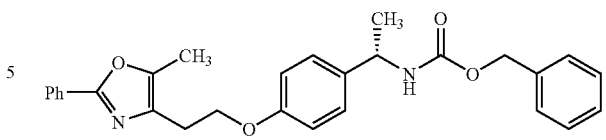

A mixture of Part B compound (1.10 g; 4.1 mmol), K$_2$CO$_3$ (680 mg; 4.9 mmol) and the mesylate (1.25 g; 4.4 mmol)

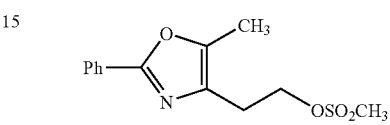

in MeCN (30 mL) was heated at 90° C. for 18 h, then cooled to RT. Volatiles were removed in vacuo, and the residue was partitioned between EtOAc and H$_2$O (100 mL each). The organic phase was washed with brine (100 mL), dried (MgSO$_4$) and concentrated in vacuo. The residue was chromatographed (SiO$_2$; stepwise gradient from 9:1 to 3:2 hexane:EtOAc) to give Part C compound (1.40 g; 78%) as a white solid.

D.

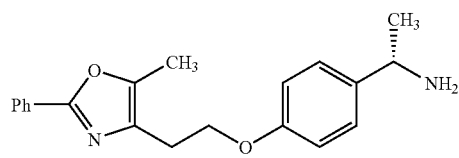

A mixture of Part C compound (1.30 g; 2.85 mmol) and 10% palladium on carbon (200 mg) in MeOH (50 mL) was stirred under an atmosphere of H$_2$ (balloon) at RT for 2 h, at which point the reaction was complete by HPLC. The catalyst was filtered off through Celite® and the filtrate was concentrated in vacuo to give Part D compound (600 mg; 65%) as a white solid.

E.

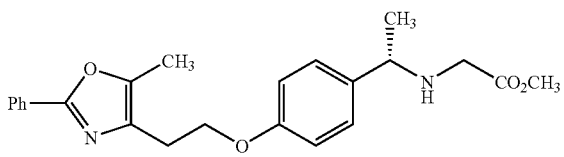

A solution of Part D compound (600 mg; 1.86 mmol), methyl bromoacetate (230 μL; 2.42 mmol) and Et$_3$N (337 μL; 2.42 mmol) in THF (10 mL) was stirred at RT for 20 h. The reaction mixture was partitioned between H$_2$O and EtOAc (60 mL) each. The organic phase was washed with brine, dried (MgSO$_4$) and concentrated in vacuo. The residue was chromatographed (SiO$_2$; stepwise gradient from hex:EtOAc 4:1 to 1:1) to furnish Part E compound (640 mg; 87%) as an oil.

F.

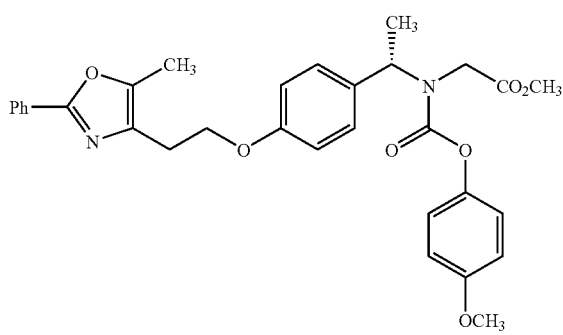

A solution of Part E compound (600 mg; 1.52 mmol), 4-methoxyphenyl chloroformate (271 μL; 1.82 mmol) and DMAP (30 mg; 0.25 mmol) in pyridine (10 mL) was heated at 70° C. for 2 h. Since starting material still remained at this point, additional 4-methoxyphenyl chloroformate (271 μL; 1.82 mmol) was added and the reaction was heated at 70° C. for an additional 1 h. Volatiles were removed in vacuo, and the residue was partitioned between EtOAc (100 mL) and 1M aqueous HCl (60 mL). The organic phase was washed with brine, dried (MgSO$_4$), and concentrated in vacuo. The residue was chromatographed (SiO$_2$; stepwise gradient from hex:EtOAc 9:1 to 4:1) to furnish Part F compound (880 mg) as an oil.

G.

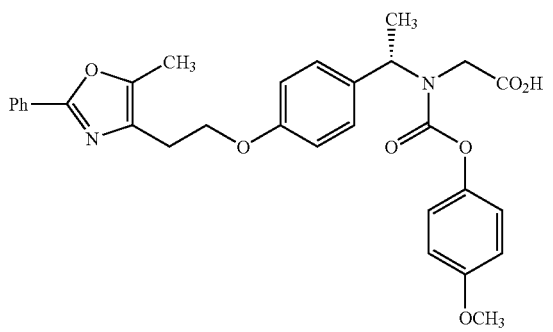

To a solution of Part F compound (880 mg; 1.62 mmol) in THF:H$_2$O (22 mL of a 2:1 solution) was added LiOH.H$_2$O (203 mg; 4.86 mmol). The reaction was stirred at RT for 18 h; then EtOAc (100 mL) was added and the solution acidified with 1 N HCl solution to pH2. The organic phase was washed with water and brine (100 mL each), dried (MgSO$_4$) and concentrated in vacuo. The residue was purified by preparative HPLC (YMC ODS 30×250 mm column; flow rate=25 mL/min; 22 min continuous gradient from 70:30 B:A to 100% B+5 min hold-time at 100% B, where solvent A=90:10:0.1 H$_2$O:MeOH:TFA and solvent B=90:10:0.1 MeOH:H$_2$O:TFA; retention time=17.8 min) and then lyophilized from dioxane to give the title compound (665 g; 78%) as a white solid.

EXAMPLE 499A

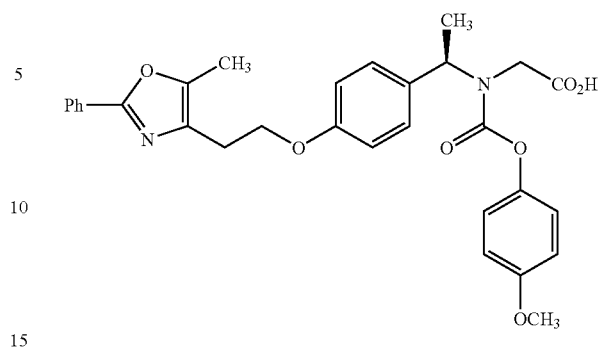

The alternative synthesis of Example 499 was done using the identical sequence described for Example 498A except that (R)-1-(4-methoxyphenyl)ethylamine was used instead of the (S) isomer.

Alternative Synthesis of Example 498 Part B Compound

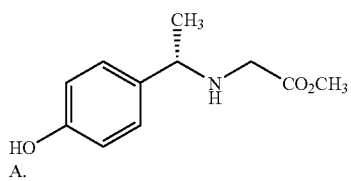

A.

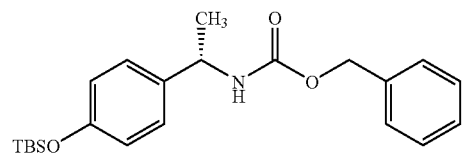

A mixture of tert-butyldimethylsilyl chloride (357 mg; 2.36 mmol), (alternative) Example 498A Part B compound from above (535 mg; 1.97 mmol) and imidazole (161 mg; 2.36 mmol) in DMF (5 mL) was was stirred at RT for 2 h. The reaction was partitioned between EtOAc (20 mL) and water (50 mL). The organic phase was washed with water (2×50 mL), dried (Na$_2$SO$_4$), and concentrated in vacuo. The residue was chromatographed (SiO$_2$; hex:EtOAc 3:1) to give Part A compound (320 mg; 42%) as an oil in addition to recovered starting phenol (150 mg; 20%).

B.

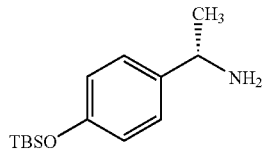

A mixture of Part A compound (320 mg; 0.83 mmol) and 10% palladium on carbon (30 mg) in MeOH (30 mL) was stirred under an atmosphere of H$_2$ (balloon) at RT for 1 h, at which point the reaction was complete by HPLC. The catalyst was filtered off through Celite® and the filtrate was concentrated in vacuo to give Part B compound (230 mg) as a white solid which was used in the next step without further purification.

C.

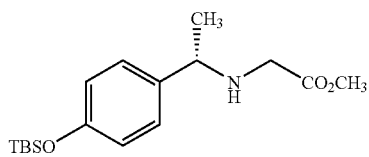

A solution of Part B compound (230 mg), methyl bromoacetate (86 μL; 0.91 mmol) and Et₃N (127 μL; 0.91 mmol) in THF (10 mL) was stirred at RT for 15 h. The reaction mixture was partitioned between H O and EtOAc (30 mL) each. The organic phase was washed with brine, dried (MgSO₄) and concentrated in vacuo. The residue was chromatographed (SiO₂; stepwise gradient from hex:EtOAc 9:1 to 1:1) to furnish Part C compound (177 mg; 66% over 2 steps) as an oil.

EXAMPLE 498

Part B Compound

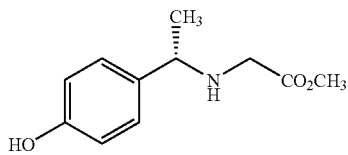

To a solution of Part C compound (177 mg; 0.55 mmol) in THF (5.5 mL) was slowly added tetrabutylammonium fluoride (1.65 mL of a 1 M solution in THF). The reaction was stirred at RT for 10 min, then partitioned between water and EtOAc. The organic phase was washed with brine, dried (MgSO₄) and concentrated in vacuo. The residue was purified by preparative HPLC (YMC reverse phase ODS 20×100 mm column; flow rate=20 mL/min; 10 min continuous gradient from 100% A to 100% B+10 min hold-time at 100% B, where solvent A=90:10:0.1 H₂O:MeOH:TFA and solvent B=90:10:0.1 MeOH:H₂O:TFA; retention time=2.6 min) to provide the title compound (97 mg; 84%).

EXAMPLE 500

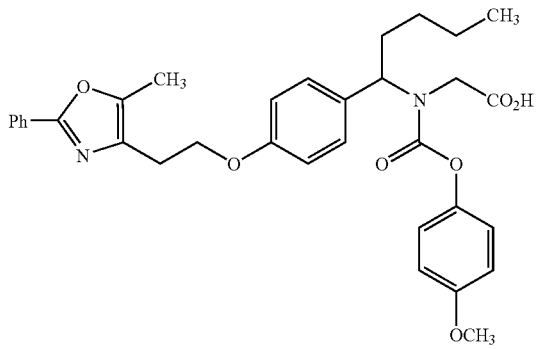

A.

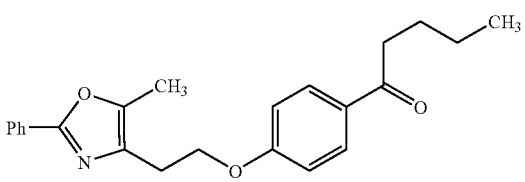

A mixture of 4-hydroxyphenyl butyl ketone (2.50 g; 14.0 mmol), 2-phenyl 5-methyl oxazole-4-ethanol mesylate (3.30 g; 11.7 mmol) and K₂CO₃ (1.94 g; 14.0 mmol) in acetonitrile (50 mL) was refluxed under Ar for 18 h. Volatiles were removed in vacuo and the residue was partitioned between H O and EtOAc. The aqueous phase was extracted with EtOAc. The combined organic extracts were washed with aqueous 1M NaOH and H₂O, dried (MgSO₄) and concentrated in vacuo. The residue was chromatographed (SiO₂; stepwise gradient from 3:1 to 9:1 hex:EtOAc) to give Part A compound (3.42 g; 80%) as a white solid.

B.

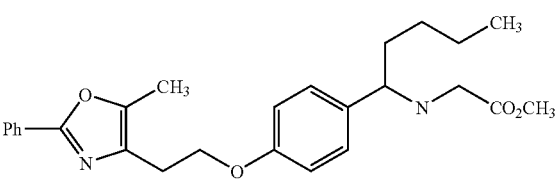

A mixture of Part A compound (3.42 g; 9.42 mmol), glycine methyl ester HCl salt (1.18 g; 9.42 mmol), Et₃N (1.97 mL; 14.1 mmol), NaBH(OAc)₃ (2.80 g; 13.2 mmol) and HOAc (0.54 mL; 9.42 mmol) in DCE (20 mL) was stirred at RT for 6 days. At this point the reaction was incomplete, but was not progressing any further. The reaction was quenched with saturated aqueous NaHCO₃ (6 mL), then concentrated in vacuo. The residue was partitioned between saturated aqueous NaHCO₃ and EtOAc. The organic phase was washed with saturated aqueous NaHCO₃ and H₂O, then extracted with 1M aqueous HCl (the unreacted starting material remained in the organic phase). The aqueous phase was basified with NaOH, then extracted with EtOAc. The organic phase was washed with H₂O and brine, dried (MgSO₄) and concentrated in vacuo to give Part B compound (365 mg; 9%) as an oil.

C.

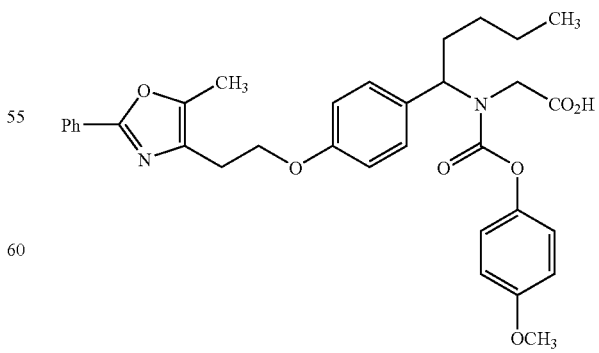

To a solution of Part C compound (50 mg; 0.11 mmol) in pyridine (1 mL) was added 4-methoxyphenyl chloroformate (40 µL) and DMAP (5 mg). The reaction mixture was heated at 60° C. for 6 h, then was cooled to RT and volatiles were removed in vacuo. The residue was dissolved in THF/MeOH/H₂O (1 mL of a 2:2:1 mixture) and LiOH (30 mg) was added. The reaction was stirred at RT for 18 h, then was acidified with aqueous 1 M HCl to pH~2. The mixture was extracted with EtOAc (30 mL), washed with H₂O and brine (15 mL each), dried (MgSO₄) and concentrated in vacuo to give the crude product. This material was purified by preparative HPLC (YMC S5 ODS 30×250 mm column; continuous gradient from 60:40 A:B to 100% B over 30 min) to give, after lyophilization from MeOH/H₂O, the title compound (52 mg; 79%) as a white solid. [M+H]⁺=573.3

EXAMPLE 501

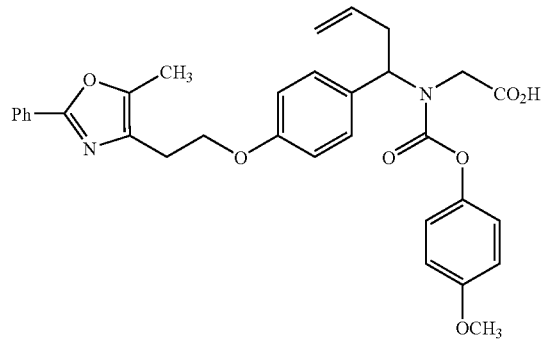

A.

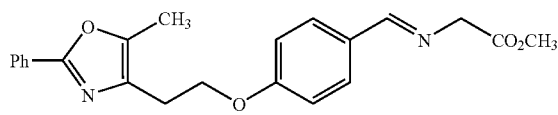

A mixture of glycine methyl ester hydrochloride (245 mg; 1.95 mmol), Et₃N (271 µL; 1.95 mmol) and the aldehyde

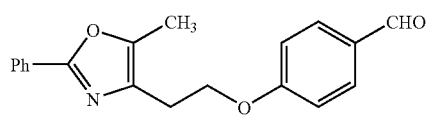

(400 mg; 1.3 mmol) and anhydrous MgSO₄ (200 mg) in THF (4 mL) was stirred at RT overnight, then filtered. The filtrate was concentrated in vacuo to give crude Part A compound, which was used in the next step without further purification.

B.

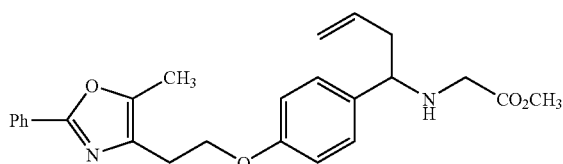

A mixture of indium metal (448 mg; 3.9 mmol) and allyl bromide (334 µL; 3.9 mmol) in anhydrous DMF (2 mL) was stirred at 0° C. for 50 min. A solution of the crude Part A compound (from above) in anhydrous DMF (2 mL) was added to this mixture, and the reaction was stirred vigorously at RT for 3 h. Analytical HPLC/MS showed that the reaction was complete at this point. The reaction was partitioned between saturated aqueous NH₄Cl and EtOAc. The organic phase was washed with H₂O (an emulsion formed) and brine, dried (MgSO₄) and concentrated in vacuo to give crude Part B compound (300 mg; 55% for 2 steps). This material was used in the next step without further purification.

C.

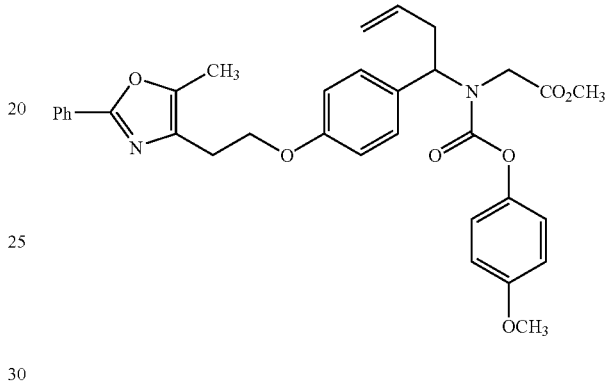

To a 0° C. solution of Part B compound (150 mg; 0.36 mmol) and Et₃N (51 µL; 0.36 mmol) in CH₂Cl₂ (4 mL) was added dropwise 4-methoxyphenyl chloroformate (53 µL; 0.36 mmol). The reaction was allowed to warm to RT and stirred at RT for 1 h, then concentrated in vacuo. The residue was chromatographed (SiO₂; hexane:EtOAc 2:1) to give Part C compound (200 mg; 98%) as an oil.

D.

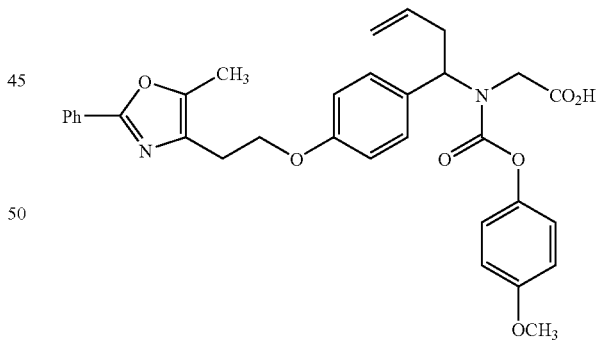

A solution of Part C compound (100 mg, 0.18 mmol) and LiOH.H₂O (30 mg, 0.72 mmol) in THF:MeOH:H₂O (1 mL of a 1:1:1 solution) was stirred at RT for 2 h. The reaction mixture was then acidified to pH~2 with aqueous 1N HCl. The aqueous phase was extracted with EtOAc (2×). The combined organic extracts were dried (Na₂SO₄), concentrated in vacuo and lyophilized from dioxane to provide title compound (80 mg; 82%) as a white solid.

[M+H]⁺=557.2

EXAMPLE 502

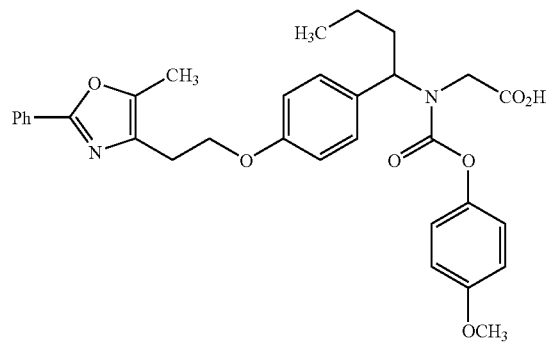

A.

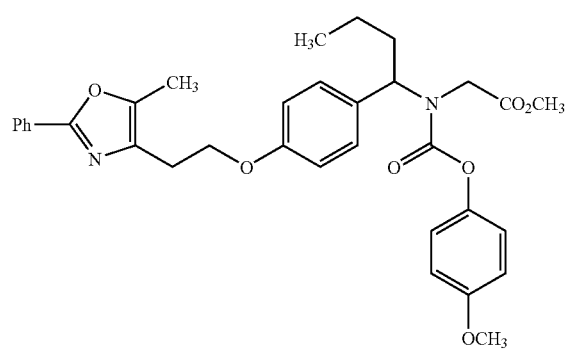

A solution of Example 501 Part C compound (100 mg; 0.18 mmol) in MeOH (10 mL) in the presence of 10% Pd/C (50 mg) was stirred under an $H_2$ atmosphere for 2 h at RT. The catalyst was then filtered off using a pad of Celite®. The filtrate was concentrated in vacuo to give Part A compound (100 mg; 100%) as an oil.

B.

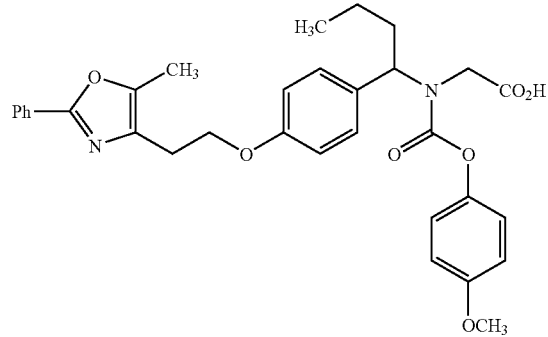

Title compound (87 mg; 90%; white solid lyophilate) was obtained from Part A compound in the same way as Example 501 compound was synthesized from Example 501 Part C compound. $[M+H]^+$=559.2

EXAMPLE 503

A.

To a solution of 5-methyl 2-phenyl-thiazol-4-yl-ethanol (50 mg; 0.23 mmol) in $CH_2Cl_2$ (3 mL) were successively added $Et_3N$ (50 μL; 0.36 mmol) and methanesulfonyl chloride (20 μL; 0.26 mmol). The reaction was stirred at RT for 2 h, then was partitioned between $CH_2CO_2$ and aqueous 1 M HCl. The organic phase was washed with brine, dried ($Na_2SO_4$), and concentrated in vacuo to give Part A compound (68 mg; 100%) as a colorless oil. This material was used in the next step without further purification.

B.

A mixture of the phenol (prepared using the identical procedures as described for the synthesis of Example 498 Part C compound except that ethyl bromoacetate was used instead of methyl bromoacetate)

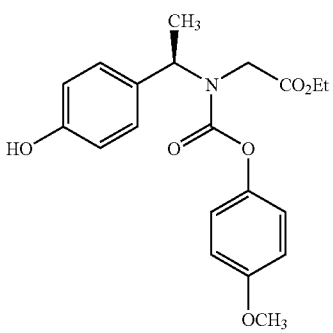

(18 mg; 0.048 mmol) and K$_2$CO$_3$ (30 mg; 0.22 mol) in MeCN (2 mL) was heated at 60° C. overnight, then cooled to RT and partitioned between EtOAc and excess aqueous 1 M HCl. The aqueous phase was extracted with EtOAc (2×); the combined organic extracts were dried (Na$_2$SO$_4$) and concentrated in vacuo. The residue was purified by preparative HPLC (as described for Example 498) to provide Part B compound (12 mg; 43%).

C.

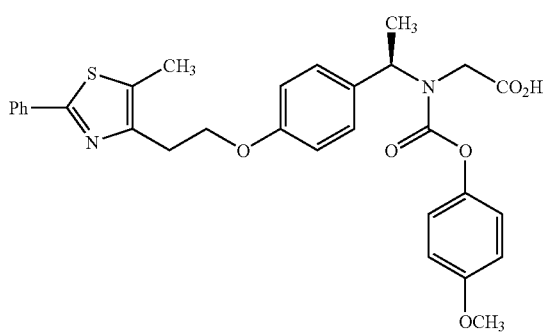

A solution of Part B compound (12 mg; 0.02 mmol) and LiOH.H$_2$O (10 mg; 0.24 mmol) in THF (2 mL) and H$_2$O (1 mL) was stirred at RT for 4 h. The reaction mixture was acidified with excess aqueous 1 M HCl and extracted with EtOAc (3×). The combined organic extracts were dried (Na$_2$SO$_4$) and concentrated in vacuo; the residue was purified by preparative HPLC (as described for Example 498) to give the title compound (3 mg; 26%) as a colorless oil. [M+H]$^+$=547.2

EXAMPLE 504

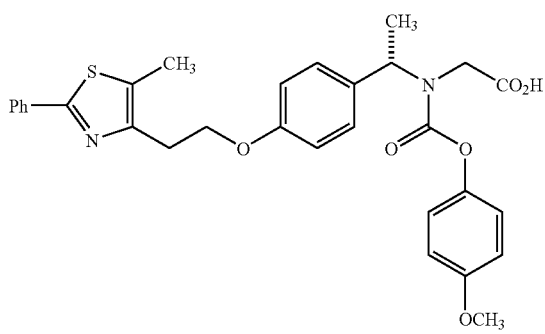

The title compound was prepared in exactly the same way as for Example 503 except that the [S]-enantiomer

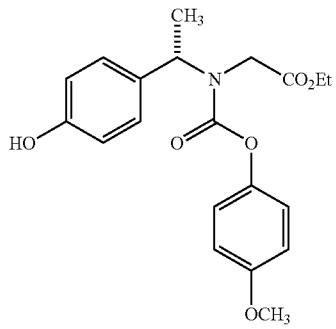

was used for the alkylation step. [M+H]$^+$=547.2

EXAMPLE 505

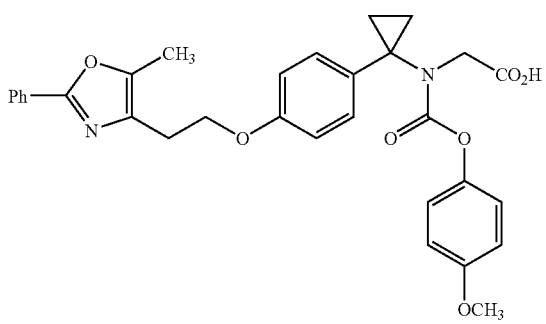

A.

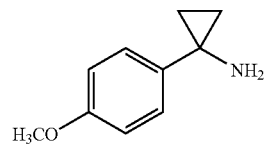

To a solution of 1-(4-methoxyphenyl)-1-cyclopropanecarboxylic acid (250 mg; 1.3 mmol) in dioxane (8 ml) were successively added Et$_3$N (198 μL; 1.43 mmol) and diphenylphosphoryl azide (307 μL; 1.43 mmol). The reaction was stirred at RT for 5 min, then heated to 80° C. for 3 h. Volatiles were removed in vacuo, and the residue was partitioned between EtOAc and H$_2$O. The organic phase was dried (Na$_2$SO$_4$) and concentrated in vacuo to give the crude product (presumably the corresponding isocyanate). This material was dissolved in aqueous 8 M HCl (1.8 mL), stired at RT for 5 min, then heated to 100° C. for 1 h. After cooling to RT, Et$_2$O was added, and the solution was cautiously basified with excess solid NaOH. The aqueous phase was extracted with Et$_2$O (3×15 mL), dried (MgSO$_4$) and concentrated in vacuo to provide compound A (100 mg; 47%) as an oil. This material was used in the next step without further purification.

B.

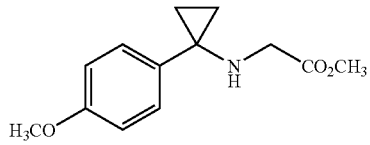

A solution of Part A Compound (100 mg; 0.61 mmol), methyl bromoacetate (103 mg; 0.67 mmol) and Et₃N (102 μL; 0.73 mmol) in THF was stirred at RT for 16 h. The reaction mixture was partitioned between EtOAc and H₂O. The organic phase was washed with brine, dried (MgSO₄), and concentrated in vacuo. The residue was chromatographed (SiO₂; CH₂Cl₂:MeOH 9:1) to give Part B compound (90 mg; 62%) as an oil.

C.

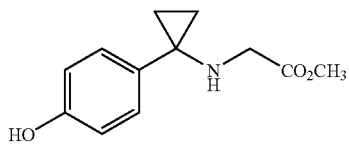

To a 0° C. solution of Part B compound (90 mg; 0.38 mmol) in CH₂Cl₂ (12.7 mL) was slowly added neat BBr₃ (82 μL; 0.87 mmol) The reaction was stirred at 0° C. for 3 h, then was partitioned between ice cold saturated aqueous NH₄Cl and EtOAc. The organic phase was discarded and the aqueous layer was neutralized by addition of NaHCO₃, then extracted with EtOAc (2×). The combined organic extracts were washed with brine, dried (MgSO₄), and concentrated in vacuo to give Part C compound (50 mg; 59%).

D.

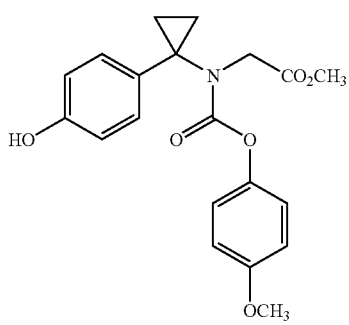

A mixture of Part C compound (50 mg; 0.22 mmol), 4-methoxyphenyl chloroformate (33 mg; 0.22 mol) and NaHCO₃ (25 mg; 0.29 mmol) in 1:1 aqueous dioxane (7.5 mL) was stirred at RT for 2 h. The reaction mixture was partitioned between EtOAc and H₂O. The organic phase was washed with brine, dried (MgSO₄) and concentrated in vacuo to give Part D compound (45 mg; 52%).

E.

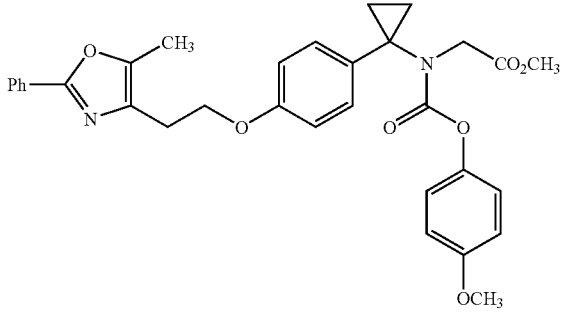

A mixture of Part D compound (45 mg; 0.12 mmol), K₂CO₃ (30 mg; 0.22 mol) and the mesylate (33 mg; 0.12 mmol)

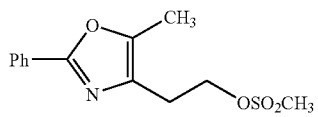

in MeCN (4 mL) was heated at 90° C. for 20 h. The reaction was cooled to RT and partitioned between EtOAc and H₂O. The aqueous phase was extracted with EtOAc (2×); the combined organic extracts were dried (MgSO₄) and concentrated in vacuo. The residue was chromatographed (SiO₂; stepwise gradient from 9:1 to 1:1 hex:EtOAc) to provide Part E compound (42 mg; 65%).

F.

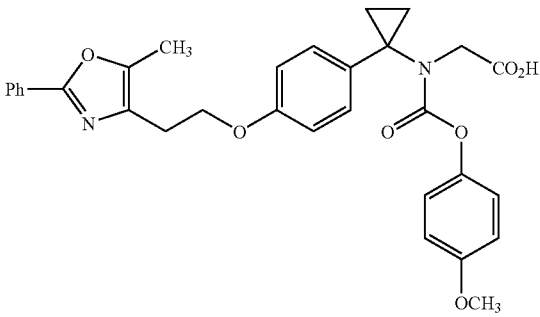

A solution of Part E compound (42 mg; 0.08 mmol) and LiOH.H₂O (6 mg; 0.15 mmol) in 2:1 THF:H₂O (3.8 mL) was stirred at RT overnight. The reaction mixture was acidified to pH2 with excess aqueous 1 M HCl and extracted with EtOAc (2×). The combined organic extracts were dried (Na₂SO₄) and concentrated in vacuo; the residue was purified by preparative HPLC (as described for Example 498) to give the title compound (28 mg; 68%) as a colorless oil. [M+H]⁺=543.2

Following procedures as described above, the Examples 506 to 518 compounds were prepared.

| Example No. | Rᵃ | [M + H]⁺ |
|---|---|---|
| 506 | (±) -Me | 515.3 |
| 507 | (±) n-Bu | 557.4 |

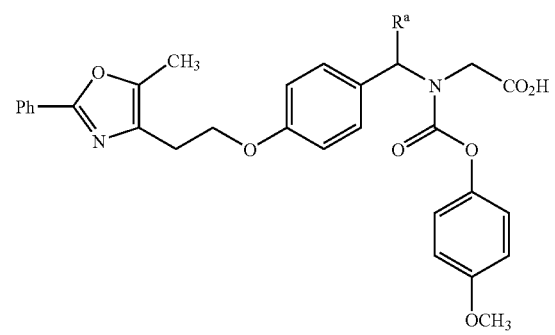
| Example No. | Rᵃ | [M + H]⁺ |
|---|---|---|
| 508 | (±) Me | 531.3 |
| 509 | (±) Et | 545.1 |
| 510 | (±) i-Bu | 573.3 |
| 511 | (±) -CH₂-C(=CH₂)-CH₃ | 571.3 |
EXAMPLE 506
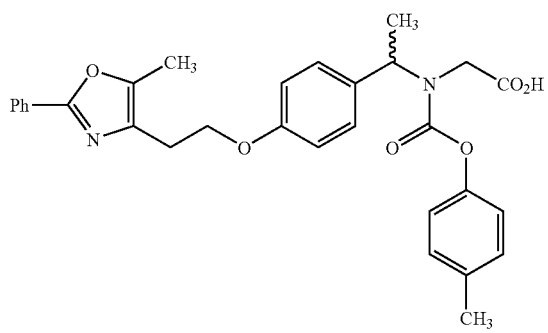
$^1$H NMR (DMSO-$d_6$; 400 MHz): δ 1.47 and 1.54 (2d, J=7.5 Hz; 3H), 2.29 (s, 3H), 2.37 (s, 3H), 2.93 (t, J=6.6 Hz, 2H), 3.81 (2d, J=18 Hz; 2H), 4.21 (t, J=6.6 Hz, 2H), 5.3 (m, 1H), 6.94 (m, 4H), 7.18 (d, J=8.4 Hz, 2H), 7.31 (m, 2H), 7.49 (m, 2H)
EXAMPLE 508
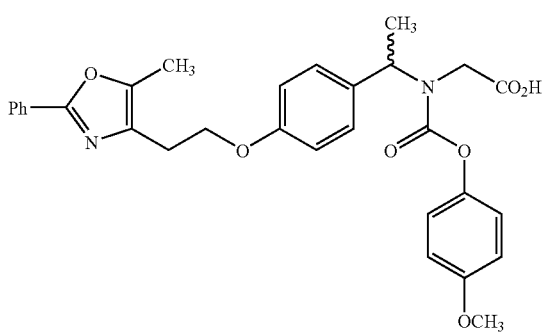
$^1$H NMR (DMSO-$d_6$; 400 MHz) δ 1.47 and 1.54 (2d, J=7.5 Hz; 3H), 2.37 (s, 3H), 2.94 (t, J=6.6 Hz, 2H), 3.74 (s, 3H), 3.81 (m, 2H), 4.21 (t, J=6.6 Hz, 2H), 5.36 (m, 1H), 6.94 (m, 4H), 7.29 (m, 2H), 7.49 (m, 3H), 7.91 (m, 2H)
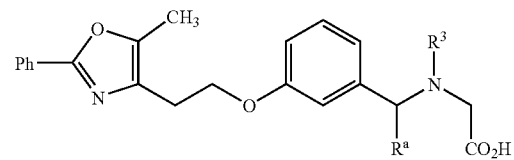
| Example No. | Structure | [M + H]⁺ |
|---|---|---|
| 512 | (±) | 531.3 |

The synthesis of Examples 513–518 involved the use of Example 541 Part B compound as the alkylating agent.
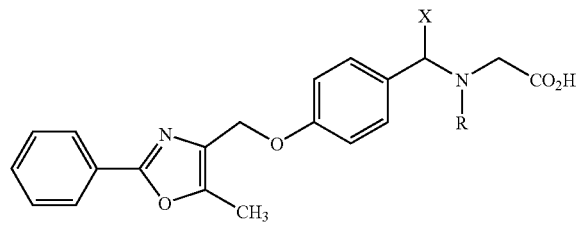
| Example No. | Structure | [M + H]+ |
|---|---|---|
| 513 | 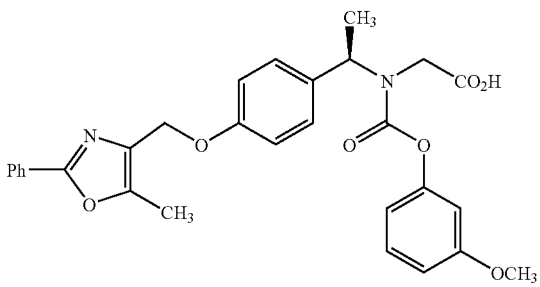 | 517.2 |
| 514 | 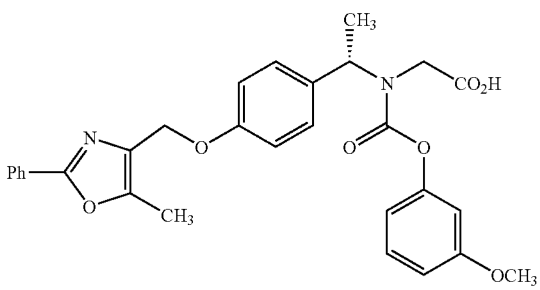 | 517.2 |
| 515 | 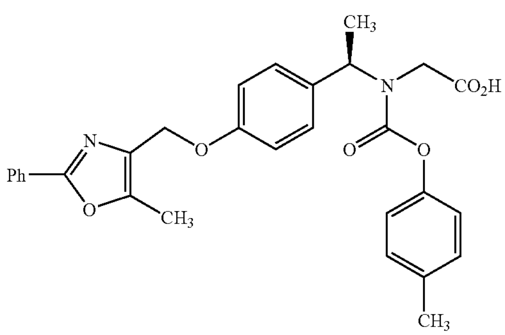 | 501.2 |
| 516 | 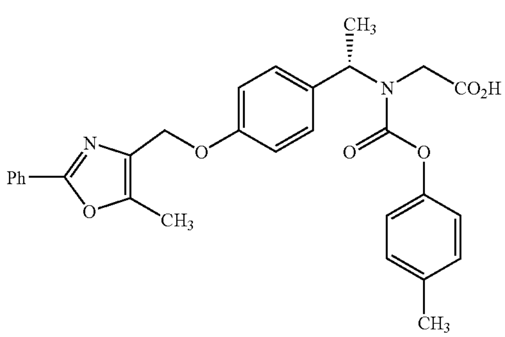 | 501.2 |

-continued

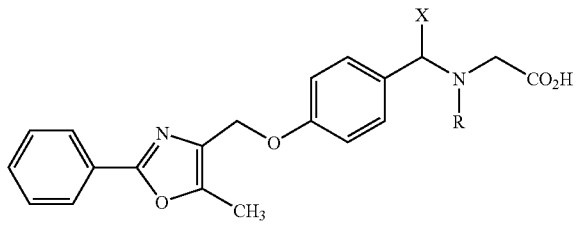

| Example No. | Structure | [M + H]+ |
|---|---|---|
| 517 | 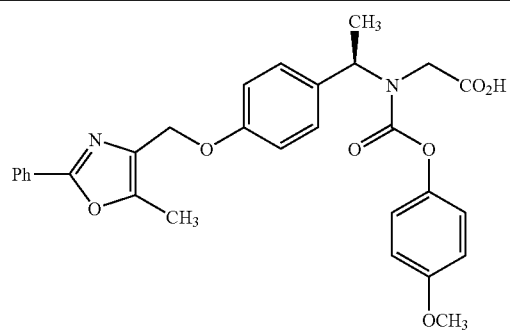 | 517.2 |
| 518 | 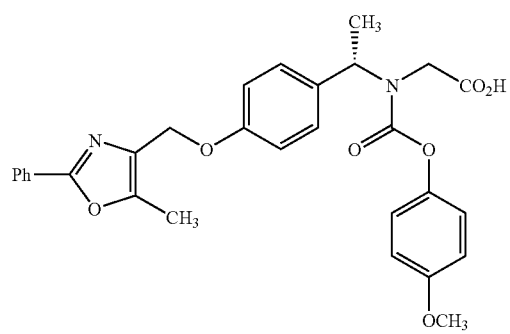 | 517.2 |

EXAMPLE 519

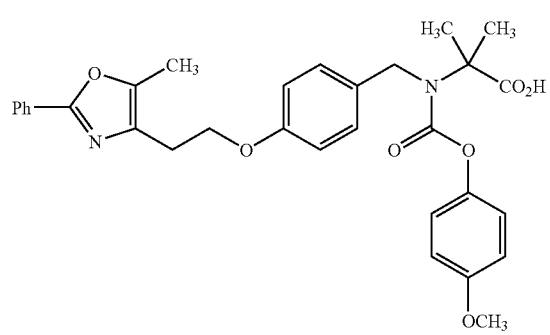

A.

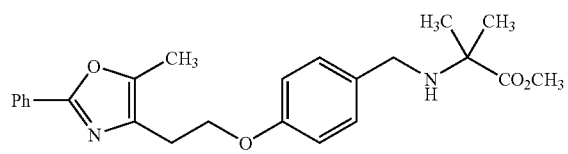

A mixture of methyl α-aminoisobutyrate hydrochloride (108 mg; 0.7 mmol), $Et_3N$ (146 μL; 111 mmol), NaBH(OAc), (222 mg; 11 mmol) and the aldehyde (215 mg; 07 mmol)

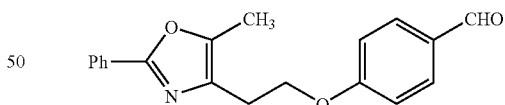

in DCE (5 mL) was stirred at RT for 21 h. Some starting material remained, so the reaction was heated at 55° C. for 4 h (no further reaction). Saturated aqueous $NaHCO_3$ was added, and volatiles were removed in vacuo. The residue was partitioned between $H_2O$ and EtOAc. The aqueous phase was extracted with EtOAc (2×). The combined organic extracts were washed with brine and extracted with aqueous 1 M HCl. The aqueous phase was basified with solid NaOH and extracted with EtOAc (2×). The organic extracts were dried ($Na_2SO_4$) and concentrated in vacuo to give crude Part A compound (174 mg; 61%).

B.

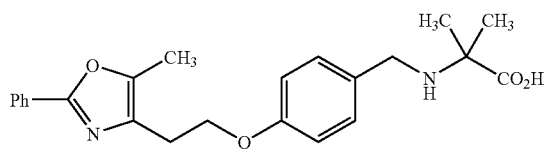

C.

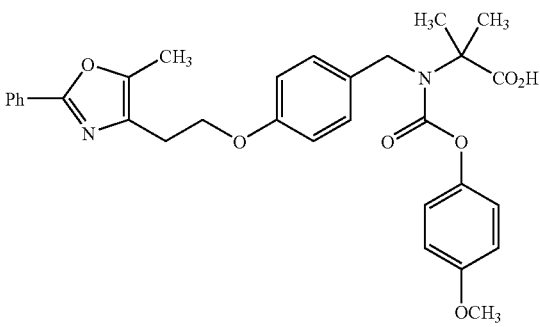

A solution of Part A compound (120 mg; 0.29 mmol) aqueous LiOH (2.0 mL of a 0.3 M solution of a 1:1:1 mixture of THF:MeOH:H$_2$O) was stirred at RT overnight. The reaction was acidified to pH~2 with aqueous 1 M HCl, then was concentrated in vacuo and purified by preparative HPLC (YMC S5 ODS 30×250 mm column; flow rate=25 mL/min; continuous gradient from 40:60 B:A to 100% B over 30 min, where solvent A=90:10:0.1 H$_2$O:MeOH:TFA; solvent B=90:10:0.1 MeOH:H$_2$O:TFA) to furnish Part B compound (60 mg; 53%) as a syrup.

A solution of Part B compound (25 mg; 0.06 mmol), 4-methoxyphenyl chloroformate (20 μL) in pyridine (1 mL) was heated at 60° C. for 6 h. Volatiles were removed in vacuo and the residue was partitioned between EtOAc (2 mL) and aqueous 1 M HCl (1 mL). The organic phase was concentrated in vacuo and the residue was purified by preparative HPLC (YMC S5 ODS 30×250 mm column; flow rate=25 mL/min; continuous gradient from 40:60 B:A to 100% B over 20 min, where solvent A=90:10:0.1 H$_2$O:MeOH: TFA; solvent B=90:10:0.1 MeOH:H$_2$O:TFA) to furnish title compound (4 mg; 12%) as a white foam. [M+H]$^+$=545.3

Following the procedures as set out hereinbefore, the following Examples 520 to 535 compounds were prepared.

EXAMPLES 520 TO 535

| Example No. | Structure | [M + H]$^+$ |
|---|---|---|
| 520 | 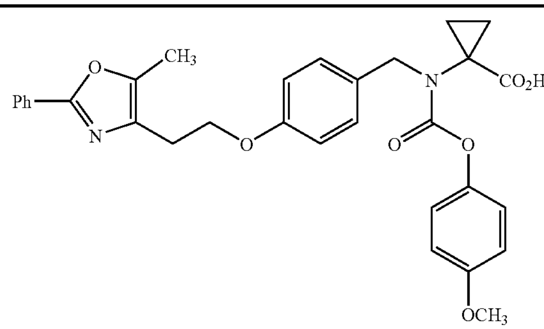 | 543.4 |
| 521 | 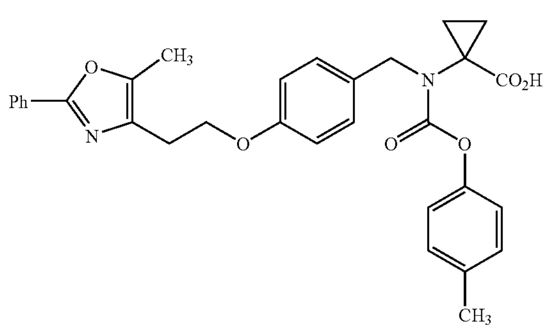 | 527.3 |

-continued
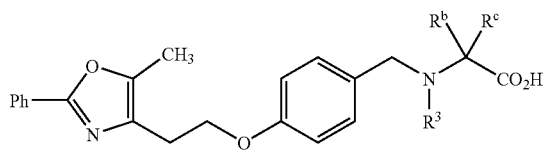
| Example No. | Structure | [M + H]+ |
|---|---|---|
| 522 | 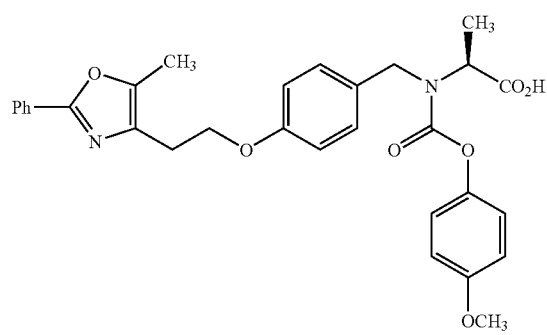 | 531.2 |
| 523 | 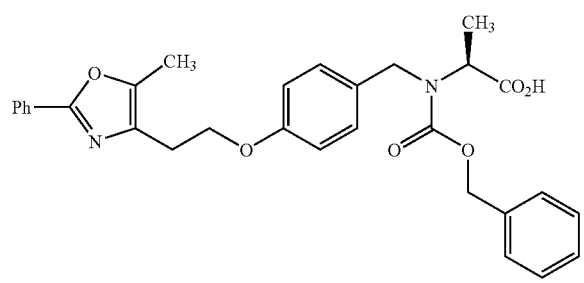 | 515.2 |
| 524 | 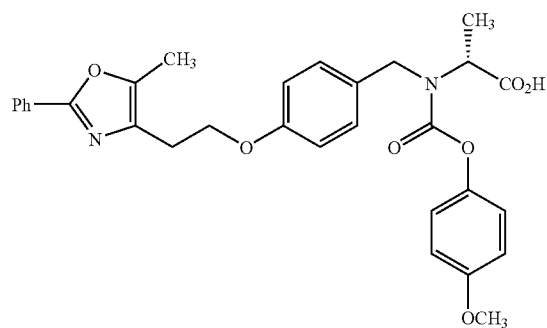 | 531.2 |
| 525 | 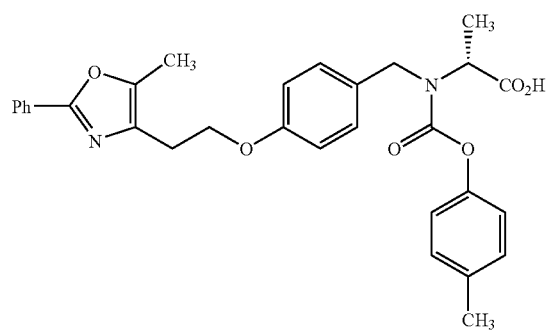 | 515.2 |

-continued
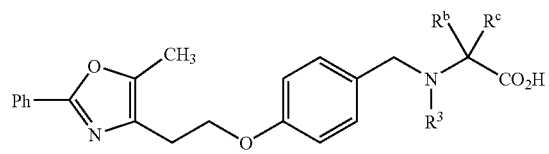
| Example No. | Structure | [M + H]+ |
|---|---|---|
| 526 | 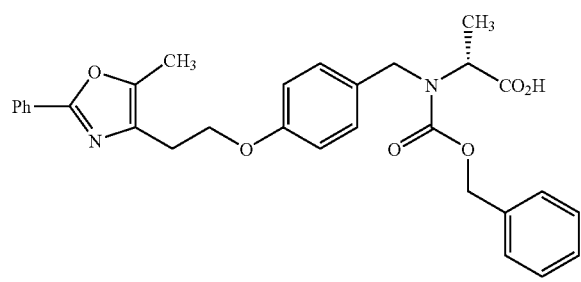 | 515.2 |
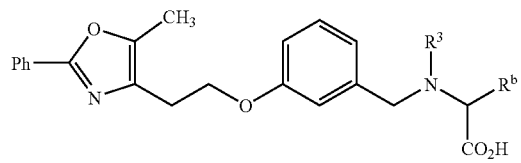
| Example No. | Structure | [M + H]+ |
|---|---|---|
| 527 | 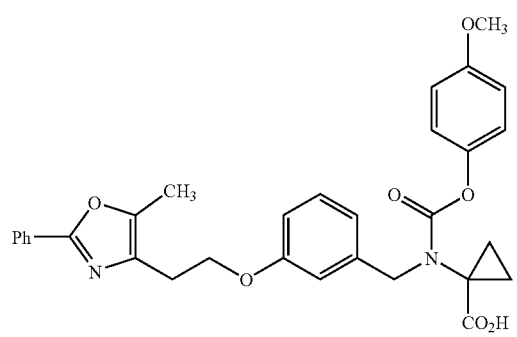 | 543.3 |
| 528 | 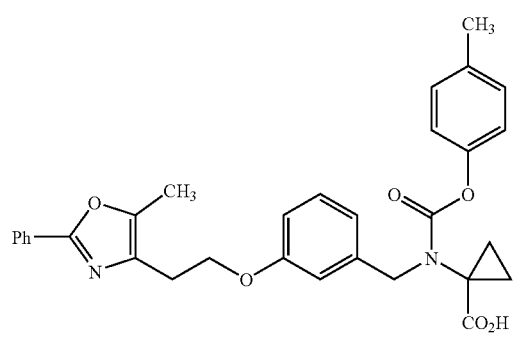 | 527.3 |

-continued
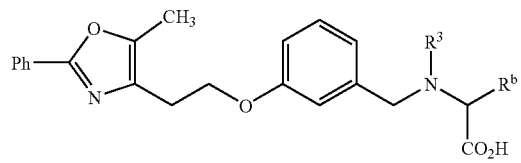
| Example No. | Structure | [M + H]⁺ |
|---|---|---|
| 529 | 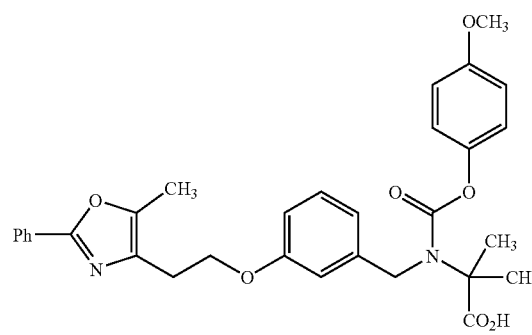 | 545.3 |
| 530 | 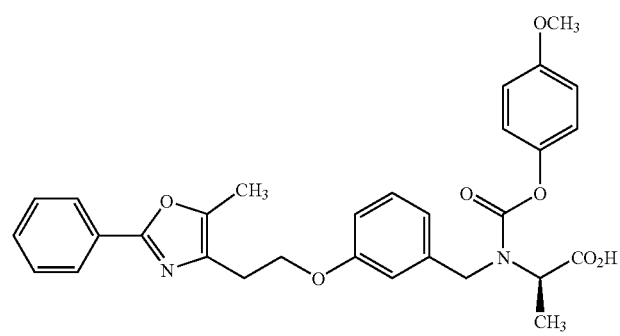 | 531.2 |
| 531 | 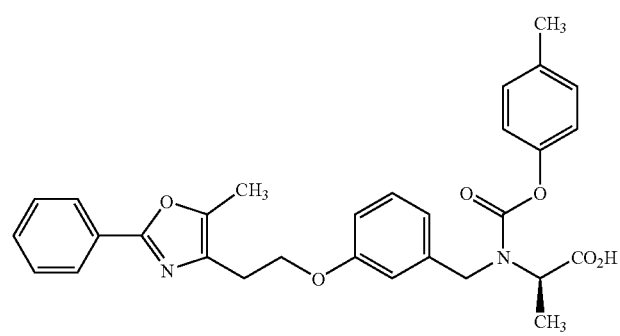 | 515.2 |
| 532 | 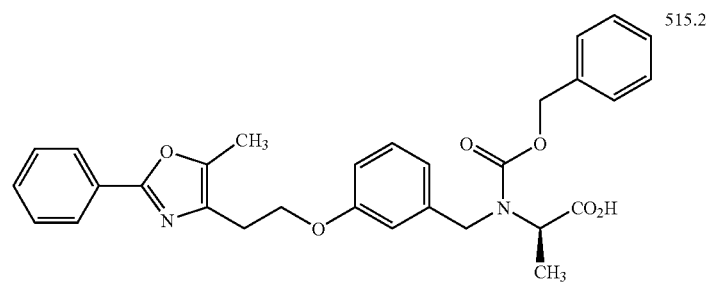 | 515.2 |

-continued
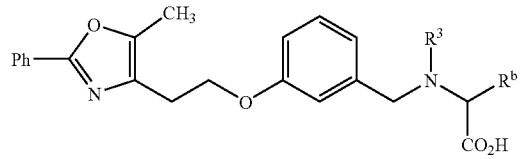
| Example No. | Structure | [M + H]+ |
|---|---|---|
| 533 | 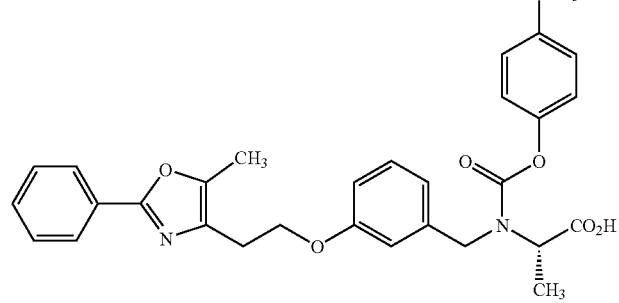 | 531.2 |
| 534 | 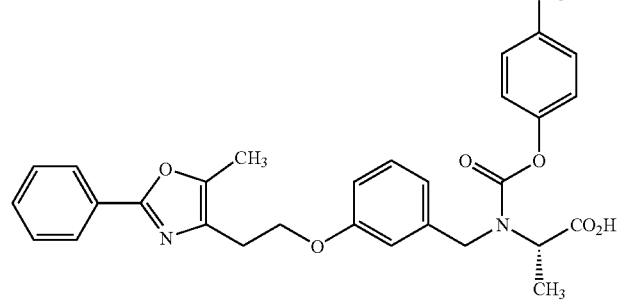 | 515.2 |
| 535 | 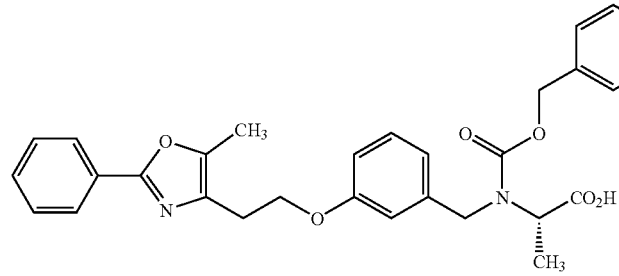 | 515.2 |
EXAMPLE 536
A.
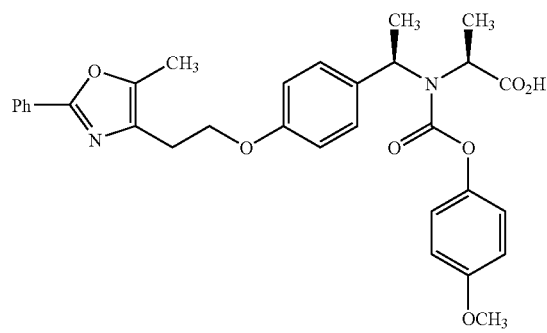
-continued
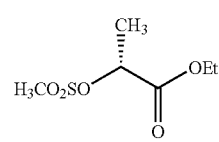
To a 0° C. solution of (R)-(−)-lactate (3.0 g; 29 mmol) and Et₃N (4.8 mL; 35 mmol) in CH₂Cl₂ (60 mL) was added methanesulfonyl chloride (2.67 mL; 35 mmol). The mixture was stirred at 0° C. for 1 h, then partitioned between CH₂Cl₂ and 1M aqueous HCl (100 mL each). The organic phase was washed with H₂O and brine, dried (MgSO₄), and concentrated in vacuo without heating to give Part A compound as an oil (4.5 g; 86%), which was used in the next step without further purification.

B.

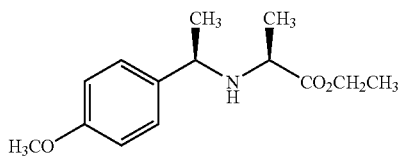

A mixture of Part A compound (1.42 g; 6.0 mmol), (R)-4-methoxy-α-methyl benzylamine (300 mg, 2.0 mmol), and K₂CO₃ (828 mg; 6.0 mmol) in MeCN (20 mL) was heated at 70° C. for 17 h (some amine starting material still remained). The reaction cooled to RT, filtered, and the volatiles were removed in vacuo. The residue was partitioned between EtOAc and H₂O. The organic phase was washed with brine, dried (MgSO₄), and concentrated in vacuo. The residue was chromatographed (SiO₂; stepwise gradient from 99:1 to 97:3 CHCl₃:MeOH) to give Part B compound (330 mg; 70%) as an oil.

C.

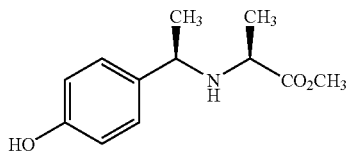

To a 0° C. solution of Part B compound (330 mg; 1.39 mmol) in CH₂Cl₂ (3 mL) was slowly added dropwise BBr₃ (3.0 mL of a 1 M solution in CH₂cl2; 30 mmol). The reaction was stirred at 10° C. for 3 h, then quenched by cautious addition of saturated aqueous NH₄Cl and CH₂Cl₂. The isolated aqueous phase was neutralized by slow addition of solid NaHCO₃, then extracted with EtOAc (2×). The combined organic extracts were washed with brine, dried (MgSO₄) and concentrated in vacuo to furnish crude Part C compound (150 mg; 48%), which was used in the next reaction without further purification.

D.

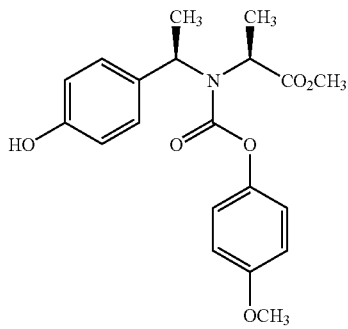

To a solution of Part C compound (300 mg; 1.35 mmol) in dioxane:H₂O (6 mL of a 1:1 solution) were successively added NaHCO₃ (500 mg; 5.95 mmol) and 4-methoxyphenyl chloroformate (300 μL; 2.0 mmol) slowly. The reaction was stirred at RT for 1 h, then partitioned between EtOAc and H₂O. The organic phase was washed with brine, dried (MgSO₄), and concentrated in vacuo to give a crude residue, which was chromatographed (SiO₂; stepwise gradient from 3:1 to 1:1 hexane:EtOAc) to furnish Part D compound (330 mg; 66%).

E.

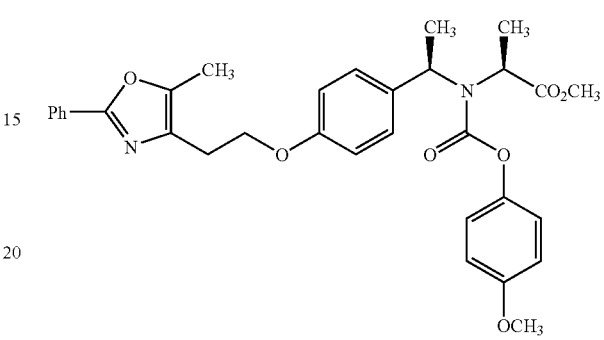

To a solution of Part D compound (330 mg; 0.88 mmol) in MeCN (20 mL) were successively added K₂CO₃ (165 mg; 1.2 mmol) and the mesylate (337 mg; 1.2 mmol).

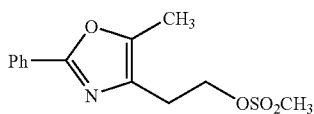

The reaction mixture was heated at 95° C. for 16 h, then cooled to RT and filtered. The filtrate was concentrated in vacuo and then partitioned between EtOAc and H₂O. The organic phase was washed with brine, dried (MgSO₄) and concentrated in vacuo. The residue was chromatographed (SiO₂; 3:1 hexane:EtOAc) to give Part E compound (350 mg; 71%).

F.

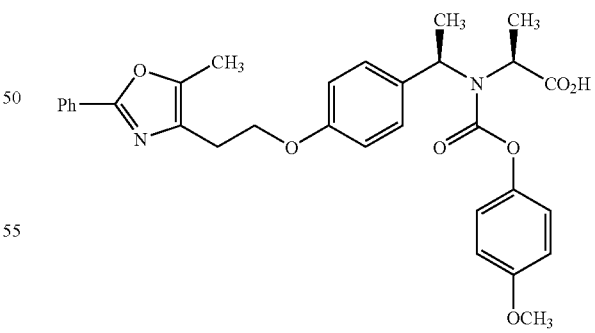

To a solution of Part E compound (350 mg; 0.62 mmol) in THF:H₂O (15 mL of a 2:1 solution) was added LiOH.H₂O (52 mg; 1.2 mmol). The reaction was stirred at RT overnight for 14 h; then EtOAc was added and the solution acidified with 1 N HCl solution to pH~2. The organic phase was washed with brine, dried (MgSO₄) and concentrated in vacuo. The residue was purified by preparative HPLC (YMC S5 ODS 30×250 mm column; flow rate=25 mL/min; 20 min continuous gradient from 50:50 B:A to 100% B, where solvent A=90:10:0.1 H₂O:MeOH:TFA and solvent B=90:10:0.1 MeOH:H₂O:TFA; retention time=26 min) and lyophilized from dioxane to give the title compound (208 mg; 61% yield) as a white solid.

[M+H]⁺=545.3

Alternative Synthesis of Example 536

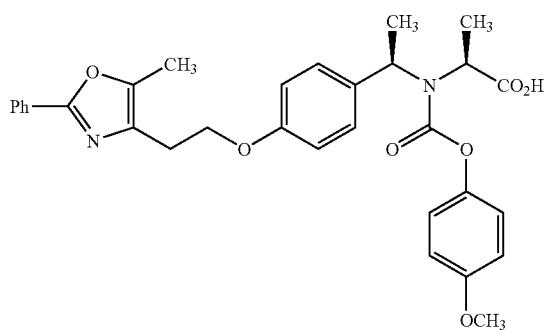

A.

A mixture of the phenol [500 mg; 1.94 mmol; prepared from (R)-1-(4-methoxyphenyl)ethylamine as for the alternative synthesis of Example 498],

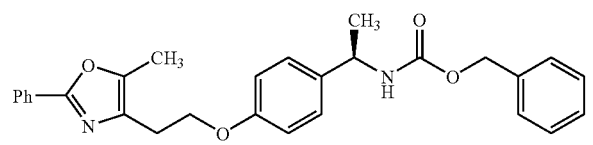

K₂CO₃ (400 mg; 2.89 mmol) and the mesylate (710 mg; 2.52 mmol)

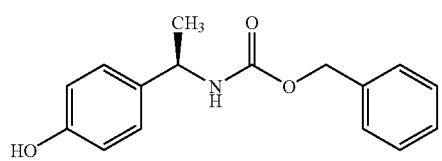

in MeCN (6.5 mL) was heated at 90° C. in an oil bath under an atmosphere of Ar for 20 h. The reaction was allowed to cool to RT, diluted with CH₂Cl₂ (40 mL) and filtered. The filtrate was concentrated in vacuo. The residue was chromatographed (SiO₂; continuous gradient from 100% hex to 4:1 hexane:EtOAc over 20 min, then 4:1 hex:EtOAc to 100% EtOAc over 20 min, then EtOAc for 5 min) to furnish Part A compound (414 mg; 47%) as a white solid.

B.

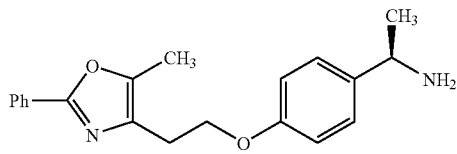

A mixture of Part A compound (300 mg; 0.66 mmol) and 10% palladium on carbon (50 mg) in MeOH (20 mL) was stirred under an atmosphere of H₂ (balloon) at RT for 2 h, at which point the reaction was complete by HPLC. The reaction mixture was filtered through Celite® and the filtrate was concentrated in vacuo to provide Part B compound (208 mg; 79%) as an oil which eventually became a white solid upon standing.

C.

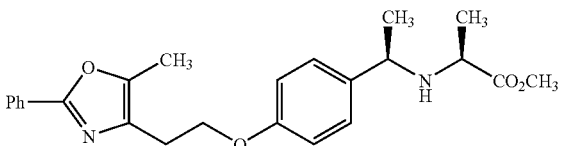

A mixture of Part B compound (160 mg; 0.50 mmol), K₂CO₃ (206 mg; 1.49 mmol) and the mesylate (292 mg; 1.49 mmol; Example 536 Part A compound)

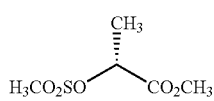

in MeCN (5 mL) was heated at 70° C. for 24 h. At this point more mesylate (97 mg; 0.50 mmol) was added, and the reaction was heated at 70° C. for a further 16 h. The reaction mixture was cooled to RT and filtered. The filtrate was concentrated in vacuo, and the residue was chromatographed (SiO₂; stepwise gradient from hex:EtOAc 3:1 to 1:1) to furnish Part C compound (98 mg; 47%) as an oil. This intermediate was then used for the preparation of Example 536 in an identical manner to that previously shown.

EXAMPLES 537 TO 539

Following the procedures set out hereinbefore, the Examples 537 to 539 compounds were prepared.

| Example No. | Structure | [M + H]+ |
|---|---|---|
| 537 | 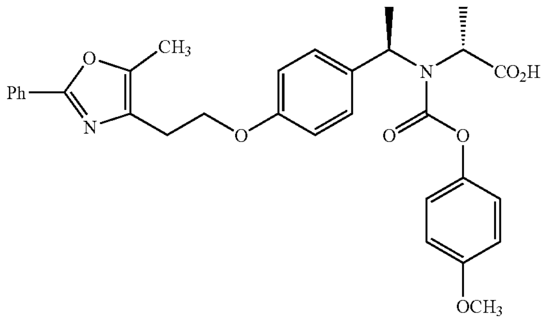 | 545.3 |
| 538 | 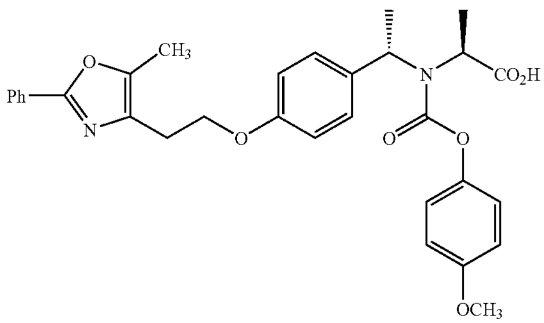 | 545.3 |
| 539 | 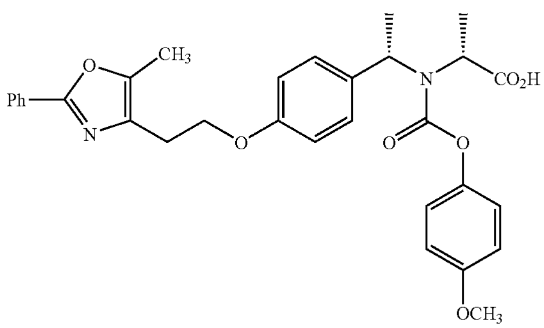 | 545.3 |

EXAMPLE 540

A.

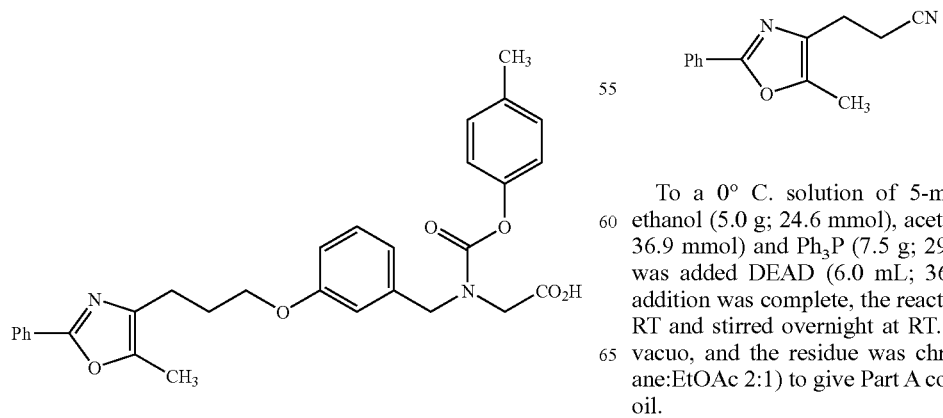

To a 0° C. solution of 5-methyl-2-phenyl-oxazol-4-yl ethanol (5.0 g; 24.6 mmol), acetone cyanohydrin (3.35 mL; 36.9 mmol) and Ph₃P (7.5 g; 29.5 mmol) in THF (60 mL) was added DEAD (6.0 mL; 36.9 mmol) dropwise. After addition was complete, the reaction mixture was warmed to RT and stirred overnight at RT. Volatiles were removed in vacuo, and the residue was chromatographed (SiO₂; hexane:EtOAc 2:1) to give Part A compound (4.5 g; 86%) as an oil.

B.

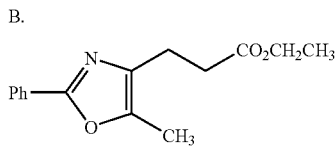

A solution of Part A compound (4.5 g; 21.2 mmol) and H₂SO₄ (concentrated; 20 mL) in EtOH (100 mL) was heated under reflux overnight. The solution was concentrated in vacuo to ⅓ its original volume, then EtOAc (150 mL) and H₂O (100 mL) were cautiously added. The organic phase was washed with saturated aqueous NaHCO₃ (2×100 mL) and brine (150 mL), dried (MgSO₄), and concentrated in vacuo to give a crude oil. This material was chromatographed (SiO₂; hexane:EtOAc 2:1) to give Part B compound (2.1 g; 38%) as a crystalline solid.

C.

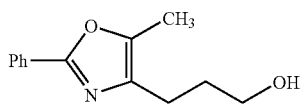

To a −78° C. solution of Part B compound (2.1 g; 8.1 mmol) in THF (6 mL) was added dropwise LiAlH₄ (16 mL of a 1.0 M solution in THF; 16 mmol) under an atmosphere of N₂. The mixture was allowed to warm to 0° C. and stirred at 0° C. for 30 min, after which the reaction was determined to be complete by TLC (hex:EtOAc 1:1). Aqueous HCl (1.0 mL of a 1 M solution; 1 mmol) and saturated aqueous sodium potassium tartrate (10 mL) were successively added and the mixture was stirred at RT for 30 min. The mixture was extracted with EtOAc (100 mL), washed with H₂O and brine, dried (Na₂SO₄) and concentrated in vacuo to give crude Part C compound (1.78 g; 97%) as a white solid, which was used in the next step without further purification.

D.

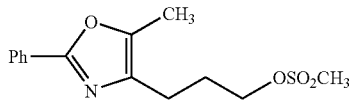

To a solution of Part C compound (670 mg; 3.09 mmol) and Et₃N (516 µL; 3.71 mmol) in CH₂Cl₂ (4 mL) was added methanesulfonyl chloride (286 µL; 3.71 mmol). The reaction mixture was stirred at RT for 30 min, at which point the reaction was complete by TLC (hex:EtOAc 2:1). The mixture was partitioned between CH₂Cl₂ (60 mL) and H₂O (40 mL). The organic phase was washed with brine (40 mL), dried (MgSO₄), and concentrated in vacuo to give Part D compound (910 mg; 100%) which was used in the next step without further purification.

E.

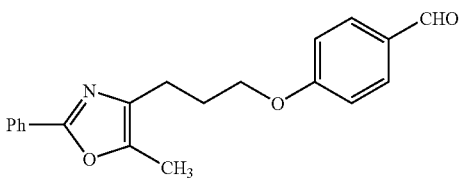

A mixture of Part D compound (380 mg; 1.29 mmol), 4-hydroxybenzaldehyde (188 mg; 1.55 mmol) and K₂CO₃ (214 mg; 1.55 mg) in MeCN (12 mL) was refluxed in an oil bath for 17 h. At this point all starting Part D compound had been consumed (but there was a significant quantity of the hydrolysis by-product, Part C compound) by HPLC/MS. The reaction was cooled to RT and the solid precipitates were filtered off. The filtrate was concentrated in vacuo and partitioned between EtOAc (60 mL) and H₂O (40 mL). The organic phase was washed with brine (40 mL), dried (MgSO₄), and concentrated in vacuo to give the crude product. This material was chromatographed (SiO₂; stepwise gradient from 4:1 to 1:2 hex:EtOAc) to give Part E compound (150 mg; 36%) as an oil in addition to Part C compound (100 mg; 36%).

F.

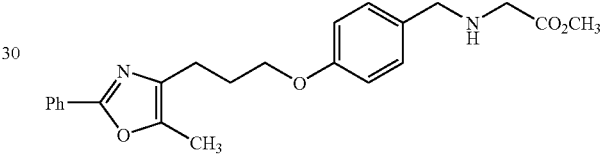

A mixture of Part E compound (150 mg; 0.50 mmol), glycine methyl ester hydrochloride (75 mg; 0.60 mmol) and Et₃N (84 µL; 0.60 mmol) in MeOH (5 mL) was stirred at RT for 6 h, after which NaBH₄ (50 mg) was added cautiously portionwise. The reaction mixture was stirred at RT overnight, after which volatiles were removed in vacuo. The residue was partitioned between EtOAc and H₂O. The organic phase was washed with brine, dried (Na₂SO₄) and concentrated in vacuo to give Part F compound (180 mg; 97%) as an oil.

G.

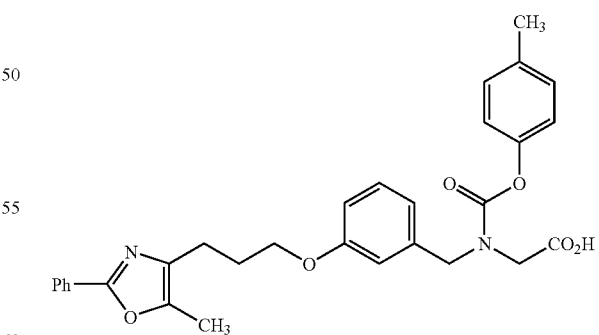

A mixture of Part F compound (23 mg; 0.060 mmol), Et₃N (10 µL; 0.66 mmol) and 4-tolyl chloroformate (10 µL; 0.066 mmol) in CH₂Cl₂ (1 mL) was stirred at RT for 2 h. Volatiles were removed in vacuo and the residue was dissolved in a solution of THF/MeOH/H₂O (1 mL of a 2:2:1 mixture); LiOH. H₂O (14 mg; 0.33 mmol) was added, and the reaction was stirred at RT for 2 h. Volatiles were removed in vacuo, and the residue was partitioned between aqueous 1 M HCl and EtOAc. The organic extract was concentrated in vacuo and the residue was purified by preparative HPLC (YMC ODS S5 30 mm×250 mm column, continuous 25 minute gradient from 40% B:60% A to 100% B, hold at 100% B for 15 min, where solvent A=90:10:0.1 H$_2$O:MeOH:TFA and solvent B=90:10:0.1 MeOH:H$_2$O:TFA; flow rate=25 mL/min) to give the title compound as a white solid (13 mg; 45% over 2 steps). [M+H]$^+$=515.3

EXAMPLE 541

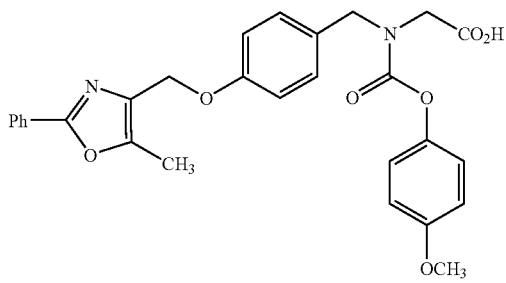

A.

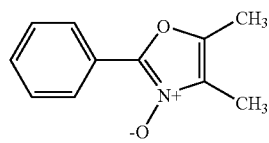

To a solution of benzaldehyde (23.8 g, 234 mmol) in EtOAc (150 mL; pre-saturated with HCl gas) was added 2,3-butanedione mono-oxime (25.0 g, 234 mmol) in one portion and the resulting solution was stirred at RT for 12 h. Analytical HPLC indicated that all starting materials had been consumed. The reaction mixture was concentrated in vacuo to yield Part A compound as a white solid, which was used in the next step without further purification.

B.

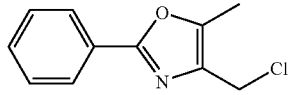

To a solution of Part A compound in CHCL$_3$ (200 mL) was added dropwise POCl$_3$ (30 mL, 320 mmol). The reaction was stirred for 12 h at 50° C., then was concentrated in vacuo. The brown residue was partitioned between EtOAc (300 mL) and 1N aqeuous NaOH. The organic phase was washed with brine, dried, (MgSO$_4$) and concentrated in vacuo. The residue was chromatographed (SiO$_2$; Et$_2$O) to give Part B compound (41.5 g; 86%) as a light brown solid (>95% pure by analytical HPLC and $^1$H-NMR analysis).

C.

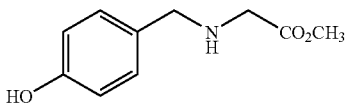

A solution of 4-hydroxybenzaldehyde (20 g, 160 mmol), glycine methyl ester hydrochloride (22 g, 180 mmol) and Et$_3$N (25 mL, 180 mmol) in MeOH (200 mL) was stirred at RT for 12 h. The reaction mixture was cooled to 0° C. and NaBH$_4$ (9.0 g, 240 mmol) was added portionwise while maintaining the reaction temperature at <RT. The reaction mixture was stirred for 5 h, then was concentrated in vacuo to give crude Part C compound, which was used in the next step without further purification.

D.

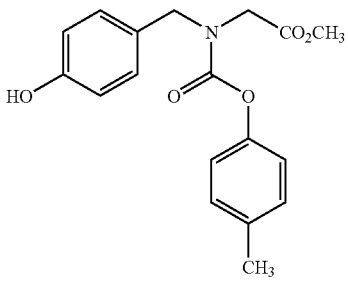

To a solution of crude Part C compound in Et$_2$O (300 mL) and H$_2$O (200 mL) were added NaHCO$_3$ (20 g, 240 mmol, in a single portion) and 4-tolyl chloroformate (15 mL, 150 mmol; dropwise). The biphasic reaction mixture was stirred for 12 h at RT. The aqueous phase was then extracted with Et$_2$O (2×200 mL). The combined organic extracts were washed with brine (2×50 mL), dried (MgSO$_4$) and concentrated in vacuo. The residue was chromatographed (SiO$_2$; stepwise gradient from 3:1 to 1:1 hexane:EtOAc) to give Part D compound (40.8 g; 76% over 2 steps) as an oil.

E.

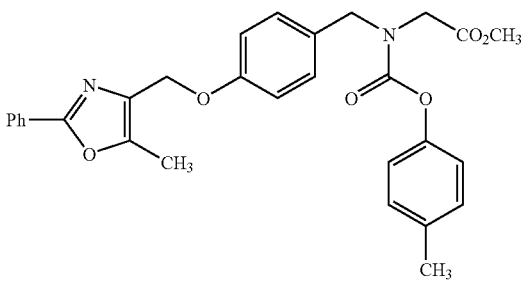

A solution of Part B compound (14.5 g, 70 mmol), Part C compound (21.6 g, 67 mmol) and K$_2$CO$_3$ (18.4 g, 134 mmol) in CH$_3$CN (150 mL) was stirred at 80° C. for 12 h. The reaction was cooled to RT and volatiles were removed in vacuo. The brown oily residue was partitioned between EtOAc (250 mL) and brine (100 mL). The aqueous layer was extracted with EtOAc (3×100 mL). The combined organic extracts were dried (MgSO$_4$) and concentrated in vacuo. The residue was chromatographed (SiO$_2$; stepwise gradient from 3:1 to 1:1 hexane:EtOAc) to give Part D compound (23.6 g; 71%) as a colorless oil.

F.

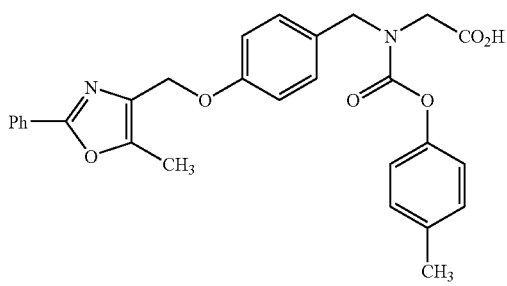

A solution of Part D compound (23.6 g, 47.4 mmol) and LiOH.H₂O (4.0 g, 95 mmol) in THF (200 mL) and H₂O (120 mL) was stirred at RT for 4 h. The reaction mixture was then acidified to pH~2 with aqueous 1N HCl. The aqueous phase was extracted with EtOAc (3×200 mL). The combined organic extracts were dried (MgSO₄) and concentrated in vacuo to yield an oily residue, which was recrystallized from EtOAc to provide title compound (19.4 g; 84%) as a white solid. [M+H]⁺=487.23;

¹H NMR (CD₃OD; 400 MHz): δ 2.32 (s, 3H), 2.46 (s, 3H) 3.99 & 4.04 (2s, 2H), 4.47 & 4.54 (2s, 2H), 5.01 and 5.00 (2s, 2H), 6.99 (d, J=8.4 Hz, 2H), 7.05 (m, 2H), 7.17 (d, J=8.4 Hz, 2H), 7.31 (m, 2H); 7.49 (m, 3H), 8.01 (m, 2H);

¹H NMR (CDCl₃; 400 MHz): δ 2.31 (s, 3H), 2.44 (s, 3H) 4.00 (s, 2H), 4.55 (2s, 2H), 5.00 (2s, 2H); 6.99 (m, 4H); 7.13 (m, 2H), 7.21 (d, J=8.8 Hz, 2H); 7.31 (m, 2H) 7.44 (s, 3H); 8.01 (s, 2H)

EXAMPLE 542

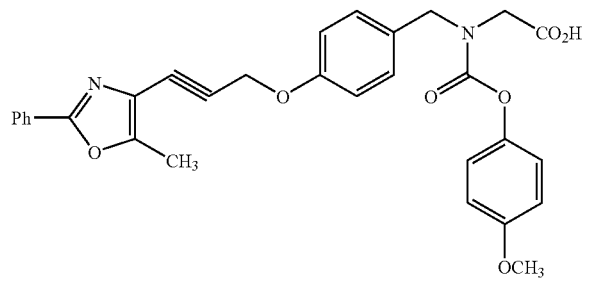

A.

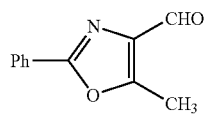

A mixture of 2-phenyl-5-methyl-oxazole-4-acetic acid (470 mg; 2.17 mmol; Maybridge) pyridine N-oxide (830 mg; 8.74 mmol) and acetic anhydride (350 mg; 3.57 mmol) in toluene (10 mL) was heated at 90° C. for 12 h, then concentrated in vacuo. The residue was then partitioned between EtOAc and 1M aqueous HCl. The organic phase was washed with saturated aqueous NaHCO₃, brine, dried (Na₂SO₄) and concentrated in vacuo to give a dark brown oil. This material was chromatographed (SiO₂; 4:1 hex:EtOAc) to give Part A compound (143 mg; 35%) as an oil.

B.

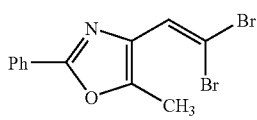

To a 0° C. solution of Part A compound (600 mg; 3.21 mmol) and Ph₃P (3.37 g; 12.9 mmol) in CH₂cl₂ (50 mL) was added dropwise a solution of CBr₄ (2.13 g; 6.4 mmol) in CH₂Cl₂ (20 mL). The solution was stirred at 0° C. for 2 h, then allowed to warm to RT and stirred at RT overnight. Volatiles were removed in vacuo and the residue was chromatographed (85:15 hexane:EtOAc) to furnish Part B compound (1.08 g; 98%) as a pale yellow solid.

C.

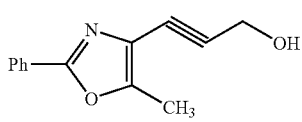

To a −78° C. solution of Part B compound (1.12 g; 3.26 mmol) in THF (60 mL) was added n-butyllithium dropwise (4.2 mL of a 1.6 M solution in hexane; 6.72 mmol) over 25 min, while maintaining the internal temperature at ≦−71° C. The reaction was stirred at −78° C. for 1 h, then allowed to warm slowly to 0° C. Paraformaldehyde (305 g) was then added in one portion and the reaction was stirred at 0° C. for 3 h and then quenched with saturated aqueous NH₄Cl. The aqueous phase was extracted with EtOAc (2×); the combined organic extracts were washed with brine, dried (Na₂SO₄) and concentrated in vacuo to give a dark oil. This material was chromatographed (SiO₂; 3:2 hex:EtOAc) to give Part C compound (466 mg; 67%) as a yellow solid.

D.

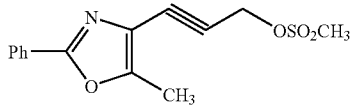

To a 0° C. solution of Part C compound (466 mg; 2.19 mmol) and Et₃N in CH₂Cl₂ was added dropwise methanesulfonyl chloride (190 μL; 2.45 mmol) and the reaction was stirred at 0° C. for 1 h. The mixture was then partitioned between CH₂Cl₂ and cold 1M aqueous HCl. The organic phase was washed with brine, dried (Na₂SO₄) and concentrated in vacuo. The crude product was chromatographed (SiO₂; 3:2 hex:EtOAc) to give Part D compound (533 mg; 84%) as an off-white solid.

E.

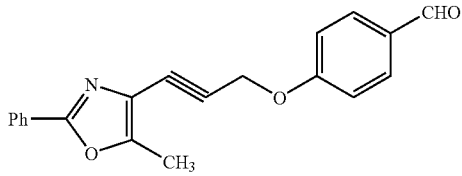

A mixture of Part D compound (198 mg; 0.68 mmol), 4-hydroxybenzaldehyde (96 mg; 0.79 mmol) and K₂CO₃ (141 mg; 1.02 mmol) in CH₃CN (13 mL) was heated at 70°

C. for 3 h, then stirred at RT overnight. Volatiles were removed in vacuo, and the residue was partitioned between EtOAc and 1 M aqueous NaOH. The organic phase was washed with brine, dried (Na$_2$SO$_4$) and concentrated in vacuo to give crude Part E compound (190 mg; 88%) as a yellow oil, which was used in the next step without further purification.

F.

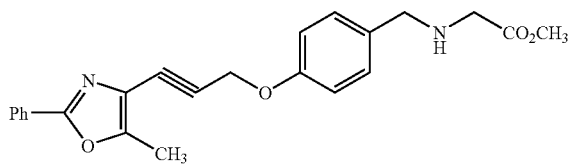

A mixture of Part E compound (123 mg; 0.39 mmol), glycine methyl ester hydrochloride (248 mg; 1.98 mmol) and Et$_3$N (600 µL; 4.3 mmol) in DCE (15 mL) was stirred at RT for 15 min, after which NaBH(OAc)$_3$H (262 mg; 1.2 mmol) was added in one portion. The reaction was stirred for 16 h at RT, after which additional NaBH(OAc)$_3$H (200 mg; 0.94 mmol) was added. Stirring was continued for 3 h, after which still more NaBH(OAc)$_3$H (200 mg; 0.94 mmol) was added. The reaction was stirred at RT for 48 h, after which all Part E compound had been consumed. The reaction mixture was partitioned between CH$_2$Cl$_2$ and aqueous NaHCO$_3$. The aqueous phase was extracted with CH$_2$Cl$_2$ (2×). The combined organic extracts were washed with brine, dried (Na$_2$SO$_4$) and concentrated in vacuo. The crude product was chromatographed (SiO$_2$; stepwise gradient from 1:1 to 2:3 hex:EtOAc) to give Part F compound (120 mg; 79%) as a colorless oil which solidified on standing.

G.

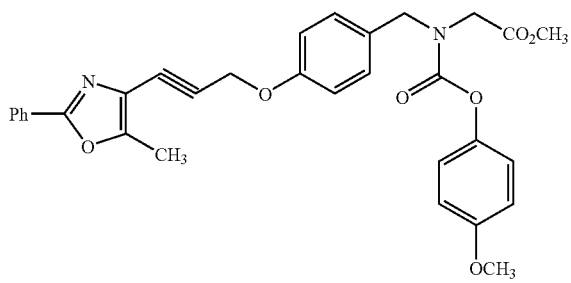

To a solution of Part F compound (180 mg; 0.46 mmol) and pyridine (100 µL; 1.24 mmol) in CH$_2$Cl$_2$ (10 mL) was added 4-methoxyphenyl chloroformate (105 µL; 0.71 mmol). The reaction was stirred at RT for 3.5 h, then partitioned between aqueous NaHCO$_3$ and EtOAc. The aqueous phase was extracted with EtOAc (2×). The combined organic extracts were washed with brine, dried (Na$_2$SO$_4$) and concentrated in vacuo. The crude product was chromatographed (SiO$_2$; hex:EtOAc 3:2) to give Part G compound (232 mg; 93%) as a colorless oil.

H.

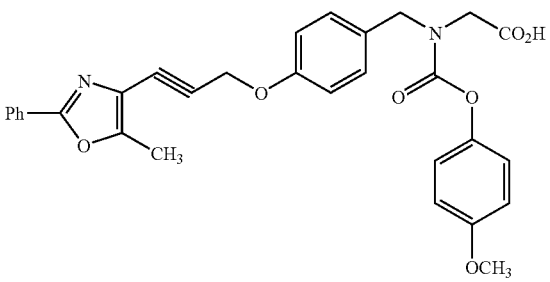

To a solution of Part G compound (232 mg; 0.43 mmol) in THF:H$_2$O (12 mL of a 5:1 mixture) was added LiOH·H$_2$O (1.3 mmol). The solution was stirred at RT overnight, then acidified with aqueous 1M HCl and extracted with EtOAc (2×). The combined organic extracts were washed with brine, dried (Na$_2$SO$_4$) and concentrated in vacuo. The crude product was purified by preparative HPLC (YMC S5 ODS 30×75 mm column, flow rate=20 mL/min; continuous gradient from 70:30 B:A to 100% B, where solvent A=90:10:0.1 H$_2$O:MeOH:TFA and solvent B=90:10:0.1 MeOH:H$_2$O:TFA) to give title compound (160 mg; 71%) as a white solid. [M+H]$^+$=527.2

EXAMPLE 543

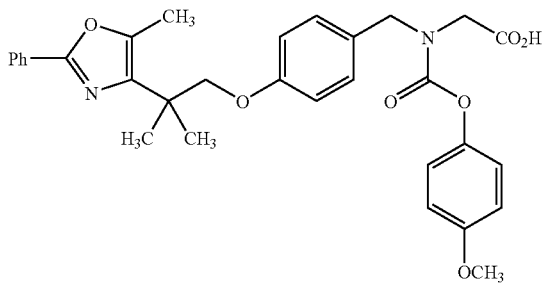

A.

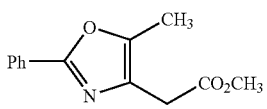

A solution of 5-methyl-2-phenyloxazole-4-yl-acetic acid (4.0 g; 18 mmol) and concentrated HCl (2 mL) in MeOH (60 mL) was heated at reflux overnight. Volatiles were removed in vacuo; the residue was partitioned between H$_2$O and EtOAc. The organic phase was washed with brine, dried (MgSO$_4$) and concentrated in vacuo to give crude Part A compound as a colorless oil (4.00 g; 94%) which was used in the next step without further purification.

B.

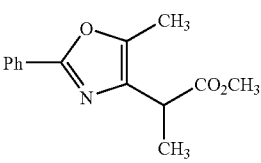

To a −78° C. solution of LDA (15.0 mL of a 2.0 M solution in heptane/THF; 30 mmol; Aldrich) were successively added dropwise a solution of Part A compound (2.3 g; 10 mmol) in THF (6 mL) and HMPA (500 µL; 2.9 mmol). The solution was stirred at −78° C. for 30 min, after which methyl iodide (1.87 mL; 30 mmol) was added dropwise. The solution was stirred at −78° C. for 1 h, then was allowed to warm to 0° C. and stirred at 0° C. for 1 h. The reaction solution was partitioned between saturated aqueous NH₄Cl and EtOAc. The aqueous phase was extracted with EtOAc (2×50 mL). The combined organic extracts were dried (MgSO₄) and concentrated in vacuo to give crude Part B compound (1.90 g; 78%) as a colorless oil, which was used in the next step without further purification.

C.

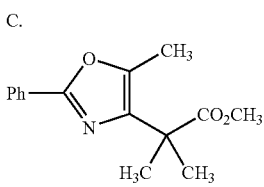

To a −78° C. solution of LDA (7.0 mL of a 2.0 M in heptane/THF; 14 mmol; Aldrich) were successively added dropwise a solution of Part B compound (1.8 g; 7.3 mmol) in THF (5 mL) and HMPA (500 µL; 2.9 mmol). The solution was stirred at −78° C. for 1 h, then a solution of methyl iodide (1 mL; 11 mmol) was added dropwise. The solution was stirred at −78° C. for 1 h, then was allowed to warm to 0° C. and stirred at 0° C. for 1 h. The reaction solution was then partitioned between saturated aqueous NH₄Cl and EtOAc. The aqueous phase was extracted with EtOAc (2×50 mL). The combined organic extracts were dried (MgSO₄) and concentrated in vacuo. The crude product was combined with the product from another reaction (from 670 mg of Part B compound) and chromatographed (SiO₂; 9:1 hexane:EtOAc) to give Part C compound (2.60 g; 95%) as a colorless oil.

D.

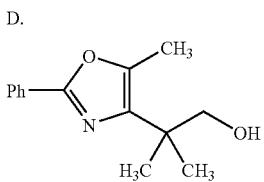

To a −78° C. solution of Part C compound (1.2 g; 4.63 mmol) in THF (3 mL) under an atmosphere of N₂ was added dropwise a solution of LiAlH₄ (1.0 mL of a 1.0 M solution in THF). The reaction was stirred at −78° C. for 1 h, then was allowed to warm to 0° C. and stirred at 0° C. for 30 min. The reaction was quenched by cautious addition of 1M aqueous potassium sodium tartrate followed by H₂O. The aqueous phase was extracted with EtOAc. The combined organic extracts were washed with H₂O, dried (MgSO₄) and concentrated in vacuo to give crude Part D compound (1.01 g; 94%) as an oil, which was used in the next step without further purification.

E.

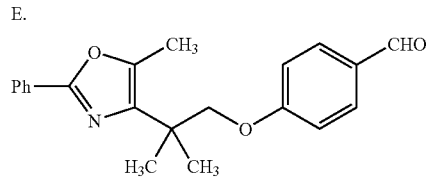

To an 80° C. solution of Part D compound (700 mg; 3.0 mmol), Ph₃P (1.2 g; 4.6 mmol) and 4-hydroxybenzaldehyde (406 mg; 3.3 mmol) in THF (10 mL) was added DEAD (720 µL; mmol) in two portions over 5 min. The solution was stirred at 80° C. for 1 h (starting material still remained), then was concentrated in vacuo. The residue was chromatographed (SiO₂; stepwise gradient from 9:1 to 5:1 hexane:EtOAc) to give Part E compound (160 mg; 16%).

F.

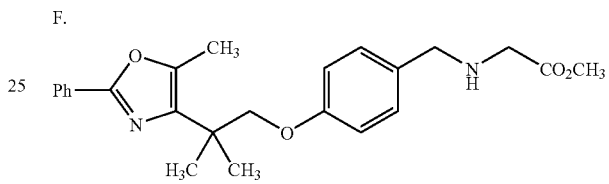

A solution of Part E compound (250 mg; 0.75 mmol), glycine methyl ester hydrochloride (141 mg; 1.13 mmol) and Et₃N (157 µL; 1.13 mmol) in MeOH (30 mL) was stirred at RT overnight. Excess solid NaBH₄ was added cautiously; the reaction was stirred at RT for 1 h, then concentrated in vacuo. The residue was partitioned between H₂O and EtOAc. The organic phase was washed with brine, dried (MgSO₄) and concentrated in vacuo to give crude Part F compound (300 mg; 98%) which was used in the next reaction without further purification.

G.

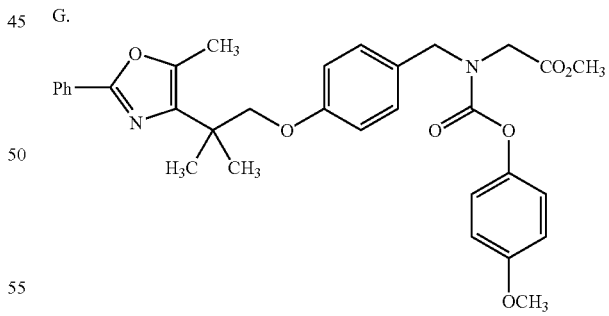

To a 0° C. solution of Part F compound (150 mg; 0.37 mmol) and Et₃N (51 µL; 0.37 mmol) in CH₂Cl₂ (5 mL) was added 4-methoxyphenyl chloroformate (55 µL; 0.37 mmol). The reaction was allowed to warm to RT and stirred at RT for 2 h. Volatiles were removed in vacuo and the residue was chromatographed (SiO₂; 5:1 hexane:EtOAc) to furnish Part G compound (130 mg; 63%).

H.

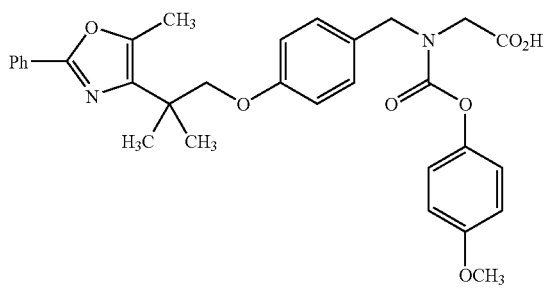

A solution of Part G compound (130 mg) and LiOH·H$_2$O (39 mg) in H$_2$O/THF/MeOH (2 mL of a 1:2:2 mixture) was stirred at RT for 2 h. Volatiles were removed in vacuo, and the residue was acidified with 1.0 M aqueous HCl, then extracted with EtOAc. The organic phase was dried (Na$_2$SO$_4$) and concentrated in vacuo to give a residue, which was purified by preparative HPLC (YMC S5 ODS reverse phase C18, 30×250 mm column; flow rate=25 mL/min; continuous gradient from 50% A:B to 100% B over 20 min, where solvent A=90:10:0.1 H$_2$O:MeOH:TFA, B=90:10:0.1 MeOH:H$_2$O:TFA), then lyophilized from dioxane to give the title compound (58 mg; 46%) as a white lyophilate. [M+H]$^+$=545.4

EXAMPLE 544

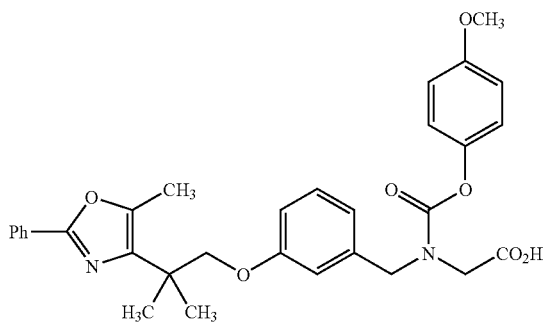

Title compound was prepared in analogous fashion to Example 543 except that 3-hydroxybenzaldehyde was used instead of 4-hydroxybenzaldehyde (in the preparation of Example 543 Part E compound). [M+H]$^+$=545.4

EXAMPLE 545

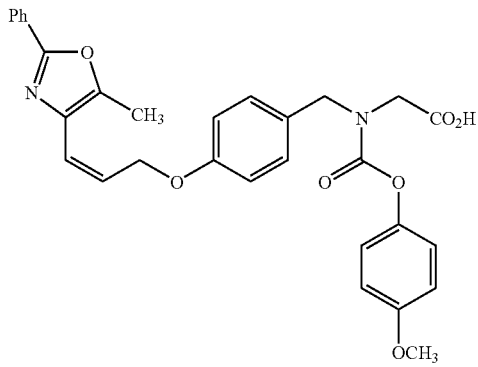

A.

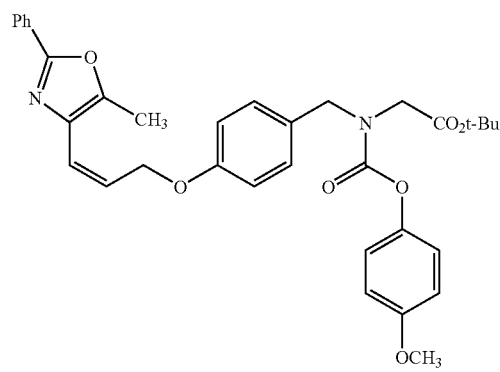

A mixture of the acetylene (38 mg; 0.065 mmol)

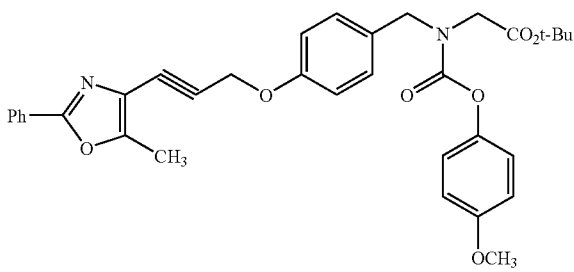

(synthesized in a completely analogous fashion to Example 542 Part G compound with glycine tert-butyl ester hydrochloride instead of glycine methyl ester hydrochloride), quinoline (80 mg; 0.62 mmol) and Lindlar's catalyst (8 mg; Pd/CaCO$_3$; Aldrich) in MeOH (8 mL) was stirred under an atmosphere of H$_2$ at 0° C. for 20 min. Additional Lindlar's catalyst (8 mg; Pd/CaCO$_3$; Aldrich) was then added and stirring was continued under an atmosphere of H$_2$ at 0° C. for 25 min, after which reaction was complete. The mixture was filtered, and the filtrate was concentrated in vacuo. The residue was purified by preparative HPLC (YMC S5 ODS 20×100 mm column; flow rate=20 mL/min; continuous 20 min gradient from 80:20 B:A to 100% B, where A=90:10:0.1 H$_2$O:MeOH:TFA and B=90:10:0.1 MeOH:H$_2$O:TFA) to give Part A compound (22 mg; 56%) as a colorless oil.

B.

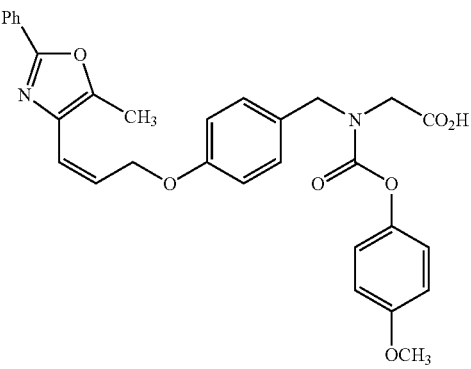

To a solution of Part A compound (3 mg; 0.005 mmol) in CH$_2$Cl$_2$ (0.5 mL) was added dropwise TFA (0.25 mL) and the reaction was stirred for 2 h at RT. Volatiles were removed in vacuo; the residue was dissolved in CDCl₃, filtered through a cotton plug and concentrated in vacuo to give the title compound (1.5 mg; 55%) as a colorless oil. [M+Na]⁺= 551.0
Following procedures set out above, Examples 546 to 556 compounds were prepared.
EXAMPLES 546 TO 556
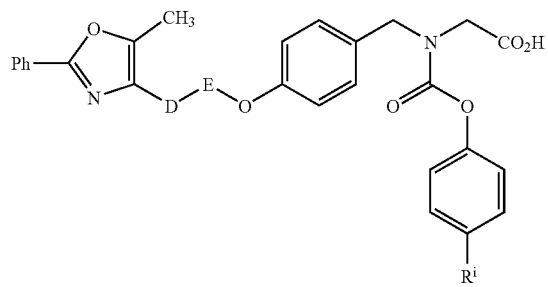
| Example No. | Structure | [M + H]⁺ |
|---|---|---|
| 546 | 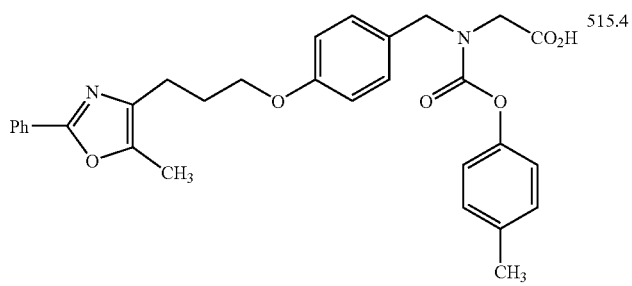 | 515.4 |
| 547 | 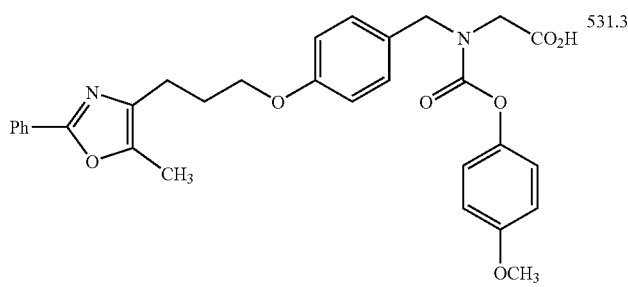 | 531.3 |
| 548 | 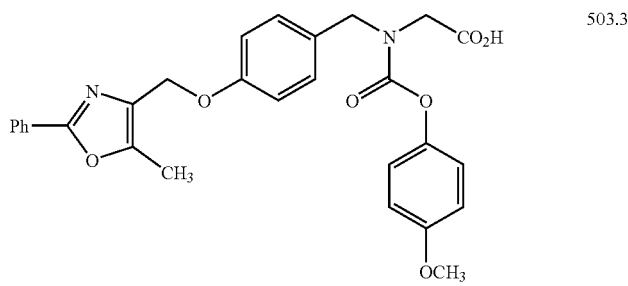 | 503.3 |

-continued
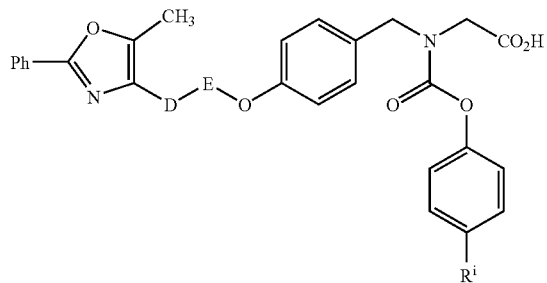
| Example No. Structure | [M + H]+ |
|---|---|
| 549 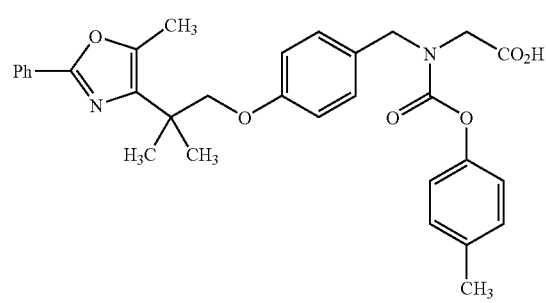 | 529.4 |
| 550 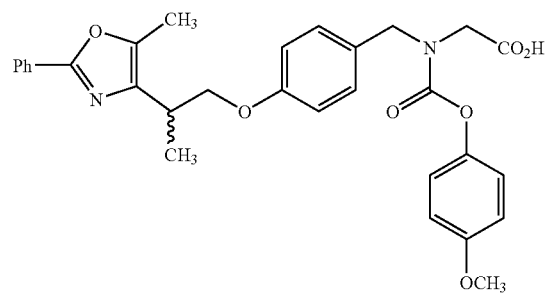 | 531.2 |
| 551 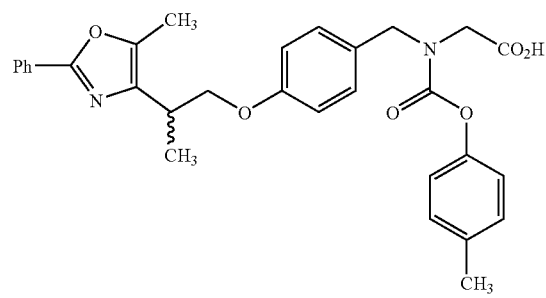 | 515.2 |

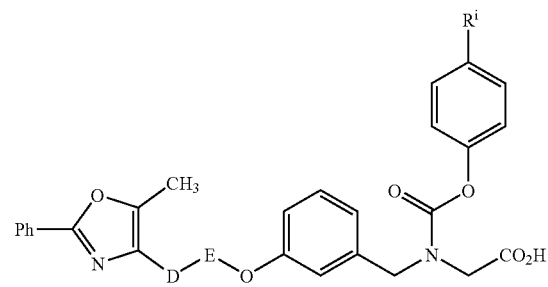
| Example No. | Structure | [M + H]+ |
|---|---|---|
| 552 | 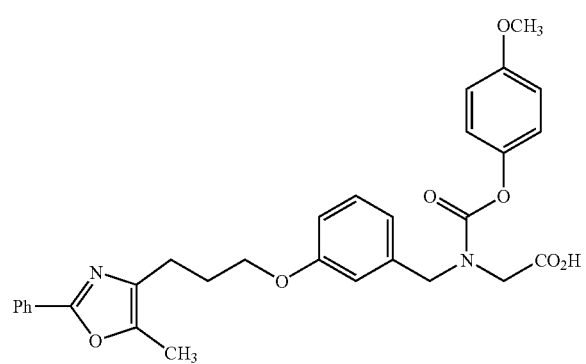 | 531.3 |
| 553 | 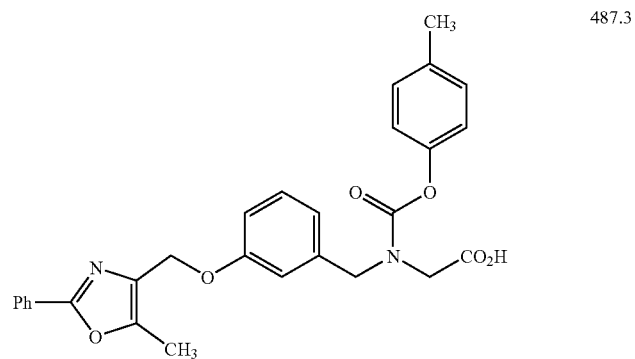 | 487.3 |
| 554 | 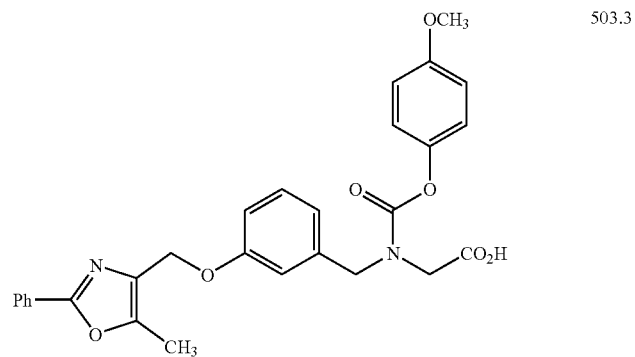 | 503.3 |

-continued
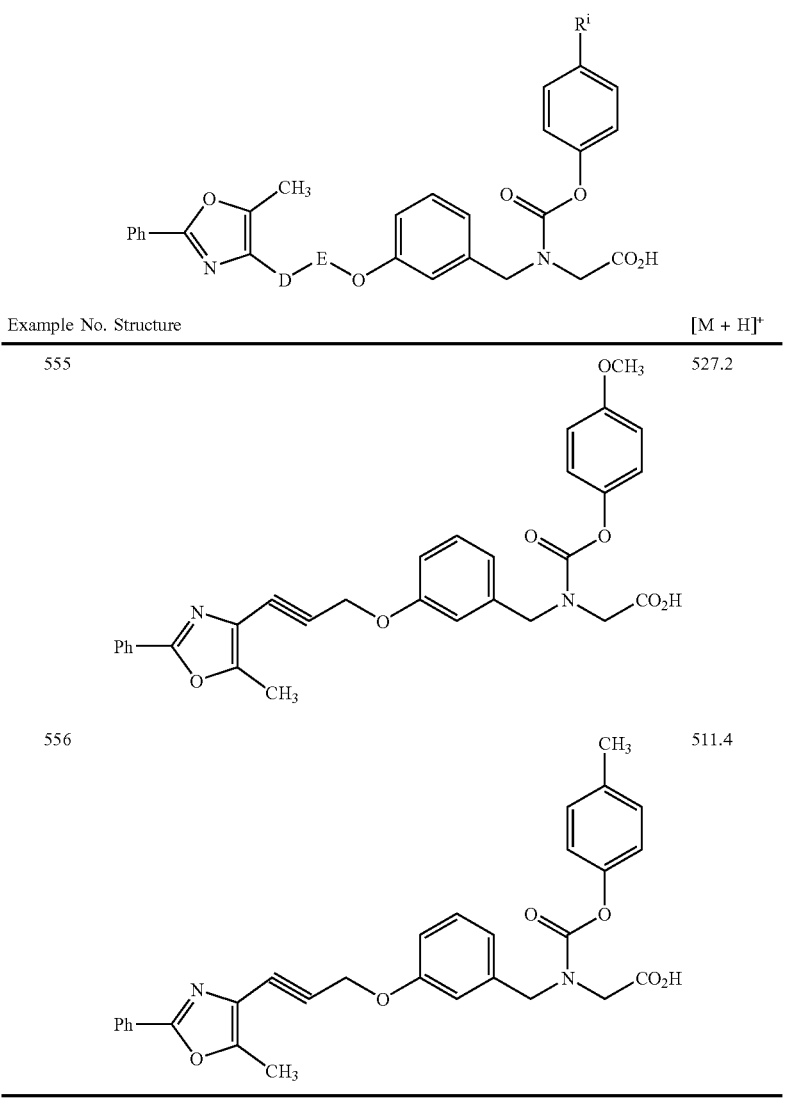
| Example No. Structure | [M + H]+ |
|---|---|
| 555 | 527.2 |
| 556 | 511.4 |
EXAMPLE 555
A.
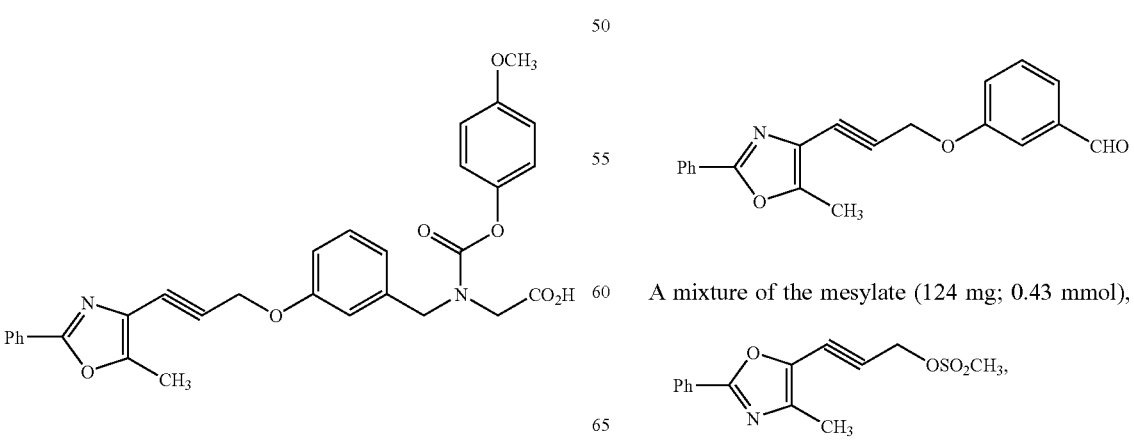
A mixture of the mesylate (124 mg; 0.43 mmol), 3-hydroxybenzaldehyde (62 mg; 0.51 mmol) and K$_2$CO$_3$ (94 mg; 0.68 mmol) in CH$_3$CN (10 mL) were heated at 70° C. for 48 h. The reaction was cooled to RT, EtOAc was added, and the mixture was washed with aq 1M NaOH and brine. The organic phase was dried (Na$_2$SO$_4$) and concentrated in vacuo. The residue was chromatographed (SiO$_2$; hex:EtOAc 4:1) to give Part A compound (71 mg; 52%) as a colorless oil. [M+H]$^+$=318.2

B.

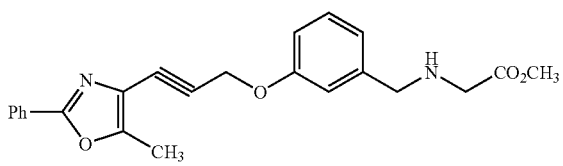

To a mixture of Part A compound (71 mg; 0.22 mmol), glycine.HCl (140 mg; 1.11 mmol) and Et$_3$N (0.3 mL; 2.16 mmol) in 1,2 dichloroethane (10 mL) was added NaBH(OAc)$_3$ (150 mg). After stirring at RT for 16 h (reaction incomplete), more NaBH(OAc)$_3$ (150 mg) was added. A final addition of NaBH(OAc)$_3$ (150 mg; in total 2.12 mmol) was made after another 3 h and the reaction stirred for 48 h at RT. The reaction was complete at this point; saturated aqueous NaHCO$_3$ was added and the aqueous phase was extracted with CH$_2$Cl$_2$ (2×). The combined organic extracts were washed with brine, dried (Na$_2$SO$_4$) and concentrated in vacuo. The residue was chromatographed (SiO$_2$; hex:EtOAc=4:6) to give Part B compound (81 mg; 93%) as a colorless oil.

C.

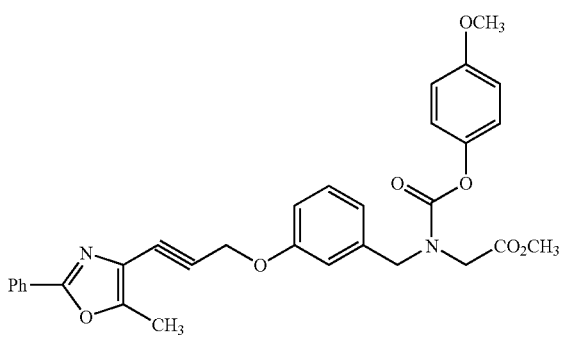

To a solution of Part B compound (10 mg; 0.026 mmol) in CH$_2$Cl$_2$ (2 mL) were successively added pyridine (10 μL; 0.12 mmol) and 4-methoxyphenyl chloroformate (10 μL; 0.067 mmol) (each in 0.1 mL CH$_2$Cl$_2$). The reaction was stirred at RT for 16 h, then partitioned between aqueous 1N HCl and EtOAc. The organic phase was washed with brine, dried (Na$_2$SO$_4$), and concentrated in vacuo. The residue was purified by preparative HPLC (YMC S5 ODS 30×75 mm column, flow rate=20 mL/min; continuous gradient from 70:30 A:B to 100% B, where solvent A=90:10:0.1 H$_2$O:MeOH:TFA and solvent B=90:10:0.1 MeOH:H$_2$O:TFA) to give Part C compound (9 mg; 65%).

D.

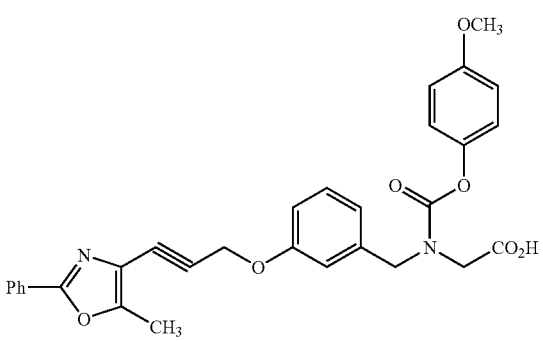

A solution of Part C compound (9 mg; 0.017 mmol) in 2:1 THF:H$_2$O (3 mL) was added LiOH (6 mg; 0.14 mmol). The solution was stirred at RT for 4 h, then acidified with excess 1M HCl (aq). The solution was extracted with EtOAc (2×5 mL). The combined organic extracts were washed with brine, dried (Na$_2$SO$_4$), and concentrated in vacuo. The crude product was purified by preparative HPLC using the same conditions as above to give title compound (6 mg; 68%) as a colorless film.

[M+H]$^+$=527.2

EXAMPLE 556

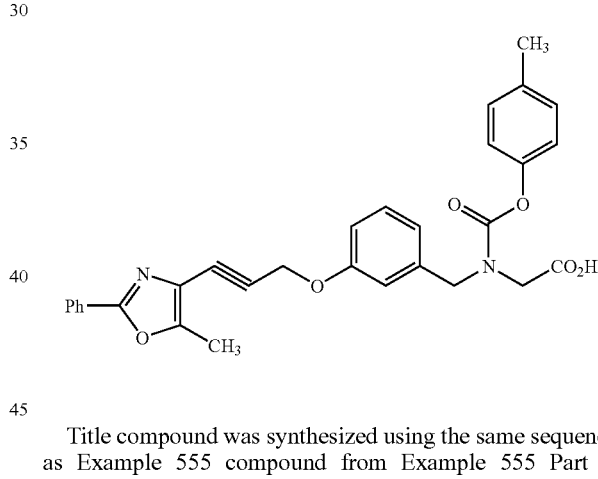

Title compound was synthesized using the same sequence as Example 555 compound from Example 555 Part B compound. Acylation with 4-methyl chloroformate (67% after HPLC purification) followed by LiOH hydrolysis furnished title compound (5 mg; 57% after HPLC purification). [M+H]$^+$=511.4

EXAMPLE 557

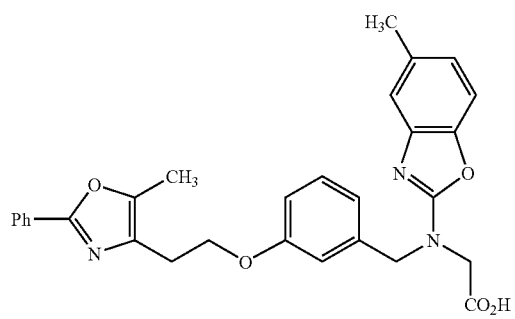

A.

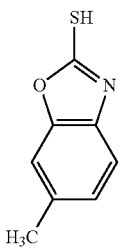

A solution of 2-amino-5-cresol (5.0 g; 40 mmol), KOH (3.2 g; 57 mmol) was refluxed in EtOH (50 mL) and CS$_2$ (40 mL) for 8 h, after which the reaction mixture was concentrated in vacuo. The residue was partitioned between aq 1M HCl (100 mL) and EtOAc (200 mL). The organic phase was washed with water (2×100 mL), dried (MgSO$_4$) and concentrated in vacuo to give Part A compound (4.0 g; 60%) as a white powder.

B.

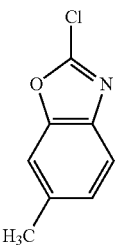

A solution of Part A compound (3.2 g; 19 mmol) and PCl5 (3.75 g; 19 mmol) in toluene (150 mL) was heated at reflux for 2 h. The reaction mixture was washed successively with water and aqueous NaHCO$_3$, then dried (Na$_2$SO$_4$) and concentrated in vacuo to give Part B compound (4.0 g) as a crude oil. This material was used in the next step without further purification.

C.

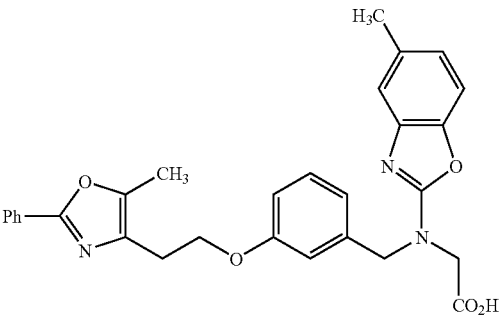

A solution of the 1,3 benzyl glycine aminoester (150 mg; 0.39 mmol), Part B compound (100 mg; 0.59 mmol) and triethylamine (0.2 mL; 1.98 mmol) in THF (5 mL) was heated at 100° C. in a sealed tube for 4 days. At this point LC/MS showed that all starting material had been consumed. Aqueous LiOH (0.5 mL of a 1 M solution) was added and the solution was stirred at RT for 5 h. The mixture was concentrated in vacuo to give an oil, which was purified by preparative HPLC (as for Example 495) to give the title compound (72 mg; 37%) as a solid.

EXAMPLE 558

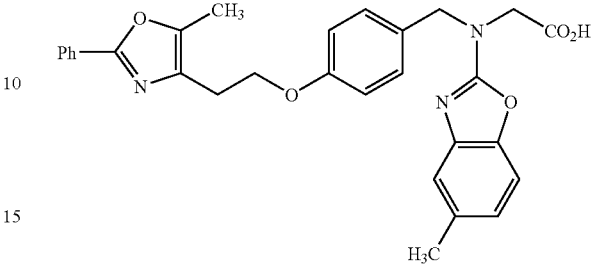

A solution of the 1,4 benzyl glycine aminoester (50 mg; 0.13 mmol), Example 557 Part B compound (100 mg; 0.59 mmol) and triethylamine (0.2 mL; 1.98 mmol) in THF (5 mL) was heated at 100° C. in a sealed tube for 4 days. At this point LC/MS showed that all starting material had been consumed. Aqueous LiOH (0.5 mL of a 1 M solution) was added and the solution was stirred at RT for 5 h. The mixture was concentrated in vacuo to give an oil, which was purified by preparative HPLC (as for Example 495) to give the title compound (26 mg; 40%) as a solid.

EXAMPLE 559

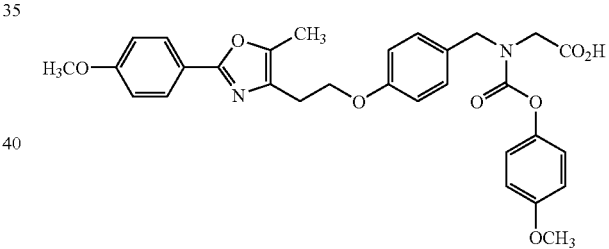

A.

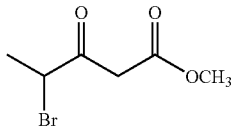

To a solution of methyl propionylacetate (4.6 g, 35 mmol) in CHCl$_3$ (40 mL) was added dropwise a solution of Br$_2$ (5.6 g; 35 mmol) in CHCl$_3$ (10 mL) and the resulting mixture was stirred at 0° C. for 0.5 h. The reaction was allowed to warm to RT and then air was bubbled into the mixture for 1 h. Volatiles were then removed in vacuo to yield an oily residue, which was partitioned between EtOAc (100 mL) and saturated aqueous NaHCO$_3$. The organic phase was washed with brine, dried (MgSO$_4$) and concentrated in vacuo to provide crude Part A compound (7.4 g, >95% yield; >90% purity) as an oil which was used in the next reaction without further purification.

B.

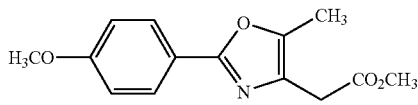

A mixture of Part A compound (1.5 g, 7.2 mmol) and 4-methoxybenzamide (1.0 g, 6.6 mmol) was heated at 100° C. for 2.5 h. The reaction mixture was chromatographed (SiO$_2$; 5% acetone/CH$_2$Cl$_2$) to yield Part B compound (0.57 g, 33%).

C.

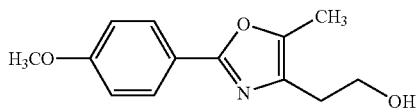

To a solution of the ester (0.57 g, 2.3 mmol) in THF (10 mL) was added LiAH$_4$ (2.5 mL of a 1 M solution in THF, 2.5 mmol) dropwise over 10 min and the reaction was stirred at RT for 0.5 h. The reaction was quenched by adding a few drops of water and then partitioned between EtOAc (50 mL) and brine (10 mL). The organic phase was dried (MgSO$_4$) and concentrated in vacuo to give Part C (0.52 g, >95%) as an oil which was used in the following reaction without further purification.

D.

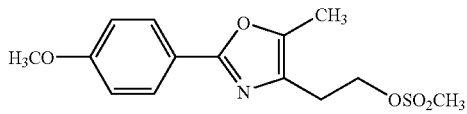

A mixture of Part C compound (0.52 g, 2.3 mmol), CH$_3$SO$_2$Cl (0.25 ml, 3.3 mmol) and Et$_3$N (0.5 ml, 3.6 mmol) in CH$_2$Cl$_2$ (10 mL) was stirred at RT for 12 h. Volatiles were removed in vacuo, and the residue was chromatographed (SiO$_2$; 4% acetone/CH$_2$Cl$_2$) to provide Part D compound (0.61 g, 85% for 2 steps) as a colorless oil.

E.

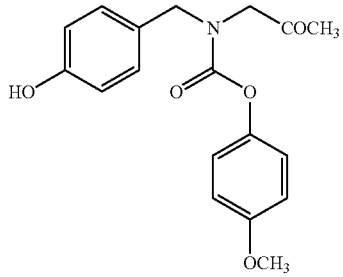

To a mixture of crude Example 541 Part C compound (synthesized using 4-hydroxybenzaldehyde [2.0 g; 16 mmol] and glycine methyl ester hydrochloride [2.3 g; 18 mmol]) in dioxane:H$_2$O (100 mL of a 1:1 mixture) were successively added NaHCO$_3$ (2.5 g; 30 mmol; in one portion) and 4-methoxyphenyl chloroformate (2.0 mL; 14 mmol) dropwise. The reaction was stirred at RT for 12 h and then extracted with EtOAc (4×150 mL). The combined organic extracts were dried (MgSO$_4$) and concentrated in vacuo. The residue was chromatographed (SiO$_2$; 3% acetone/CH$_2$Cl$_2$) to provide Part E compound (2.4 g; 44%) as a colorless oil.

F.

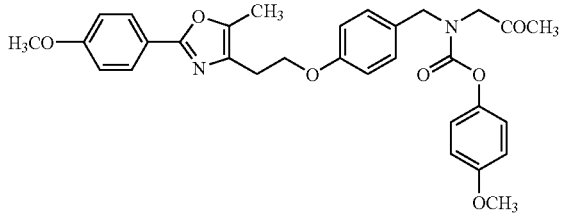

A mixture of Part E compound (86 mg, 0.25 mmol), Part D compound (60 mg, 0.20 mmol) and K$_2$CO$_3$ (50 mg, 3.7 mmol) in DMF (3 mL) was heated at 80° C. for 12 h. The reaction was cooled to RT and filtered. Volatiles were removed in vacuo and the residue was chromatographed (SiO$_2$; 7:3 hexane:EtOAc) to provide title compound (41 mg; 36%) as a colorless oil.

G.

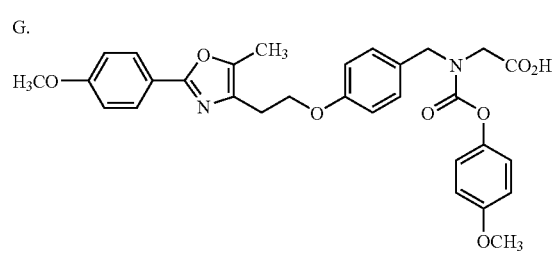

A solution of Part F compound (41 mg, 0.071 mmol) and LiOH.H$_2$O (34 mg; 0.8 mmol) in THF-H$_2$O (2 mL of a 2:1 mixture) was stirred at RT for 2 h. The reaction mixture was acidified to pH~2 with 1 M aqueous HCl, then was extracted with EtOAc. The combined organic extracts were concentrated in vacuo and the residue was purified by preparative HPLC (YMC S5 ODS 30×250 mm column; flow rate=25 mL/min; 30 min continuous gradient from 50% A:50% B to 100% B, where solvent A=90:10:0.1 H$_2$O:MeOH:TFA and solvent B=90:10:0.1 MeOH:H$_2$O:TFA) to provide title compound (17 mg, 40%) as a colorless oil.

[M+H]$^+$=547.23

EXAMPLE 560

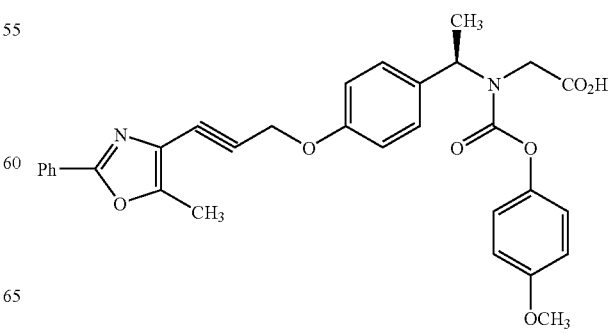

A.

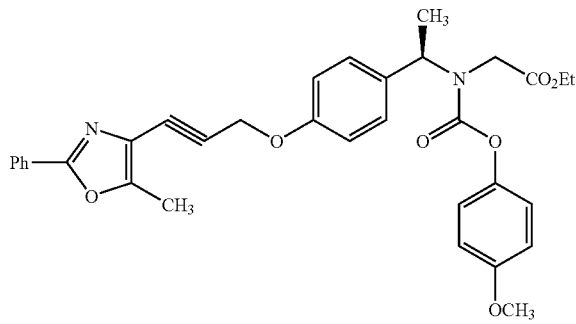

A mixture of the mesylate (18 mg; 0061 mmol)

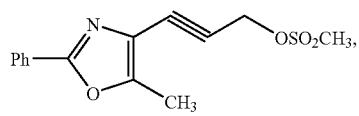

the ester,

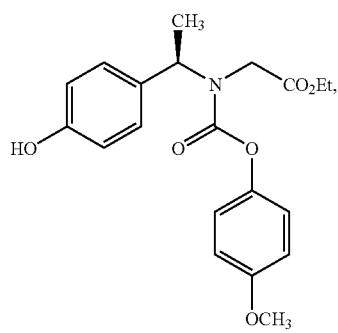

[described in the synthesis of Example 503 Part B compound (50 mg; 0.13 mmol)], K₂CO₃ (17 mg; 0.34 mmol) in CH₃CN (1 mL) were heated at 70° C. for 24 h. Additional K₂CO₃ (30 mg) and CH₃CN (1 mL) were added and the mixture was heated at 75° C. for another 48 h. The reaction was cooled to RT, EtOAc was added, and the mixture was washed with aq 1M NaOH and brine. The organic phase was dried (Na₂SO₄) and concentrated in vacuo to give the crude product. This was purified by preparative HPLC (YMC S5 ODS 50×75 mm column; continuous gradient from 70:30 B:A to 100% B, where A=90:10:0.1 H₂O:MeOH:TFA and B=90:10:0.1 MeOH:H₂O:TFA) to give Part A compound (13 mg; 35%) as a colorless oil.

B.

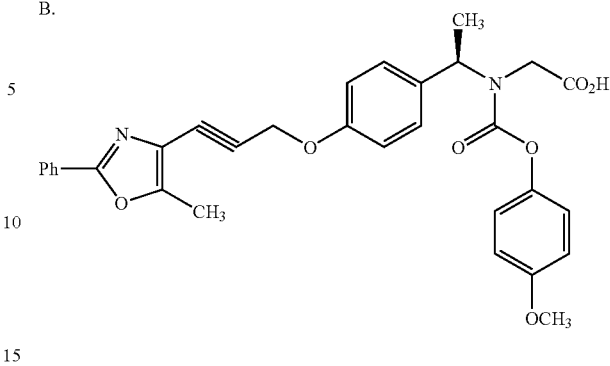

To a solution of Part A compound (12 mg; 0.021 mmol) in 2:1 THF:H₂O (1.5 mL) was added LiOH (8 mg; 0.19 mmol). The solution was stirred at RT for 24 h, then acidified with excess 1M HCl (aq). The solution was extracted with EtOAc (2×5 mL). The combined organic extracts were washed with brine, dried (Na₂SO₄), and concentrated in vacuo. The crude product was purified by preparative HPLC using the same conditions as above to give title compound (6.4 mg) as a colorless film. [M+H]⁺=541.3

EXAMPLE 561

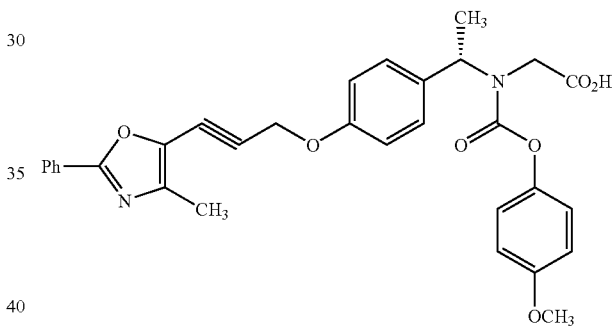

A.

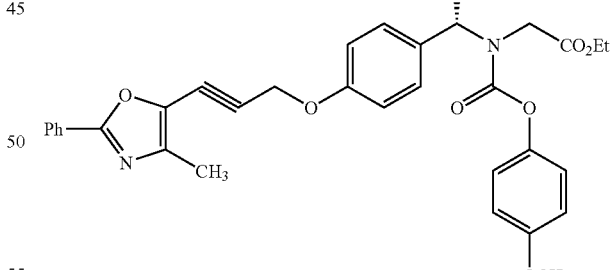

A mixture of the mesylate (18 mg; 0061 mmol)

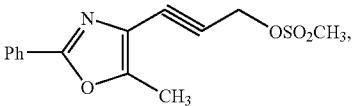

the phenol (50 mg; 0.13 mmol)

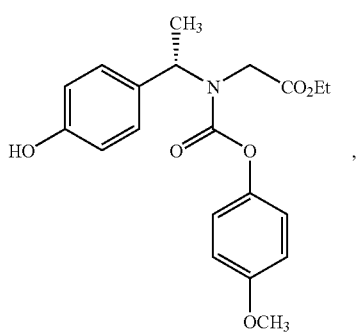

K$_2$CO$_3$ (17 mg; 0.34 mmol) in CH$_3$CN (1 mL) were heated at 70° C. for 24 h. Additional K$_2$CO$_3$ (30 mg) and CH$_3$CN (1 mL) were added and the mixture was heated at 75° C. for another 48 h. The reaction was cooled to RT, EtOAc was added, and the mixture was washed with aq 1M NaOH and brine. The organic phase was dried (Na$_2$SO$_4$) and concentrated in vacuo to give the crude product. This was purified by preparative HPLC (YMC 55 ODS 50×75 mm column; continuous gradient from 70:30 B:A to 100% B, where A=90:10:0.1 H$_2$O:MeOH:TFA and B=90:10:0.1 MeOH:H$_2$O:TFA) to give Part A compound (13 mg; 35%) as a colorless oil.

B.

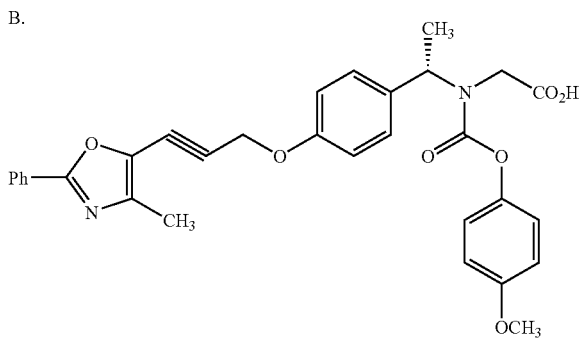

To a solution of Part A compound (12 mg; 0.021 mmol) in 2:1 THF:H$_2$O (1.5 mL) was added LiOH (8 mg; 0.19 mmol). The solution was stirred at RT for 24 h, then acidified with excess 1M HCl (aq). The solution was extracted with EtOAc (2×5 mL). The combined organic extracts were washed with brine, dried (Na$_2$SO$_4$), and concentrated in vacuo. The crude product was purified by preparative HPLC using the same conditions as above to give title compound. [M+H]$^+$=541.3

EXAMPLE 562

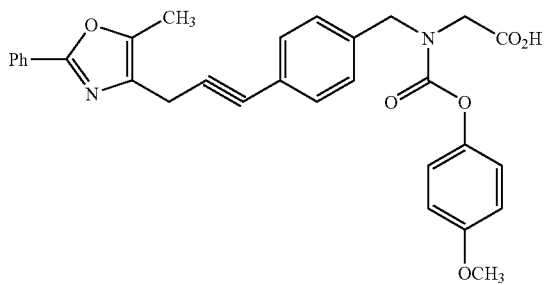

A.

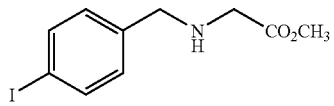

A solution of 4-iodobenzaldehyde (1.0 g; 4.31 mmol) and glycine methyl ester hydrochloride (0.65 g; 5.17 mmol) and Et$_3$N (0.50 g; 4.95 mmol) in MeOH (15 mL) was stirred at RT for 4 h. The mixture was cooled to 0° C. and a solution of NaBH$_4$ (230 mg; 6.0 mmol) in MeOH was added portionwise. The mixture was allowed to warm to RT and stirred overnight at RT. Volatiles were removed in vacuo (without heating) and the residue was partitioned between aq NaHCO$_3$ and EtOAc. The aqueous phase was extracted with EtOAc (3×). The combined organic extracts were dried (Na$_2$SO$_4$) and concentrated in vacuo to give Part A compound as an oil. This material was used in the next step without further purification.

B.

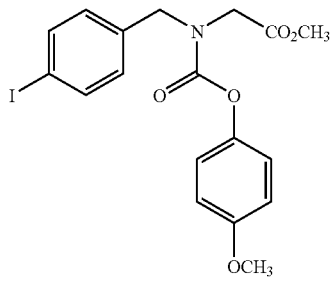

To a solution of the crude Part A compound and Et$_3$N (0.80 g; 8.00 mmol) in CH$_2$Cl$_2$ was added a solution of 4-methoxyphenyl chloroformate (0.93 g; 5.00 mmol) in CH$_2$Cl$_2$. The reaction mixture was stirred at RT overnight, then partitioned between saturated aq NaHCO$_3$ and EtOAc. The aqueous phase was extracted with EtOAc (2×); the combined organic extracts were dried (Na$_2$SO$_4$) and concentrated in vacuo to give a residue, which was chromatographed (SiO$_2$; hex:EtOAc 3:1) to give Part B compound (1.2 g; 61%) as an oil.

C.

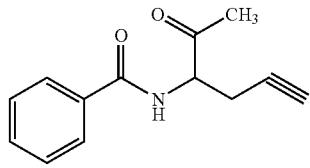

To a 0° C. solution of DL-propargyl glycine (3.0 g; 26.5 mmol) in pyridine (20 mL; 247 mmol) was added dropwise benzoyl chloride (3.73 g; 26.5 mmol). The solution was allowed to warm to RT and stirred at RT for 1 h. Acetic anhydride (10 mL) was added and the mixture was stirred at 90° C. for 2 h. The reaction mixture was diluted with H$_2$O (35 mL) and extracted with EtOAc (3×); the combined organic extracts were washed with aqueous 1N HCl, H$_2$O, aqueous NaHCO$_3$, and finally water. The organic phase was dried (Na$_2$SO$_4$) and concentrated in vacuo. The crude product was chromatographed (SiO$_2$; stepwise gradient from 5:1 to 3:1 hex:EtOAc) to give Part C compound (1.0 g; 17%) as an orange solid.

D.

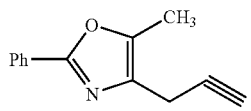

A solution of Part C compound (1.0 g; 4.65 mmol), trifluoroacetic anhydride (3 mL) and TFA (3 mL) in a sealed tube was heated at 40° C. for 8 h. Volatiles were removed in vacuo and the residue was dissolved in EtOAc (50 mL). The solution was washed repeatedly with saturated aq NaHCO$_3$ (until all acid had been removed from the organic phase), then brine, dried (Na$_2$SO$_4$) and concentrated in vacuo. The residue was chromatographed (SiO$_2$; 6:1 hex:EtOAc) to give Part D compound (800 mg; 87%; >98% pure by HPLC) as an oil.

E.

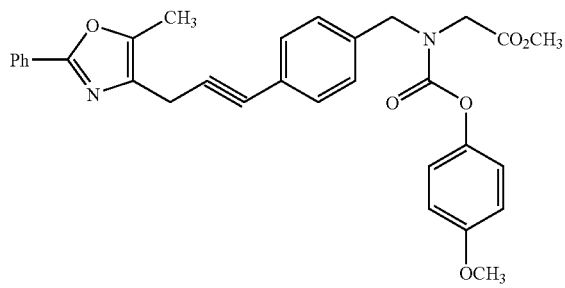

A mixture of Part D compound (100 mg; 0.507 mmol), Part B compound (254 mg; 0.558 mmol), CuI (2 mg; 0.01 mmol) and (Ph$_3$P)$_2$PdCl$_2$ (4 mg; 0.005 mmol) in diethylamine (2 mL) was stirred at RT for 3 h under N$_2$. At this point HPLC/MS showed that all starting material had been consumed and the presence of a peak which corresponded to the desired product. The reaction mixture was filtered and the filtrate was concentrated in vacuo. The residue was chromatographed (SiO$_2$; stepwise gradient from 5:1 to 2:1 hex:EtOAc) to provide Part E compound (200 mg; 75%) as an oil.

F.

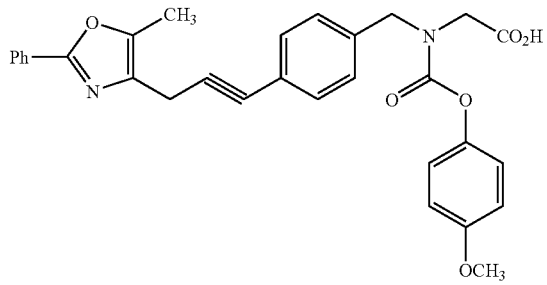

A solution of Part E compound (20 mg; 0.038 mol) in HOAc/conc HCl (1 mL of a 10:1 solution) was stirred at 45° C. overnight. Volatiles were removed in vacuo and the residue was purified by preparative HPLC (YMC S5 ODS reverse phase column; 30×250 mm; flow rate=25 mL/min; 30 min continuous gradient from 50:50 A:B to 100% B, where solvent A=90:10:0.1 H$_2$O:MeOH:TFA and solvent B=90:10:0.1 MeOH:H$_2$O:TFA) to give the title compound (6.8 mg; 35%) as a lyophilate. [M+H]$^+$=511.2

EXAMPLE 563

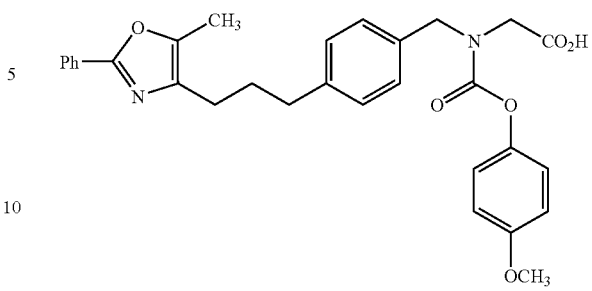

A.

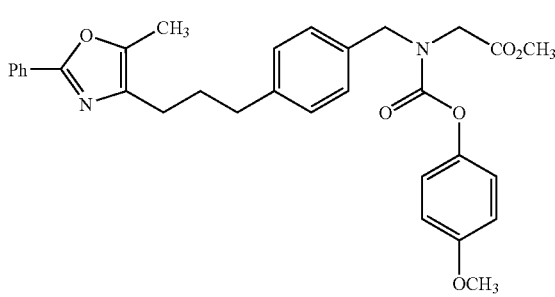

A solution of Example 562 Part E compound

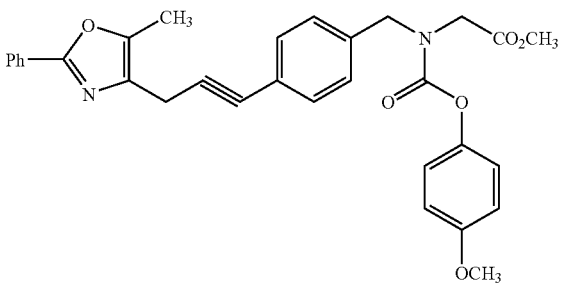

(38 mg; 0.072 mmol) in MeOH (5 mL) was stirred under an atmosphere of H$_2$ in the presence of 10% Pd/C catalyst (10 mg) at RT for 2 h. The catalyst was filtered off and the filtrate was concentrated in vacuo to give Part A compound (35 mg; 92%) as an oil.

B.

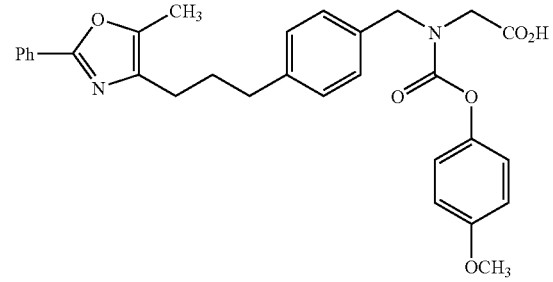

A solution of Part A compound (35 mg; 0.066 mmol) in aqueous LiOH (1 mL of a 1M solution) and THF (5 mL) was stirred at RT for 2 h. The reaction was acidified to pH3 with excess aqueous 1M HCl and extracted with EtOAc (2×5 mL). The combined organic extracts were dried (Na$_2$SO$_4$) and concentrated in vacuo. The residue was purified by preparative HPLC (YMC S5 ODS reverse phase column; 30×250 mm; flow rate=25 mL/min; 30 min continuous gradient from 50:50 A:B to 100% B, where solvent A=90:10:0.1 H$_2$O:MeOH:TFA and solvent B=90:10:0.1 MeOH:H$_2$O:TFA) to give, after lyophilization from dioxane, the title compound (31 mg; 87%) as a white solid. [M+H]$^+$=515.9

EXAMPLE 564

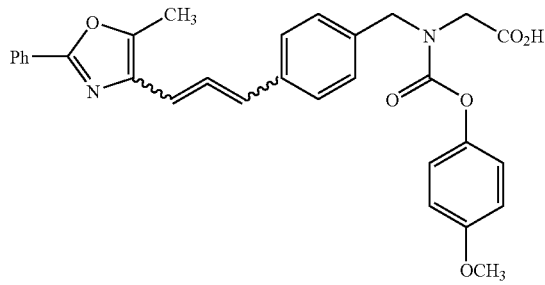

A solution of Example 562 Part E compound

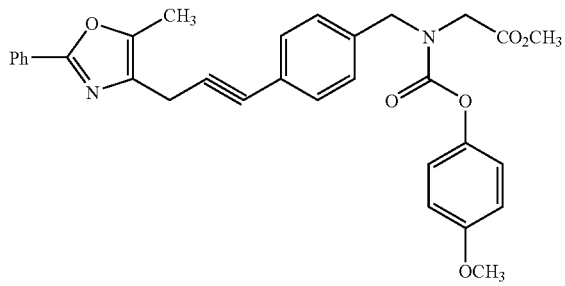

(20 mg; 0.038 mmol) and aqueous LiOH (1 mL of a 1 M solution; 1 mmol) in THF (2 mL) was stirred at RT for 2 h. The reaction mixture was acidified with excess aqueous 1 M HCl and extracted with EtOAc. The combined organic extracts were concentrated in vacuo. The residue was purified by preparative HPLC ((YMC S5 ODS reverse phase column; 30×250 mm; flow rate=25 mL/min; 30 min continuous gradient from 50:50 A:B to 100% B, where solvent A=90:10:0.1 H$_2$O:MeOH:TFA and solvent B=90:10:0.1 MeOH:H$_2$O:TFA) to give (9 mg; 46%) as a white solid. [M+H]$^+$=511.2

EXAMPLE 565

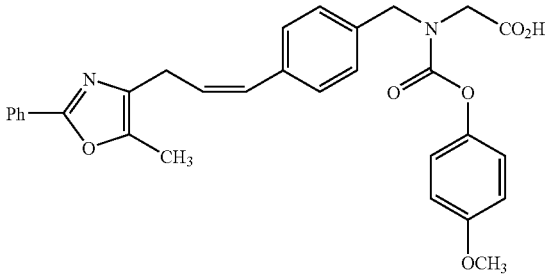

A.

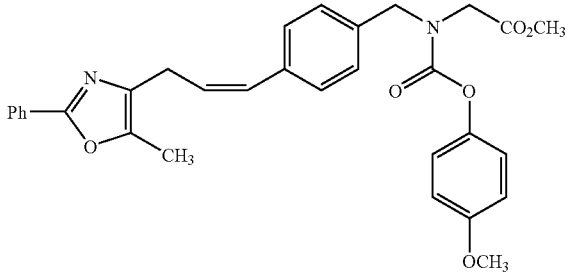

A mixture of Example 562 Part E compound

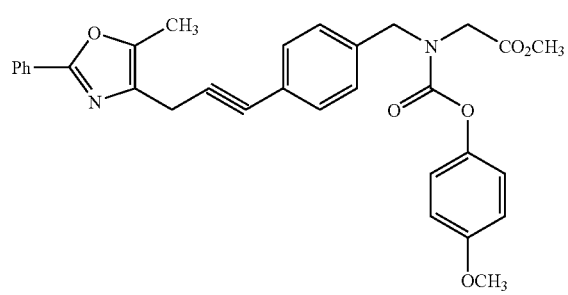

(80 mg; 0.15 mmol), quinoline (2 μL; 0.01 mmol) and Lindlar's catalyst (7 mg; 5% Pd/CaCO$_3$) in toluene (2 mL) was stirred under an atmosphere of H$_2$ for 2 h. More Lindlar's catalyst (20 mg) was then added and stirring was continued under H$_2$ for another 2 h, after which the reaction was complete by analytical HPLC. The reaction mixture was filtered (Celite®) and the filtrate was concentrated in vacuo. The residue was chromatographed (SiO$_2$; stepwise gradient from 3:1 to 2:1 hexane:EtOAc) to give Part A compound.

B.

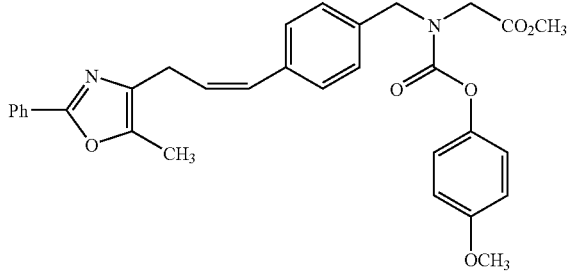

A solution of Part A compound and aqueous LiOH (1 mL of a 1 M solution; 1 mmol) in THF was stirred at RT overnight. The reaction mixture was acidified with excess aqueous 1 M HCl and extracted with EtOAc (2×). The combined organic extracts were concentrated in vacuo. The residue was purified by preparative HPLC (as for Example 495) to give the title compound (14 mg; 18%) as a white solid. [M+H]$^+$=513.3

EXAMPLE 566

Racemic

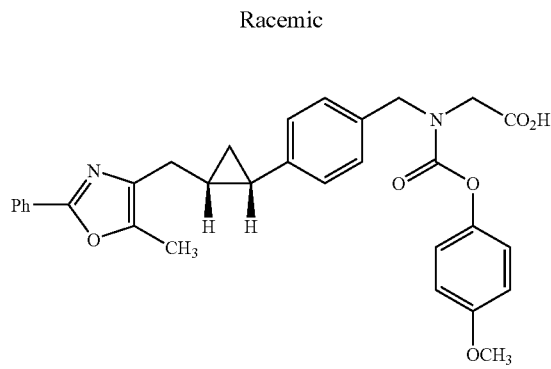

A.

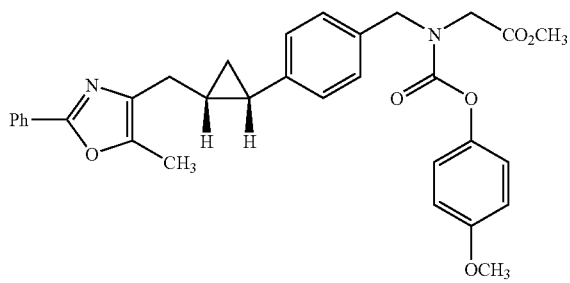

To a 0° C. solution of Example 565 Part A compound

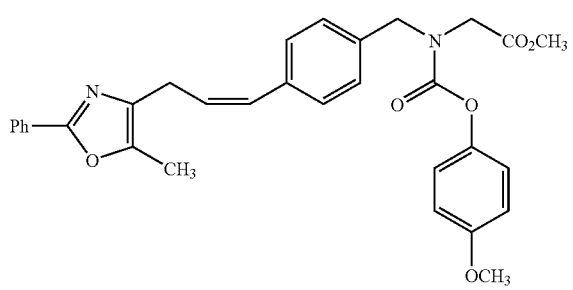

(60 mg; 0.11 mmol) in DCE (3 mL) was added dropwise diethylzinc (43 μL; 0.29 mmol). The solution was stirred at 0° C. for 10 min and iodochloromethane (244 μL; 0.57 mmol) was then added. The reaction was allowed to warm to RT and stirred at RT for 3 h, then was cautiously quenched by addition of aqueous HCl (1 mL of a 1 M solution). The aqueous layer was extracted with EtOAc (2×); the combined organic extracts were dried (Na₂SO₄) and concentrated in vacuo. The residue was chromatographed (SiO₂; stepwise gradient from 3:1 to 2:1 hexane:EtOAc) to give crude Part A compound, which was used in the next step without further purification.

B.

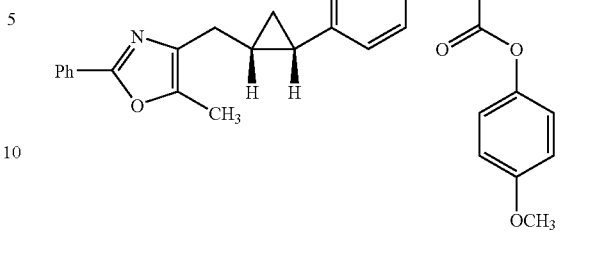

A solution of crude Part A compound and aqueous LiOH (1 mL of a 1 M solution; 1 mmol) in THF was stirred at RT overnight. The reaction mixture was acidified with excess aqueous 1 M HCl and extracted with EtOAc. The combined organic extracts were concentrated in vacuo. The residue was purified by preparative HPLC (conditions) to give the title compound (7 mg; 12% over 2 steps) as a white solid. [M+H]⁺=527.2.

EXAMPLE 567

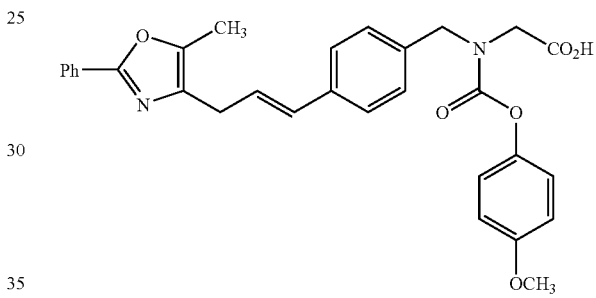

A.

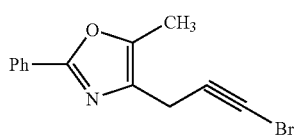

A mixture of Example 562 Part D compound

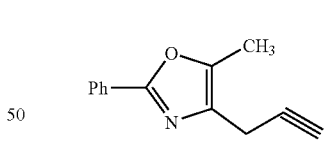

(300 mg; 1.52 mmol), N-bromo-succinimide (297 mg; 1.67 mmol) and AgNO₃ (28 mg; 0.19 mmol) in acetone (2 mL) was stirred at RT for 30 min. The mixture was filtered and the filtrate was concentrated in vacuo. The residue was chromatographed (SiO₂; hexane:EtOAc 5:1) to give Part A compound (320 mg; 76%) as yellow crystals.

B.

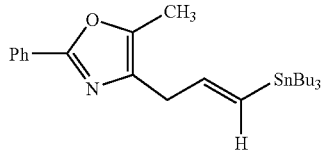

To a solution of Part A compound (320 mg; 1.2 mmol), Ph₃P (13 mg; 0.05 mmol) and Tris(dibenzylideneacetone)dipalladium(0) (5 mg; 0.006 mmol) in THF (1 mL) was added Bu₃SnH (700 μL; 2.5 mmol) dropwise under an atmosphere of N₂. The mixture was stirred at RT for 2 h, then was quenched by addition of aqueous KF (7 mL of a 1 M solution). The mixture was stirred vigorously overnight, then extracted with EtOAc (2×). The combined organic extracts were washed with H₂O, dried (Na₂SO₄) and concentrated in vacuo. The residual oil was chromatographed (SiO₂; hexane:EtOAc 3:1) to give Part B compound (200 mg; 35%) as an oil. In addition, the byproduct vinyl compound

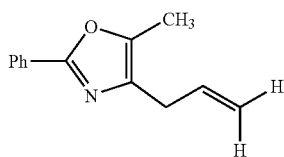

(100 mg; 43%) was also obtained.

C.

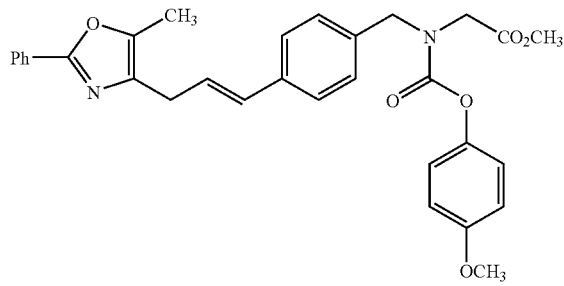

A solution of Part B compound (100 mg; 0.020 mmol) and Example 562 Part B compound

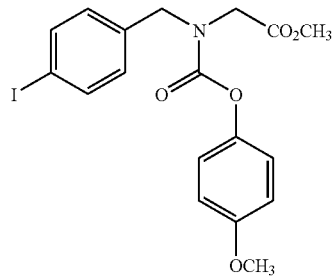

(100 mg; 0.22 mmol) and (Ph₃P)₄Pd° (3 mg; 0.002 mmol) in toluene was heated at 100° C. overnight under an atmosphere of N₂. Volatiles were removed in vacuo and the residue was chromatographed (SiO₂; stepwise gradient from 3:1 to 2:1 hexane:EtOAc) to give Part C compound.

D.

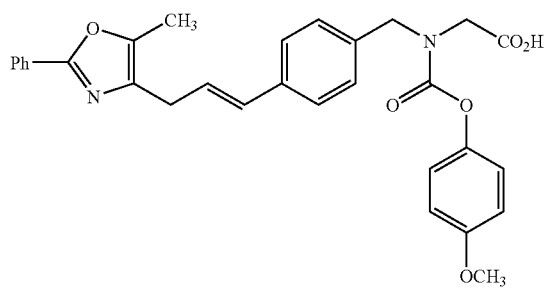

A solution of crude Part C compound (in aqueous LiOH (1 mL of a 1M solution) and THF (5 mL) was stirred at RT overnight. The reaction was acidified to pH3 with excess aqueous 1 M HCl and extracted with EtOAc (2×5 mL). The combined organic extracts were dried (Na₂SO₄) and concentrated in vacuo. The residue was purified by preparative HPLC (YMC S5 ODS reverse phase column; 30×250 mm; flow rate=25 mL/min; 30 min continuous gradient from 50:50 A:B to 100% B, where solvent A=90:10:0.1 H₂O:MeOH:TFA and solvent B=90:10:0.1 MeOH:H₂O:TFA) to give, after lyophilization from dioxane, title compound (23 mg; 20%) as a white solid. $[M+H]^+=513.3$

EXAMPLES 568 TO 572

Following the procedures set out hereinbefore and in the working Examples, the following compounds were prepared.

| Example No. | Structure | $[M + H]^+$ |
|---|---|---|
| 568 | 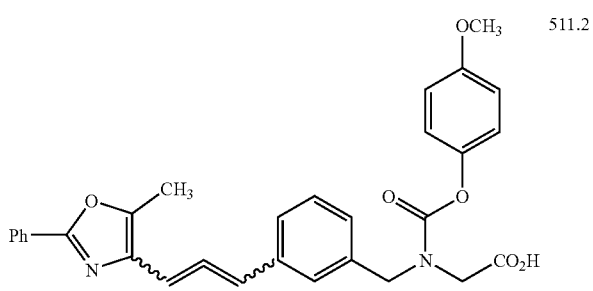 | 511.2 |

-continued
| Example No. | Structure | [M + H]+ |
|---|---|---|
| 569 | 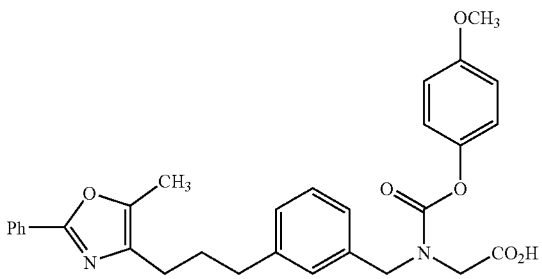 | 515.9 |
| 570 | 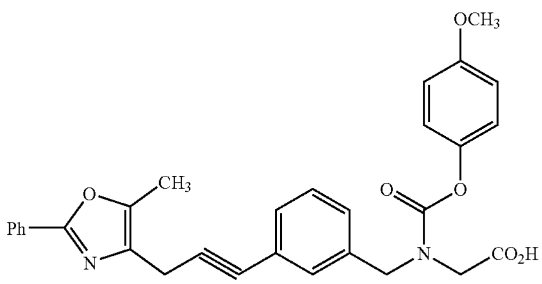 | 511.2 |
| 571 | 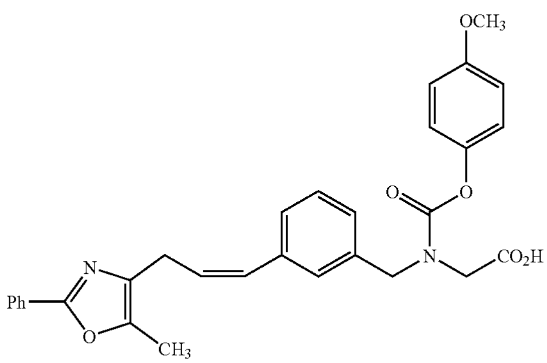 | 513.2 |
| 572 | 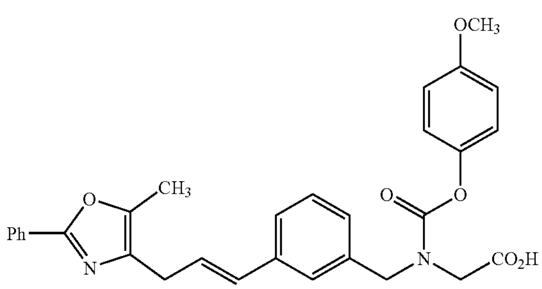 | 513.3 |
EXAMPLE 573
-continued
A.
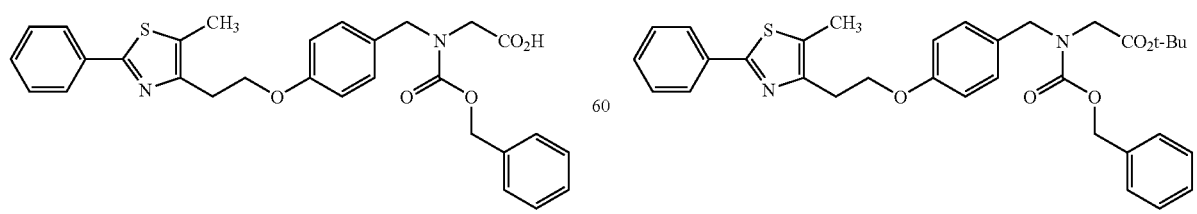

285

To a mixture of the amino-ester (27 mg; 0.073 mmol)

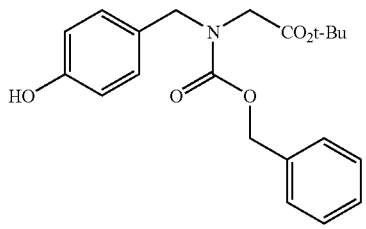

5-methyl-2-phenyl-thiazol-4-yl-ethanol (25 mg; 0.11 mmol; Maybridge) resin-bound Ph$_3$P (27 mg; 0.081 mmol) in CH$_2$Cl$_2$ (0.5 mL) was added DEAD (20 µL; 0.13 mmol). The reaction was stirred at RT for 6 h, then was filtered. The filtrate was concentrated in vacuo and the residue was purified by preparative HPLC (YMC S5 ODS 30×100 mm column; flow rate=50 mL/min; continuous gradient from 30:70 B:A to 100% B, where solvent A=90:10:0.1 H$_2$O:MeOH:TFA and solvent B=90:10:0.1 MeOH:H$_2$O:TFA) to furnish Part A compound.

B.

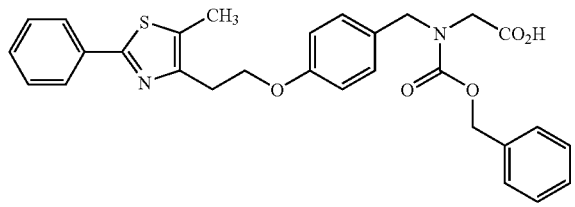

A solution of Part A compound in TFA (1 mL) was stirred at RT overnight, then was concentrated in vacuo to furnish title compound (11 mg; 26%) as a brown oil (94% purity by analytical HPLC). [M+H]$^+$=517.2

EXAMPLE 574

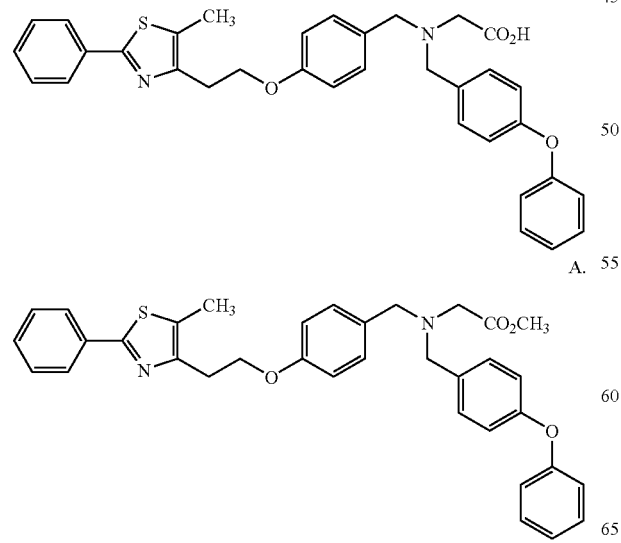

286

To a mixture of the amino-ester (31 mg; 0.082 mmol)

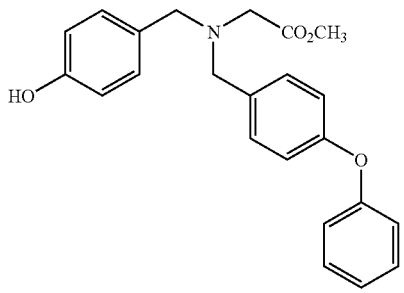

5-methyl-2-phenyl-thiazol-4-yl-ethanol (25 mg; 0.11 mmol; Maybridge) resin-bound Ph$_3$P (32 mg; 0.096 mmol) in CH$_2$cl$_2$ (0.5 mL) was added DEAD. (20 µL; 0.13 mmol). The reaction was stirred at RT for 6 h, then was filtered. The filtrate was concentrated in vacuo to give crude Part A compound.

B.

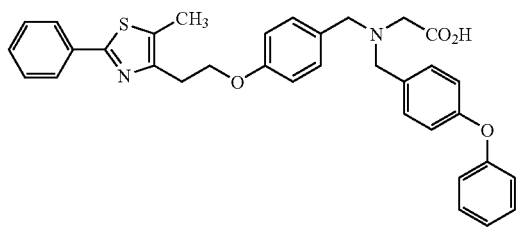

A solution of crude Part A compound and LiOH.H$_2$O (20 mg; 0.48 mmol) in THF:MeOH:H$_2$O (1 mL of a 3:1:1 mixture) was stirred at RT overnight. The reaction was acidified to pH~4 with aqueous 1N HCl, then was extracted with EtOAc (2×). The combined organic extracts were concentrated in vacuo and the residue was purified by preparative HPLC (YMC S5 ODS 30×100 mm column; flow rate=50 mL/min; 10 min continuous gradient from 30:70 B:A to 100% B, where solvent A=90:10:0.1 H$_2$O:MeOH:TFA and solvent B=90:10:0.1 MeOH:H$_2$O:TFA) to furnish title compound (16 mg; 34%) as a brown oil (95% purity by analytical HPLC). [M+H]$^+$= 565.2

EXAMPLE 575

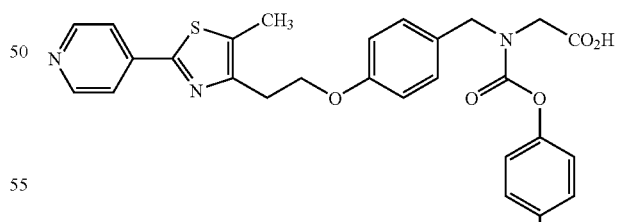

A.

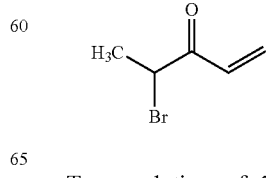

To a solution of 2,4-dibromo-3-pentanone (Avocado Chemicals, 19.6 g, 80 mmol) in CH$_2$Cl$_2$ (50 mL) was added dropwise Et₃N (30 mL, 210 mmol) over 30 min; the resulting solution was heated to reflux for 12 h. The reaction mixture was cooled to RT, then was poured into ice and acidified with concentrated HCl. The organic phase was concentrated in vacuo to give an oil, which was fractionally distilled (b.p.=42'–45° C. at 13 mm Hg) to give Part A compound (6.0 g, 46%; with ~20% of the starting material) as an oil.

B.

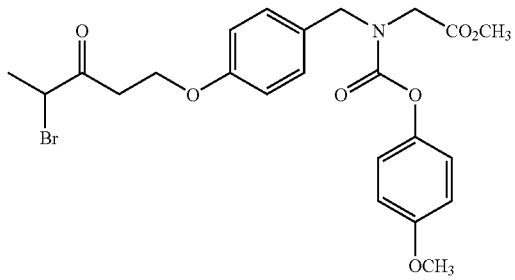

A mixture of Example 559 Part E compound (0.60 g, 1.7 mmol),

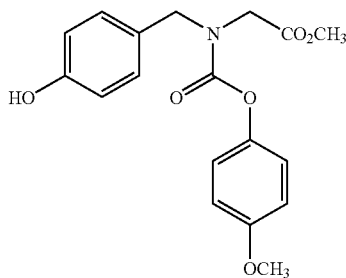

Part A compound (0.60 g, 3.7 mmol) and K₂CO₃ (1.0 g, 7.3 mmol) in benzene (20 mL) was stirred at RT for 12 h. TLC at this point indicated that ~50% of the starting material had been consumed and that the reaction had stalled. The reaction mixture was filtered and the filtrate was concentrated in vacuo. The residue was chromatographed (SiO₂; 3% acetone/CH₂Cl₂) to provide Part B compound (0.41 g; 47%) as an oil.

C.

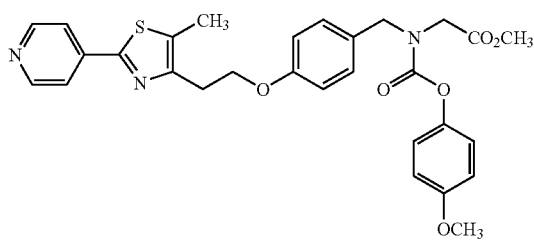

A solution of Part B compound (40 mg, 0.080 mmol) and thioisonicotinamide (50 mg, 0.36 mmol) in toluene-EtOH (3 mL of a 1:1 mixture) was heated at 55° C. for 12 h. The reaction was cooled to RT and volatiles were removed in vacuo. The crude product was purified by preparative HPLC (YMC S5 ODS 30×250 mm, continuous 30 min gradient from 30% B:70% A to 100% B at 30 min, where solvent A=90:10:0.1 H₂O:MeOH:TFA and solvent B=90:10:0.1 MeOH:H₂O:TFA) to give Part C compound (17; 39%) as an oil.

D.

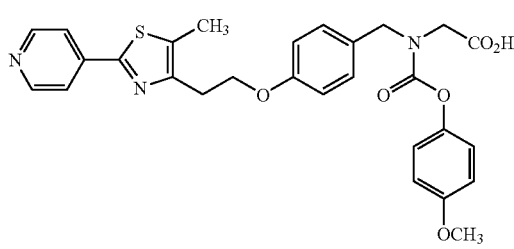

A solution of Part C compound (17 mg, 0.031 mmol) and LiOH.H₂O (40 mg, 1 mmol) in THF-H₂O (3 mL of a 2:1 mixture) was stirred at RT for 2 h. The reaction mixture was acidified by addition of acetic acid and then partitioned between H₂O (2 mL) and EtOAc (5 mL). The organic phase was dried (MgSO₄) and concentrated in vacuo to provide the title compound (13.7 mg, 81%) as a white solid. [M+H]⁺= 534.2

EXAMPLES 576 TO 580

Following the procedures set out hereinbefore and in the working Examples, the following compounds were prepared.

| Example No. | Structure | [M + H]⁺ |
|---|---|---|
| 576 | ![structure] | 551.2; 553.2 |

-continued
| Example No. | Structure | [M + H]+ |
|---|---|---|
| 577 | 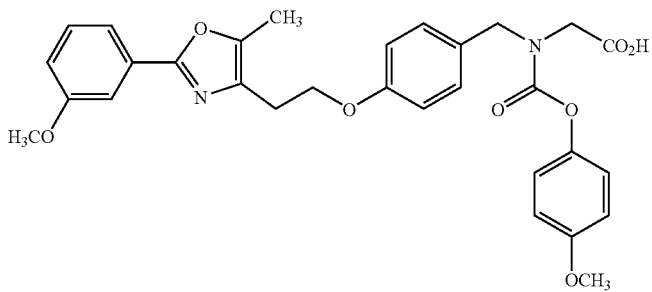 | 547.2 |
| 578 | 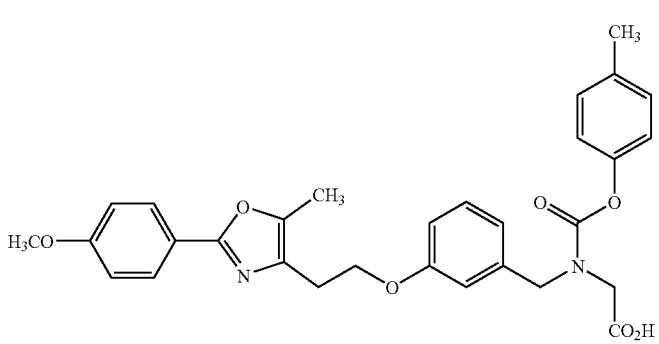 | 531.2 |
| 579 | 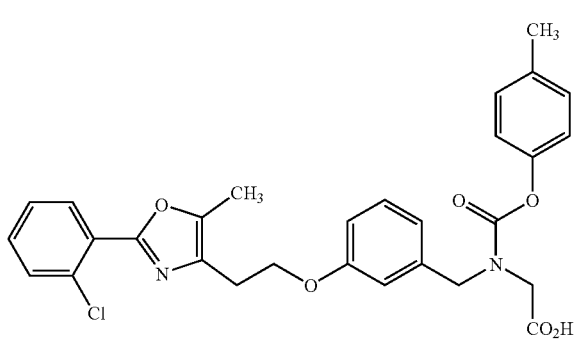 | 535.2; 537.2 |
| 580 | 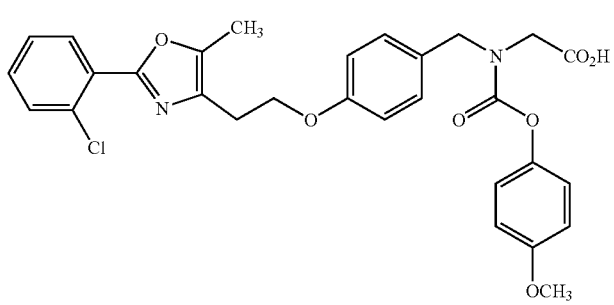 | 551.2; 553.2 |

Examples 581 and 582 were synthesized according to the general procedures described for Examples 313 and 314.
| Example | Structure | [M + H]⁺ |
|---|---|---|
| 581 | 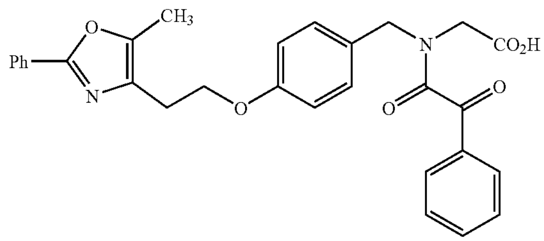 | 499.2 |
| 582 | 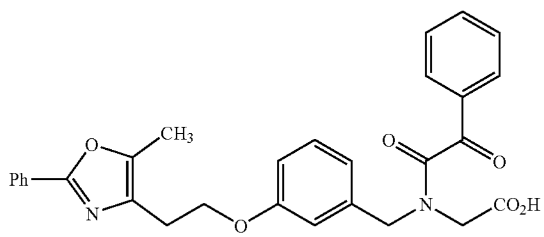 | 499.1 |
Examples 583 and 584 were synthesized according to the general methods described hereinbefore (e.g. for Example 139) using 4-methoxy thiophenol.
| Example | Structure | [M + H]⁺ |
|---|---|---|
| 583 | 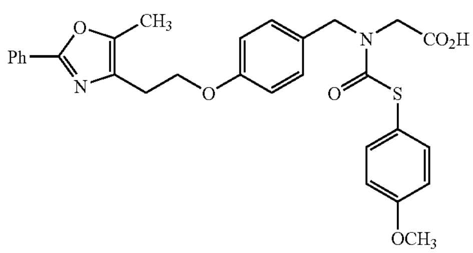 | 533.3 |
| 584 | 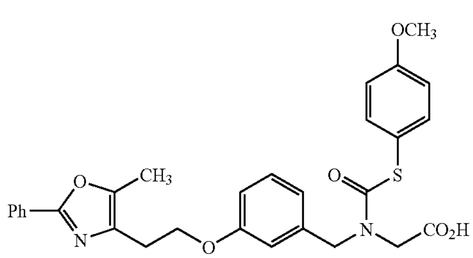 | 533.3 |
EXAMPLE 584
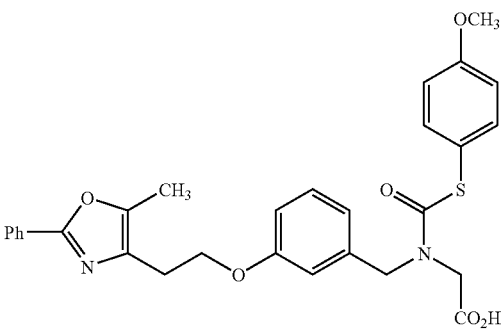
$^1$H NMR (CDCl$_3$; 400 MHz): δ 2.42 (s, 3H), 3.04 (br s; 2H), 3.79 (s, 3H), 4.03 (br s, 2H), 4.25 (br s, 2H), 4.70 (br s, 2H), 6.8–7.0 (m, 5H), 7.15–7.30 (m, 1H), 7.35–7.50 (m, 5H), 7.95–8.05 (m, 2H); 8.95 (br s, 1H)
EXAMPLE 585
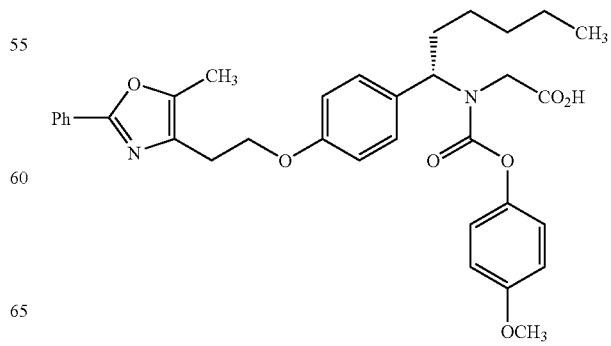

A.

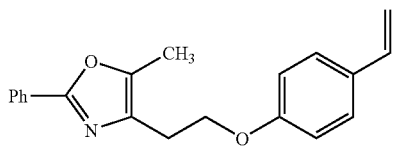

To a −78° C. solution of methyltriphenylphosphonium bromide (4.2 g; 11.8 mmol) in THF (60 mL) was added dropwise n-butyllithium (4.7 mL of a 2.5 M solution in hexane; 11.8 mmol). The solution was allowed to warm to RT and stirred at RT for 45 min. To this mixture was added dropwise a solution of the aldehyde (3.0 g; 9.8 mmol)

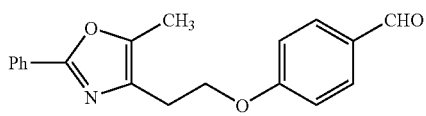

in THF (15 mL). The reaction was stirred at RT for 30 min and at 50° C. for 13 h. After cooling to RT, the reaction mixture was partitioned between EtOAc and saturated aqueous NH₄Cl. The organic phase was washed with brine, dried (MgSO₄) and concentrated in vacuo. The residue was chromatographed (SiO₂; Hexane:EtOAc; stepwise gradient from 9:1 to 4:1) to provide Part A compound (2.0 g; 67%).

B.

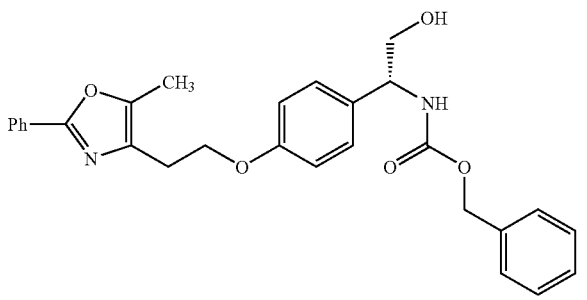

To a solution of benzyl carbamate (3.07 g; 20.3 mmol) in n-propanol (26 mL) was added a freshly prepared solution of aqueous NaOH (800 mg in 48 mL H₂O) and tert-butyl hypochlorite (2.17 g; 20.0 mmol). After stirring at RT for 5 min, a solution of hydroquinidine 1,4-phthalazinediyl diether [(DHQD)₂PHAL; Aldrich; 256 mg; 0.33 mmol] in n-propanol (23 mL) was added, after which the mixture became homogeneous. A solution of Part A compound (2.0 g; 6.56 mmol) in n-propanol (32 mL) was added, followed by a solution of potassium osmate dihydrate [K₂OsO₄(OH₂)₂; 97 mg; 0.26 mmol] in aqueous NaOH (5 mL of a 0.4 M solution). The light green reaction solution was stirred at RT for 30 min, after which it became yellow, and was cooled to 0° C. The reaction was quenched by addition of saturated aqueous sodium sulfite (60 mL) and stirring for 15 min. The aqueous phase was extracted with EtOAc (2×100 mL); the combined organic extracts were washed with water and brine, dried (MgSO₄) and concentrated in vacuo. The residue was chromatographed (SiO₂; Hex:EtOAc; stepwise gradient from 9:1 to 1:1) to furnish Part B compound (1.80 g; 58%) and the byproduct Part C compound (0.93 g; 30%).

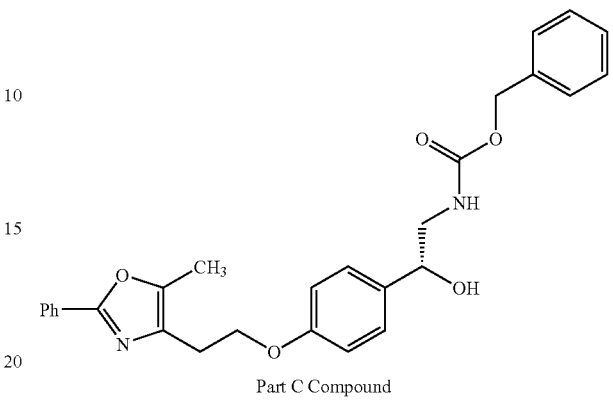

Part C Compound

D.

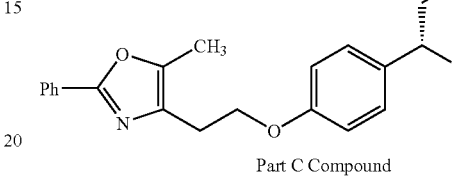

To a 0° C. solution of Part B compound (1.10 g; 2.33 mmol) in CH₂Cl₂ (12 mL) were successively added methanesulfonyl chloride (220 μL; 2.80 mmol) and Et₃N (420 μL; 3.03 mmol) dropwise. The reaction was stirred at 0° C. for 2 h, then was partitioned between CH₂Cl₂ and aqueous 1N HCl. The organic phase was washed with water and brine, dried (MgSO₄) and concentrated in vacuo to provide Part D compound (1.10 g; 86%) as a solid.

E.

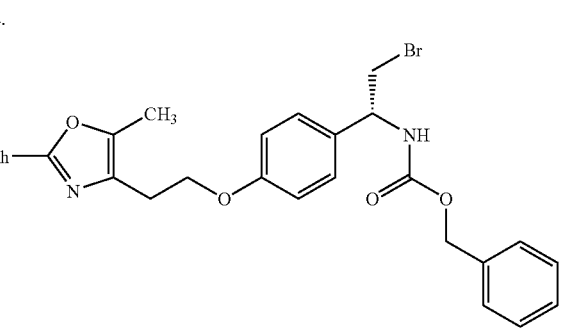

A mixture of Part D compound (1.10 g; 2.0 mmol) and LiBr (260 mg; 3.0 mmol) in acetone (4 mL) was heated at 50° C. for 14 h. The reaction was then cooled to RT and concentrated in vacuo. The residue was chromatographed (SiO₂; stepwise gradient from 9:1 to 4:1 hex:EtOAc) to give Part E compound (481 mg; 45%) as an oil.

F.

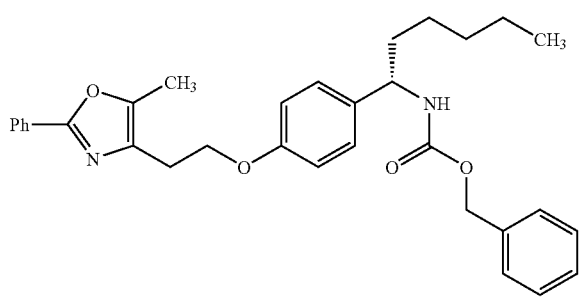

To a −78° C. slurry of CuCN (17 mg; 0.19 mmol) in freshly distilled anhydrous THF (0.54 mL) was added dropwise n-butyllithium (150 μL of a 2.5 M solution in hexanes). The mixture was allowed to warm slowly to 0° C. to generate the higher-order cuprate reagent as a clear tan solution. The reaction was then cooled to −50° C. and a solution of Part E compound (50 mg; 0.094 mmol) in THF (0.4 mL) was added dropwise. The reaction was stirred at −50° C. for 1 h and then allowed to warm slowly to 0° C. over 2 h. The mixture was then quenched at 0° C. by addition of 9:1 saturated aqueous $NH_4Cl$:concentrated $NH_4OH$ (2 mL), and then allowed to warm to RT with vigorous stirring until complete dissolution had occurred. The aqueous phase was extracted with EtOAc (2×), and the combined organic extracts were washed with saturated aqueous $NH_4Cl$ and brine, dried ($MgSO_4$) and concentrated in vacuo. The residue was chromatographed ($SiO_2$; stepwise gradient from 9:1 to 2:1 hex:EtOAc) to provide Part F compound (26 mg; 54%) as a solid.

G.

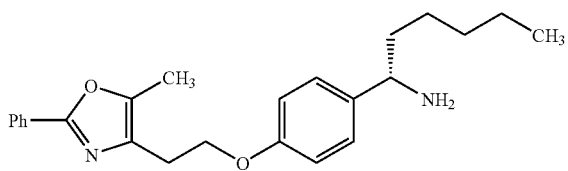

A mixture of Part F compound (26 mg; 0.051 mmol) and 10% palladium on carbon (10 mg) in 2:1 MeOH:EtOAc (1.2 mL) was stirred under an atmosphere of $H_2$ (balloon) at RT for 2 h, at which point the reaction was complete by HPLC. The catalyst was filtered off through Celite® and the filtrate was concentrated in vacuo to give Part G compound (18 mg; 93%) as an oil.

H.

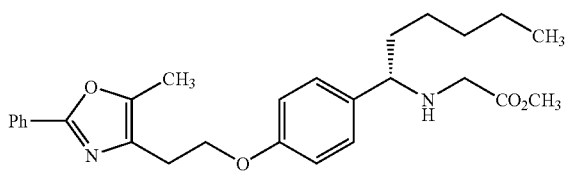

A solution of Part G compound (18 mg; 0.048 mmol), methyl bromoacetate (9 μL; 0.095 mmol) and $Et_3N$ (15 μL; 0.10 mmol) in THF (500 μL) was stirred at RT for 15 h. The reaction mixture was partitioned between $H_2O$ and EtOAc (60 mL) each. The organic phase was washed with brine, dried ($MgSO_4$) and concentrated in vacuo to furnish crude Part H compound, which was used in the next step without further purification.

I.

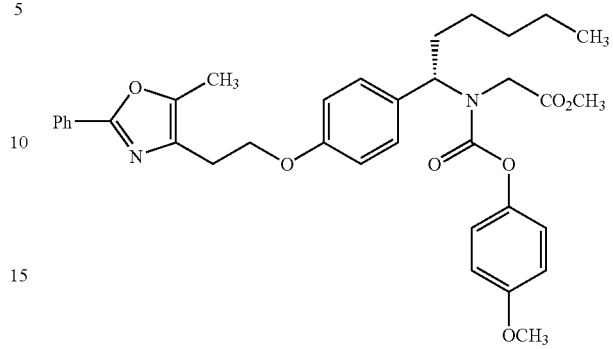

A solution of crude Part H compound, 4-methoxyphenyl chloroformate (21 μL; 0.143 mmol) and 4-dimethylaminopyridine (4 mg; 0.033 mmol) in pyridine (10 mL) was heated at 70° C. for 2 h. The reaction mixture was partitioned between EtOAc and 1M aqueous HCl. The organic phase was washed with brine, dried ($MgSO_4$), and concentrated in vacuo. The residue was purified by preparative HPLC (YMC reverse phase ODS 20×100 mm column; 10 min continuous gradient from 50% A:50% B to 100% B+10 min hold-time at 100% B, where Solvent A=90:10:0.1 $H_2O$:MeOH:TFA, and Solvent B=90:10:0.1 MeOH:$H_2O$:TFA; flow rate=20 mL/min; retention time= 14.6 min) to furnish Part I compound (16 mg; 56% over 2 steps) as an oil.

J.

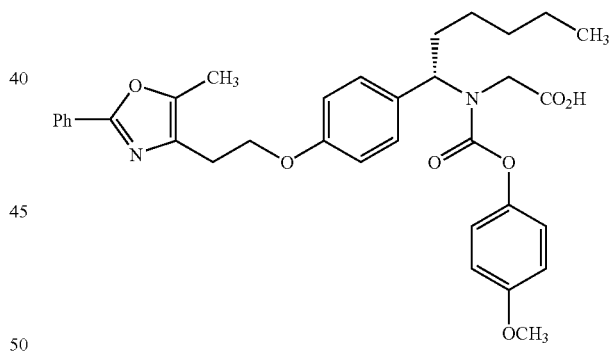

To a solution of Part I compound (9.0 mg; 0.015 mmol) in THF:$H_2O$ (750 μL of a 2:1 solution) was added LiOH.$H_2O$ (2.5 mg; 0.06 mmol). The reaction was stirred at RT for 15 h; then EtOAc (2 mL) was added and the solution acidified with 1 N HCl solution to pH~2. The organic phase was washed with water and brine, dried ($MgSO_4$) and concentrated in vacuo. The residue was purified by preparative HPLC (YMC reverse phase ODS 20×100 mm column; flow rate=20 mL/min; 10 min continuous gradient from 50:50 B:A to 100% B+10 min hold-time at 100% B, where solvent A=90:10:0.1 $H_2O$:MeOH:TFA and solvent B=90:10:0.1 MeOH:$H_2O$:TFA; retention time=13.2 min) to provide the title compound (6.0 mg; 68%) as a white solid.

$[M+H]^+$=587.3

EXAMPLE 586

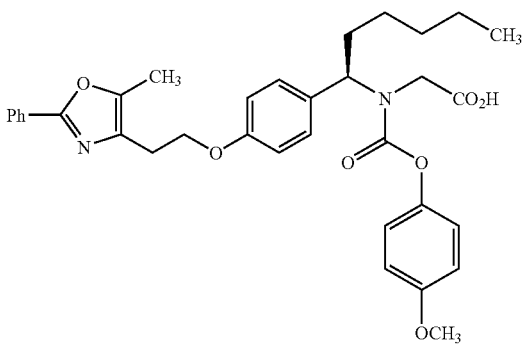

The synthesis of Example 586 was performed using the identical sequence as described for Example 585 except that the catalyst used in the aminohydroxylation procedure (step 2) for the preparation of the key intermediate

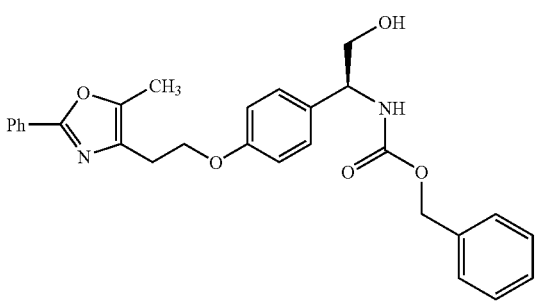

was hydroquinine 1,4-phthlazinediyl diether [(DHQ)$_2$PHAL; Aldrich] instead of hydroquinidine 1,4-phthlazinediyl diether [(DHQD)$_2$PHAL; Aldrich].

EXAMPLE 587

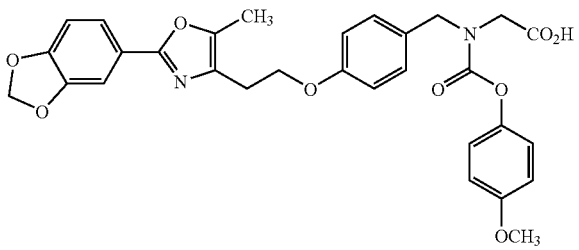

A.

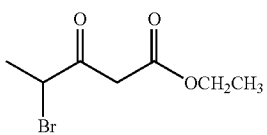

To a 0° C. solution of ethyl propionylacetate (10.0 g, 69.4 mmol) in CHCl$_3$ (60 mL) was added dropwise a solution of Br$_2$ (3.6 mL; 69.4 mmol) in CHCl$_3$ (20 mL) and the resulting mixture was stirred at 0° C. for 0.5 h. The reaction was allowed to warm to RT and stirred at RT for 0.5 h. Air was then bubbled into the mixture for 1 h. Volatiles were then removed in vacuo to yield an oily residue to provide crude Part A compound (15.3 g, >95% yield) as an oil which was used in the next reaction without further purification.

B.

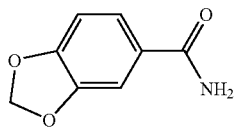

To a mixture of piperonylic acid (2.0 g; 12 mmol), HOBT.H$_2$O (2.44 g; 18.1 mmol) and NH$_4$Cl (1.28 g; 23.7 mmol) in DMF (48 mL) were successively added EDCI.HCl (3.45 g; 18.1 mmol) and iPr$_2$NEt (2.3 mL; 48 mmol). The reaction mixture was stirred at RT overnight until the starting acid had been completely consumed(by HPLC). The mixture was partitioned between H$_2$O (80 mL) and EtOAc (250 mL). The aqueous phase was extracted with EtOAc (250 mL). The combined organic extracts were washed with aqueous 1 N HCl (40 mL), dried (Na$_2$SO$_4$) and concentrated in vacuo. The crude product was chromatographed (SiO$_2$; stepwise gradient from hex:EtOAc 1:1 to 100% EtOAc) to give Part B compound (1.5 g; 76%) as a white solid.

C.

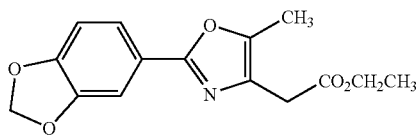

A mixture of Part A compound (2.11 g, 9.5 mmol) and Part B compound (1.41 g, 8.54 mmol) was heated with a heat gun until the mixture became homogeneous, after which the solution was heated at 130° C. in an oil bath for 5 h. The reaction mixture was chromatographed (SiO$_2$; continuous gradient from hex to 4:1 Hex:EtOac over 20 min, then continuous gradient from 4:1 Hex:EtOAc to 100% EtOAc over 15 min) to yield Part C compound (0.95 g, 39%) as a yellow solid.

D.

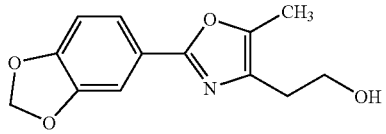

To a −78° C. solution of Part C compound (0.95 g, 3.3 mmol) in anhydrous THF (20 mL) was added LiAH$_4$(3.55 mL of a 1 M solution in THF, 3.55 mmol) dropwise over 10 min and the reaction was stirred at −78° C. for 0.5 h, then at 0° C. for 5 min. The reaction was quenched by sequential cautious addition of water (0.13 mL), aqueous NaOH (20 mg in 0.13 mL H$_2$O) and water (0.20 mL). Anhydrous MgSO$_4$ (400 mg) was then added to the mixture, which was stirred at RT for 10 min, then filtered. The filtrate was concentrated in vacuo and the residue was chromatographed (SiO$_2$; stepwise gradient from hex:EtOAc 1:1 to 100% EtOAc) to give Part D compound (350 mg; 43%) as an oil.

E.

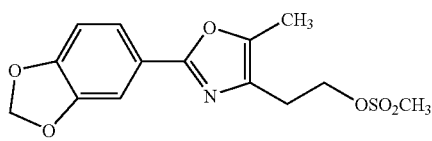

A mixture of Part D compound (0.35 g, 1.41 mmol), CH₃SO₂Cl (0.131 ml, 1.69 mmol) and Et₃N (355 μL, 2.55 mmol) in anhydrous CH₂Cl₂ (6 mL) was stirred at RT for 4 h, then partitioned between EtOAc (150 mL) and H₂O (10 mL). The organic phase was dried (MgSO₄) and concentrated in vacuo. The residue was chromatographed (SiO₂; stepwise gradient from hex:EtOAc 1:1 to 100% EtOAc) to provide Part E compound (0.395 g, 86%) as a white solid.

F.

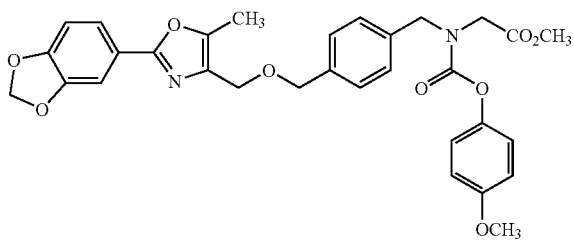

A mixture of Part E compound (25 mg; 0.076 mmol), Example 559 Part E compound (25 mg, 0.073 mmol),

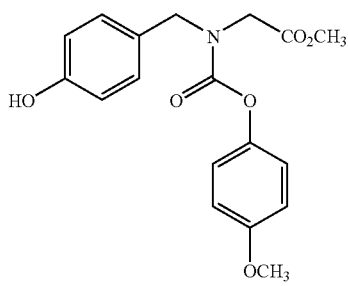

and K₂CO₃ (15 mg, 0.109 mmol) in acetonitrile (1 mL) was shaken and heated at 80° C. for 22 h. The reaction was cooled to RT and filtered. The filtrate was concentrated in vacuo and the residue was purified by preparative HPLC (YMC reverse-phase ODS 20×100 mm column; continuous gradient over 10 min from 70:30 A:B to 100% B, where A=90:10:0.1 H₂O:MeOH:TFA, and B=90:10:0.1 MeOH:H₂O:TFA, with 7 min hold time at 100% B; flow rate=20 mL/min) to provide Part F compound (21 mg; 51%) as a colorless oil.

G.

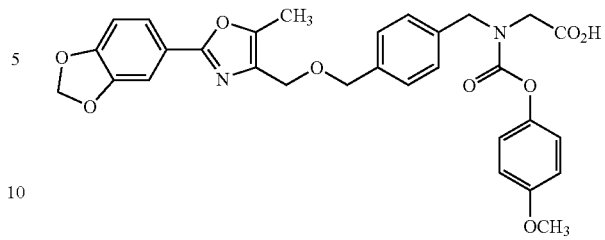

A solution of Part F compound (21 mg, 0.037 mmol) and LiOH.H₂O (4.0 mg; 0.095 mmol) in THF-H₂O (2.0 mL of a 1:1 mixture) was shaken at RT for 4 h. The reaction mixture was acidified to pH5 with 1 M aqueous HCl, then was extracted with EtOAc (3 mL) by shaking for 10 min. The organic phase was washed with H₂O (2 mL) and concentrated in vacuo to provide Example 586 (16.3 mg, 75%) as a solid foam.

[M+H]⁺=561.2

Examples 588 to 596 were prepared according to the scheme described above.

EXAMPLES 588 TO 591

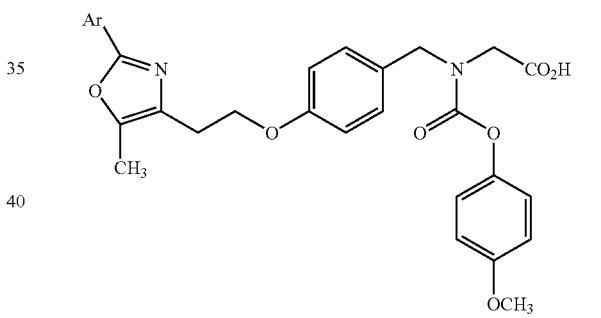

| Example No. | Ar | [M + H]⁺ |
|---|---|---|
| 588 | 3-Cl-C₆H₄ | 551.1 |
| 589 | 2-OCH₃-C₆H₄ | 547.2 |
| 590 | 3-CF₃-C₆H₄ | 585.3 |

-continued

| Example No. | Ar | [M + H]⁺ |
|---|---|---|
| 591 | 4-(F₃C)-phenyl | 585.2 |

EXAMPLES 592 TO 596

| Example No. | Ar | [M + H]⁺ |
|---|---|---|
| 592 | 3-Cl-phenyl | 551.1 |
| 593 | 2-OCH₃-phenyl | 547.2 |
| 594 | benzo[1,3]dioxol-5-yl | 561.2 |
| 595 | 3-(F₃C)-phenyl | 585.3 |
| 596 | 4-(F₃C)-phenyl | 585.2 |

What is claimed is:

1. A compound having the structure amino ester (a)

or amino acid (b)

wherein PG is a carboxylic acid protecting group which is methyl, ethyl or t-butyl, and $R^5 =$ [structure shown]

wherein $X^1_x$ is an alkylene chain of two carbons, alkenylene chain of two carbons or an alkynylene chain of two carbons;

$X^1_m$ is an alkylene chain of one carbon; and $X^1_n$ is an alkylene chain of one carbon;

Q is C;

A is O;

$R^1$ is methyl;

X is CH;

$R^2$ is H, alkyl, alkoxy, halogen, amino or substituted amino;

$R^{2a}$, $R^{2b}$ and $R^{2c}$ are each H;

or stereoisomers thereof, or a prodrug ester thereof, and pharmaceutically acceptable salt thereof.

2. The compound as defined in claim 1 wherein $X^1_x$ is $(CH_2)_2$;
$X^1_m$ is $CH_2$, or
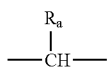
wherein $R_a$ is or alkyl alkenyl, $X^1_n$ is $CH_2$, $R^1$ is lower alkyl, $R^{2a}$ H, $^4X$ is CH; and PG is methyl, ethyl or t-butyl.
3. The compound as defined in claim 1 having the structure
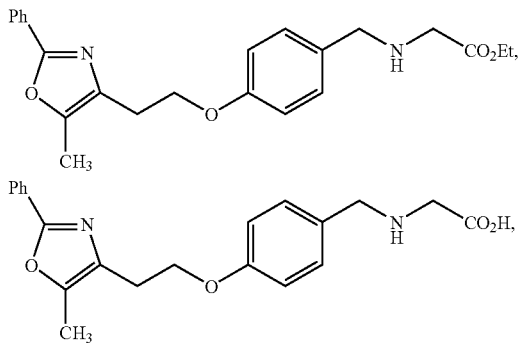
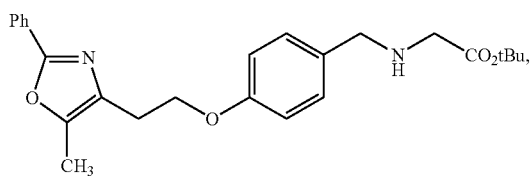
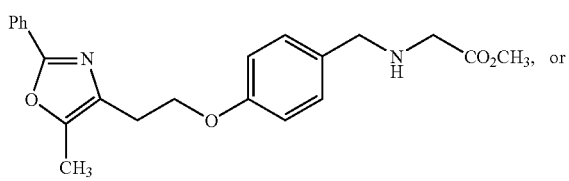
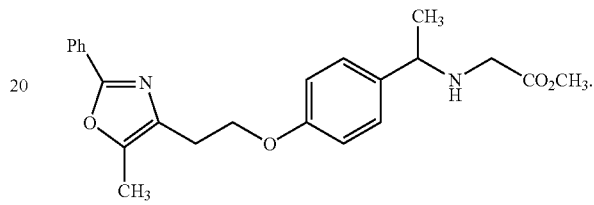
* * * * *

UNITED STATES PATENT AND TRADEMARK OFFICE
CERTIFICATE OF CORRECTION

| | | |
|---|---|---|
| PATENT NO. | : 7,084,162 B2 | Page 1 of 1 |
| APPLICATION NO. | : 10/655876 | |
| DATED | : August 1, 2006 | |
| INVENTOR(S) | : Cheng et al. | |

It is certified that error appears in the above-identified patent and that said Letters Patent is hereby corrected as shown below:

On Title page, column 2, foreign patent documents, "WO 00/64676" should read --WO 00/64876--

Claim 1, column 302, line 66, "and" should be replaced with -- or a --

Claim 2, column 303, lines 9 and 10 should read as follows:

-- wherein $R_a$ is alkyl or alkenyl, $X^1_n$ is $CH_2$, $R^1$ is lower alkyl, and $R^{2a}$ H, X is CH; and PG is methyl, ethyl or t-butyl--.

Signed and Sealed this

Seventh Day of August, 2007

JON W. DUDAS
*Director of the United States Patent and Trademark Office*